(12) United States Patent
Triebel et al.

(10) Patent No.: US 11,680,104 B2
(45) Date of Patent: Jun. 20, 2023

(54) ANTI-LAG-3 ANTIBODIES

(71) Applicant: IMMUTEP S.A.S., Orsay (FR)

(72) Inventors: Frédéric Triebel, Versailles (FR); Chrystelle Brignone, Chatenay-Malabry (FR)

(73) Assignee: IMMUTEP S.A.S., Orsay (FR)

( * ) Notice: Subject to any disclaimer, the term of this patent is extended or adjusted under 35 U.S.C. 154(b) by 174 days.

(21) Appl. No.: 15/756,767

(22) PCT Filed: Sep. 1, 2016

(86) PCT No.: PCT/EP2016/070664
§ 371 (c)(1),
(2) Date: Mar. 1, 2018

(87) PCT Pub. No.: WO2017/037203
PCT Pub. Date: Mar. 9, 2017

(65) Prior Publication Data
US 2019/0153112 A1  May 23, 2019

(30) Foreign Application Priority Data

Sep. 2, 2015 (GB) .................................... 1515572
Jul. 18, 2016 (GB) .................................... 1612437

(51) Int. Cl.
*A61P 29/00* (2006.01)
*C07K 16/28* (2006.01)
*A61P 37/06* (2006.01)

(52) U.S. Cl.
CPC .......... *C07K 16/2896* (2013.01); *A61P 29/00* (2018.01); *A61P 37/06* (2018.01); *C07K 2317/24* (2013.01); *C07K 2317/565* (2013.01); *C07K 2317/70* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,703,039 A | 10/1987 | Hawiger et al. |
| 4,816,397 A | 3/1989 | Boss et al. |
| 4,816,567 A | 3/1989 | Cabilly et al. |
| 4,866,132 A | 9/1989 | Obligin et al. |
| 4,873,316 A | 10/1989 | Meade et al. |
| 4,946,778 A | 8/1990 | Ladner et al. |
| 5,225,539 A | 7/1993 | Winter |
| 5,256,334 A | 10/1993 | Smid et al. |
| 5,346,981 A | 9/1994 | Sarpeshkar et al. |
| 5,476,786 A | 12/1995 | Huston |
| 5,514,548 A | 5/1996 | Krebber et al. |
| 5,530,101 A | 6/1996 | Queen et al. |
| 5,585,089 A | 12/1996 | Queen et al. |
| 5,643,575 A | 7/1997 | Martinez et al. |
| 5,677,425 A | 10/1997 | Bodmer et al. |
| 5,693,762 A | 12/1997 | Queen et al. |
| 5,714,350 A | 2/1998 | Co et al. |
| 5,739,277 A | 4/1998 | Presta et al. |
| 5,747,035 A | 5/1998 | Presta et al. |
| 5,849,860 A | 12/1998 | Hakimi et al. |
| 5,869,046 A | 2/1999 | Presta et al. |
| 5,874,304 A | 2/1999 | Zolotukhin et al. |
| 5,919,445 A | 7/1999 | Chao |
| 5,939,045 A | 8/1999 | Suzuki et al. |
| 5,958,713 A | 9/1999 | Thastrup et al. |
| 5,968,738 A | 10/1999 | Anderson et al. |
| 5,968,750 A | 10/1999 | Zolotukhin et al. |
| 5,976,796 A | 11/1999 | Szalay et al. |
| 5,976,877 A | 11/1999 | Hercend et al. |
| 5,985,577 A | 11/1999 | Bulinski |
| 6,020,192 A | 2/2000 | Muzyczka et al. |
| 6,046,305 A | 4/2000 | Choi |
| 6,066,476 A | 5/2000 | Tsien et al. |
| 6,121,022 A | 9/2000 | Presta et al. |
| 6,165,745 A | 12/2000 | Ward et al. |

(Continued)

FOREIGN PATENT DOCUMENTS

| | | |
|---|---|---|
| EP | 0054951 B1 | 12/1984 |
| EP | 0154316 B1 | 9/1989 |

(Continued)

OTHER PUBLICATIONS

Edwards, B.M., et al. J. Mol. Biol. 2003;334:103-118 (Year: 2003).*
Torres, M., and Casadevall, A. Trends Immunol. 2008;91-97 (Year: 2008).*
Khan, T., and Salunke, D.M. J. Immunol. 2014;192:5398-5405 (Year: 2014).*
Poosarla, V.G., et al. Biotechnol. Bioengin. 2017; 114(6): 1331-1342 (Year: 2017).*
Lauffer, Randall B., et al."Preparation and Water Relaxation Properties of Proteins Labeled with Paramagnetic Metal Chelates"; Magnetic Resonance Imaging; vol. 3; pp. 11-16; 1985.
Lefranc, Marie-Paule, et al."IMGT, the International ImMunoGeneTics Database"; Nucleic Acids Research; vol. 27, No. 1; pp. 209-212; 1999.
Lefranc, Marie-Paule, et al."IMGT Unique Numbering for Immunoglobulin and T Cell Receptor Variable Domains and Ig Superfamily V-Like Domains"; Developmental and Comparative Immunology; vol. 27; p. 55-77; 2003.

(Continued)

*Primary Examiner* — G. R. Ewoldt
(74) *Attorney, Agent, or Firm* — Scully, Scott, Murphy & Presser, P.C.

(57) ABSTRACT

Antibodies, or antigen-binding fragments thereof, that bind to Lymphocyte-activation gene-3 (LAG-3) are described, in particular antibodies, or antigen-binding fragments thereof, that are agonists of LAG-3. The antibodies bind to LAG-3 and inhibit antigen-induced $CD4^+$ and/or $CD8^+$ T cell proliferation, or antigen-induced $CD4^+$ and/or $CD8^+$ T cell activation. The antibodies may be used as medicaments, in particular for the treatment of conditions associated with proliferation and/or activation of $CD4^+$ and/or $CD8^+$ T cells, such as inflammatory and autoimmune disorders.

7 Claims, 31 Drawing Sheets
Specification includes a Sequence Listing.

(56) References Cited

U.S. PATENT DOCUMENTS

| | | |
|---|---|---|
| 6,180,370 B1 | 1/2001 | Queen et al. |
| 6,197,524 B1 | 3/2001 | Romagnani |
| 6,277,375 B1 | 8/2001 | Ward |
| 6,350,861 B1 | 2/2002 | Co et al. |
| 6,447,784 B1 | 9/2002 | Bermudes et al. |
| 6,946,292 B2 | 9/2005 | Kanda et al. |
| 7,214,775 B2 | 5/2007 | Hanai et al. |
| 7,521,051 B2 | 4/2009 | Collins et al. |
| 7,632,924 B2 | 12/2009 | Cho et al. |
| 8,551,481 B2 * | 10/2013 | Pardoll .......... A61P 31/00 424/139.1 |
| 8,859,739 B2 | 10/2014 | Kontermann et al. |
| 9,244,059 B2 | 1/2016 | Triebel et al. |
| 9,908,936 B2 | 3/2018 | Triebel et al. |
| 2003/0153043 A1 | 8/2003 | Carr et al. |
| 2004/0131637 A1 | 7/2004 | Chatfield |
| 2005/0053973 A1 | 3/2005 | Kolkman et al. |
| 2005/0089932 A1 | 4/2005 | Kolkman et al. |
| 2005/0164301 A1 | 7/2005 | Kolkman et al. |
| 2007/0148165 A1 | 6/2007 | Shitara et al. |
| 2010/0233183 A1 | 9/2010 | Triebel et al. |
| 2011/0008331 A1 | 1/2011 | Triebel |
| 2011/0027295 A1 | 2/2011 | Powell et al. |
| 2011/0070238 A1 | 3/2011 | Triebel et al. |
| 2011/0150892 A1 | 6/2011 | Thudium et al. |
| 2011/0229461 A1 | 9/2011 | Lyson |
| 2014/0093511 A1 | 4/2014 | Lonberg et al. |
| 2014/0220021 A1 | 8/2014 | Shibayama et al. |
| 2014/0286935 A1 | 9/2014 | Hamblin et al. |
| 2016/0017037 A1 | 1/2016 | Hamblin et al. |
| 2016/0176965 A1 | 6/2016 | Haudebourg et al. |

FOREIGN PATENT DOCUMENTS

| | | |
|---|---|---|
| EP | 0125023 B1 | 6/1991 |
| EP | 0519596 A1 | 12/1992 |
| EP | 0120694 B2 | 7/1993 |
| EP | 0194276 B1 | 8/1993 |
| EP | 0239400 B1 | 8/1994 |
| EP | 0401384 B1 | 3/1996 |
| EP | 1158004 A2 | 11/2001 |
| EP | 1229125 A1 | 8/2002 |
| EP | 1374902 A1 | 1/2004 |
| EP | 1 921 090 A1 | 5/2008 |
| EP | 1987839 A1 | 11/2008 |
| EP | 1 075 496 B1 | 3/2010 |
| WO | 86/01533 A1 | 3/1986 |
| WO | 91/14438 A1 | 10/1991 |
| WO | 93/03769 A1 | 3/1993 |
| WO | 93/06213 A1 | 4/1993 |
| WO | 93/09239 A1 | 5/1993 |
| WO | 93/11161 A1 | 6/1993 |
| WO | 94/12649 A2 | 6/1994 |
| WO | 94/28938 A1 | 12/1994 |
| WO | 95/00655 A1 | 1/1995 |
| WO | 95/11984 A2 | 5/1995 |
| WO | 96/16990 A1 | 6/1996 |
| WO | 96/17951 A2 | 6/1996 |
| WO | 96/32478 A1 | 10/1996 |
| WO | 97/03695 A1 | 2/1997 |
| WO | 97/35614 A1 | 10/1997 |
| WO | 97/43316 A1 | 11/1997 |
| WO | 99/15553 A2 | 4/1999 |
| WO | 99/43713 A1 | 9/1999 |
| WO | 99/58679 A1 | 11/1999 |
| WO | 00/09560 A2 | 2/2000 |
| WO | 00/42072 A2 | 7/2000 |
| WO | 02/31240 A2 | 4/2002 |
| WO | 02/060919 A2 | 8/2002 |
| WO | 03/011878 A2 | 2/2003 |
| WO | 03/076567 A2 | 9/2003 |
| WO | 2004/078928 A2 | 9/2004 |
| WO | 2004081026 A2 | 9/2004 |
| WO | 2005077042 A2 | 8/2005 |
| WO | 2005103086 A1 | 11/2005 |
| WO | 2006/012508 A2 | 2/2006 |
| WO | 2006/014679 A1 | 2/2006 |
| WO | 2007/011041 A1 | 1/2007 |
| WO | 2008/096158 A2 | 8/2008 |
| WO | 2008/132601 A1 | 11/2008 |
| WO | 2010/019570 A2 | 2/2010 |
| WO | 2011/014438 A1 | 2/2011 |
| WO | 2011/016238 A1 | 2/2011 |
| WO | 2011/110621 A1 | 9/2011 |
| WO | 2014/008218 A1 | 1/2014 |
| WO | 2014/140180 A1 | 9/2014 |
| WO | 2015/138920 A1 | 9/2015 |
| WO | 2015138920 A1 | 9/2015 |

OTHER PUBLICATIONS

Lewis, Alan P., et al."Immunoglobulin Complementarity-determining Region Grafting by Recombinant Polymerase Chain Reaction to Generate Humanised Monoclonal Antibodies"; Gene; vol. 101; pp. 297-302; 1991.

Li, Tiansen, et al."In Vivo Transfer of a Reporter Gene to the Retina Mediated by an Adenoviral Vector"; Investigative Ophthalmology & Visual Science; vol. 35, No. 5; Apr. 1994; pp. 2543-2549.

Li, Tiansen, et al."Phenotype Correction in Retinal Pigment Epithelium in Murine Mucopolysaccharidosis VII by Adenovirus-Mediated Gene Transfer"; Proc. Natl. Acad. Sci. USA; vol. 92; pp. 7700-7704; Aug. 1995.

MacCallum, Robert M., et al."Antibody-Antigen Interactions: Contact Analysis and Binding Site Topography"; J. Mol. Biol.; vol. 262; pp. 732-745; 1996.

Macon-Lemaitre, Laetitia, et al."The Negative Regulatory Function of the Lymphocyte-Activiation Gene-3 Co-Receptor (CD223) on Human T Cells"; Immunology; vol. 115; pp. 170-178; 2005.

Matz, Mikhail V., et al."Fluorescent Proteins from Nonbioluminescent Anthozoa Species"; Nature Biotechnology; vol. 17; Oct. 1999; pp. 969-973.

McKelvie, Nicola D., et al."Expression of Heterologous Antigens in *Salmonella typhimurium* Vaccine Vectors Using the in vivo-inducible, SPI-2 Promoter, ssaG"; Vaccine; vol. 22; pp. 3243-3255; 2004.

Rolling, Fabienne, et al."Evaluation of Adeno-Associated Virus-Mediated Gene Transfer into the Rat Retina by Clinical Fluorescence Photography"; Human Gene Therapy; vol. 10; pp. 641-648; Mar. 1, 1999.

Saji, Hideo "Targeted Delivery of Radiolabeled Imaging and Therapeutic Agents: Bifunctional Radiopharmaceuticals"; Critical Reviews in Therapeutic Drug Carrier Systems; vol. 16, No. 2; pp. 209-244; 1999.

Samulski, Richard Jude, et al."Helper-Free Stocks of Recombinant Adeno-Associated Viruses: Normal Integration Does Not Require Viral Gene Expression"; Journal of Virology; vol. 63, No. 9; pp. 3822-3828; Sep. 1989.

Sato, Koh, et al."Reshaping a Human Antibody to Inhibit the Interleukin 6-dependent Tumor Cell Growth"; Cancer Research; vol. 53; pp. 851-856; Feb. 15, 1993.

Shetron-Rama, Lynne M., et al."Intracellular Induction of Listeria Monocytogenes actA Expression"; Infection and Immunity; vol. 70, No. 3; pp. 1087-1096; Mar. 2002.

Sipkins, Dorothy A., et al."Detection of Tumor Angiogenesis in vivo by avB3-targeted Magnetic Resonance Imaging"; Nature Medicine; vol. 4, No. 5; May 1998; pp. 623-626.

Sizemore, Donata R., et al."Attenuated Shigella as a DNA Delivery Vehicle for DNA-Mediated Immunization"; Science; vol. 270; Oct. 13, 1995; pp. 299-302.

Takahashi, Masayo, et al."Rescue from Photoreceptor Degeneration in the rd Mouse by Human Immunodeficiency Virus Vector-Mediated Gene Transfer"; Journal of Virology; vol. 73, No. 9; pp. 7812-7816; Sep. 1999.

Triebel, Frederic "LAG-3: A Regulator of T-cell and DC Responses and its Use in Therapeutic Vaccination"; Trends in Immunology; vol. 24, No. 12; Dec. 2003; pp. 619-622.

(56) References Cited

OTHER PUBLICATIONS

Murphy, Michael, et al."Using Biacore to Measure the Binding Kinetics of an Antibody-Antigen Interaction"; Current Protocols in Protein Science; Chapter 19, Unit 19.14; 2006.

Valdivia, Raphael H., et al."Bacterial Genetics by Flow Cytometry; Rapid Isolation of *Salmonella typhimurium* Acid-Inducible Promoters by Differential Fluorescence Induction"; Molecular Microbiology; vol. 22, No. 2; pp. 367-378; 1996.

Zapata, Gerardo, et al."Engineering Linear F(ab')2 Fragments for Efficient Production in *Escherichia coli* and Enhanced Antiproliferative Activity"; Protein Engineering; vol. 8, No. 10; pp. 1057-1062; 1995.

Melton, D.A., et al."Efficient in vitro Synthesis of Biologically Active RNA and RNA Hybridization Probes from Plasmids Containing a Bacteriophage SP6 Promoter"; Nucleic Acids Research; vol. 12, No. 18; 1984.

Mendelson, Ella, et al."Expression and Rescue of a Nonselected Marker from an Integrated AAV Vector";Virology; vol. 166; pp. 154-165; 1988.

Miyoshi, Hiroyuki, et al."Stable and Efficient Gene Transfer into the Retina Using an HIV-Based Lentiviral Vector"; Proc. Natl. Acad. Sci. USA; vol. 94; pp. 10319-10323; Sep. 1997.

Muller-Gartner, Hans W."Imaging Techniques in the Analysis of Brain Function and Behaviour"; Tibtech; vol. 16; Mar. 1998; pp. 122-130.

Pulkkinen, Wendy S., et al."A *Salmonella typhimurium* Virulence Protein is Similar to a Yersinia Enterocolitica Invasion Protein and a Bacteriophage Lambda Outer Membrane Protein"; Journal of Bacteriology; vol. 173, No. 1; pp. 86-93; Jan. 1991.

Queen, Cary, et al."A Humanized Antibody that Binds to the Interleukin 2 Receptor"; Proc. Natl. Acad. Sci. USA; vol. 86; pp. 10029-10033; Dec. 1989.

Queen, Cary, et al."Cell-Type Specific Regulation of a K Immunoglobulin Gene by Promoter and Enhancer Elements"; Immunological Reviews; Copenhagen, Denmark; No. 89; 1986; pp. 49-53.

Riechmann, Lutz, et al."Reshaping Human Antibodies for Therapy"; Nature; vol. 332;pp. 323-327; Mar. 24, 1988.

Pluckthein, A., et al."The Pharmacology of Monoclonal Antibodies"; vol. 113; New York; pp. 269-315; 1994.

Reddy, Manjula P., et al."Elimination of Fc Receptor-Dependent Effector Functions of a Modified IgG4 Monoclonal Antibody to Human CD4"; The Journal of Immunology; vol. 164; pp. 1925-1933; 2000.

Uchida et al., "The innate mononuclear phagocyte network depletes B lymphocytes through Fc receptor-dependent mechanisms during anti-CD20 antibody immunotherapy", The Journal of Experimental Medicine, vol. 199, No. 12, pp. 1659-1669 (2004).

Velders et al., "The Impact of Antigen Density and Antibody Affinity on Antibody-Dependent Cellular Cytotoxicity: Relevance for Immunotherapy of Carcinomas", British Journal of Cancer, vol. 78, No. 4, pp. 478-483 (1998).

Virella, et al., "Biosynthesis, Metabolism, and Biological Properties", Introduction to Medical Immunology, Chapter 6, 4th Edition, pp. 99-100 (1998).

Wacker et al., "N-Linked Glycosylation in Campylobacter jejuni and its Functional Transfer into *E. coli*", Science, 298; 1790-1793 (2002).

Waldmann, Herman, "The new immunosuppression: just kill the T cell", Nature Medicine, vol. 9, No. 10, pp. 1259-1260 (2003).

Woo, et al., "Differential subcellular localization of the regulatory T-cell protein LAG-3 and the coreceptor CD4", Eur J Immunol, 40;1768-1777 (2010).

Workman and Vignali, "The CD4-related molecule, LAG-3 (CD223), regulates the expansion of activated T cells", Eur J Immunol, 33; 970-979 (2003).

Worn and Pluckthun, "Stability Engineering of Antibody Single-chain Fv Fragments", J Mol Biol, 305; 989-1010 (2001).

Yamane-Ohnuki, et al., "Establishment of FUT8 knockout Chinese hamster ovary cells: an ideal host cell line for producing completely defucosylated antibodies with enhanced antibody-dependent cellular cytotoxicity", Biotechnology and Bioengineering 87(5); 614-622 (2004).

Yousaf, et al., "Targeting behavior of rat monoclonal IgG antibodies in vivo: role of antibody isotype, specificity and the target cell antigen density", Eur. J Immunol, vol. 21, pp. 943-950 (1991).

Zhang, et al., "A New Strategy for the Synthesis of Glycoproteins", Science, 303; 371-373 (2004).

Zhang, et al., "CD8+ T Cells: Foot Soldiers of the Immune System", Immunity Review, vol. 35, pp. 161-168 (2011).

Yasuda, et al. "Humanization of Murine Antibodies by CDR-Grafting", Japanese Journal of Thrombosis and Hemostasis, 4(3): 193-200 (1993). (Translation attached).

"Recombinant Antibodies for in vivo research use", http://absolutelyantibody.com/catalog/in-vivo-research, 2015.

Dotti, "The Other Face of Chimeric Antigen Receptors", Molecular Therapy, vol. 22, No. 5, pp. 899-900, (2014).

De Pascalis, et al. "Grafting of 'Abbreviated' Complementarity-Determining Regions Containing Specificity-Determining Residues Essential for Ligand Contact to Engineer a Less Immunogenic Humanized Monoclonal Antibody", The Journal of Immunology, vol. 169, pp. 3076-3084 (2002).

Miyahira, Andrea, "Types of immune cells present in human PBMC", Sanguine Biosciences, 2012, http://technical.sanguinebio.com.

Kisielow et al., "Expression of lymphocyte activation gene 3 (LAG-3) on B cells is induced by T cells", European Journal of Immunology, vol. 35, pp. 2081-2088 (2005).

"The European Committee on Antimicrobial Susceptibility Testing. Breakpoint tables for interpretation of MICs and zone diameters. Version 5.0, 2015. http://www.eucast.org."

InvivoGen (www.invivogen.com)—Immunoglobulin G Review, 2011.

Nobel-Jamieson, et al., "Auto-immune cholangiopathy in a juvenile patient with systemic lupus erythematosus", Acta Paediatrica, Foundation Acta Paediatrica, 10 1.e262-264 (2012).

Peggs, et al., "Cancer immunotherapy: co-stimulatory agonists and co-inhibitory antgaonists", The Journal of Translational Immunology, vol. 157, pp. 9-19 (2009).

Stewart, et al., "The role of Fc gamma receptors in the activity of immunomodulatory antibodies for cancer", Journal for ImmunoTherapy of Cancer, vol. 2, No. 29, (2014).

T-Cell Research, T Cell Brochure, 2014, pp. 1-14, BD Biosciences, https://www.bdbiosciences.com > documents > cell.

InvivoGen (www.invivogen.com)—Antibody Isotype Families (2015).

Andre, et al., "CD40L stabilizes arterial thrombi by a B3 integrin-dependent mechanism," Nature Medicine, vol. 8, No. 3, pp. 247-252 (2002).

Andreae et al., "Maturation and Activation of Dendritic Cells Induced by Lymphocyte Activation Gene-3 (CD223)1", The Journal of Immunology, vol. 168, pp. 3874-3880 (2002).

Andreae, et al., "MHC class II signal transduction in human dendritic cells induced by a natural ligand, the LAG-3 protein (CD223)", Blood, vol. 102, No. 6, pp. 2130-2137 (2003).

Annunziato, et al., "Expression and release of LAG-3-encoded protein by human CD4+ T cells are associated with IFN-γ production", The FASEB Journal, vol. 10, pp. 769-776 (1996).

Avice, et al., "Lymphocyte Activation Gene-3, a MHC Class II Ligand Expressed on Activated T Cells, Stimulates TNF-a and IL-12 Production by Monocytes and Dendritic CellsT", The Journal of Immunology, vol. 162, pp. 2748-2753 (1999).

Baixeras, et al., "Characterization of the Lymphocyte Activation Gene 3-Encoded Protein. A New Ligand for Human .leukocyte Antigen Class II Antigens", J. Exp. Med., vol. 176, pp. 327-337 (1992).

Bayry, et al., "Rescuing CD4+CD25+ regulatory T-cell functions in rheumatoid arthritis by cytokine-targeted monoclonal antibody therapy", Drug Discovery Today, vol. 12, No. 13/14, pp. 548-552 (2007).

Belson, et al., "Characterisation of the clinical and activated T cell response to repeat delayed-type hypersensitivity skin challenges in human subjects, with KLH and PPD, as potential model to test T-cell targeted therapies", Inflammation Research, vol. 65, pp. 389-404 (2016).

(56) References Cited

OTHER PUBLICATIONS

Bettini, et al., "Cutting Edge: Accelerated Autoimmune Diabetes in the Absence of LAG-3", The Journal of Immunology, vol. 187, pp. 3493-3498 (2011).
Bindon, et al., "Importance of antigen specificity for complement-mediated lysis by monoclonal antibodies", Eur. J Immunol., vol. 18, pp. 1507-1514 (1988).
Bostrom, et al., "Chapter 19: Improving Antibody Binding Affinity And Specificity for Therapeutic Development", Therapeutic Antibodies: Methods and Protocols, vol. 525; pp. 353-376 (2009).
Boyd, et al., "The Effect of the Removal of Sialic Acid, Galactose and Total Carbohydrate on the Functional Activity of Campath-1H", Molecular Immunology, vol. 32, No. 17/18, pp. 1311-1318 (1995).
Brignone, et al., "A Soluble Form of Lymphocyte Activation Gene-3 (IMP321) Induces Activation of a Large Range of Human Effector Cytotoxic Cells", The Journal of Immunology, vol. 179, pp. 4202-4211 (2007).
Buchholz, et al., "The smallest unit: effector and memory CD8+ T cell differentiation on the single cell level", Frontiers in Immunology, vol. 4, Article 31, pp. 1-10 (2013).
Buckner, Jane Hoyt, "Mechanisms of impaired regulation by CD4+CD25+FOXP3+ regulatory T cells in human autoimmune diseases", Nature Rev. Immunol., vol. 10, No. 12, pp. 849-859 (2010).
Camisaschi, et al., "LAG-3 Expression Defines a Subset of CD4+CD25highFoxp3+ Regulatory T Cells That Are Expanded at Tumor Sites", The Journal of Immunology, vol. 184, pp. 6545-6551 (2010).
Campbell, et al. "Collagen-induced arthritis in C57BL/6 (H-2b) mice: new insights into an important disease model of rheumatoid arthritis", Eur. J Immunol., vol. 30, pp. 1568-1575 (2000).
Chan, et al., "Variable region domain exchange in human IgGs promotes antibody complex formation with accompanying structural changes and altered effector functions", Molecular Immunology, vol. 41, pp. 527-538 (2004).
Chavele and Ehrenstein, "Regulatory T-cells in systemic lupus erythematosus and rheumatoid arthritis", FEBS Letters, vol. 585, pp. 3603-3610 (2011).
Chothia, et al., "Conformations of immunoglobulin hypervariable regions", Nature, vol. 342, No. 21/28, pp. 877-883(1989).
Coles, et al., "Alemtuzumab vs. interferon Beta-1a in Early Multiple Sclerosis", The New England Journal of Medicine, vol. 359, No. 17, pp. 1786-1801 (2008).
Collin, "Immune checkpoint inhibitors: a patent review (2010-2015)", Expert Opinion on Therapeutic Patents, vol. 26, No. 5, pp. 555-564 (2016).
Dall' Acqua, et al., "Increasing the Affinity of a Human IgG1 for the Neonatal Fc Receptor: Biological Consequences", The Journal of Immunology, vol. 169, pp. 5171-5180 (2002).
Dall'Acqua, et al., "Modulation of the Effector Functions of a Human IgG1 through Engineering of its Hinge Region", The Journal of Immunology, vol. 177, pp. 1129-1138 (2006).
Davis, B.G., "Synthesis of Glycoproteins", Chem. Rev., vol. 102, pp. 579-601 (2002).
De Groot and Martin, "Reducing Risk, Improving Outcomes: Bioengineering Less Immunogenic Protein Therapeutics", Clinical Immunology, vol. 131, pp. 189-201 (2009).
Doria, et al., "Autoinflammation and autoimmunity: Bridging the divide", Autoimmunity Reviews, vol. 12, pp. 22-30 (2012).
Ehrenstein, et al., "Compromised Function of Regulatory T Cells in Rheumatoid Arthritis and Reversal by Anti-TNFa Therapy", J. Exp. Med., vol. 200, No. 3, pp. 277-285 (2004).
Ewert, et al., "Stability improvement of antibodies for extracellular and intracellular applications: CDR grafting to stable frameworks and structure-based framework engineering", Methods, vol. 34, pp. 184-199 (2004).
Freeman, et al., "Regulation of innate CD8+ T-cell activation mediated by cytokines", PNAS, vol. 109, No. 25, pp. 3971-9976, (2012).
Galli, et al., "Unequivocal Delayed Hypersensitivity in Mast Cell-Deficient and Beige Mice", Science, vol. 226, pp. 710-713 (1984).

Ghetie and Ward, "Multiple Roles for the Major Histocompatibility Complex Class I-Related Receptor FcRn", Annu. Rev. Immunol., vol. 18, pp. 739-766 (2000).
Ghetie, et al., "Increasing the serum persistence of an IgG fragment by random mutagenesis", Nature Biotechnol, vol. 15. pp. 637-640 (1997).
Hang and Bertozzi, "Chemoselective Approaches to Glycoprotein Assembly", Acc. Chem. Res., vol. 34, pp. 727-736 (2001).
Hannier, et al., "CD3/TCR Complex-Associated Lymphocyte Activation Gene-3 Molecules Inhibit CD3/TCR Signaling", The Journal of Immunology, vol. 161, pp. 4058-4065 (1998).
Hargreaves, et al., "Selective depletion of activated T cells: the CD40L-specific antibody experience", Trends in Molecular Medicine, vol. 10, No. 3, pp. 130-135 (2004).
Haudebourg, et al., "Depletion of LAG-3 Positive Cells in Cardiac Allograft Reveals Their Role in Rejection and Tolerance", Transplantation, vol. 84, No. 11, pp. 1500-1506 (2007).
Herwijnen, et al., "Regulatory T cells that recognize a ubiquitous stress-inducible self-antigen are long-lived suppressors of autoimmune arthritis", PNAS, vol. 109, No. 35, pp. 14134-14139 (2012).
Hinton, et al., Engineered Human IgG Antibodies with Longer Serum Half-lives in Primates, J. Biological Chem., vol. 279, No. 8, pp. 6213-6216 (2004).
Saito, et al., "A Tumor Necrosis Factor Receptor Loop Peptide Mimic Inhibits Bone Destruction to the Same Extent as Anti-Tumor Necrosis Factor Monoclonal Antibody in Murine Collagen-Induced Arthritis", Arthritis & Rheumatism, vol. 56, No. 4, pp. 1164-1174 (2007).
Hodgson, John, "Making Monoclonals in Microbes", Bio/Technology, vol. 9, pp. 421-425 (1991).
Holliger and Hudson, "Engineered Antibody Fragments and The Rise of Single Domains", Nature Biotechnology, vol. 23, No. 9, pp. 1126-1136 (2005).
Huang, et al., "Role of LAG-3 in Regulatory T Cells", Immunity, vol. 21, pp. 503-513 (2004).
Huard, et al., "Cellular expression and tissue distribution of the human LAG-3-encoded protein, an MHC class II Ligand", Immunogenetics, vol. 39, pp. 213-217 (1994).
Huard, et al., "Lymphocyte-activation gene 3/major histocompatibility complex class II interaction modulates the antigenic response of CD4+ T lymphocytes", Eur J. Immunol, vol. 24, pp. 3216-3221 (1994).
Huard, et al., "Characterization of the major histocompatibility complex class II binding site on LAG-3 protein", Proc. Natl. Acad. Sci. USA, vol. 94, pp. 5744-5749 (1997).
Huard, et al., "LAG-3 does not define a specific mode of natural killing in human", Immunology Letters, vol. 61, pp. 109-112 (1998).
Inglis, et al., "Collagen-Induced arthritis in C57BL/6 mice is associated with a robust and sustained T-cell response to type II collagen", Arthritis Research & Therapy, vol. 9, R113, pp. 1-8 (2007).
Adelman, John P., et al."In Vitro Deletional Mutagenesis for Bacterial Production of the 20,000-Dalton Form of Human Pituitary Growth Hormone"; DNA; vol. 2, No. 3; 1983.
Adib-Conquy, Minou, et al."Effect of Amino Acid Substitutions in the Heavy Chain CDR3 of an Autoantibody on its Reactivity"; International Immunology; vol. 10, No. 3; pp. 341-346; Published 1998.
Albrecht, Huguette, et al."Monospecific Bivalent scFv-SH: Effects of Linker Length and Location of an Engineered Cysteine on Production, Antigen Binding Activity and Free SH Accessibility"; Journal of Immunologial Methods; 310; 2006; pp. 100-116.
Ali, Robin R., et al."Adeno-Associated Virus Gene Transfer to Mouse Retina"; Human Gene Therapy; 9:81-86; Jan. 1, 1998.
Alpuche-Aranda, Celia M., et al."*Salmonella typhimurium* Activates Virulence Gene Transcription within Acified Macrophage Phagosomes"; Proc Natl. Acad. Sci USA; vol. 89; pp. 10079-10083; Nov. 1992.
Altschul, Stephen F., et al."Gapped Blast and PSI-Blast: a New Generation of Protein Database Search Programs"; Nucleic Acids Research; vol. 25, No. 17; pp. 3389-3402; 1997.

(56) References Cited

OTHER PUBLICATIONS

Amit, A.G., et al."Three-Dimensional Structure of an Antigen-Antibody Complex at 2.8 Å Resolutions"; Science; vol. 233, pp. 747-753; Aug. 15, 1986.

Angal, S., et al."A Single Amino Acid Substitution Abolishes the Heterogeneity of Chimeric Mouse/Human (IgG4) Antibody"; Molecular Immunology; vol. 30, No. 1; pp. 105-108; Great Britain; 1993.

Baixeras, Elena, et al."Characterization of the Lymphocyte Activation Gene 3-Encoded Protein. A New Ligand for Human Leukocyte Antigen Class II Antigens"; J. Exp Med.; vol. 176; pp. 327-337; Published Aug. 1, 1992.

Merrifield, R.B."Solid Phase Peptide Synthesis. I. The Synthesis of a Tetrapeptide"; J. Am. Chem. Soc.; vol. 85; pp. 2149-2156; Jul. 20, 1963.

Beers, Richard, et al."Immunotoxins with Increased Activity Against Epidermal Growth Factor Receptor vIII-expressing Cells Produced by Antibody Phage Display"; Clinical Cancer Research; vol. 6; pp. 2835-2843; Jul. 2000.

Bennett, Jean, et al."Real-time, Noninvasive In Vivo Assessment of Adeno-Associated Virus-Mediated Retinal Transduction"; Investigative Opthalmology and Visual Science; vol. 38, No. 13; pp. 2857-2863; Dec. 1997.

Bird, Robert E., et al."Single-Chain Antigen-Binding Proteins"; Science; vol. 242; pp. 423-426; Oct. 21, 1988.

Borras, T., et al."Adenoviral Reporter Gene Transfer to the Human Trabecular Meshwork Does Not Alter Aqueous Humor Outflow. Relevance for Potential Gene Therapy of Glaucoma"; Gene Therapy; vol. 6; pp. 515-524; 1999.

Brekke, Ole Henrik, et al."Therapeutic Antibodies for Human Diseases at the Dawn of the Twenty-First Century"; Nature Reviews Drug Discovery; pp. 52-62; vol. 2; Jan. 2003.

Brummell, David A., et al."Probing the Combining Site of an Anti-Carbohydrate Antibody by Saturation-Mutagenesis: Role of the Heavy-Chain CDR3 Residues"; Biochemistry; vol. 32; pp. 1180-1187; Published 1993.

Camarero, Julio A., et al."Synthesis of Proteins by Native Chemical Ligation Using Fmoc-Based Chemistry"; Protein & Peptide Letters; vol. 12; pp. 723-728; 2005.

Caravan, Peter, et al."Gadolinium (III) Chelates as MRI Contrast Agents: Structure, Dynamics, and Applications"; Chem. Rev.; vol. 99; pp. 2293-2352; 1999.

Carrier, MJ, et al."Expression of Human IL-1 Beta in *Salmonella typhimurium*. A Model System for the Delivery of Recombinant Therapeutic Proteins in vivo"; The Journal of Immunology; vol. 148; pp. 1176-1181; 1992.

Chatfield, S.N., et al."Use of the nirB Promoter to Direct the Stable Expression of Heterologous Antigens in *Salmonella* Oral Vaccine Strains: Development of a Single-Dose Oral Tetanus Vaccine"; Bio/Technology; vol. 10; Aug. 1992.

Chen, Tracy "Formulation Concerns of Protein Drugs" Drug Development and Industrial Pharmacy: 18:11-12, 1311-1354; 1992.

Chothia, Cyrus, et al."Domain Association in Immunoglobulin Molecules. The Packing of Variable Domains"; J. Mol. Biol.: vol. 186; pp. 651-663; 1985.

Chothia, Cyrus, et al."Canonical Structures for the Hypervariable Regions of Immunoglobulins"; J. Mol. Biol.; vol. 196; pp. 901-917; 1987.

Chothia, Cyrus, et al."Conformations of Immunoglobulin Hypervariable Regions"; Nature; vol. 342, pp. 877-883; Dec. 1989.

Co, MS, et al."Chimeric and Humanized Antibodies with Specificity for the CD33 Antigen"; The Journal of Immunology vol. 148; pp. 1149-1154; 1992.

Cox, Jonathan P.L., et al."A Directory of Human Germ-Line Vx Segments Reveals a Strong Bias in their Usage"; Eur. J. Immunol. vol. 24; pp. 827-836; 1994.

Curtet, Chantal, et al."Polylysine-Gd-DTPAn and Polylysine-Gd-DOTAn Couple to Anti-CEA F(ab')2 Fragments as Potential Immunocontrast Agents; Relaxometry, Biodistribution, and Magnetic Resonance Imaging in Nude Mice Grafted with Human Colorectal Carcinoma"; Investigative Radiology; vol. 33, Issue 10; pp. 752-761; Oct. 1998.

Daugherty, Bruce L., et al."Polymerase Chain Reaction Facilitates the Cloning, CDR-Grafting, and Rapid Expression of a Murine Monoclonal Antibody Directed Against the CD18 Component of Leukocyte Integrins"; Nucleic Acids Research; vol. 19, No. 9; pp. 2471-2476; 1991.

De Boer, Herman A., et al."The TAG Promoter: A Functional Hybrid Derived from the TRP and LAC Promoters"; Proc. Natl. Acad. Sci. USA; vol. 80; pp. 21-25; Jan. 1983.

De Wildt, Ruud M.T., et al."Heavy Chain CDR3 Optimization of a Germline Encoded Recombinant Antibody Fragment Predisposed to Bind the U1A Protein"; Protein Engineering; vol. 10, No. 7; pp. 835-841; 1997.

Dunstan, Sarah J., et al."Use of In Vivo-Regulated Promoters to Deliver Antigens from Attenuated *Salmonella enterica* var. *typhimurium*"; Infection and Immunity; vol. 67, No. 10; pp. 5133-5141; Oct. 1999.

Flannery, John G., et al."Efficient Photoreceptor-Trageted Gene Expression in vivo by Recombinant Adeno-Associated Virus"; Proc. Natl. Acad. Sci. USA; vol. 94; pp. 6916-6921; Jun. 1997.

Flotte, Terence R., et al."Stable in vivo Expression of the Cystic Fibrosis Transmembrane Conductance Regulator with an Adeno-Associated Virus Vector"; Proc. Natl. Acad. Sci USA; vol. 90; pp. 10613-10617; Nov. 1993.

Ganesan, A. "Solid-Phase Synthesis in the Twenty-First Century"; Mini-Reviews in Medical Chemistry; vol. 6 pp. 3-10; 2006.

Hall, BL, et al."A Single Amino Acid Mutation in CDR3 of the 3-14-9 L Chain Abolished Expression of the IDA 10-defined Idiotope and Antigen Binding"; The Journal of Immunology; vol. 149; pp. 1605-1612; 1992.

Hannier, Sigrid, et al."CD3/TCR Complex-Associated Lymphocyte Activation Gene-3 Molecules Inhibit CD3/TCR Signaling"; The Journal of Immunology; vol. 161; pp. 4058-4065; 1998.

Harborne, Nerina R., et al."Transcriptional Control, Translation and Function of the Products of the Five Open Reading Frames of the *Escherichia coli* Nir Operon"; Moleculare Microbiology; vol. 6, No. 19; pp. 2805-2813; 1992.

Hillen, Wolfgang, et al."Tet Repressor-tet Operator Interaction"; Protein Nucleic Acid Ineraction; vol. 10, pp. 143-162; 1989.

Holliger, Philipp, et al."Diabodies: Small Bivalent and Bispecific Antibody Fragments"; Proc. Natl. Acad. Sci. USA; vol. 90; pp. 6444-6448; Jul. 1993.

Holt, Lucy J., et al."Domain Antibodies: Proteins for Therapy"; Trends in Biotechnology; vol. 21, No. 11 pp. 484-490; Nov. 2003.

Huard, Bertrand, et al."T Cell Major Histocompatibility Complex Class II Molecules Down-Regulate CD4+ T Cell Clone Responses Following LAG-3 Binding"; Eur. J. Immunol.; vol. 26; pp. 1180-1186; 1996.

Huard, Bertrand, et al."Characterization of the Major Histocompatibility Complex Class II Binding Site on LAG-3 Protein"; Proc. Natl. Acad. Sci. USA; vol. 94; pp. 5744-5749; May 1997.

Jomary, C., et al."Rescue of Photoreceptor Function by AAV-Mediated Gene Transfer in a Mouse Model of Inherited Retinal Degeneration"; Gene Therapy; vol. 4; pp. 683-690; 1997.

Jones, Peter T., et al."Replacing the Complementarity-determining Regions in a Human Antibody with Those from a Mouse"; Nature; vol. 321; May 1986; pp. 522-525.

Kabat, Elvin A., et al."Unusual Distribtions of Amino Acids in Complementarity-Determining (Hypervariable) Segments of Heavy and Light Chains of Immunoglobulins and Their Possible Roles in Specificity of Antibody-Combining Sites"; The Journal of Biological Chemistry; vol. 252, No. 19; pp. 6609-6616; Oct. 10, 1977.

Kammann, Matthias, et al."Rapid Insertional Mutagenesis of DNA by Polymerase Chain Reaction (PCR)"; Nucleic Acids Research; vol. 17, No. 13; 1989; p. 5404.

Kelley, Robert F., et al."Thermodynamic Analysis of an Antibody Functional Epitope"; Biochemistry; vol. 32; pp. 6828-6835; 1993.

Klechevsky, Eynav, et al."Cross-priming CD8+ T Cells by Targeting Antigens to Human Dendritic Cells Through DCIR"; Blood ; vol. 116, No. 10; Sep. 9, 2010; pp. 1685-1698.

(56) References Cited

OTHER PUBLICATIONS

Komissarov, Andrey A., et al. "Site-Specific Mutagenesis of a Recombinant Anti-Single-Stranded DNA Fab"; The Journal of Biological Chemistry; vol. 272, No. 43; pp. 26864-26870; Oct. 24, 1997.

Laffleur, Brice, et al. "Production of Human or Humanized Antibodies in Mice"; Antibody Method and Protocols, Methods in Molecular Biology; vol. 901; 2012; pp. 149-159.

Ssacs, J D, "From bench to bedside; discovering rules for antibody design, and improving serotherapy with monoclonal antibodies", Rheumatology, vol. 40, pp. 724-738 (2001).

Iwai, et al., "Involvement of Inducible Costimulator-B7 Homologous Protein Costimulatory Pathway in Murine Lupus Nephritis I", J Immunol., vol. 171. pp. 2848-2854 (2003).

Chappel, et al., "Identification of a Secondary FcγRI Binding Site within a Genetically Engineered Human IgG Antibody", (1993) J Biological Chem 268(33); 25124-25131.

Jamali et al., "Kinetics of Anti-CD4-Induced T Helper Cell Depletion and Inhibition of Function. Activation of T Cells by the CD3 Pathway Inhibits Anti-CD4-Mediated T Cell Elimination and Down-Regulation of Cell Surface CD4", The Journal of Immunology, vol. 148, No. 6, Mar. 15, 1992 (Mar. 15, 1992), pp. 1613-1619, XP055213914, ISSN: 0022-1767.

Jones, et al., Chapter 21; Deimmumization of Monoclonal Antibodies; Antony Dimitrov (Ed), Therapeutic Antibodies: Methods and Protocols 525; 405-423 (2009).

Junghans, R.P., "Finally! The Brambell Receptor (FcRB), Mediator of Transmission of Immunity and Protection from Catabolism for IgG", Immunol Res 16(1): pp. 29-57 (1997).

Kim, et al., "Antibody Engineering for the Development of Therapeutic Antibodies", Mol. Cells, vol. 20, No. 1, pp. 17-29 (2005).

Kisielow, et al, "Expression of lymphocyte activation gene 3 (LAG-3) on B cells is induced by T cells", Eur. J. Immunol., vol. 35, pp. 2081-2088 (2005).

Kitade, et al., "Early Presence of Regulatory Cells in Transplanted Rats Rendered Tolerant by Donor-Specific Blood Transfusion", J Immunol, 75:4963-4970 (2005).

Kohler et al., "Continuous cultures of fused cells secreting antibody of predefined specificity", Nature, vol. 256, pp. 495-497 (1975).

Koretzky, "Multiple Roles of CD4 and CD8 in T Cell Activation", Journal of Immunology, vol. 185, pp. 2643-2644, (2010).

Kunstfeld, et al., "Induction of cutaneous delayed-type hypersensitivity reactions in VEGF-A transgenic mice results in chronic skin inflammation associated with persistent lymphatic hyperplasia", Blood, vol. 104, No. 4, pp. 1048-1057 (2004).

Lamminmaki, et al., "Crystal Structure of a Recombinant Anti-estradiol Fab Fragment in Complex with 17B-Estradiol", The Journal of Biological Chemistry, vol. 276, No. 39, pp. 36687-36694 (2001).

Lange-Asschenfeldt, et al., "Increased and prolonged inflammation and angiogenesis in delayed type hypersensitivity reactions elicited in the skin of thrombospondin-2-deficient mice", Blood, vol. 99, No. 2, pp. 538-545 (2002).

Lazaret et al., "Engineered antibody Fc variants with enhanced effector function", (2006) PNAS 103(11); 4005-4010.

Leinhardt, et al., "Active tuberculosis in Africa is associated with reduced Th1 and increased Th2 activity in vivo", Eur J Immunol 32: 1605-1613 (2002).

MacCallum, et al., "Antibody-antigen interactions: Contact analysis and binding site topography", (1996) J Mol Biol. 262: 732-745.

Macon-Lemaitre, et al., "The negative regulatory function of the Lymphocyte-activation gene-3 co-receptor (CD223) on human T cells", Immunology, vol. 115, No. 2, pp. 170-178 (2005).

Mages, et al., "Molecular cloning and characterization of murine ICOS and identification of B7h as COS ligand", Eur. J Immunol, vol. 30, pp. 1040-1047 (2000).

Monk, et al., "Fc-dependent depletion of activated T cells occurs through CD40L-specific antibody rather than costimulation blockade", Nature Medicine, vol. 9, No. 10, pp. 1275-1280 (2003).

Seok, et al., "Genomic responses in mouse models poorly mimic human inflammatory diseases", PNAS, vol. 110, No. 9, pp. 3507-3512, Feb. 26, 2013.

Nechansky, et al., "Compensation of endogenous IgG mediated inhibition of antibody-dependent cellular cytotoxicity by glyco-engineering of therapeutic antibodies", (2007) Molecular Immunol., vol. 44; 1815-1817.

Nicholson, et al., "Monocyte Dependent Regulation of Autoimmune Inflammation", Current Molecular Medicine, vol. 9, pp. 23-29, 2009.

Nishida, et al., "Novel humanized anti-CD20 monoclonal antibodies with unique germline VH and VL gene recruitment and potent effector functions", International Journal of Oncology, vol. 32, pp. 1263-1274 (2008).

Ono, et al., "Improved technique of heart transplantation in rats", Journal of Thoracic and Cardiovascular Surgery, vol. 57, No. 2, pp. 225-229 (1969).

Nobel-Jamieson, et al., "Auto-immune cholangiopathy in a juvenile patient with systemic lupus erythematosus", Acta Paediatrica, Foundation Acta Paediatrica, 101, pp. e262-e264 (2012).

Ozkaynak, et al., "Importance of iCOS-B7RP-1 costimulation in acute and chronic allograft rejection", Nature Immunology, vol. 2, No. 7, pp. 591-596 (2001).

Patel and Boyd, "An improved assay for antibody dependent cellular cytotoxicity based on time resolved fluorometry", (1995) J Immunol Meth 184:29-38.

Pluckthun, Andreas, "Mono-and Bivalent Antibody Fragments Produced in *Escherichia coli* Engineering, Folding and Antigen Binding", (1992) Immunol Rev, 130; 151-188.

Poirier et al., "Antibody-mediated depletion of lymphocyte-activation gene-3 (LAG-3+)-activated T lymphocytes Prevents delayed-type hypersensitivity in non-human primates", Clin Experimental Immunol., 164(2): 265-274 (2011).

Queen, et al., "A humanized antibody that binds to the interleukin 2 receptor", (1989) Proc Natl Acad Sci USA, 86: 10029-10032.

Raju, et al., "Glycoengineering of Therapeutic Glycoproteins: In Vitro Galactosylation and Sialylation of Glycoproteins with Terminal N-Acetylglucosamine and Galactose Residues", (2001) Biochem 40; 8868-8876.

Rothe, et al., "Ribosome display for improved biotherapeutic molecules", (2006) Expert Opinion on Biological Therapy 6(2); 177-187.

Sakamoto, et al., "AILIM/ICOS: Its Expression and Functional Analysis with Monoclonal Antibodies", Hybridoma and Hybridomics, vol. 20, No. 5, pp. 293-303 (2001).

Saldanha, Jose W., Molecular Engineering I; Humanization—found in Chapter 6, pp. 119-144 of The Handbook of Therapeutic Antibodies, edited by Stephan Dubel, Jan. 1, 2007, Wiley-VCH, Weinheim, XP007913671, ISBN; 978-3-527-31453-9.

Sears and Wong, "Toward Automated Synthesis of Oligosaccharides and Glycoproteins", (2001) Science 291; 2344-2350.

Shields, et al., "High Resolution Mapping of the Binding Site on Human IgG1 for FcγRI, FcγRII, FcγRIII, and FcRn and Design of IgG1 Variants with Improved Binding to the FcγR", (2001) J Biol Chem 276(9); 6591-6604.

Siawaya, et al., "Immune parameters as markers of tuberculosis extent of disease and early prediction of anti-tuberculosis chemotherapy response", (2008) J Infect 56: 340-347.

Sierro, et al., "The CD4-like molecule LAG-3, biology and therapeutic applications" Expert Opinion on Therapeutic Targets 15(1): 91-101 (2011).

Song, et al., "Rat and Human Natural Killers Exhibit Contrasting Immunoglobulin G Subclass Specificities in Antibody-Dependent Cellular Cytotoxicity Reflecting Differences in Their Fc Receptors FcγR)", Journal of Leukocyte Biology, vol. 48, pp. 524-530 (1990).

Sporici, et al., "ICOS Ligand Costimulation is Required for T-Cell Encephalitogenicity", Clinical Immunology, vol. 100, No. 3, pp. 277-288 (2001).

Stasiuk, et al., "Collagen-Induced Arthritis in DBA/1 Mice: Cytokine Gene Activation Following Immunization with Type II Collagen", Cellular Immunology, vol. 173, pp. 269-275 (1996).

(56) References Cited

OTHER PUBLICATIONS

Steplewski et al., "Biological activity of human-mouse IgG1, IgG2, IgG3, and IgG4 chimeric monoclonal antibodies with antitumor specificity", (1988) Proc Nat'l Acad Sci 85:4852-4856.

Teeling, et al., "The Biological Activity of Human CD20 Monoclonal Antibodies is Linked to Unique Epitopes on CD201", The Journal of Immunology, vol. 177, pp. 362-371 (2006).

Thie, et al., Chapter 16: "Affinity Maturation by Phage Display", Antony Dimitrov (Ed). Therapeutic Antibodies; Methods and Protocols 525; 309-322 (2009) [Methods Mol Biol (2011).

Thomson, et al., "FK506; a novel immunosuppressant for treatment of autoimmune disease; Rationale and preliminary clinical experience at the University of Pittsburgh", Springer Semin Immunopathol. 14(4); 323-344 (1993).

Totsuka, et al., "Ameliorating Effect of Anti-inducible Costimulator Monoclonal Antibody in a Murine Model of Chronic Colitis", Gastroenterology, vol. 124, pp. 410-421 (2003).

Triebel, et al., "A soluble lymphocyte activation gene-3 (sLAG-3) protein as a prognostic factor in human breast cancer expressing estrogen or progesterone receptors", (2006) Cancer Letters 235; 147-153.

Triebel, "LAG-3: a regulator of T-cell and DC responses and its use in therapeutic vaccination", Trends in Immunology, vol. 24, No. 12, pp. 619-622 (2003).

Cole, et al., "The EBV-Hybridoma Technique and its Application to Human Lung Cancer", pp. 77-96, 1985.

Ellis et al. 'Selective depletion of LAG3+ cells in T-cell-driven inflammation: a randomized, double-blind, placebo-controlled FTIH phase I/Ib clinical trial' Poster Presentations, S336, 2018.

Legat, et al., "Vaccination with LAG-31g (IMP321) and Peptides Induces Specific CD4 and CD8 T-Cell Responses in Metastatic Melanoma Patients-Report of a Phase I/IIa Clinical Trial", Clinical Cancer Research, vol. 22, No. 6, 2016.

Liu, et al., "Kaempferol attenuates imiquimod-induced psoriatic skin inflammation in a mouse model", British Society for Immunology, Clinical and Experimental Immunology, vol. 198, pp. 403-415 (2019).

Clinical Trial Summary, Safety, Tolerability, Efficacy and Dose-response of GSK2831781 in Ulcerative Colitis, https://clinicaltrials.gov.ct2/show/CCT03893565, 2019.

Slevin et al. 'Lymphocytle Activation Gene (LAG)-3 is Associated with Mucosal Inflammation and Disease Activity in Ulcerative Colitis' Journal of Crohn's and Colitis, Jan. 16, 2020.

Rudikoff S. et al., "Single Amino Acid Substitution Altering Antigen-Binding Specificity", Pro. Natl. Acad. Sci. USA 79:1979-1983 (Mar. 1982).

Bruniquel D. et al., "Regulation of Expression of the Human Lymphocyte Activation Gene-3 (LAG-3) Molecule, a LIgand for MHC Class II", Immunogenetics 48:116-124 (1998).

Drake C.G. et al., "Blocking the Regulatory T Cell Molecule LAG-3 Augments In Vivo Anti-Tumor Immunity in an Autochthonous Model of Prostate Cancer", Journal of Clinical Oncology 24(ISS):2573 (2006), abstract only.

Tomlinson I.M. et al., "The Repertoire of Human Germline VH Sequences Reveals About Fifty Groups of VH Segments With Different Hypervariable Loops", J. Mol. Biol. 227:776-798 (1992).

Townsend S. et al., "Augmented Binary Substitution: Single-Pass CDR Germ-Lining and Stabilization of Therapeutic Antibodies", PNAS 112(50):15354-15359 (Dec. 15, 2015).

\* cited by examiner

Figure 1

```
         10         20         30         40         50         60
 LQPGAEVPVV WAQEGAPAQL PCSPTIPLQD LSLLRRAGVT WQHQFDSGPP AAAPGHPLAP 70         80         90        100        110        120
 GPHPAAPSSW GPRPRRYTVL SVGPGGLRSG RLPLQPRVQL DERGRQRGDF SLWLRPARRA 130        140        150        160        170        180
 DAGEYRAAVH LRDRALSCRL RLRLGQASMT ASFPGSLRAS DWVILNCSFS RPDRPASVHW 190        200        210        220        230        240
 FRNRGQGRVP VRESPHHHLA ESFLFLPQVS PMDSGPWGCI LTYRDGFNVS IMYNLTVLGL 250        260        270        280        290        300
 EPPTFLTVYA GAGSRVGLFC RLPAGVGTRS FLTAKWTPPG GGFDLLVTGD NGDFTLPLED 310        320        330        340        350        360
 VSQAQAGTYT CRIHLQEQQL NATVTLAIIT VTPKSFGSPG SLGKLLCEVT PVSGQERFVW 370        380        390        400        410        420
 SSLDTPSQRG FSGPWLEAQE AQLLSQPWQC QLYQGERLLG AAVYFTELSS PGAQRSGRAP 430        440        450        460        470        480
 GALPAGHLLL FLTLGVLSLL LLVTGAFGFH LWRRQWRPRR FSALEQGIHP QAQSKIEELE 490        500
 QEPEPEPEPE PEPEPEPEPE QL
```

```
<-------------------FR1-IMGT---------------------><----CDR1
  Q  V  T  L  K  E  S  G  P  G  I  L  Q  P  S  Q  T  L  S  L  T  C  S  F  S  G  F  S  L  S
CAGGTTACTCTGAAAGAGTCTGGCCCTGGGATATTGCAGCCCTCCCAGACCCTCAGTCTCACTTGTTCTTTCTCTGGGTTTTCACTCAGC   90

-IMGT-----><----------FR2-IMGT-------------------><------CDR2-IMGT-----><-----
  T  S  G  M  G  W  I  R  Q  P  S  G  K  G  L  E  W  L  H  I  W  W  D  D  I  K  R
ACTTCTGGTATGGGCTGGATTCGTCAGCCTTCAGGGAAGGGTCTGGAGTGGCTGCACATTTGGTGGGATGATATCAAGCGC           180

--------------FR3-IMGT------------------------------><-----
  Y  N  P  D  L  R  S  R  L  T  I  S  K  D  T  S  S  S  Q  I  F  L  K  I  A  S  V  D  T  A
TATAACCCAGACCTGAGGAGCCGACTGACTATCTCCAAGGATACCTCCAGCAGCCAGATTTTCCTCAAGATCGCCAGTGTGGACACTGCA   270

----CDR3-IMGT-------------><-----
  D  T  A  T  Y  Y  C  A  R  I  V  E  G  S  Y  S  S  Y  F  D  V  W  G  A  G  T  T  V  T
GATACTGCCACATATTACTGTGCTCGAATAGTTGAAGGTTCATACAGTAGTTACTTCGATGTCTGGGGCGCAGGGACCACGGTCACC     360

V  S  S
GTCTCCTCAG   370
```

```
<------------------------FR1-IMGT----------------------><----CDR1-IM
 D  I  V  M  T  Q  P  H  K  F  M  S  T  S  V  G  D  R  V  T  I  T  C  K  A  S  Q  D  V  I
GACATTGTGATGACCCAGCCTCACAAATTCATGTCCACATCAGTGGGAGACAGGGTCACCATCACCTGCAAGGCCAGTCAGGATGTGATT      90

GT----><---------------FR2-IMGT----------------><--CDR2-IM><--------
 F  D  V  A  W  Y  Q  Q  K  P  G  Q  S  P  K  L  L  I  Y  S  A  S  S  R  V  S  G  V  P  D
TTTGATGTAGCCTGGTATCAACAGAAACCAGGACAATCCCCTAAATTACTGATTTACTCGGCATCCTCCCGGGTCAGTGGAGTCCCTGAT    180

------------------------FR3-IMGT-------------------------><---------
 R  F  T  G  S  G  T  D  F  T  F  T  I  S  S  V  Q  A  E  D  L  A  V  Y  Y  C  Q  Q
CGCTTCACTGGCAGTGGATCTGGGACGGATTTCACTTTCACCATCAGCAGTGTGCAGGCTGAGGACCTGGCAGTTTATTACTGTCAGCAA    270

-----CDR3-IMGT----------->
 H  Y  S  T  P  Y  T  F  G  G  G  T  T  L  E  I  K
CACTATAGTACTCCGTACACGTTCGGAGGGGGGACCACGCTGGAAATAAAAC                                          322
```

```
<-----------------------FR1-IMGT------------------------><---------CDR1
  Q  V  T  L  K  E  S  G  P  G  I  L  Q  P  S  Q  T  L  S  L  T  C  S  F  S  G  F  S  L  N
CAGGTTACTCTGAAAGAGTCTGGGCCTGGGATATTGCAGCCCTCCCAGACCCTCAGTCTCACTTGTTCTTTCTCTGGGTTTTCACTGAAC  90

-IMGT----------><----------------FR2-IMGT---------------><-------CDR2-IMGT--------><-------
  T  S  G  M  G  V  G  W  I  R  Q  P  S  G  K  G  L  E  W  L  T  H  I  W  W  D  D  V  K  R
ACTTCTGGTATGGGTGTAGGCTGGATTCGTCAGCCATCAGGGAAGGGTCTGGAGTGGCTGACACACATTTGGTGGGATGATGTCAAGCGC  180

-----------------------------FR3-IMGT----------------------------------->
  Y  N  P  A  L  K  S  R  L  T  I  S  K  D  T  S  S  N  Q  V  F  L  K  I  A  S  V  D  T  A
TATAATCCAGCCCTGAAGAGCCGACTGACTATCTCCAAGGATACCTCCAGCAGCCAGGTATTCCTAAAGATCGCCAGTGTGGACACTGCA  270

<---------CDR3-IMGT------------><----
  D  T  A  T  Y  Y  C  A  R  I  E  G  Q  T  Y  Y  D  Y  Y  F  D  Y  W  G  Q  G  V  T  L  T
GATACTGCCACATACTACTGTGCTCGAATAGAGGGGCAAACTTACTACGACTATTACTTTGACTACTGGGGCCAAGGCGTCACTCTCACA  360

V  S  S
GTCTCCTCAG  370
```

```
<----------------------------FR1-IMGT-----------------------><----CDR1-IM
 D   I   V   M   T   Q   S   H   K   L   M   S   T   S   V   G   D   G   L   S   I   T   C   R   A   S   Q   D   V   S
GACATTGTGATGACCCAGTCTCACAAACTCATGTCCACAGTCAGTGGAGATGGGCTCAGCATCACCTGCAGGGCCAGTCAAGGATGTGAGC  90
GT---><----------------------FR2-IMGT-------------------><CDR2-IM><-----------------------FR3-IMGT-----------
 I   A   V   V   W   Y   Q   Q   K   P   G   Q   S   P   K   L   L   I   Y   S   A   S   F   R   Y   T   G   V   P   D
ATTGCTGTAGTGTGGTATCAACAGAAACCAGGACAATCTCCTAAACTGCTGATTTACTCTGCATCCTTCCGGTACACTGGAGTCCCTGAT  180
--------------------FR3-IMGT-----------------------------><----
 R   F   T   G   S   G   S   G   T   D   F   T   F   T   I   S   S   V   Q   A   E   D   L   A   V   Y   Y   C   Q   Q
CGCTTCACTGGCAGTGGATCTGGGACGGATTTCACTTTCACCATCAGCAGTGTGCAGGCTGAAGACCTGGCAGTTTATTACTGTCAGCAA  270
-----CDR3-IMGT----->
 H   Y   S   I   P   W   T   F   G   G   G   T   K   L   E   I   K
CATTATAGTATTCCGTGGACGTTCGGTGGAGGCACCAAGCTGGAAATCAAAC  322
```

Figure 15
A)
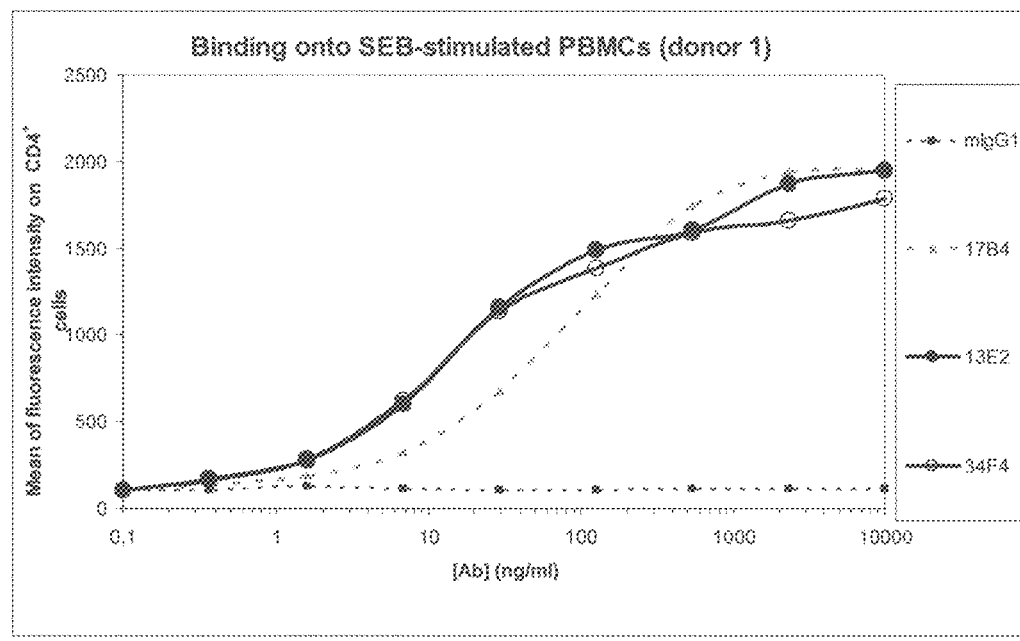
B)
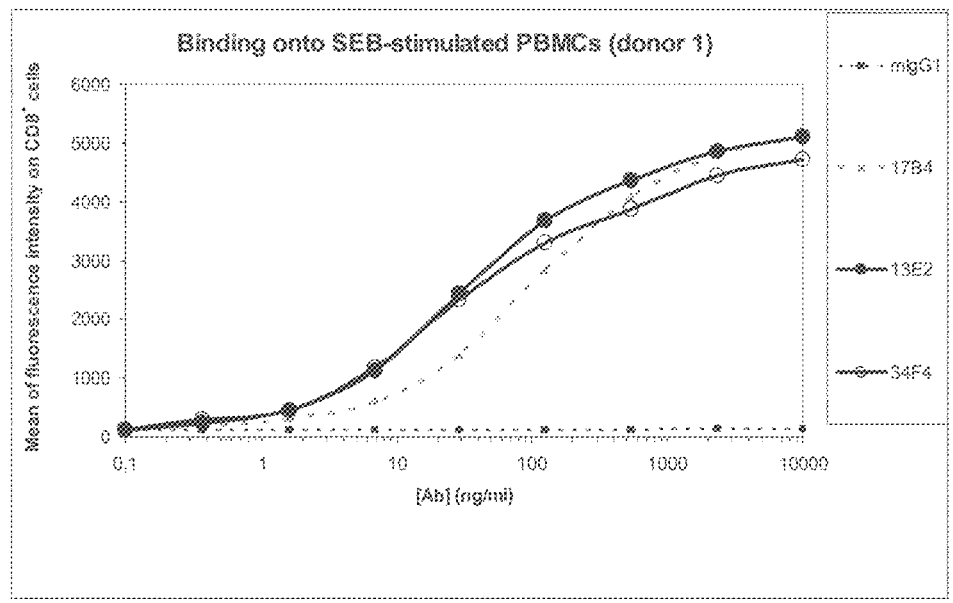

Figure 16
A)
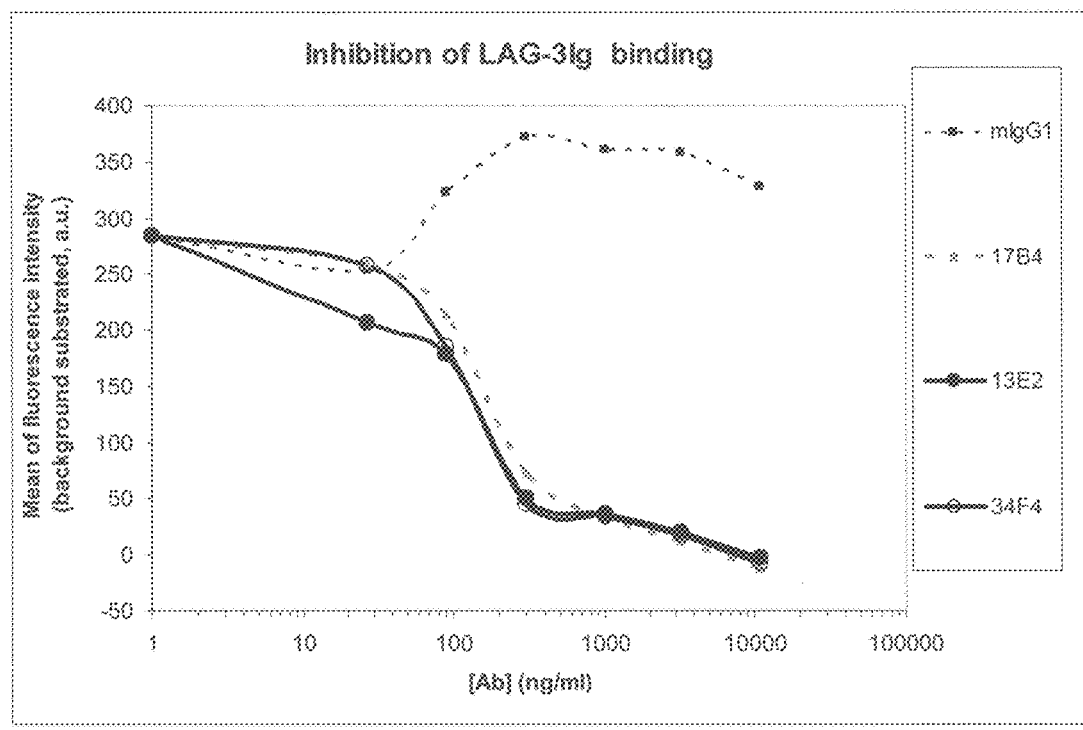
B)
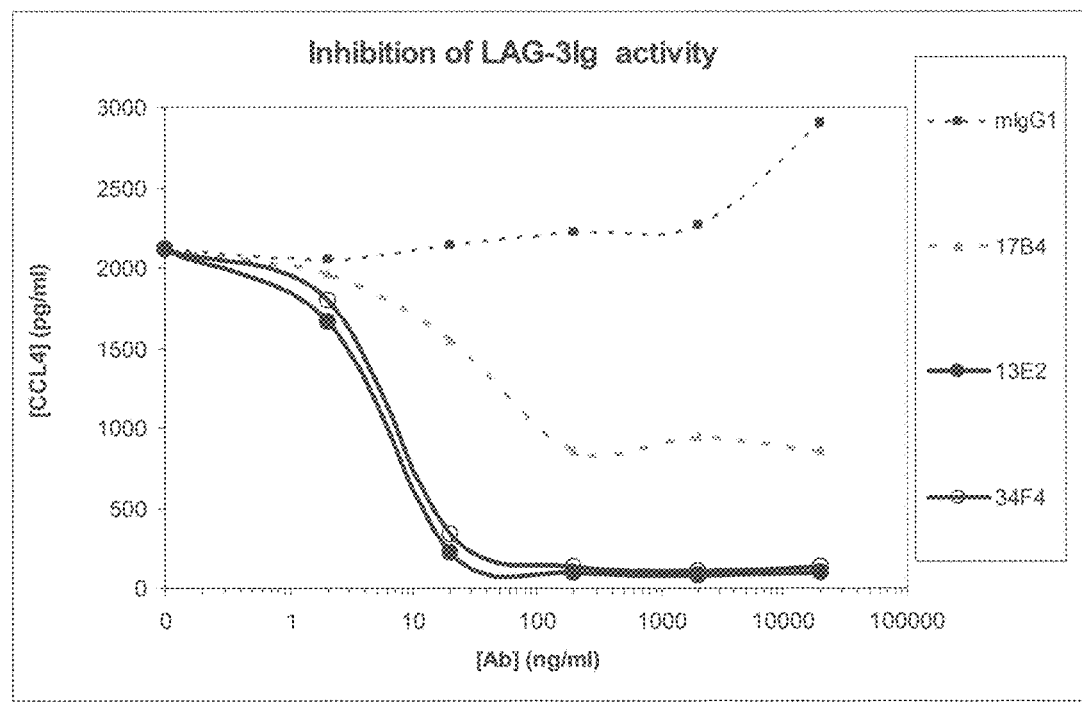

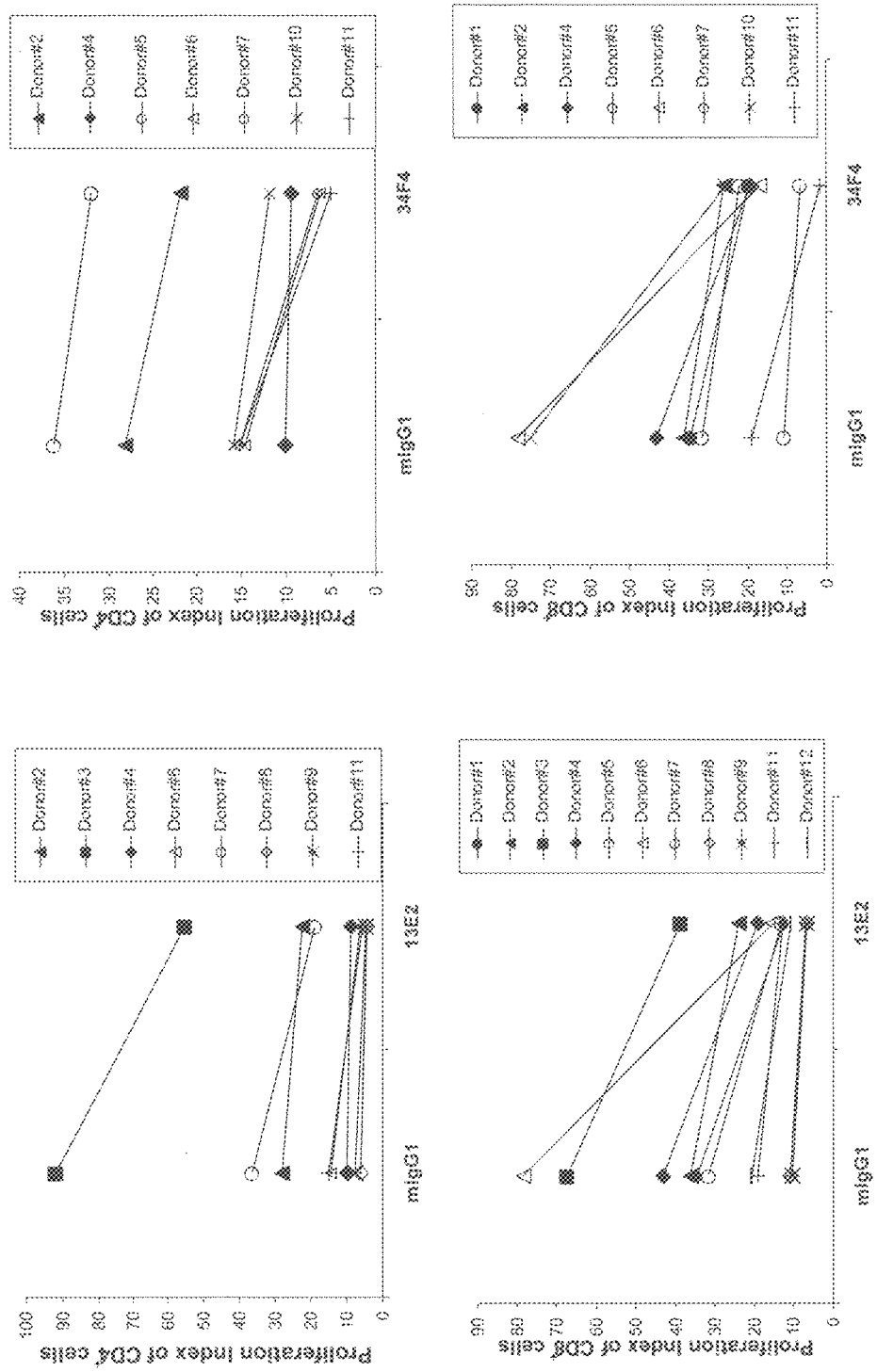

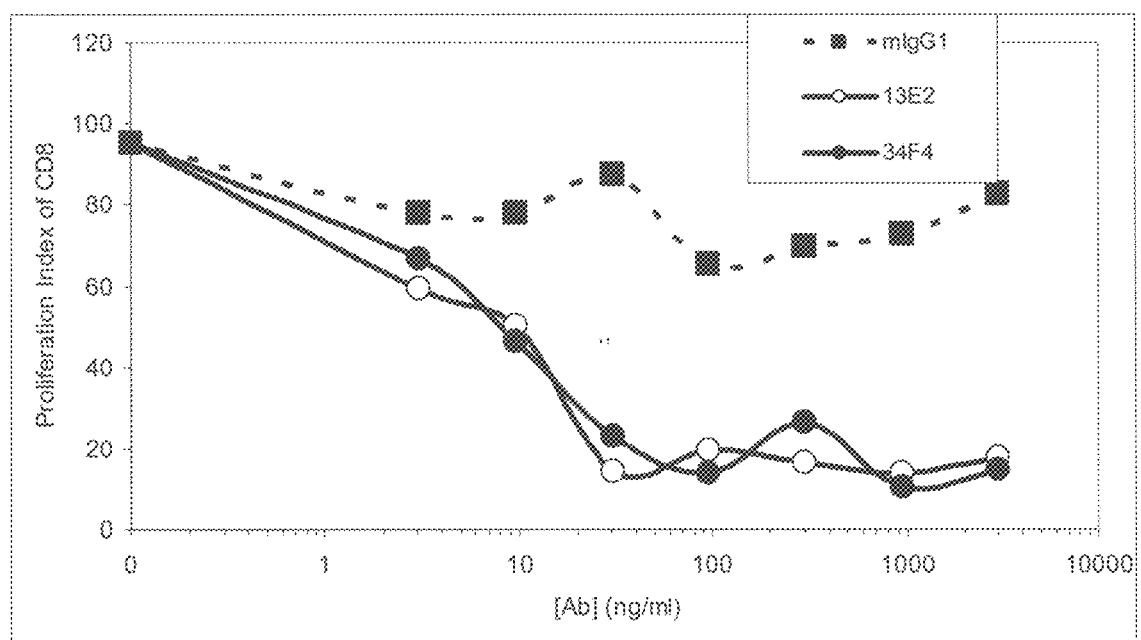

Figure 20

A) 13E2IgG4mut (heavy chain of chimeric antibody Chim13E2IgG4)

```
MGWTLVFLFLLSVTAGVHSQVTLKESGPGILQPSQTLSLTCSFSGFSLSTSGMGLGWIRQ    60
PSGKGLEWLTHIWWDDIKRYNPDLRSRLTISKDTSSQIFLKIASVDTADTATYYCARIV   120
EGSYSSSYFDVWGAGTTVTVSSASTKGPSVFPLAPCSRSTSESTAALGCLVKDYFPEPVT  180
VSWNSGALTSGVHTFPAVLQSSGLYSLSSVVTVPSSSLGTKTYTCNVDHKPSNTKVDKRV  240
ESKYGPPCPPCPAPEFLGGPSVFLFPPKPKDTLMISRTPEVTCVVVDVSQEDPEVQFNWY  300
VDGVEVHNAKTKPREEQFNSTYRVVSVLTVLHQDWLNGKEYKCKVSNKGLPSSIEKTISK  360
AKGQPREPQVYTLPPSQEEMTKNQVSLTCLVKGFYPSDIAVEWESNGQPENNYKTTPPVL  420
DSDGSFFLYSRLTVDKSRWQEGNVFSCSVMHEALHNHYTQKSLSLSLGK   469
```

B) 13E2IgK (light chain of chimeric antibody Chim13E2IgG4)

```
MVSSAQFLGLLLLCFQGTRCDIVMTQPHKFMSTSVEDRVTITCKASQDVIFDVAWYQQKP    60
GQSPKLLIYSASSRVSGVPDRFTGSGSGTDFTFTISSVQAEDLAVYYCQQHYSTPYTFGG  120
GTTLEIKRTVAAPSVFIFPPSDEQLKSGTASVVCLLNNFYPREAKVQWKVDNALQSGNSQ  180
ESVTEQDSKDSTYSLSSTLTLSKADYEKHKVYACEVTHQGLSSPVTKSFNRGEC   234
```

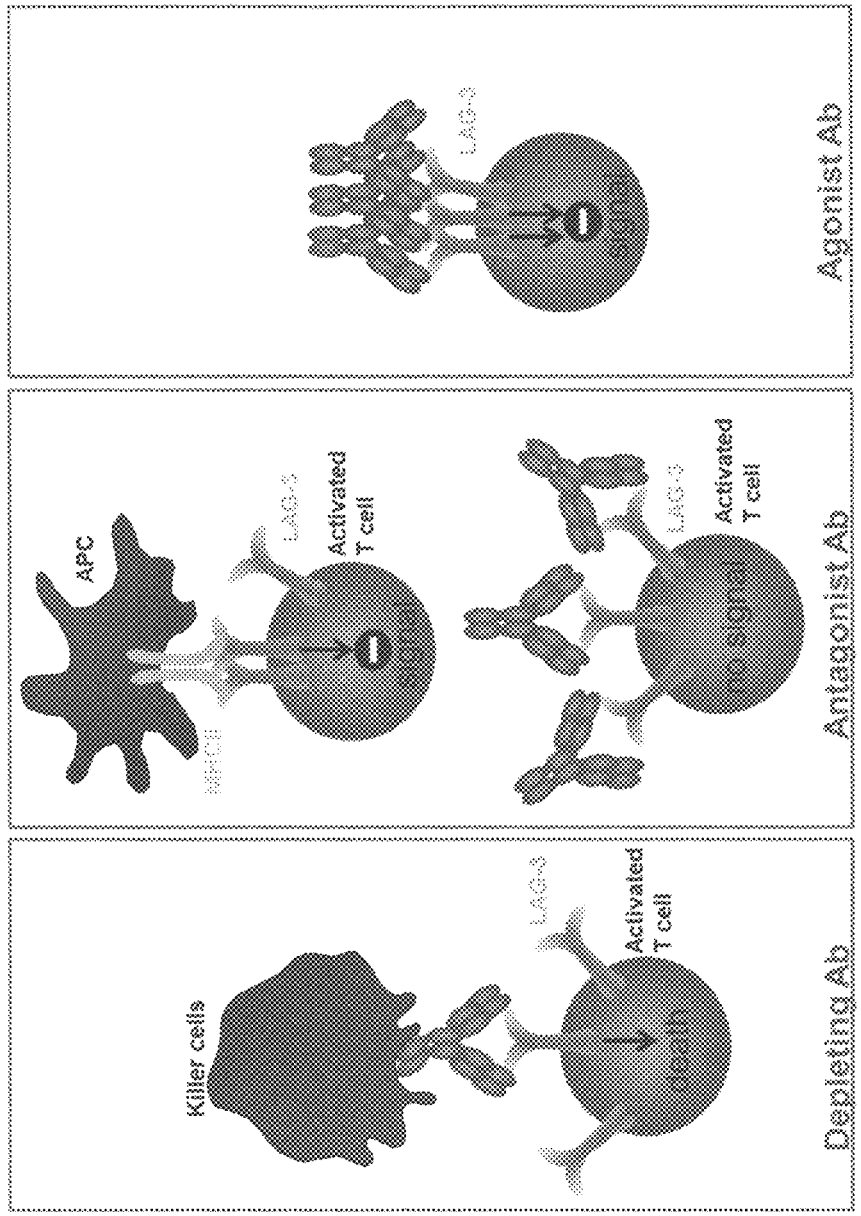

Figure 22

```
               20
13E2 VH        QVTLKESSGPG ILQPSQTLSL TCSFSGFSLS TSGMGLGWIR QPSGKGLEWL THIWWDDIKP
VH1            QVTLKESSGPA LVKPTQTLTL TCTFSGFSLS TSGMGLGWIR QPPGKALEWL AHIWWDDIKP
VH2            QITLKESSPA LVKPTQTLTL TCTFSGFSLS TSGMGLGWIR QPPGKALEWL AHIWWDDIKP
VH3            QITLKETGFT LVKPTQTLTL TCTFSGFSLS TSGMGLGWIR QPPGKALEWV THIWWDDIKP
VH4 (IMP761-H) QITLKESGPT LVKPTQTLTL TCTFSGFSLS TSGMGLGWIR QPPGKTLEWL THIWWDDIKP 80
13E2 VH        YNPDLRSRLT ISKDTSSSQI FLKIASVDTA DTATYYCARI DVWGAGTTVT
VH1            YNPDLRSRLT ISKDTSKSQV ILNMTNMDPV DTATYYCARI VKGSYSSSYF DVWGQGTTVT
VH2            YNPDLRSRLT ISKDTSKNQV VLTMANMDPV DTATYYCARI VEGSYSSSVF DVWGQGTTVT
VH3            YNEDLRSRVT IRKDTSKNQV ALTMTNMDPL DTGTYYCARI VEGSYSSSYF DVWGQGTLVT
VH4 (IMP761-H) YNPDLRSRIS IRKDTSKNQV VLTMTNMDPL DTGTYYCARI VEGSYSSSYF DVWGQGTLVT 140
13E2 VH        VSS
VH1            VSS
VH2            VSS
VH3            VSS
VH4 (IMP761-H) VSS 21
13E2 VL        DIVMTQPHKF MSTSVEDRVT ITCKASQDVI EDVAWYQQKP GQSPKLLIYS ASSRVSGVPD
VL1            DIVMTQSPDS LAVSLGERAT INCKASQDVI EDVAWYQQKP GQPPKLLIYS ASSRVSGVPD
VL2            DIQMTQSPSS LSASVGDRVT ITCKASQDVI EDVAWYQQKP GQAPKLLIES ASSRVSGVPS
VL3            DIVMTQSPDS LSASVGDRVT ITCKASQDVI EDVAWYQQRP GQAPKLLIYS ASSRVSGVPS
VL4 (IMP761-L) DIVLTQSPDS LAVSLGERAT INCRASQDVI EDVAWYQQKA GQSPKLLIYS ASSRVSGVPD 91
13E2 VL        RFTGSGSGTD FTFTISSVQA EDLAVYYCQQ HYSTPYTFGG GTTLEIK
VL1            RFSGSGSGTD FTLTISSLQA EDVAVYYCQQ HYSTPYTFGG GTKLEIK
VL2            RFSGSGSGTD FTLTISSLQP EDFATYYCQQ HYSTPYTFGQ GTKVEIK
VL3            RFSGSGSGTD FTLTISSLQP EDFATYYCQQ HYSTPYTFGQ GTRIDIK
VL4 (IMP761-L) RFSGSGSGTD FTLTIDSLQA EDVAVYYCQQ HYSTPYTFGG GTKVEIK
```

Figure 23

```
13E2IgG4mut     1 MGWTLVFLFL LSVTAGVHSQ VTLKESGPGI LQPSQTLSLT CSFSGFSLST SGMGLGWIRQ
IMP761-H        1 MGWTLVFLFL LSVTAGVHSQ ITLKESGPTL VKPTQTLTLT CTFSGFSLST SGMGLGWIRQ 13E2IgG4mut    61 PSGKGLEWLT HIWWDDIKRY NPDLRSRLTI SKDTSSSQIF LKIASVDTAD TATYYCARIV
IMP761-H       61 PPGKTLEWLT HIWWDDIKRY NPDLRSRLST IKDTSKNQVV LTMTNMDPLD TGTYYCARIV 13E2IgG4mut   121 EGSYSSSYFD VWCAGTIVTV SSASTKGPSV FPLAPCSRST SESTAALGCL VKDYFPEPVT
IMP761-H      121 EGSYSSSYFD VWGQGTLVTV SSASTKGPSV FPLAPCSRST SESTAALGCL VKDYFPEPVT 13E2IgG4mut   181 VSWNSGALTSG VHTFPAVLQ SSGLYSLSSV VTVPSSSLGT KTYTCNVDHK PSNTKVDKRV
IMP761-H      181 VSWNSGALTSG VHTFPAVLQ SSGLYSLSSV VTVPSSSLGT KTYTCNVDHK PSNTKVDKRV 13E2IgG4mut   241 ESKYGPPCPPC PAPEFLGGP SVFLFPPKPK DTLMISRTPE VTCVVVDVSQ EDPEVQFNWY
IMP761-H      241 ESKYGPPCPPC PAPEFLGGP SVFLFPPKPK DTLMISRTPE VTCVVVDVSQ EDPEVQFNWY 13E2IgG4mut   301 VDGVEVHNAKT KPREEQFNS TYRVVSVLTV LHQDWLNGKE YKCKVSNKGL PSSIEKTISK
IMP761-H      301 VDGVEVHNAKT KPREEQFNS TYRVVSVLTV LHQDWLNGKE YKCKVSNKGL PSSIEKTISK 13E2IgG4mut   361 AKGQPREPQVY TLPPSQEEM TKNQVSLTCL VKGFYPSDIA VEWESNGQPE NNYKTTPPVL
IMP761-H      361 AKGQPREPQVY TLPPSQEEM TKNQVSLTCL VKGFYPSDIA VEWESNGQPE NNYKTTPPVL 13E2IgG4mut   421 DSDGSFFLYSR LTVDKSRWQ EGNVFSCSVM HEALHNHYTQ KSLSLSLGK
IMP761-H      421 DSDGSFFLYSR LTVDKSRWQ EGNVFSCSVM HEALHNHYTQ KSLSLSLGK
```

Figure 24

```
             1   MVSSAQFLGL LLLCFQGTRC DIVMTQPHKF MSTSVEDRVT ITCKASQDVI FDVAWYQQKP
13E2IgK
IMP761-L     1   MVSSAQFLGL LLLCFQGTRC DIVMTQTPSS LSASVGDRVT ITCKASQDVI FDVAWYQQRP

13E2IgK     61   GQSPKLLIYS ASSRVSGVPD RFTGSGSGTD FTFTISSVQA EDLAVYYCQQ HYSTPYTFGG
IMP761-L    61   GQAPKLLIYS ASSRYSGVPS RFSGSGSGTD FTLTISSLQP EDFATYYCQQ HYSTPYTFGQ

13E2IgK    121   GTTLEIKRTV AAPSVFIFPP SDEQLKSGTA SVVCLLNNFY PREAKVQWKV DNALQSGNSQ
IMP761-L   121   GTRLDIKRTV AAPSVFIFPP SDEQLKSGTA SVVCLLNNFY PREAKVQWKV DNALQSGNSQ

13E2IgK    181   ESVTEQDSKD STYSLSSTLT LSKADYEKHK VYACEVTHQG LSSPVTKSFN RGEC
IMP761-L   181   ESVTEQDSKD STYSLSSTLT LSKADYEKHK VYACEVTHQG LSSPVTKSFN RGEC
```

Figure 29
a) 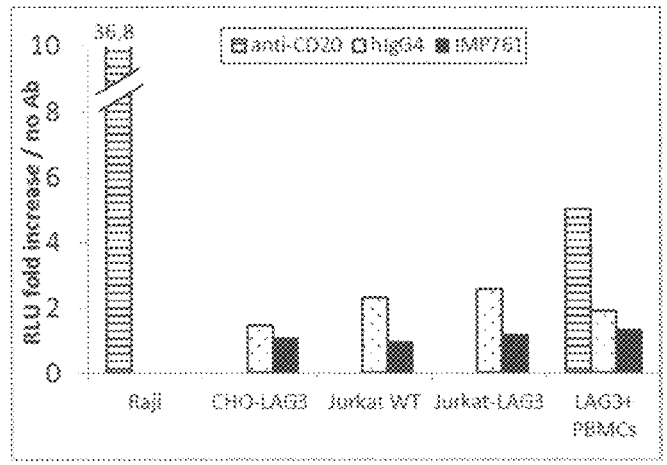
b) 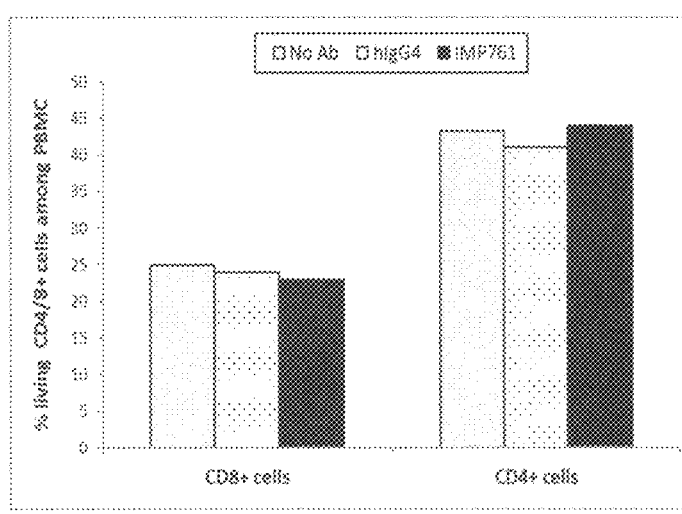
c) 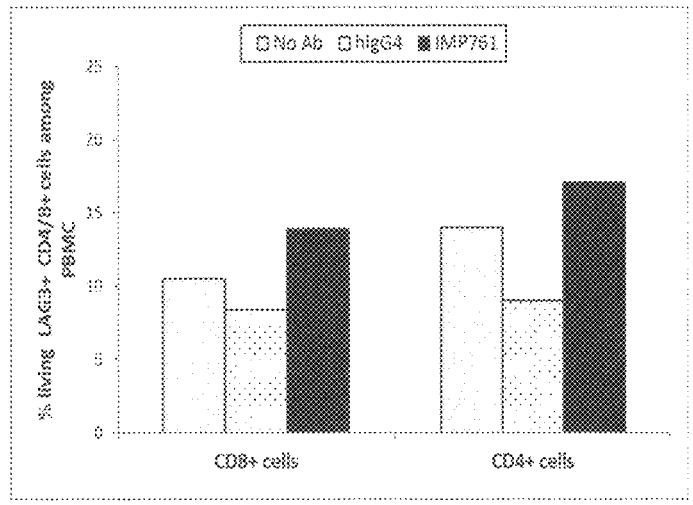

Figure 30
a)
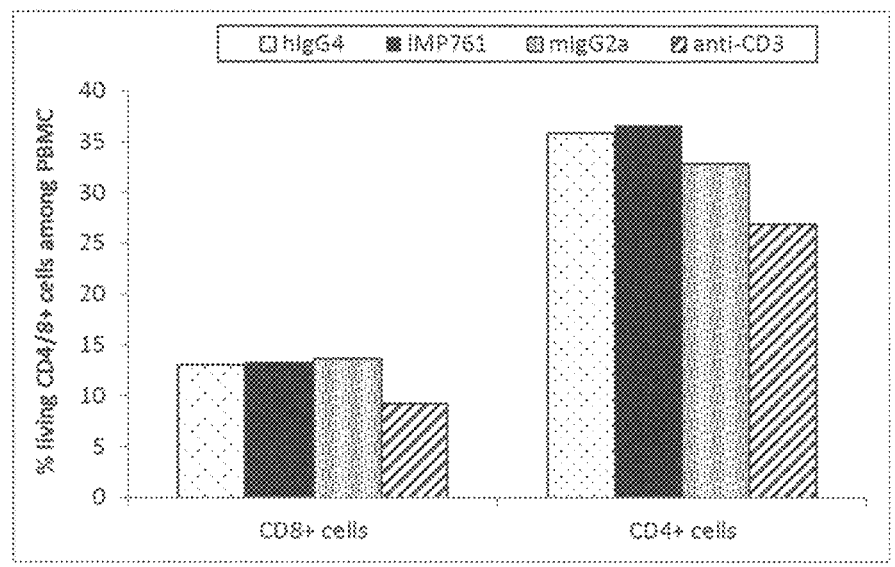
b)
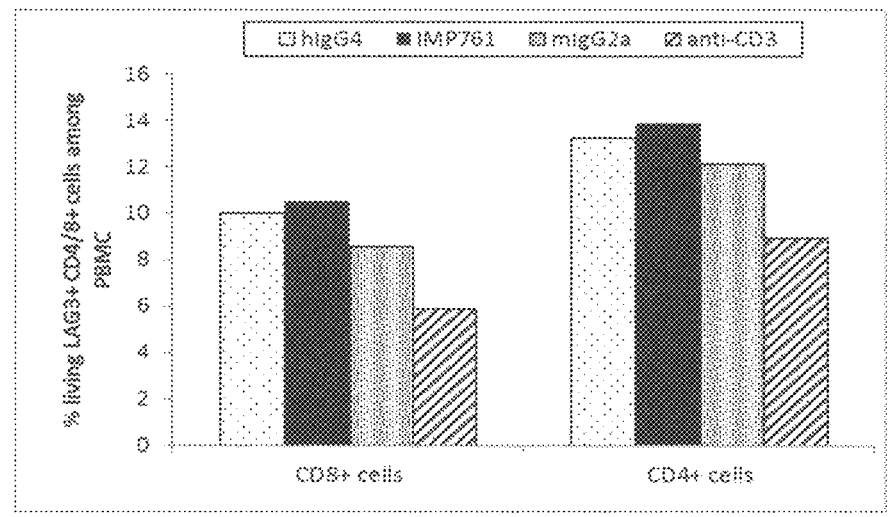

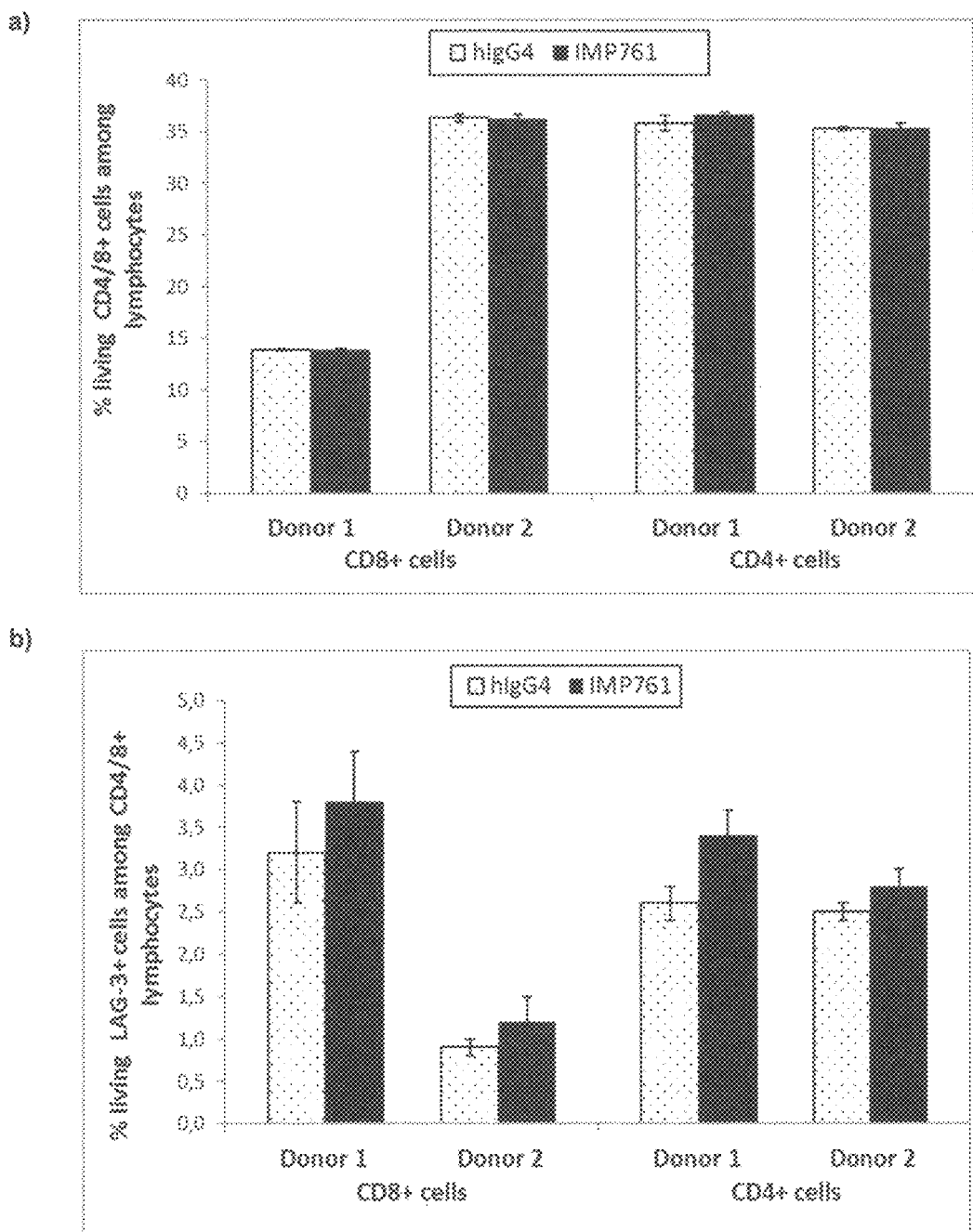

ANTI-LAG-3 ANTIBODIES

INCORPORATION BY REFERENCE OF SEQUENCE LISTING

The Sequence Listing in the ASCII text file, named as SequenceListingST25.txt of 47,062 bytes, created Feb. 13, 2018, and submitted to the United States Patent and Trademark Office via EFS-Web, is incorporated herein by reference.

This invention relates to antibodies, or antigen-binding fragments thereof, that bind to Lymphocyte-activation gene-3 (LAG-3), especially antibodies, or antigen-binding fragments thereof, that are agonists of LAG-3, and to use of the antibodies or fragments as medicaments, in particular for the treatment of conditions associated with proliferation and/or activation of $CD4^+$ and/or $CD8^+$ T cells, in particular inflammatory and autoimmune disorders.

The lymphocyte activation gene 3 (LAG-3) is a CD4 homolog type I membrane protein with four extracellular Ig superfamily domains. Similar to CD4, LAG-3 oligomerizes at the surfaces of T cells and binds to MHC class II molecules on antigen-presenting cells (APCs) but with significantly higher affinity than CD4. LAG-3 is expressed on activated CD4-positive and CD8-positive T lymphocytes where it associates with the CD3-TCR complex at the cell surface and negatively regulates signal transduction. As a consequence, it negatively regulates T cell proliferation, function, and homeostasis. When recognition of the MHC class II-peptide complex by a specific TCR occurs, intracellular signals are transduced in the T cell through the TCR and in the APC through MHC class II molecules. The negative regulatory role of LAG-3 signalling into T cells operates in primary CD4 and CD8 human T-cell responses (Macon-Lemaitre, et al., Immunology. 2005 June; 115(2): 170-178).

LAG-3 also encodes an alternative splice variant that is translated to a soluble form of LAG-3 (sLAG-3). As a soluble molecule, LAG-3 activates antigen-presenting cells (APCs) through MHC class II signalling, leading to increased antigen-specific T-cell responses in vivo (Triebel, Trends Immunol., 2003, 24: 619-622).

The amino acid sequence of human and murine LAG-3 protein is provided in Figure 1 of Huard et al (*Proc. Natl. Acad. Sci. USA*, 11: 5744-5749, 1997). The sequence of human LAG-3 protein is repeated in FIG. 1 below (SEQ ID NO: 27). The amino acid sequences of the four extracellular Ig superfamily domains (D1, D2, D3, and D4) of human LAG-3 are at amino acid residues: 1-149 (D1) (SEQ ID NO:28); 150-239 (D2) (SEQ ID NO:29); 240-330 (D3) (SEQ ID NO:39); and 331-412 (D4) (SEQ ID NO:51).

Baixeras, et al. (J. Exp. Med., 1992, Vol. 176: 327-337) describes production of 17G4, a mouse monoclonal antibody (isotype IgG1) to human LAG-3 protein. This antibody recognizes a 30 amino acid extra-loop of the first N-terminal D1 domain of human LAG-3. 17B4 inhibits LAG-3/MHC class interactions, and increases T cell proliferation as a LAG-3 signalling antagonist (Huard at al, Eur J Immunol. 1996; 26:1180-6). 17B4 mAb has no agonist activity, as determined by its inability to induce intracellular free calcium elevation into T cells in the absence of a secondary cross-linking reagent (Hannier et al, J Immunol. 1998; 161:4058-65.).

Agents capable of modulating the activation and/or effector functions of CD8-positive and CD4-positive T cells are highly desirable. In particular, many autoimmune disorders are known to involve autoreactive T cells and autoantibodies. There is a need, therefore, for agents that are capable of inhibiting or eliminating autoreactive lymphocytes without compromising the immune system's ability to defend against pathogens.

Poirier et al (Clinical and Experimental Immunology, 2011, 164: 265-274) describe evaluation of a cytotoxic LAG-3 chimeric antibody (chimeric A9H12). In vivo, the antibody depleted LAG-3$^+$-activated T cells in lymph nodes and showed efficacy at reducing skin inflammation in a tuberculin-induced delayed-type hypersensitivity (DTH) model in baboons. Antibodies that specifically deplete activated T cells present a promising therapeutic strategy to prevent and/or treat autoimmune disorders.

As an alternative strategy, the Applicant has appreciated that LAG-3 agonists will negatively regulate T cell proliferation and/or function without depleting the T cells, and that such agonists can also be used to treat inflammatory or autoimmune disorders.

The applicant has been able to produce monoclonal anti-LAG-3 agonistic antibodies. These antibodies inhibit antigen-induced proliferation of CD4-positive and CD8-positive T cells. Such antibodies, and antigen-binding fragments thereof, can be used for the treatment of immune disorders, in particular T-cell-mediated immune disorders, including inflammatory and autoimmune disorders.

According to the invention, there is provided an agonistic anti-LAG-3 antibody, or an antigen-binding fragment thereof. In particular, the antibody is a monoclonal agonistic anti-LAG-3 antibody, or an antigen-binding fragment thereof.

The term "LAG-3" used herein refers to Lymphocyte Activation Gene-3. The term "LAG-3" includes variants, isoforms, homologs, orthologs and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species but not all other species (e.g., cross-react with monkey LAG-3 but not mouse LAG-3). The term "human LAG-3" refers to human sequence LAG-3, such as the complete amino acid sequence of human LAG-3 having Genbank Accession No. NP 002277 (SEQ ID NO: 38), or the amino acid sequence of human LAG-3 protein given in FIG. 1 (SEQ ID NO: 27). The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

The term "monkey LAG-3" is intended to encompass LAG-3 proteins expressed by Old World and New World monkeys, including but not limited to cynomolgus monkey LAG-3 and rhesus monkey LAG-3. A representative amino acid sequence for monkey LAG-3 is the rhesus monkey LAG-3 amino acid sequence which is also deposited as Genbank Accession No. XM_001108923. Another representative amino acid sequence for monkey LAG-3 is the alternative rhesus monkey sequence of clone pa23-5 as described in US 2011/0150892 A1. This alternative rhesus sequence exhibits a single amino acid difference, at position 419, as compared to the Genbank-deposited sequence.

A particular human LAG-3 sequence will generally be at least 90% identical in amino acid sequence to human LAG-3 of Genbank Accession No. NP_002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of Genbank Accession No. NP_002277. In certain embodiments, a human LAG-3 sequence will display no more than 10 amino acid differences from the LAG-3 sequence of Genbank Accession No. NP_002277. In certain embodiments, the human LAG-3 can display no more than 5, or even no more than 4, 3, 2, or 1 amino acid difference from the LAG-3 sequence of Genbank Accession No. NP_002277. Percent identity can be determined as described herein.

According to some embodiments, an agonistic anti-LAG-3 antibody of the invention, or antigen-binding fragment thereof, inhibits antigen-induced $CD4^+$ and/or $CD8^+$ T cell proliferation, or antigen-induced $CD4^+$ and/or $CD8^+$ T cell activation.

An agonistic anti-LAG-3 antibody of the invention, or antigen-binding fragment thereof, may be an isolated agonistic anti-LAG-3 antibody, or antigen-binding fragment thereof.

The term "agonistic" is used herein interchangeably with the term "agonist".

There is also provided according to the invention an isolated antibody, or an antigen-binding fragment thereof, that binds to LAG-3 and inhibits antigen-induced $CD4^+$ and/or $CD8^+$ T cell proliferation, or antigen-induced $CD4^+$ and/or $CD8^+$ T cell activation.

In some embodiments, the antibody, or antigen-binding fragment thereof, inhibits antigen-induced $CD4^+$ T cell proliferation, and/or antigen-induced $CD8^+$ T cell proliferation. In some embodiments, the antibody, or antigen-binding fragment thereof, inhibits antigen-induced $CD4^+$ T cell proliferation, and antigen-induced $CD8^+$ T cell proliferation. In particular embodiments, the antibody, or antigen-binding fragment thereof, inhibits antigen-induced $CD8^+$ T cell proliferation more than antigen-induced $CD4^+$ T cell proliferation.

FIG. 21 illustrates the differences between depleting anti-LAG-3 antibodies, antagonist anti-LAG-3 antibodies, and antibodies of the invention (i.e. agonistic anti-LAG-3 antibodies, and antibodies that bind to LAG-3 and inhibit antigen-induced $CD4^+$ and/or $CD8^+$ T cell proliferation, or antigen-induced $CD4^+$ and/or $CD8^+$ T cell activation).

A depleting anti-LAG-3 antibody causes depletion of activated T cells by binding to LAG-3 expressed on the surface of the cells. Depletion can occur by antibody-dependent cell-mediated cytotoxicity (ADCC), or by complement-dependent cytotoxicity (CDC). In ADCC, the Fc region of the depleting antibody binds to Fc receptors (FcγRs) on the surface of immune effector cells, such as natural killers and macrophages, leading to lysis of the targeted cells. In CDC, the Fc region of the depleting antibody binds to the C1q component of complement, and the targeted cell is killed by triggering the complement cascade at the cell surface. Thus, depleting anti-LAG-3 antibodies inhibit T cell-mediated immune responses. It will be appreciated that the effects of depleting anti-LAG-3 antibodies are long-lasting, and irreversible because they cause the destruction of activated T cells. Such antibodies are useful, for example, for the treatment of inflammatory and autoimmune disorders, and for the prevention of transplant rejection An antagonist anti-LAG-3 antibody binds to LAG-3 on the surface of activated T cells, and prevents interaction of LAG-3 with MHC class II molecules on the surface of antigen-presenting cells (APCs). This blocks the negative regulation of signal transduction that occurs when APCs bind to LAG-3 on activated T cells. Consequently, antagonist anti-LAG-3 antibodies prevent the negative regulation of T cell proliferation, function and homeostasis normally mediated by LAG-3. Such antibodies are useful, for example, for the treatment of cancer and infectious disease.

Antibodies of the invention bind to LAG-3 on the surface of activated T cells, and negatively regulate signal transduction through agonism of LAG-3, causing negative regulation of T cell proliferation and/or activation. Thus, antibodies of the invention inhibit T cell-mediated immune responses, in particular by inhibiting antigen-induced $CD4^+$ and/or $CD8^+$ T cell proliferation, and/or antigen-induced $CD4^+$ and/or $CD8^+$ T cell activation. The effects of such antibodies are reversible, and may be less long-lasting than the effects of depleting anti-LAG-3 antibodies since they do not cause the destruction of activated T cells. It will be appreciated that the length of time for which an antibody of the invention is effective will depend on the plasma half-life of the antibody.

Inhibition of antigen-induced $CD4^+$ and/or $CD8^+$ T cell proliferation may be determined by any suitable method known to the skilled person. An example of a suitable method is by measuring the proliferation of $CD4^+$ and/or $CD8^+$ T cells induced by antigenic peptides in the presence of the antibody or fragment, compared with the corresponding proliferation in the presence of a negative control antibody of the same isotype. The $CD4^+$ and $CD8^+$ T cells may be present, for example, in a sample of peripheral blood mononuclear cells (PBMCs) obtained from a healthy donor. Proliferation of the cells may be induced by any suitable antigenic peptides, such as a pool of peptides covering the sequence of CMV pp35. Proliferation of the cells may be measured by labelling the cells, for example with a fluorescent cell staining dye, such as carboxyfluorescein succinimidyl ester (CFSE). An example of a method for measuring inhibition of antigen-induced $CD4^+$ and/or $CD8^+$ T cell proliferation is described in more detail in Example 10 below.

The percentage inhibition of antigen-induced $CD4^+$ and/or $CD8^+$ T cell proliferation may be determined as a percentage inhibition of the proliferation index (PI), calculated as the sum of: the percentage of $CD4^+$ and/or $CD8^+$ T cells under each division peak (assessed by FACS), multiplied by the division number, as described in more detail in Example 10 below.

In some embodiments, an antibody of the invention, or antigen-binding fragment thereof, inhibits antigen-induced $CD4^+$ T cell proliferation by at least 10%, 20%, 30%, 40%, 50%, 60%, 70%, 80%, or 90%, compared to antigen-induced $CD4^+$ T cell proliferation in the absence of the antibody or fragment.

In some embodiments, an antibody of the invention, or antigen-binding fragment thereof, inhibits antigen-induced $CD8^+$ T cell proliferation by at least 10%, 20%, 30%, 40%, 50%, 60%, 70%, 80%, or 90%, compared to antigen-induced $CD8^+$ T cell proliferation in the absence of the antibody or fragment.

In some embodiments, an antibody of the invention, or antigen-binding fragment thereof, inhibits antigen-induced CD4+ T cell proliferation, and antigen-induced CD8+ T cell proliferation, each by at least 10%, 20%, 30%, 40%, 50%, 60%, 70%, 80%, or 90%, compared to antigen-induced CD4+ T cell proliferation, and antigen-induced CD8+ T cell proliferation, respectively, in the absence of the antibody or fragment.

In one embodiment, an antibody of the invention, or antigen-binding fragment thereof, inhibits antigen-induced CD4+ T cell proliferation by at least 20% compared to antigen-induced CD4+ T cell proliferation in the absence of the antibody or fragment, and inhibits antigen-induced CD8+ T cell proliferation by at least 30% compared to and antigen-induced CD8+ T cell proliferation in the absence of the antibody or fragment.

Inhibition of antigen-induced CD4+ and/or CD8+ T cell proliferation by an antibody of the invention, or fragment thereof, may be compared to antigen-induced CD4+ and/or CD8+ T cell proliferation in the presence of a negative control antibody of the same isotype, or fragment thereof.

In some embodiments, an antibody of the invention, or antigen-binding fragment thereof, inhibits antigen-induced CD8+ T cell proliferation by at least 10%, 20%, 30%, 40%, 50%, 60%, 70%, 80%, or 90%, more than the antibody or fragment inhibits antigen-induced CD4+ T cell proliferation.

According to some embodiments, the inhibition of antigen-induced CD8+ T cell proliferation is LAG-3 dependent and IL-2 independent.

According to some embodiments, an antibody of the invention, or antigen-binding fragment thereof, inhibits antigen-induced CD4+ and/or CD8+ T cell activation. In certain embodiments, an antibody of the invention, or antigen-binding fragment thereof, inhibits antigen-induced CD4+ and/or CD8+ T cell proliferation and antigen-induced CD4+ and/or CD8+ T cell activation.

In particular, an antibody of the invention, or antigen-binding fragment thereof, may bind to LAG-3 and inhibit antigen-induced CD4+ and/or CD8+ T cell activation. In certain embodiments, an antibody of the invention, or antigen-binding fragment thereof, binds to LAG-3 and inhibits antigen-induced CD4+ T cell activation and antigen-induced CD8+ T cell activation.

Inhibition of activation of CD4+ and/or CD8+ T cells may be determined by any suitable method known to the skilled person. An example of a suitable method is by measuring the effect of the antibody, or fragment, on CD4+ and/or CD8+ T cell activation marker expression, or T cell activation marker secretion. For example, CD8+ T cell activation may be measured by measuring the expression of CD25, as an activation marker, on CD8+ T cells induced by antigenic peptides in the presence of the antibody or fragment, compared with the corresponding CD25 expression in the presence of a negative control antibody of the same isotype. Alternatively, T cell activation may be measured by measuring the secretion of IFN-γ in cell supernatant of T cells induced by antigenic peptides in the presence of the antibody or fragment, compared with the corresponding secretion in the presence of a negative control antibody of the same isotype. The T cells may be present, for example, in a sample of PBMCs obtained from a healthy donor. Activation of the cells may be induced by any suitable antigenic peptides, such as a pool of peptides covering the sequence of CMV pp35. An example of a method for determining inhibition of antigen-induced T cell activation by measuring T cell activation marker secretion is described in more detail in Example 15 below. An example of a method for determining inhibition of antigen-induced CD8+ T cell activation by measuring CD8+ T cell activation marker expression is described in more detail in Example 16 below.

In some embodiments, an antibody of the invention, or antigen-binding fragment thereof, inhibits antigen-induced CD4+ and/or CD8+ T cell activation by at least 10%, 20%, 30%, 40%, 50%, 60%, 70%, 80%, or 90%, compared to antigen-induced CD4+ and/or CD8+ T cell activation in the absence of the antibody or fragment.

Inhibition of antigen-induced CD4+ and/or CD8+ T cell activation by an antibody of the invention, or fragment thereof, may be compared to antigen-induced CD4+ and/or CD8+ T cell activation in the presence of a negative control antibody of the same isotype, or fragment thereof.

According to some embodiments, an antibody of the invention, or an antigen-binding fragment thereof, inhibits binding of IMP321 to MHC class II-positive cells.

IMP321 (also referred to as "LAG-3Ig" below) is a recombinant soluble human LAG-3Ig fusion protein. The fusion protein is obtained as a 200-kDa dimer produced in Chinese hamster ovary (CHO) cells transfected with a plasmid encoding for the extracellular domain of human LAG-3 fused to the human IgG1 Fc. The sequence of IMP321 is provided in SEQ ID NO: 17 of US Patent Application No. 2011/0008331.

Binding of IMP321 to MHC class II-positive cells may be determined by measuring binding of an IMP321-label conjugate (for example an IMP321-Alex 488 conjugate) to Raji cells (these are MHC class II-positive B cells), for example as described in Example 8 below.

In some embodiments, an antibody of the invention, or an antigen-binding fragment thereof, inhibits binding of IMP321 to MHC class II-positive cells by at least 10%, at least 20%, at least 30%, at least 40%, at least 50%, at least 60%, at least 70%, at least 80%, or at least 90% compared to the binding of IMP321 to MHC class II-positive cells in the absence of the antibody or fragment.

In some embodiments, an antibody of the invention, or an antigen-binding fragment thereof, inhibits binding of IMP321 to MHC class II-positive cells by at least 30%, compared to the binding of IMP321 to MHC class II-positive cells in the absence of the antibody or fragment, wherein the ratio of the concentration of the antibody, or fragment, to IMP321 is 0.1:1.

In some embodiments, an antibody of the invention, or an antigen-binding fragment thereof, inhibits binding of IMP321 to MHC class II-positive cells by at least 80%, compared to the binding of IMP321 to MHC class II-positive cells in the absence of the antibody or fragment, wherein the ratio of the concentration of the antibody, or fragment, to IMP321 is 0.3:1 or 1:1.

In some embodiments, an antibody of the invention, or an antigen-binding fragment thereof, inhibits IMP321-induced monocyte activation.

IMP321 is able to activate cells of the human monocytic cell line THP-1. Activation of THP-1 cells can be determined by the level of secretion of chemokine ligand 4 (CCL4, also known as Macrophage inflammatory protein-1β, MIP-1β) by the THP-1 cells. Pre-incubation of an antibody, or fragment, of the invention with IMP321 prior to incubation of the mixture with THP-1 cells can be used to determine whether the antibody, or fragment, inhibits IMP321-induced monocyte activation. A method for determining inhibition of IMP321-induced monocyte activation is described in more detail in Example 9 below.

In some embodiments, an antibody of the invention, or an antigen-binding fragment thereof, inhibits IMP321-induced monocyte activation by at least 10%, at least 20%, at least 30%, at least 40%, at least 50%, at least 60%, at least 70%, at least 80%, or at least 90% compared to the amount of IMP321-induced monocyte activation in the absence of the antibody or fragment.

In some embodiments, an antibody of the invention, or an antigen-binding fragment thereof, inhibits IMP321-induced monocyte activation by at least 70% compared to the amount of IMP321-induced monocyte activation in the absence of the antibody or fragment, wherein the ratio of the concentration of the antibody, or fragment, to IMP321 is 1:1.

Huard et al (*Proc. Natl. Acad. Sci. USA,* 11: 5744-5749, 1997) describes characterization of the MHC class II binding site on LAG-3 protein. Many of the residues essential for binding MHC class II proteins are clustered at the base of a large 30 amino acid extra-loop structure in the LAG-3 D1 domain. The amino acid sequence of the extra-loop structure of the D1 domain of human LAG-3 protein is GPPAAAPGHPLAPGPHPAAPSSWGPRPRRY (SEQ ID NO: 40), the underlined sequence in FIG. 1.

An antibody of the invention, or antigen-binding fragment thereof, may bind to an epitope of human LAG-3 that overlaps with the MHC class II binding site on LAG-3.

An antibody of the invention, or antigen-binding fragment thereof, may bind to an epitope that overlaps with the 30 amino acid extra-loop of the first N-terminal D1 domain of human LAG-3.

In other embodiments, an antibody of the invention, or antigen-binding fragment thereof, does not bind to the 30 amino acid extra-loop sequence (SEQ ID NO: 40) of the first N-terminal D1 domain of human LAG-3 protein.

An antibody of the invention may inhibit binding of LAG-3 to MHC class II molecules in vivo. In particular, an antibody of the invention may antagonise the MHC class II-activating signal into antigen-presenting cells (APCs). Thus, an antibody of the invention may inhibit LAG-3-induced APC activation, for example dendritic cell activation, for example LAG-3-induced monocyte or macrophage activation.

In some embodiments, an antibody of the invention, or an antigen-binding fragment thereof, inhibits binding of LAG-3 to MHC class II-positive cells by at least 10%, at least 20%, at least 30%, at least 40%, at least 50%, at least 60%, at least 70%, at least 80%, or at least 90% compared to the binding of LAG-3 to MHC class II-positive cells in the absence of the antibody or fragment.

In some embodiments, an antibody of the invention, or an antigen-binding fragment thereof, inhibits LAG-3-induced APC activation by at least 10%, at least 20%, at least 30%, at least 40%, at least 50%, at least 60%, at least 70%, at least 80%, or at least 90% compared to the amount of LAG-3-induced APC activation in the absence of the antibody or fragment.

A monoclonal antibody of the invention, or antigen-binding fragment thereof, may comprise one, two, or three complementarity determining regions (CDRs) of an antibody heavy chain variable (VH) region comprising amino acid sequence SEQ ID NO:7, and/or one, two, or three CDRs of an antibody light chain variable (VL) region comprising amino acid sequence SEQ ID NO:8.

There is also provided according to the invention an anti-LAG-3 antibody, or antigen-binding fragment thereof, which comprises one, two, or three complementarity determining regions (CDRs) of an antibody heavy chain variable (VH) region comprising amino acid sequence SEQ ID NO:7, and/or one, two, or three CDRs of an antibody light chain variable (VL) region comprising amino acid sequence SEQ ID NO:8.

The CDRs of the antibody VH region may be CDRs of amino acid sequence SEQ ID NO:1, 2, and 3, and the CDRs of the antibody VL region may be CDRs of amino acid sequence SEQ ID NO:4, 5, and 6.

An antibody of the invention, or antigen-binding fragment thereof, may comprise an antibody VH region with CDRs comprising amino acid sequences of SEQ ID NOs:1, 2, and 3, and/or an antibody VL region with CDRs comprising amino acid sequences of SEQ ID NOs:4, 5, and 6.

The CDRs of amino acid sequence SEQ ID NOs:1, 2, and 3 may be present in any order in the VH region, and the CDRs of amino acid sequence SEQ ID NOs:4, 5, and 6 may be present in any order in the VL region. However, in a preferred embodiment, the antibody, or fragment thereof, comprises CDR-H1 having amino acid sequence SEQ ID NO:1, CDR-H2 having amino acid sequence SEQ ID NO:2, and CDR-H3 having amino acid sequence SEQ ID NO:3, and/or CDR-L1 having amino acid sequence SEQ ID NO:4, CDR-L2 having amino acid sequence SEQ ID NO:5, and CDR-L3 having amino acid sequence SEQ ID NO:6.

The CDRs of the antibody VH region may be CDRs of amino acid sequence SEQ ID NO:21, 22, and 23, and the CDRs of the antibody VL region may be CDRs of amino acid sequence SEQ ID NO:24, 25, and 26.

An antibody of the invention, or antigen-binding fragment thereof, may comprise an antibody VH region with CDRs comprising amino acid sequences of SEQ ID NOs:21, 22, and 23, and/or an antibody VL region with CDRs comprising amino acid sequences of SEQ ID NOs:24, 25, and 26.

The CDRs of amino acid sequence SEQ ID NOs:21, 22, and 23 may be present in any order in the VH region, and the CDRs of amino acid sequence SEQ ID NOs:24, 25, and 26 may be present in any order in the VL region. However, in a preferred embodiment, the antibody, or fragment thereof, comprises CDR-H1 having amino acid sequence SEQ ID NO:21, CDR-H2 having amino acid sequence SEQ ID NO:22, and CDR-H3 having amino acid sequence SEQ ID NO:23, and/or CDR-L1 having amino acid sequence SEQ ID NO:24, CDR-L2 having amino acid sequence SEQ ID NO:25, and CDR-L3 having amino acid sequence SEQ ID NO:26.

In some embodiments, the CDRs of the antibody VH region are selected from CDRs of amino acid sequence SEQ ID NO:1, 2, 3, 21, 22, and 23, and the CDRs of the antibody VL region are selected from CDRs of amino acid sequence SEQ ID NO:4, 5, 6, 24, 25, and 26.

In some embodiments, an antibody of the invention, or antigen-binding fragment thereof, comprises an antibody VH region comprising a VH CDR1, a VH CDR2, and a VH CDR3, wherein the VH CDR1 has an amino acid sequence selected from SEQ ID NO:1 and 21, and/or the VH CDR2 has an amino acid sequence selected from SEQ ID NO:2 and 22, and/or the VH CDR3 has an amino acid sequence selected from SEQ ID NO:3 and 23.

In some embodiments:
  the VH CDR1 has an amino acid sequence selected from SEQ ID NO:1 and 21, and the VH CDR2 has an amino acid sequence selected from SEQ ID NO:2 and 22;
  the VH CDR1 has an amino acid sequence selected from SEQ ID NO:1 and 21, and the VH CDR3 has an amino acid sequence selected from SEQ ID NO:3 and 23;
  the VH CDR2 has an amino acid sequence selected from SEQ ID NO:2 and 22, and the VH CDR3 has an amino acid sequence selected from SEQ ID NO:3 and 23; or the VH CDR1 has an amino acid sequence selected from SEQ ID NO:1 and 21, the VH CDR2 has an amino acid sequence selected from SEQ ID NO:2 and 22, and the VH CDR3 has an amino acid sequence selected from SEQ ID NO:3 and 23.

In some embodiments, an antibody of the invention, or antigen-binding fragment thereof, comprises an antibody VL region comprising a VL CDR1, a VL CDR2, and a VL CDR3, wherein the VL CDR1 has an amino acid sequence selected from SEQ ID NO:4 and 24, and/or the VL CDR2 has an amino acid sequence selected from SEQ ID NO:5 and 25, and/or the VL CDR3 has an amino acid sequence selected from SEQ ID NO:6 and 26.

In some embodiments:
the VL CDR1 has an amino acid sequence selected from SEQ ID NO:4 and 24, and the VL CDR2 has an amino acid sequence selected from SEQ ID NO:5 and 25;
the VL CDR1 has an amino acid sequence selected from SEQ ID NO:4 and 24, and the VL CDR3 has an amino acid sequence selected from SEQ ID NO:6 and 26;
the VL CDR2 has an amino acid sequence selected from SEQ ID NO:5 and 25, and the VL CDR3 has an amino acid sequence selected from SEQ ID NO:6 and 26; or
the VL CDR1 has an amino acid sequence selected from SEQ ID NO:4 and 24, the VL CDR2 has an amino acid sequence selected from SEQ ID NO:5 and 25, and the VL CDR3 has an amino acid sequence selected from SEQ ID NO:6 and 26.

In particular embodiments, an antibody of the invention, or antigen-binding fragment thereof, comprises: an antibody VH region comprising: a VH CDR1 with an amino acid sequence selected from SEQ ID NO:1 and 21; a VH CDR2 with an amino acid sequence selected from SEQ ID NO:2 and 22; and a VH CDR3 with an amino acid sequence selected from SEQ ID NO:3 and 23; and an antibody VL region comprising: a VL CDR1 with an amino acid sequence selected from SEQ ID NO:4 and 24; a VL CDR2 with an amino acid sequence selected from SEQ ID NO:5 and 25; and a VL CDR3 with an amino acid sequence selected from SEQ ID NO:6 and 26.

An antibody of the invention, or antigen-binding fragment thereof, may comprise an antibody VH region comprising amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO:7, and/or an antibody VL region comprising amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO:8.

In a preferred embodiment, an antibody of the invention, or antigen-binding fragment thereof, comprises an antibody VH region comprising amino acid sequence SEQ ID NO:7, and/or an antibody VL region comprising amino acid sequence SEQ ID NO:8.

An antibody of the invention, or antigen-binding fragment thereof, may comprise an antibody VH region and/or an antibody VL region comprising amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical, or that is identical, to the amino acid sequence of the VH and/or VL regions of mouse monoclonal anti-LAG-3 antibody 13E2, described herein in Examples 1, 2 and 3 (13E2 VH amino acid sequence: SEQ ID NO:7; 13E2 VL amino acid sequence: SEQ ID NO:8).

There is also provided according to the invention an antibody, or antigen-binding fragment thereof, that competes for binding to LAG-3 with an antibody that comprises an antibody VH region comprising amino acid sequence SEQ ID NO:7, and an antibody VL region comprising amino acid sequence SEQ ID NO:8.

There is further provided according to the invention an antibody, or antigen-binding fragment thereof, that competes for binding to LAG-3 with mouse monoclonal anti-LAG-3 antibody 13E2.

A monoclonal antibody of the invention, or antigen-binding fragment thereof, may comprise one, two, or three complementarity determining regions (CDRs) of an antibody heavy chain variable (VH) region comprising amino acid sequence SEQ ID NO:17, and/or one, two, or three CDRs of an antibody light chain variable (VL) region comprising amino acid sequence SEQ ID NO:18.

There is also provided according to the invention an anti-LAG-3 antibody, or antigen-binding fragment thereof, which comprises one, two, or three complementarity determining regions (CDRs) of an antibody heavy chain variable (VH) region comprising amino acid sequence SEQ ID NO:17, and/or one, two, or three CDRs of an antibody light chain variable (VL) region comprising amino acid sequence SEQ ID NO:18.

The CDRs of the antibody VH region may be CDRs of amino acid sequence SEQ ID NO:11, 12, and 13, and the CDRs of the antibody VL region may be CDRs of amino acid sequence SEQ ID NO:14, 15, and 16.

An antibody of the invention, or antigen-binding fragment thereof, may comprise an antibody VH region with CDRs comprising amino acid sequences of SEQ ID NOs:11, 12, and 13, and/or an antibody VL region with CDRs comprising amino acid sequences of SEQ ID NOs:14, 15, and 16.

The CDRs of amino acid sequence SEQ ID NOs:11, 12, and 13 may be present in any order in the VH region, and the CDRs of amino acid sequence SEQ ID NOs:14, 15, and 16 may be present in any order in the VL region. However, in a preferred embodiment, the antibody, or fragment thereof, comprises CDR-H1 having amino acid sequence SEQ ID NO:11, CDR-H2 having amino acid sequence SEQ ID NO:12, and CDR-H3 having amino acid sequence SEQ ID NO:13, and/or CDR-L1 having amino acid sequence SEQ ID NO:14, CDR-L2 having amino acid sequence SEQ ID NO:15, and CDR-L3 having amino acid sequence SEQ ID NO:16.

The CDRs of the antibody VH region may be CDRs of amino acid sequence SEQ ID NO:31, 32, and 33, and the CDRs of the antibody VL region may be CDRs of amino acid sequence SEQ ID NO:34, 35, and 36.

An antibody of the invention, or antigen-binding fragment thereof, may comprise an antibody VH region with CDRs comprising amino acid sequences of SEQ ID NOs:31, 32, and 33, and/or an antibody VL region with CDRs comprising amino acid sequences of SEQ ID NOs:34, 35, and 36.

The CDRs of amino acid sequence SEQ ID NOs:31, 32, and 33 may be present in any order in the VH region, and the CDRs of amino acid sequence SEQ ID NOs:34, 35, and 36 may be present in any order in the VL region. However, in a preferred embodiment, the antibody, or fragment thereof, comprises CDR-H1 having amino acid sequence SEQ ID NO:31, CDR-H2 having amino acid sequence SEQ ID NO:32, and CDR-H3 having amino acid sequence SEQ ID NO:33, and/or CDR-L1 having amino acid sequence SEQ ID NO:34, CDR-L2 having amino acid sequence SEQ ID NO:35, and CDR-L3 having amino acid sequence SEQ ID NO:36.

In some embodiments, the CDRs of the antibody VH region are selected from CDRs of amino acid sequence SEQ ID NO:11, 12, 13, 31, 32, and 33, and the CDRs of the antibody VL region are selected from CDRs of amino acid sequence SEQ ID NO:14, 15, 16, 34, 35, and 36.

In some embodiments, an antibody of the invention, or antigen-binding fragment thereof, comprises an antibody VH region comprising a VH CDR1, a VH CDR2, and a VH CDR3, wherein the VH CDR1 has an amino acid sequence selected from SEQ ID NO:11 and 31, and/or the VH CDR2 has an amino acid sequence selected from SEQ ID NO:12 and 32, and/or the VH CDR3 has an amino acid sequence selected from SEQ ID NO:13 and 33.

In some embodiments:
the VH CDR1 has an amino acid sequence selected from SEQ ID NO:11 and 31, and the VH CDR2 has an amino acid sequence selected from SEQ ID NO:12 and 32;
the VH CDR1 has an amino acid sequence selected from SEQ ID NO:11 and 31, and the VH CDR3 has an amino acid sequence selected from SEQ ID NO:13 and 33;
the VH CDR2 has an amino acid sequence selected from SEQ ID NO:12 and 32, and the VH CDR3 has an amino acid sequence selected from SEQ ID NO:13 and 33; or
the VH CDR1 has an amino acid sequence selected from SEQ ID NO:11 and 31, the VH CDR2 has an amino acid sequence selected from SEQ ID NO:12 and 32, and the VH CDR3 has an amino acid sequence selected from SEQ ID NO:13 and 33.

In some embodiments, an antibody of the invention, or antigen-binding fragment thereof, comprises an antibody VL region comprising a VL CDR1, a VL CDR2, and a VL CDR3, wherein the VL CDR1 has an amino acid sequence selected from SEQ ID NO:14 and 34, and/or the VL CDR2 has an amino acid sequence selected from SEQ ID NO:15 and 35, and/or the VL CDR3 has an amino acid sequence selected from SEQ ID NO:16 and 36.

In some embodiments:
the VL CDR1 has an amino acid sequence selected from SEQ ID NO:14 and 34, and the VL CDR2 has an amino acid sequence selected from SEQ ID NO:15 and 35;
the VL CDR1 has an amino acid sequence selected from SEQ ID NO:14 and 34, and the VL CDR3 has an amino acid sequence selected from SEQ ID NO:16 and 36;
the VL CDR2 has an amino acid sequence selected from SEQ ID NO:15 and 35, and the VL CDR3 has an amino acid sequence selected from SEQ ID NO:16 and 36; or
the VL CDR1 has an amino acid sequence selected from SEQ ID NO:14 and 34, the VL CDR2 has an amino acid sequence selected from SEQ ID NO:15 and 35, and the VL CDR3 has an amino acid sequence selected from SEQ ID NO:16 and 36.

In particular embodiments, an antibody of the invention, or antigen-binding fragment thereof, comprises: an antibody VH region comprising: a VH CDR1 with an amino acid sequence selected from SEQ ID NO:11 and 31, a VH CDR2 with an amino acid sequence selected from SEQ ID NO:12 and 32, and a VH CDR3 with an amino acid sequence selected from SEQ ID NO:13 and 33; and an antibody VL region comprising: a VL CDR1 with an amino acid sequence selected from SEQ ID NO:14 and 34, a VL CDR2 with an amino acid sequence selected from SEQ ID NO:15 and 35, and a VL CDR3 with an amino acid sequence selected from SEQ ID NO:16 and 36.

An antibody of the invention, or antigen-binding fragment thereof, may comprise an antibody VH region comprising amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO:17, and/or an antibody VL region comprising amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO:18.

In a preferred embodiment, an antibody of the invention, or antigen-binding fragment thereof, comprises an antibody VH region comprising amino acid sequence SEQ ID NO:17, and/or an antibody VL region comprising amino acid sequence SEQ ID NO:18.

An antibody of the invention, or antigen-binding fragment thereof, may comprise an antibody VH region and an antibody VL region comprising amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical, or that is identical, to the amino acid sequence of the VH and VL regions of mouse monoclonal anti-LAG-3 antibody 34F4, described herein in Examples 4, 5 and 6 (34F4 VH amino acid sequence: SEQ ID NO:17; 34F4 VL amino acid sequence: SEQ ID NO:18).

There is also provided according to the invention an antibody, or antigen-binding fragment thereof, that competes for binding to LAG-3 with an antibody that comprises an antibody VH region comprising amino acid sequence SEQ ID NO:17, and an antibody VL region comprising amino acid sequence SEQ ID NO:18.

There is further provided according to the invention an antibody, or antigen-binding fragment thereof, that competes for binding to LAG-3 with mouse monoclonal anti-LAG-3 antibody 34F4.

In certain embodiments, antibodies of the invention comprise a heavy chain variable region comprising CDR1, CDR2 and CDR3 sequences, and a light chain variable region comprising CDR1, CDR2, and CDR3 sequences, which differ from those of antibody 13E2 or 34F4 by one or more conservative modifications, for example up to five conservative modifications. It is understood in the art that certain conservative sequence modifications can be made which do not remove antigen binding. See, e.g., Brummell et al. (1993) *Biochem* 32:1180-8; de Wildt et al. (1997) *Prot. Eng.* 10:835-41; Komissarov et al. (1997) *J. Biol. Chem.* 272:26864-26870; Hall et al. (1992) *J. Immunol.* 149:1605-12; Kelley and O'Connell (1993) *Biochem.* 32:6862-35; Adib-Conquy et al. (1998) *Int. Immunol.* 10:341-6 and Beers et al. (2000) *Clin. Can. Res.* 6:2835-43.

As used herein, the term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Antibodies of the invention can be prepared using an antibody having one or more of the VH and/or VL sequences of 13E2 or 34F4 as starting material to engineer a modified antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) Nature 332:323-327; Jones et al. (1986) Nature 321: 522-525; Queen et al. (1989) Proc. Natl. Acad. Sci. U.S.A. 86:10029-10033; U.S. Pat. Nos. 5,225, 539; 5,530,101; 5,585,089; 5,693,762 and 6,180,370).

There is also provided according to the invention an antibody of the invention, or antigen-binding fragment thereof, for example a monoclonal antibody, or antigen-binding fragment thereof, comprising CDR1, CDR2, and CDR3 of an antibody heavy chain variable region comprising amino acid sequence SEQ ID NO:7, and/or comprising CDR1, CDR2, and CDR3 of an antibody light chain variable region comprising amino acid sequence SEQ ID NO:8 (i.e., the CDRs of 13E2). While such antibodies contain the VH and VL CDR sequences of monoclonal antibody 13E2, they can contain differing framework sequences.

Similarly, there is also provided according to the invention an antibody of the invention, or antigen-binding fragment thereof, for example a monoclonal antibody, or antigen-binding fragment thereof, comprising CDR1, CDR2, and CDR3 of an antibody heavy chain variable region comprising amino acid sequence SEQ ID NO:17, and/or comprising CDR1, CDR2, and CDR3 of an antibody light chain variable region comprising amino acid sequence SEQ ID NO:18 (i.e., the CDRs of 34F4). While such antibodies contain the VH and VL CDR sequences of monoclonal antibody 34F4, they can contain differing framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline V$_H$ Sequences Reveals about Fifty Groups of V$_H$ Segments with Different Hypervariable Loops" J. Mol. Biol. 227:776-798; and Cox et al. (1994) "A Directory of Human Germ-line V$_H$ Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG_0010109, NT_024637 & BC070333), 3-33 (NG_0010109 & NT_024637) and 3-7 (NG_0010109 & NT_024637). As another example, the following heavy chain germline sequences found in the HCo12 HuMAb mouse are available in the accompanying Genbank Accession Nos.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art.

Preferred framework sequences for use in antibodies of the invention are those that are structurally similar to the framework sequences of the 13E2 or 34F4 antibodies.

Sequences showing significant alignment with nucleic acid sequence encoding the VH domain of monoclonal antibody 13E2 include the following germline genes: IGHV8-8*01, IGHV8-11*01, IGHV8-12*01, IGHD2-12*01, IGHD1-1*01, IGHJ1*01, IGHJ1*02, IGHJ1*03.

Sequences showing significant alignment with nucleic acid sequence encoding the VL domain of monoclonal antibody 13E2 include the following germline genes: IGKV6-17*01, IGKV6-25*01, IGKV6-23*01, IGKJ2*01, IGKJ2*03, IGKJ2*02.

Sequences showing significant alignment with nucleic acid sequence encoding the VH domain of monoclonal antibody 34F4 include the following germline genes: IGHV8-8*01, IGHV8-12*01, IGHV8-11*01, IGHD1-1*01, IGHD1-2*01, IGHD2-3*01, IGHJ2*01, IGHJ2*02, IGHJ2*03.

Sequences showing significant alignment with nucleic acid sequence encoding the VL domain of monoclonal antibody 34F4 include the following germline genes: IGKV6-17*01, IGKV6-25*01, IGKV6-23*01, IGKJ1*01, IGKJ1*02, IGKJ2*01.

Preferred heavy chain framework sequences for use in antibodies of the invention are those that are structurally similar to the framework sequences encoded by germline V gene IGHV8-8*01, IGHV8-11*01, or IGHV8-12*01, especially IGHV8-8*01. Preferred light chain framework sequences for use in antibodies of the invention are those that are structurally similar to the framework sequences encoded by germline V gene IGKV6-17*01, IGKV6-25*01, or IGKV6-23*01, especially IGKV6-17*01.

The VH CDR1, CDR2, and CDR3 sequences, and the VL CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations can be amino acid substitutions, additions or deletions, but are preferably substitutions. Moreover, typically no more than one, two, three, four or five residues within a CDR region are altered. In some embodiments, no more than one, two, three, four or five residues are altered in total for all six CDR regions.

In particular embodiments, an antibody of the invention, or antigen-binding fragment thereof, comprises:

an antibody VH region comprising: a VH CDR1 with an amino acid sequence selected from SEQ ID NO:1 and 21; a VH CDR2 with an amino acid sequence selected from SEQ ID NO:2 and 22; and a VH CDR3 with an amino acid sequence selected from SEQ ID NO:3 and 23; and an antibody VL region comprising: a VL CDR1 with an amino acid sequence selected from SEQ ID NO:4 and 24; a VL CDR2 with an amino acid sequence selected from SEQ ID NO:5 and 25; and a VL CDR3 with an amino acid sequence selected from SEQ ID NO:6 and 26; or a variant thereof in which no more than one, two, three, four or five amino acid residues are altered by amino acid substitution, addition, or deletion, within the CDR sequences.

In particular embodiments, an antibody of the invention, or antigen-binding fragment thereof, comprises:

an antibody VH region comprising: a VH CDR1 with an amino acid sequence selected from SEQ ID NO:11 and 31, a VH CDR2 with an amino acid sequence selected from SEQ ID NO:12 and 32, and a VH CDR3 with an amino acid sequence selected from SEQ ID NO:13 and 33; and an antibody VL region comprising: a VL CDR1 with an amino acid sequence selected from SEQ ID NO:14 and 34, a VL CDR2 with an amino acid sequence selected from SEQ ID NO:15 and 35, and a VL CDR3 with an amino acid sequence selected from SEQ ID NO:16 and 36; or a variant thereof in which no more than one, two, three, four or five amino acid residues are altered by amino acid substitution, addition, or deletion, within the CDR sequences.

In another embodiment, the invention provides an anti-LAG-3 monoclonal antibody, or antigen-binding fragment thereof, comprising a heavy chain variable region comprising: (a) a VH CDR1 region comprising SEQ ID NO: 1, or an amino acid sequence having one, two, three, four or five amino acid substitutions, deletions or additions as compared to SEQ ID NO: 1; (b) a VH CDR2 region comprising SEQ ID NO: 2, or an amino acid sequence having one, two, three, four or five amino acid substitutions, deletions or additions as compared to SEQ ID NO: 2; and (c) a VH CDR3 region comprising SEQ ID NO: 3, or an amino acid sequence having one, two, three, four or five amino acid substitutions, deletions or additions as compared to SEQ ID NO: 3; and/or a light chain variable region comprising: (a) a VL CDR1 region comprising SEQ ID NO: 4, or an amino acid sequence having one, two, three, four or five amino acid substitutions, deletions or additions as compared to SEQ ID NO: 4; (b) a VL CDR2 region comprising SEQ ID NO: 5, or an amino acid sequence having one, two, three, four or five amino acid substitutions, deletions or additions as compared to SEQ ID NO: 5; and (c) a VL CDR3 region comprising SEQ ID NO: 6, or an amino acid sequence having one, two, three, four or five amino acid substitutions, deletions or additions as compared to SEQ ID NO: 6.

In a further embodiment, the invention provides an anti-LAG-3 monoclonal antibody, or antigen-binding fragment thereof, comprising a heavy chain variable region comprising: (a) a VH CDR1 region comprising SEQ ID NO: 11, or an amino acid sequence having one, two, three, four or five amino acid substitutions, deletions or additions as compared to SEQ ID NO: 11; (b) a VH CDR2 region comprising SEQ ID NO: 12, or an amino acid sequence having one, two, three, four or five amino acid substitutions, deletions or additions as compared to SEQ ID NO: 12; and (c) a VH CDR3 region comprising SEQ ID NO: 13, or an amino acid sequence having one, two, three, four or five amino acid substitutions, deletions or additions as compared to SEQ ID NO: 13; and/or a light chain variable region comprising: (a) a VL CDR1 region comprising SEQ ID NO: 14, or an amino acid sequence having one, two, three, four or five amino acid substitutions, deletions or additions as compared to SEQ ID NO: 14; (b) a VL CDR2 region comprising SEQ ID NO: 15, or an amino acid sequence having one, two, three, four or five amino acid substitutions, deletions or additions as compared to SEQ ID NO: 15; and (c) a VL CDR3 region comprising SEQ ID NO: 16, or an amino acid sequence having one, two, three, four or five amino acid substitutions, deletions or additions as compared to SEQ ID NO: 16.

In another embodiment, the invention provides an anti-LAG-3 monoclonal antibody, or antigen-binding fragment thereof, comprising a heavy chain variable region comprising: (a) a VH CDR1 region comprising SEQ ID NO: 21, or an amino acid sequence having one, two, three, four or five amino acid substitutions, deletions or additions as compared to SEQ ID NO: 21; (b) a VH CDR2 region comprising SEQ ID NO: 22, or an amino acid sequence having one, two, three, four or five amino acid substitutions, deletions or additions as compared to SEQ ID NO: 22; and (c) a VH CDR3 region comprising SEQ ID NO: 23, or an amino acid sequence having one, two, three, four or five amino acid substitutions, deletions or additions as compared to SEQ ID NO: 23; and/or a light chain variable region comprising: (a) a VL CDR1 region comprising SEQ ID NO: 24, or an amino acid sequence having one, two, three, four or five amino acid substitutions, deletions or additions as compared to SEQ ID NO: 24; (b) a VL CDR2 region comprising SEQ ID NO: 25, or an amino acid sequence having one, two, three, four or five amino acid substitutions, deletions or additions as compared to SEQ ID NO: 25; and (c) a VL CDR3 region comprising SEQ ID NO: 26, or an amino acid sequence having one, two, three, four or five amino acid substitutions, deletions or additions as compared to SEQ ID NO: 26.

In a further embodiment, the invention provides an anti-LAG-3 monoclonal antibody, or antigen-binding fragment thereof, comprising a heavy chain variable region comprising: (a) a VH CDR1 region comprising SEQ ID NO: 31, or an amino acid sequence having one, two, three, four or five amino acid substitutions, deletions or additions as compared to SEQ ID NO: 31; (b) a VH CDR2 region comprising SEQ ID NO: 32, or an amino acid sequence having one, two, three, four or five amino acid substitutions, deletions or additions as compared to SEQ ID NO: 32; and (c) a VH CDR3 region comprising SEQ ID NO: 33, or an amino acid sequence having one, two, three, four or five amino acid substitutions, deletions or additions as compared to SEQ ID NO: 33; and/or a light chain variable region comprising: (a) a VL CDR1 region comprising SEQ ID NO: 34, or an amino acid sequence having one, two, three, four or five amino acid substitutions, deletions or additions as compared to SEQ ID NO: 34; (b) a VL CDR2 region comprising SEQ ID NO: 35, or an amino acid sequence having one, two, three, four or five amino acid substitutions, deletions or additions as compared to SEQ ID NO: 35; and (c) a VL CDR3 region comprising SEQ ID NO: 36, or an amino acid sequence having one, two, three, four or five amino acid substitutions, deletions or additions as compared to SEQ ID NO: 36.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CF11 is modified such that the number of cysteine residues in the hinge region is altered, e.g., increased or decreased. This approach is described further in U.S. Pat. No. 5,677,425. The number of cysteine residues in the hinge region of CF11 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CF12-CF13 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half-life. The IgG class is the most stable and has a serum half-life of 20 days, whereas IgM and IgA persist for only 5-8 days (Brekke & Sandlie, 2003, Nature Reviews Drug Discovery 2, 52-62). Various approaches are possible. For example, one or more of the following mutations can be introduced: T252L, T254S, T256F, as described in U.S. Pat. No. 6,277,375. Alternatively, to increase the biological half-life, the antibody can be altered within the CF11 or CL region to contain a salvage receptor binding epitope taken from two loops of a CF12 domain of an Fc region of an IgG, as described in U.S. Pat. Nos. 5,869,046 and 6,121,022.

An antibody of the invention, or antigen-binding fragment thereof, should lack antibody-dependent cell-mediated cytotoxicity (ADCC) and complement-dependent cytotoxicity (CDC) so that the antibody or fragment can be used to negatively regulate T cell proliferation and/or function without depleting T cells as a result of ADCC or CDC.

In ADCC, the Fc region of an antibody binds to Fc receptors (FcγRs) on the surface of immune effector cells, such as natural killers and macrophages, leading to lysis of the targeted cells. In CDC, the Fc region binds to the C1q component of complement, and the targeted cell is killed by triggering the complement cascade at the cell surface. The ADCC and CDC activity of an antibody depends on its isotype. Both IgM and IgG can mediate complement fixation, whereas only IgG can promote antibody-dependent cellular cytotoxicity (ADCC). IgG isoforms exhibit different levels of CDC and ADCC:

IgG: CDC (hIgG3>hIgG1>hIgG2>hIgG4; mIgG2a>mIgG1);

ADCC (hIgG1hIgG3≥hIgG2≥IgG4; mIgG2a>mIgG1)

Thus, in some embodiments, an antibody of the invention, or antigen-binding fragment thereof, comprises a mouse IgG1, or human IgG4 Fc portion to ensure that the antibody or fragment lacks ADCC and CDC activity.

ADCC and CDC activity of an antibody of the invention, or antigen-binding fragment thereof, may be determined by any suitable method known to the skilled person. Examples of suitable assays for CDC and ADCC activity are described in WO 2008/132601, and below.

An anti-LAG-3 antibody exhibiting CDC activity will consistently kill LAG-3+ cells in the presence of complement, compared with its isotypic control.

For CDC testing, the target cells used to assess an anti-LAG-3 antibody may be a LAG-3-transfected cell line, or primary T cells activated to induce expression of LAG-3. For example, in one possible assay for CDC testing, the target cells are LAG-3+ CHO cells compared to wt CHO cells. Both types of cells (i.e. cells expressing LAG-3, and equivalent cells not expressing LAG-3) are incubated for 1 hour at 37° C. with either the anti-LAG-3 test antibody, or its isotype-matched negative control antibody, and rabbit serum containing active complement. Cell viability is then assessed using 7-Amino-Actinomycin D (7-AAD), a fluorescent dye labelling cells which have lost their membranous integrity, a phenomenon which appears rapidly after death. The percentage of 7-AAD-positive CHO cells (i.e. dead target cells) is determined by flow cytometry analysis. An antibody exhibiting CDC activity will only kill LAG-3+ cells (for example, LAG-3+ CHO cells) in the presence of complement. The anti-LAG-3 Ab may be titered down to determine the efficacy of the antibody to activate CDC at low concentration of antibody.

A CDC assay may also be performed on PBMCs stimulated with the superantigen SEB. The cytotoxicity of test antibody is analysed on both activated (namely CD25+/LAG-3+ cells) and non-activated (namely CD25−/LAG-3− cells) CD4+ helper T and CD8+ cytotoxic T cells. Only activated $CD4^+$ and $CD8^+$ T cells are specifically killed by an antibody exhibiting CDC.

For ADCC testing, PMBCs are stimulated for one day with IL-2 to serve as effector cells and LAG-3-expressing cells (for example, LAG-3+ CHO cells) are labelled with the vital dye CFSE to serve as target cells. In the presence of test anti-LAG-3 antibody, if effector cells (PBMCs) are able to kill a significant percentage of LAG-3-expressing cells (for example, LAG-3+ CHO cells), compared with an isotype-matched negative control antibody, the test antibody exhibits ADCC. This effect should increase with the number of effector cells. The test antibody may be titered down to determine the efficacy of the antibody to induce ADCC at low concentration of antibody.

A test anti-LAG-3 antibody can be considered not to exhibit CDC or ADCC when it kills less than twice as many LAG-3+ cells as an isotype-matched negative control antibody in any of the assays described above.

Killing of target cells is used in classic ADCC bioassays, which use donor peripheral blood mononuclear cells (PBMCs) or the natural killer (NK) cell subpopulation as effector cells. However, these cells can be variable in response, and can result in high background readings. An ADCC Reporter Bioassay available from Promega uses an alternative readout at an earlier point in ADCC pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC is quantified through the luciferase produced as a result of NFAT pathway activation; luciferase activity in the effector cell is quantified with luminescence readout. Using this assay, signal is high, and assay background is low. A good assay response is only obtained when target cells with the correct surface antigen, the correct specific antibody, and effector cells expressing FcγRIIIa are present. If any one of these is missing, there is no response.

When evaluating the ADCC activity of an antibody using an ADCC Reporter Bioassay, the tested antibody can be considered not to exhibit ADCC when the measured increase in bioluminescence is less than twice that of its isotype-matched negative control antibody.

In other embodiments, the Fc region comprises a mutant human IgG4 Fc sequence with an S228P mutation to abolish Fab arm exchange (as shown in FIG. 20(A) for chimeric antibody Chim13E2IgG4 comprising heavy chain sequence 13E2IgG4mut).

In other embodiments, the Fc region comprises a wild-type human Ig kappa (IgK) chain C portion (13E2IgK) (as shown in FIG. 20(B) for chimeric antibody Chim13E2IgG4 comprising light chain sequence 13E2IgK).

The numbering of residues in the Fc region used for the human IgG4 Fc mutant described above is the standard numbering of the Eu index as in Kabat (Kabat, E. A. et al., Sequences of proteins of immunological interest. 5th Edition—US Department of Health and Human Services, NIH publication n° 91-3242, pp 662, 680, 689 (1991)).

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Another modification of the antibodies herein that is contemplated by this disclosure is pegylation. An antibody can be pegylated to, for example, increase the biological (eg., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, eg., EP 0 154 316 and EP 0 401 384.

An antibody of the invention may be a monoclonal antibody, or an antigen-binding fragment thereof.

The terms "antibody" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab')$_2$, and or other antibody fragments that retain specific binding to antigen, and monoclonal antibodies. An antibody can be monovalent or bivalent. An antibody can be an Ig monomer, which is a "Y-shaped" molecule that consists of four polypeptide chains: two heavy chains and two light chains connected by disulfide bonds. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) Trends Biotechnol. 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, a "monoclonal antibody" is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries).

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and by MacCallum et al., J. Mol. Biol. 262:732-745 (1996). A further system is the International ImMunoGeneTics (IMGT) numbering system (Lefranc et al., Nucleic Acids Research 27:209-212 (1999)). The definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth in Table 1 below as a comparison. The CDRs listed in Table 4 in Example 2, and in Table 9 in Example 5, were defined in accordance with Lefranc 1999, and Kabat 1991.

TABLE 1

CDR Definitions

| | Kabat[1] | Chothia[2] | MacCallum[3] | Lefranc[4] |
|---|---|---|---|---|
| $V_H$ CDR-1 | 31-35 | 26-32 | 30-35 | 27-38 |
| $V_H$ CDR-2 | 50-65 | 53-55 | 47-58 | 56-65 |
| $V_H$ CDR-3 | 95-102 | 96-101 | 93-101 | 105-117 |
| $V_L$ CDR-1 | 24-34 | 26-32 | 30-36 | 27-38 |
| $V_L$ CDR-2 | 50-56 | 50-52 | 46-55 | 56-65 |
| $V_L$ CDR-3 | 89-97 | 91-96 | 89-96 | 105-117 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. An antibody of the invention binds specifically to an epitope within a LAG-3 protein, particularly a human LAG-3 protein. "Specific binding" refers to binding with an affinity of at least about $5 \times 10^{-7}$ M or greater, e.g., $10^{-7}$ M, $5 \times 10^{-8}$ M, $10^{-8}$ M, or greater. "Non-specific binding" refers to binding with an affinity of less than about $10^{-7}$ M, e.g., binding with an affinity of $10^{-6}$ M, $10^{-5}$ M, $10^{-4}$ M, etc. As used herein, an antibody that "specifically binds human LAG-3" is intended to refer to an antibody that binds to human LAG-3 protein (and possibly a LAG-3 protein from one or more non-human species) but does not substantially bind to non-LAG-3 proteins. Preferably, the antibody binds to a human LAG-3 protein with "high affinity", namely with a of $K_D$ of $1 \times 10^{-7}$ M or less, more preferably $1 \times 10^{-8}$ M or less, more preferably $5 \times 10^{-9}$ M or less, more preferably $1 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-6}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$" as used herein, is intended to refer to the dissociation constant, which is obtained from the ratio of $K_d$ to $K_a$. (i.e., $K_d/K_a$) and is expressed as a molar concentration (M).

The term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

In some embodiments, an antibody of the invention, or antigen-binding fragment thereof, binds to a human LAG-3 protein with higher affinity (i.e. with a lower dissociation constant) than the antagonistic anti-LAG-3 monoclonal antibody 17B4 (Baixeras, et al., J. Exp. Med., 1992, Vol. 176: 327-337). Example 7 below describes the results of Biacore analysis of binding of 17B4 antibody to human LAG-3Ig protein. The results show that the dissociation constant of 17B4 for human LAG-3Ig was 3.69 nM. Thus, in some embodiments, an antibody of the present invention binds a human LAG-3 protein (or a human LAG-3Ig protein) with a dissociation constant ($K_D$) of less than 3.69 nM, for example as determined by Biacore analysis.

In some embodiments, an antibody of the present invention binds a human LAG-3 protein (or a derivative thereof, such as a human LAG-3Ig protein) with a dissociation constant ($K_D$) of no more than 3.5 nM, no more than 2.5 nM, no more than 2 nM, no more than 1 nM, no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, an anti-LAG-3 antibody of the present disclosure binds a human LAG-3 protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, or no more than 1 pM.

Example 20 below describes the results of Biacore analysis of binding of chimeric 13E2 IgG4 antibody (described below), and of humanized 13E2 IgG4 (described below), to human LAG-3Ig protein. The results show that the dissociation constant of chimeric 13E2 IgG4 antibody for human LAG-3Ig was 21.9 pM, and of humanized 13E2 IgG4 for human LAG-3Ig was 22.8 pM.

In particular embodiments, an antibody of the present invention binds a human LAG-3 protein (or a human LAG-3Ig protein) with a dissociation constant ($K_D$) of no more than 100 pM, no more than 90 pM, no more than 80 pM, no more than 70 pM, no more than 60 pM, no more than 50 pM, no more than 40 pM, no more than 30 pM, or no more than 25 pM, for example as determined by Biacore analysis.

In some embodiments, the affinity of an antibody of the invention, or antigen-binding fragment thereof, may be at least 10%, 20%, 30%, 40%, 50%, 60%, 70%, 80%, or 90% higher than the affinity of 17B4 for a human LAG-3 protein. In some embodiments, an antibody of the invention, or antigen-binding fragment thereof, may be at least 1.5, 2, 2.5, 3, or 3.5 times the affinity of 17B4 for a human LAG-3 protein.

The affinity of an antibody to a human LAG-3 protein can be determined by one skilled in the art, suitably by surface plasmon resonance, for example using a biosensor system, such as a Biacore system (Murphy et al, Using Biacore to measure the binding kinetics of an antibody-antigen interaction; *Curr Protoc Protein Sci*. 2006 September; Chapter 19: Unit 19.14). For example, Biacore analysis can be used to determine the dissociation constant between an antibody of the invention and a human LAG-3 protein.

Binding to human LAG-3 can be assessed using one or more other techniques also well established in the art. For example, an antibody can be tested by a flow cytometry assay in which the antibody is reacted with a cell line that expresses human LAG-3, such as CHO cells that have been transfected to express human LAG-3 on their cell surface. Other suitable cells for use in flow cytometry assays include SEB-stimulated PBMCs, or anti-CD3-stimulated CD4+ activated T cells, which express native LAG-3. Still other suitable binding assays include ELISA assays, for example, using a recombinant LAG-3 protein.

An antibody of the invention is an isolated antibody. An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or non-reducing conditions using Coomassie blue or silver stain. Isolated antibody includes the antibody in situ within recombinant cells since at least one component of the antibody's natural environment will not be present. In some instances, isolated antibody will be prepared by at least one purification step.

In preferred embodiments, an antibody of the invention is a humanized antibody, or antigen-binding fragment thereof, particularly, a humanized monoclonal antibody, or antigen-binding fragment thereof.

A humanized antibody of the invention, or antigen-binding fragment thereof, may comprise a humanized light chain framework region and/or a humanized heavy chain framework region.

The term "humanized antibody" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The variable region amino acid sequence may be identical to the variable region amino acid sequence of the species from which it is derived (for example, mouse sequence), or may be at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to that variable region sequence. For example, the variable region amino acid sequence of a chimeric antibody of the invention may comprise one or more amino acid deletions, substitutions, or additions (for example one, two, three, four, five, six, seven, eight, nine, or ten amino acid deletions, substitutions, or additions) compared with the variable region amino acid sequence of the species from which it is derived.

Similarly, the constant region amino acid sequence may be identical to the constant region amino acid sequence of the species from which it is derived (for example, human sequence), or may be at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to that constant region amino acid sequence. For example, the constant region amino acid sequence of a chimeric antibody of the invention may comprise one or more amino acid deletions, substitutions, or additions (for example one, two, three, four, five, six, seven, eight, nine, or ten amino acid deletions, substitutions, or additions) compared with the constant region amino acid sequence of the species from which it is derived.

For example, as described above, the amino acid sequence of the Fc hinge region of a chimeric antibody may be mutated to decrease the biological half-life of the antibody, or the amino acid sequence of the Fc region may be mutated to increase the biological half-life of the chimeric antibody.

For example, in some embodiments of chimeric antibodies of the invention, the heavy chain variable region sequence comprises, or is derived from a mouse antibody, and the heavy chain constant region sequence comprises, or is derived from IgG4 Fc sequence. In other embodiments, the light chain variable region sequence comprises, or is derived from a mouse antibody, and the light chain constant region sequence comprises, or is derived from human Ig kappa (IgK) chain C sequence.

In other embodiments, the Fc region comprises a mutant human IgG4 Fc sequence with an S228P mutation to abolish Fab arm exchange (as shown in FIG. 20(A) for chimeric antibody Chim13E2IgG4 comprising heavy chain sequence 13E2IgG4mut).

In other embodiments, the Fc region comprises a wild-type human Ig kappa (IgK) chain C portion (13E2IgK) (as shown in FIG. 20(B) for chimeric antibody Chim13E2IgG4 comprising light chain sequence 13E2IgK).

The numbering of residues in the Fc region used for the human IgG4 Fc mutant described above is the standard numbering of the Eu index as in Kabat (Kabat, E. A. et al., Sequences of proteins of immunological interest. 5th Edition—US Department of Health and Human Services, NIH publication n° 91-3242, pp 662, 680, 689 (1991)).

Humanized antibodies may be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIACORE) and/or solid-phase enzyme-linked immunosorbent assay (ELISA) analysis. In many cases, a humanized antibody of the invention does not substantially elicit a HAMA response in a human subject.

Certain amino acids from the human variable region framework residues are selected for substitution based on their possible influence on CDR conformation and/or binding antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, at least 70%, at least 80%, at least 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions may be as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody can be selected for substitution into the humanized antibody. Residues that are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids can interact directly with the antigen (Amit et al., Science, 233:747 (1986)) and selecting these amino acids from the donor can be desirable to keep all the antigen contacts that provide affinity in the original antibody. Alternatively, CDR and framework regions may be as defined by MacCallum et al., or Lefranc et al. (supra—see Table 1).

In some cases, a humanized $V_H$ framework or $V_L$ framework is a consensus humanized framework. A consensus humanized framework can represent the most commonly occurring amino acid residue in a selection of human immunoglobulin $V_L$ or $V_H$ framework sequences.

In some embodiments, an antibody of the invention, or fragment thereof, comprises one or more humanized framework regions (FRs). In some embodiments, a subject anti-LAG-3 antibody comprises a light chain variable region comprising one, two, three, or four light chain FRs that have been humanized. In some embodiments, a subject antibody comprises a light chain variable region comprising, in order from N-terminus to C-terminus: a humanized light chain FR1; a CDR-L1 as set forth herein; a humanized light chain FR2; a CDR-L2 as set forth herein; a humanized light chain FR3; a CDR-L3 as set forth herein; and a humanized light chain FR4. In some embodiments, the respective amino acid sequences of CDR-L1, CDR-L2, and CDR-L3 are: SEQ ID NO:1, SEQ ID NO:2, and SEQ ID NO:3.

For example, a subject antibody can comprise a light chain variable region that comprises, in order from N-terminus to C-terminus: a humanized light chain FR1; a CDR-L1 comprising amino acid sequence SEQ ID NO:1; a humanized light chain FR2; a CDR-L2 comprising amino acid sequence SEQ ID NO:2; a humanized light chain FR3; a CDR-L3 comprising amino acid sequence SEQ ID NO:3; and a humanized light chain FR4.

In other embodiments, the respective amino acid sequences of CDR-L1, CDR-L2, and CDR-L3 are: SEQ ID NO:4, SEQ ID NO:5, and SEQ ID NO:6.

For example, a subject antibody can comprise a light chain variable region that comprises, in order from N-terminus to C-terminus: a humanized light chain FR1; a CDR-L1 comprising amino acid sequence SEQ ID NO:4; a humanized light chain FR2; a CDR-L2 comprising amino acid sequence SEQ ID NO:5; a humanized light chain FR3; a CDR-L3 comprising amino acid sequence SEQ ID NO:6; and a humanized light chain FR4.

In other embodiments, the respective amino acid sequences of CDR-L1, CDR-L2, and CDR-L3 are: SEQ ID NO:24, SEQ ID NO:25, and SEQ ID NO:26.

For example, a subject antibody can comprise a light chain variable region that comprises, in order from N-terminus to C-terminus: a humanized light chain FR1; a CDR-L1 comprising amino acid sequence SEQ ID NO:24; a humanized light chain FR2; a CDR-L2 comprising amino acid sequence SEQ ID NO:25; a humanized light chain FR3; a CDR-L3 comprising amino acid sequence SEQ ID NO:26; and a humanized light chain FR4.

In other embodiments, the respective amino acid sequences of CDR-L1, CDR-L2, and CDR-L3 are selected from: SEQ ID NO: 4 and 24 (CDR-L1); SEQ ID NO: 5 and 25 (CDR-L2); and SEQ ID NO: 6 and 26 (CDR-L3).

For example, a subject antibody can comprise a light chain variable region that comprises, in order from N-terminus to C-terminus: a humanized light chain FR1; a CDR-L1 comprising amino acid sequence selected from SEQ ID NO:4 and 24; a humanized light chain FR2; a CDR-L2 comprising amino acid sequence selected from SEQ ID NO:5 and 25; a humanized light chain FR3; a CDR-L3 comprising amino acid sequence selected from SEQ ID NO:6 and 26; and a humanized light chain FR4.

In other embodiments, the respective amino acid sequences of CDR-L1, CDR-L2, and CDR-L3 are: SEQ ID NO:11, SEQ ID NO:12, and SEQ ID NO:13.

For example, a subject antibody can comprise a light chain variable region that comprises, in order from N-terminus to C-terminus: a humanized light chain FR1; a CDR-L1 comprising amino acid sequence SEQ ID NO:11; a humanized light chain FR2; a CDR-L2 comprising amino acid sequence SEQ ID NO:12; a humanized light chain FR3; a CDR-L3 comprising amino acid sequence SEQ ID NO:13; and a humanized light chain FR4.

In other embodiments, the respective amino acid sequences of CDR-L1, CDR-L2, and CDR-L3 are: SEQ ID NO:14, SEQ ID NO:15, and SEQ ID NO:16.

For example, a subject antibody can comprise a light chain variable region that comprises, in order from N-terminus to C-terminus: a humanized light chain FR1; a CDR-L1 comprising amino acid sequence SEQ ID NO:14; a humanized light chain FR2; a CDR-L2 comprising amino acid sequence SEQ ID NO:15; a humanized light chain FR3; a CDR-L3 comprising amino acid sequence SEQ ID NO:16; and a humanized light chain FR4.

In other embodiments, the respective amino acid sequences of CDR-L1, CDR-L2, and CDR-L3 are: SEQ ID NO:34, SEQ ID NO:35, and SEQ ID NO:36.

For example, a subject antibody can comprise a light chain variable region that comprises, in order from N-terminus to C-terminus: a humanized light chain FR1; a CDR-L1 comprising amino acid sequence SEQ ID NO:34; a humanized light chain FR2; a CDR-L2 comprising amino acid sequence SEQ ID NO:35; a humanized light chain FR3; a CDR-L3 comprising amino acid sequence SEQ ID NO:36; and a humanized light chain FR4.

In other embodiments, the respective amino acid sequences of CDR-L1, CDR-L2, and CDR-L3 are selected from: SEQ ID NO: 14 and 34 (CDR-L1); SEQ ID NO: 15 and 35 (CDR-L2); and SEQ ID NO: 16 and 36 (CDR-L3).

For example, a subject antibody can comprise a light chain variable region that comprises, in order from N-terminus to C-terminus: a humanized light chain FR1; a CDR-L1 comprising amino acid sequence selected from SEQ ID NO:14 and 34; a humanized light chain FR2; a CDR-L2 comprising amino acid sequence selected from SEQ ID NO:15 and 35; a humanized light chain FR3; a CDR-L3 comprising amino acid sequence selected from SEQ ID NO:16 and 36; and a humanized light chain FR4.

In some embodiments, a subject anti-LAG-3 antibody comprises a heavy chain variable region comprising one, two, three, or four heavy chain FRs that have been humanized. In some embodiments, a subject antibody comprises a heavy chain variable region comprising, in order from N-terminus to C-terminus: a humanized heavy chain FR1; a CDR-H1 as set forth herein; a humanized heavy chain FR2; a CDR-H2 as set forth herein; a humanized heavy chain FR3; a CDR-H3 as set forth herein; and a humanized heavy chain FR4.

In some embodiments, the respective amino acid sequences of CDR-H1, CDR-H2, and CDR-H3 are: SEQ ID NO:4, SEQ ID NO:5, and SEQ ID NO:6.

For example, a subject antibody can comprise a heavy chain variable region that comprises, in order from N-terminus to C-terminus: a humanized heavy chain FR1; a CDR-H1 comprising amino acid sequence SEQ ID NO:4; a humanized heavy chain FR2; a CDR-H2 comprising amino acid sequence SEQ ID NO:5; a humanized heavy chain FR3; a CDR-H3 comprising amino acid sequence SEQ ID NO:6; and a humanized heavy chain FR4.

In other embodiments, the respective amino acid sequences of CDR-H1, CDR-H2, and CDR-H3 are: SEQ ID NO:1, SEQ ID NO:2, and SEQ ID NO:3.

For example, a subject antibody can comprise a heavy chain variable region that comprises, in order from N-terminus to C-terminus: a humanized heavy chain FR1; a CDR-H1 comprising amino acid sequence SEQ ID NO:1; a humanized heavy chain FR2; a CDR-H2 comprising amino acid sequence SEQ ID NO:2; a humanized heavy chain FR3; a CDR-H3 comprising amino acid sequence SEQ ID NO:3; and a humanized heavy chain FR4.

In other embodiments, the respective amino acid sequences of CDR-H1, CDR-H2, and CDR-H3 are: SEQ ID NO:21, SEQ ID NO:22, and SEQ ID NO:23.

For example, a subject antibody can comprise a heavy chain variable region that comprises, in order from N-terminus to C-terminus: a humanized heavy chain FR1; a CDR-H1 comprising amino acid sequence SEQ ID NO:21; a humanized heavy chain FR2; a CDR-H2 comprising amino acid sequence SEQ ID NO:22; a humanized heavy chain FR3; a CDR-H3 comprising amino acid sequence SEQ ID NO:23; and a humanized heavy chain FR4.

In other embodiments, the respective amino acid sequences of CDR-H1, CDR-H2, and CDR-H3 are selected from: SEQ ID NO: 1 and 21 (CDR-H1); SEQ ID NO: 2 and 22 (CDR-H2); and SEQ ID NO: 3 and 23 (CDR-H3).

For example, a subject antibody can comprise a heavy chain variable region that comprises, in order from N-terminus to C-terminus: a humanized heavy chain FR1; a CDR-H1 comprising amino acid sequence selected from SEQ ID NO:1 and 21; a humanized heavy chain FR2; a CDR-H2 comprising amino acid sequence selected from SEQ ID NO:2 and 22; a humanized heavy chain FR3; a CDR-H3 comprising amino acid sequence selected from SEQ ID NO:3 and 23; and a humanized heavy chain FR4.

In other embodiments, the respective amino acid sequences of CDR-H1, CDR-H2, and CDR-H3 are: SEQ ID NO:14, SEQ ID NO:15, and SEQ ID NO:16.

For example, a subject antibody can comprise a heavy chain variable region that comprises, in order from N-terminus to C-terminus: a humanized heavy chain FR1; a CDR-H1 comprising amino acid sequence SEQ ID NO:14; a humanized heavy chain FR2; a CDR-H2 comprising amino acid sequence SEQ ID NO:15; a humanized heavy chain FR3; a CDR-H3 comprising amino acid sequence SEQ ID NO:16; and a humanized heavy chain FR4.

In other embodiments, the respective amino acid sequences of CDR-H1, CDR-H2, and CDR-H3 are: SEQ ID NO:11, SEQ ID NO:12, and SEQ ID NO:13.

For example, a subject antibody can comprise a heavy chain variable region that comprises, in order from N-terminus to C-terminus: a humanized heavy chain FR1; a CDR-H1 comprising amino acid sequence SEQ ID NO:11; a humanized heavy chain FR2; a CDR-H2 comprising amino acid sequence SEQ ID NO:12; a humanized heavy chain FR3; a CDR-H3 comprising amino acid sequence SEQ ID NO:13; and a humanized heavy chain FR4.

In other embodiments, the respective amino acid sequences of CDR-H1, CDR-H2, and CDR-H3 are: SEQ ID NO:31, SEQ ID NO:32, and SEQ ID NO:33.

For example, a subject antibody can comprise a heavy chain variable region that comprises, in order from N-terminus to C-terminus: a humanized heavy chain FR1; a CDR-H1 comprising amino acid sequence SEQ ID NO:31; a humanized heavy chain FR2; a CDR-H2 comprising amino acid sequence SEQ ID NO:32; a humanized heavy chain FR3; a CDR-H3 comprising amino acid sequence SEQ ID NO:33; and a humanized heavy chain FR4.

In other embodiments, the respective amino acid sequences of CDR-H1, CDR-H2, and CDR-H3 are selected from: SEQ ID NO: 11 and 31 (CDR-H1); SEQ ID NO: 12 and 32 (CDR-H2); and SEQ ID NO: 13 and 33 (CDR-H3).

For example, a subject antibody can comprise a heavy chain variable region that comprises, in order from N-terminus to C-terminus: a humanized heavy chain FR1; a CDR-H1 comprising amino acid sequence selected from SEQ ID NO:11 and 31; a humanized heavy chain FR2; a CDR-H2 comprising amino acid sequence selected from SEQ ID NO:12 and 32; a humanized heavy chain FR3; a CDR-H3 comprising amino acid sequence selected from SEQ ID NO:13 and 33; and a humanized heavy chain FR4.

Examples of suitable humanized framework sequences include:

```
VH variant 1 (VH₁)
VH₁ FR1:
                                   (SEQ ID NO: 52)
QVTLKESGPALVKPTQTLTLTCTFS;

VH₁ FR2:
                                   (SEQ ID NO: 53)
WIRQPPGKALEWLA;

VH₁ FR3:
                                   (SEQ ID NO: 54)
RLTISKDTSKSQVILNMTNMDPVDTATYYC;
and

VH₁ FR4:
                                   (SEQ ID NO: 55)
WGQGTTVTVSS;

VH variant 2 (VH₂)
VH₂ FR1:
                                   (SEQ ID NO: 56)
QITLKESGPALVKPTQTLTLTCSFS;

VH₂ FR2:
                                   (SEQ ID NO: 57)
WIRQPPGKALEWLA;

VH₂ FR3:
                                   (SEQ ID NO: 58)
RLTISKDTSKNQVVLTMANMDPVDTATYYC;

VH₂ FR4:
                                   (SEQ ID NO: 59)
WGQGTTVTVSS;

VH variant 3 (VH₃)
VH₃ FR1:
                                   (SEQ ID NO: 60)
QITLKETGPTLVKPTQTLTLTCTFS;

VH₃ FR2:
                                   (SEQ ID NO: 61)
WIRQPPGKALEWVT;

VH₃ FR3:
                                   (SEQ ID NO: 62)
RVTIRKDTSKNQVALTMTNMDPLDTGTYYC;

VH₃ FR4:
                                   (SEQ ID NO: 63)
WGQGTLVTVSS;

VH variant 4 (VH₄)
VH₄ FR1:
                                   (SEQ ID NO: 64)
QITLKESGPTLVKPTQTLTLTCTFS;

VH₄ FR2:
                                   (SEQ ID NO: 65)
WIRQPPGKTLEWLT;

VH₄ FR3:
                                   (SEQ ID NO: 66)
RLSITKDTSKNQVVLTMTNMDPLDTGTYYC;

VH₄ FR4:
                                   (SEQ ID NO: 67)
WGQGTLVTVSS;

VL variant 1 (VL₁)
VL₁ FR1:
                                   (SEQ ID NO: 68)
DIVMTQSPDSLAVSLGERATINC;

VL₁ FR2:
                                   (SEQ ID NO: 69)
WYQQKPGQPPKLLIY;

VL₁ FR3:
                                   (SEQ ID NO: 70)
GVPDRFSGSGSGTDFTLTISSLQAEDVAVYYC;
and

VL₁ FR4:
                                   (SEQ ID NO: 71)
FGQGTKLEIK;

VL variant 2 (VL₂)
VL₂ FR1:
                                   (SEQ ID NO: 72)
DIQMTQSPSSLSASVGDRVTITC;

VL₂ FR2:
                                   (SEQ ID NO: 73)
WYQQKPGQAPKLLIF;

VL₂ FR3:
                                   (SEQ ID NO: 74)
GVPSRFSGSGSGTDFTLTLSSLQPEDFATYYC;
and

VL₂ FR4:
                                   (SEQ ID NO: 75)
FGQGTKVEIK;

VL variant 3 (VL₃)
VL₃ FR1:
                                   (SEQ ID NO: 76)
DIVMTQTPSSLSASVGDRVTITC;

VL₃ FR2:
                                   (SEQ ID NO: 77)
WYQQRPGQAPKLLIY;

VL₃ FR3:
                                   (SEQ ID NO: 78)
GVPSRFSGSGSGTDFTLTISSLQPEDFATYYC;
and

VL₃ FR4:
                                   (SEQ ID NO: 79)
FGQGTRLDIK;

VL variant 4 (VL₄)
VL₄ FR1:
                                   (SEQ ID NO: 80)
EIVLTQSPDSLAVSLGERATINC;

VL₄ FR2:
                                   (SEQ ID NO: 81)
WYQQKAGQSPKLLIY;

VL₄ FR3:
                                   (SEQ ID NO: 82)
GVPDRFSGSGSGTDFTLTIDSLQAEDVAVYYC;
and
```

-continued

VL₄ FR4:
(SEQ ID NO: 83)
FGGGTKVEIK

The sequences of the variable regions of humanized VH variants 1-4, and VL variants 1-4, are shown aligned with the corresponding sequence of the original mouse antibody 13E2 in FIG. 22. CDR sequences are highlighted in grey. Changes in the humanized framework sequences of the variants, compared with the original mouse sequence, are shown underlined and in bold. The changed residues in the humanized sequence for each variant are also set out in Tables 26 (heavy chain sequences) and 27 (light chain sequences) in Example 18.

In some embodiments, a humanized antibody of the invention (or antigen-binding fragment thereof) comprises a humanized heavy chain which comprises any of the amino acid substitutions depicted for $VH_1$, $VH_2$, $VH_3$, or $VH_4$ in Table 26 and/or a humanized light chain which comprises any of the amino acid substitutions depicted for $VL_1$, $VL_2$, $VL_3$, or $VL_4$ in Table 27.

An antibody of the invention, or antigen-binding fragment thereof (in particular, a humanized antibody of the invention, or antigen-binding fragment thereof), may comprise any of the above humanized framework sequences (SEQ ID NOs: 52-83), or any combination of the above humanized framework sequences (SEQ ID NOs:52-83).

In some embodiments, the humanized heavy chain framework region may comprise an amino acid sequence of: any of SEQ ID NOs: 52, 53, 54, or 55; any of SEQ ID NOs: 56, 57, 58, or 59; any of SEQ ID NOs: 60, 61, 62, or 63; or any of SEQ ID NOs: 64, 65, 66, or 67.

In particular embodiments, an antibody of the invention, or antigen-binding fragment thereof (in particular, a humanized antibody of the invention, or antigen-binding fragment thereof), may comprise:

a VH framework region 1 (VH FR1) of SEQ ID NO: 52; a VH FR2 of SEQ ID NO: 53; a VH FR3 of SEQ ID NO: 54; and a VH FR4 of SEQ ID NO: 55;

a VH framework region 1 (VH FR1) of SEQ ID NO: 56; a VH FR2 of SEQ ID NO: 57; a VH FR3 of SEQ ID NO: 58; and a VH FR4 of SEQ ID NO: 59;

a VH framework region 1 (VH FR1) of SEQ ID NO: 60; a VH FR2 of SEQ ID NO: 61; a VH FR3 of SEQ ID NO: 62; and a VH FR4 of SEQ ID NO: 63; or a VH framework region 1 (VH FR1) of SEQ ID NO: 64; a VH FR2 of SEQ ID NO: 65; a VH FR3 of SEQ ID NO: 66; and a VH FR4 of SEQ ID NO: 67.

Alternatively, or additionally, in some embodiments, the humanized light chain framework region may comprise an amino acid sequence of: any of SEQ ID NOs: 68, 69, 70, or 71; any of SEQ ID NOs: 72, 73, 74, or 75; any of SEQ ID NOs: 76, 77, 78, or 79; or any of SEQ ID NOs: 80, 81, 82, or 83.

In particular embodiments, an antibody of the invention, or antigen-binding fragment thereof (in particular, a humanized antibody of the invention, or antigen-binding fragment thereof), may comprise:

a VL framework region 1 (VL FR1) of SEQ ID NO: 68; a VL FR2 of SEQ ID NO: 69; a VL FR3 of SEQ ID NO: 70; and a VL FR4 of SEQ ID NO: 71;

a VL framework region 1 (VL FR1) of SEQ ID NO: 72; a VL FR2 of SEQ ID NO: 73; a VL FR3 of SEQ ID NO: 74; and a VL FR4 of SEQ ID NO: 75;

a VL framework region 1 (VL FR1) of SEQ ID NO: 76; a VL FR2 of SEQ ID NO: 77; a VL FR3 of SEQ ID NO: 78; and a VL FR4 of SEQ ID NO: 79; or a VL framework region 1 (VL FR1) of SEQ ID NO: 80; a VL FR2 of SEQ ID NO: 81; a VL FR3 of SEQ ID NO: 82; and a VL FR4 of SEQ ID NO: 83.

In particular embodiments, an antibody of the invention, or antigen-binding fragment thereof (in particular, a humanized antibody of the invention, or antigen-binding fragment thereof), may comprise any of the following combinations of humanized framework sequences:

$VH_1$ FR1-FR4; and $VL_1$ FR1-FR4;
$VH_1$ FR1-FR4; and $VL_2$ FR1-FR4;
$VH_1$ FR1-FR4; and $VL_3$ FR1-FR4;
$VH_1$ FR1-FR4; and $VL_4$ FR1-FR4;
$VH_2$ FR1-FR4; and $VL_1$ FR1-FR4;
$VH_2$ FR1-FR4; and $VL_2$ FR1-FR4;
$VH_2$ FR1-FR4; and $VL_3$ FR1-FR4;
$VH_2$ FR1-FR4; and $VL_4$ FR1-FR4;
$VH_3$ FR1-FR4; and $VL_1$ FR1-FR4;
$VH_3$ FR1-FR4; and $VL_2$ FR1-FR4;
$VH_3$ FR1-FR4; and $VL_3$ FR1-FR4;
$VH_3$ FR1-FR4; and $VL_4$ FR1-FR4;
$VH_4$ FR1-FR4; and $VL_1$ FR1-FR4;
$VH_4$ FR1-FR4; and $VL_2$ FR1-FR4;
$VH_4$ FR1-FR4; and $VL_3$ FR1-FR4;
$VH_4$ FR1-FR4; and $VL_4$ FR1-FR4.

In a particular embodiment, an antibody of the invention, or antigen-binding fragment thereof (in particular, a humanized antibody of the invention, or antigen-binding fragment thereof), comprises the following humanized framework sequences:

VH₄ FR1:
(SEQ ID NO: 64)
QITLKESGPTLVKPTQTLTLTCTFS;

VH₄ FR2:
(SEQ ID NO: 65)
WIRQPPGKTLEWLT;

VH₄ FR3:
(SEQ ID NO: 66)
RLSITKDTSKNQVVLTMTNMDPLDTGTYYC;
and

VH₄ FR4:
(SEQ ID NO: 67)
WGQGTLVTVSS;
and

VL₃ FR1:
(SEQ ID NO: 76)
DIVMTQTPSSLSASVGDRVTITC;

VL₃ FR2:
(SEQ ID NO: 77)
WYQQRPGQAPKLLIY;

VL₃ FR3:
(SEQ ID NO: 78)
GVPSRFSGSGSGTDFTLTISSLQPEDFATYYC;
and

VL₃ FR4:
(SEQ ID NO: 79)
FGQGTRLDIK

In particular embodiments, an isolated antibody of the invention, or antigen-binding fragment thereof, comprises an antibody VH region comprising:

a VH FR1 having an amino acid sequence of SEQ ID NO: 52; a VH CDR1 having an amino acid sequence selected from SEQ ID NO: 1 and 21; a VH FR2 having an amino acid sequence of SEQ ID NO: 53; a VH CDR2 having an amino acid sequence selected from SEQ ID NO: 2 and 22; a VH FR3 having an amino acid sequence of SEQ ID NO: 54; a VH CDR3 having an amino acid sequence selected from SEQ ID NO: 3 and 23; and a VH FR4 having an amino acid sequence of SEQ ID NO: 55;

a VH FR1 having an amino acid sequence of SEQ ID NO: 52; a VH CDR1 having an amino acid sequence of SEQ ID NO: 1; a VH FR2 having an amino acid sequence of SEQ ID NO: 53; a VH CDR2 having an amino acid sequence of SEQ ID NO: 2; a VH FR3 having an amino acid sequence of SEQ ID NO: 54; a VH CDR3 having an amino acid sequence of SEQ ID NO: 3; and a VH FR4 having an amino acid sequence of SEQ ID NO: 55;

a VH FR1 having an amino acid sequence of SEQ ID NO: 52; a VH CDR1 having an amino acid sequence of SEQ ID NO: 21; a VH FR2 having an amino acid sequence of SEQ ID NO: 53; a VH CDR2 having an amino acid sequence of SEQ ID NO: 22; a VH FR3 having an amino acid sequence of SEQ ID NO: 54; a VH CDR3 having an amino acid sequence of SEQ ID NO: 23; and a VH FR4 having an amino acid sequence of SEQ ID NO: 55;

a VH FR1 having an amino acid sequence of SEQ ID NO: 56; a VH CDR1 having an amino acid sequence selected from SEQ ID NO: 1 and 21; a VH FR2 having an amino acid sequence of SEQ ID NO: 57; a VH CDR2 having an amino acid sequence selected from SEQ ID NO: 2 and 22; a VH FR3 having an amino acid sequence of SEQ ID NO: 58; a VH CDR3 having an amino acid sequence selected from SEQ ID NO: 3 and 23; and a VH FR4 having an amino acid sequence of SEQ ID NO: 59;

a VH FR1 having an amino acid sequence of SEQ ID NO: 56; a VH CDR1 having an amino acid sequence of SEQ ID NO: 1; a VH FR2 having an amino acid sequence of SEQ ID NO: 57; a VH CDR2 having an amino acid sequence of SEQ ID NO: 2; a VH FR3 having an amino acid sequence of SEQ ID NO: 58; a VH CDR3 having an amino acid sequence of SEQ ID NO: 3; and a VH FR4 having an amino acid sequence of SEQ ID NO: 59;

a VH FR1 having an amino acid sequence of SEQ ID NO: 56; a VH CDR1 having an amino acid sequence of SEQ ID NO: 21; a VH FR2 having an amino acid sequence of SEQ ID NO: 57; a VH CDR2 having an amino acid sequence of SEQ ID NO: 22; a VH FR3 having an amino acid sequence of SEQ ID NO: 58; a VH CDR3 having an amino acid sequence of SEQ ID NO: 23; and a VH FR4 having an amino acid sequence of SEQ ID NO: 59;

a VH FR1 having an amino acid sequence of SEQ ID NO: 60; a VH CDR1 having an amino acid sequence selected from SEQ ID NO: 1 and 21; a VH FR2 having an amino acid sequence of SEQ ID NO: 61; a VH CDR2 having an amino acid sequence selected from SEQ ID NO: 2 and 22; a VH FR3 having an amino acid sequence of SEQ ID NO: 62; a VH CDR3 having an amino acid sequence selected from SEQ ID NO: 3 and 23; and a VH FR4 having an amino acid sequence of SEQ ID NO: 63;

a VH FR1 having an amino acid sequence of SEQ ID NO: 60; a VH CDR1 having an amino acid sequence of SEQ ID NO: 1; a VH FR2 having an amino acid sequence of SEQ ID NO: 61; a VH CDR2 having an amino acid sequence of SEQ ID NO: 2; a VH FR3 having an amino acid sequence of SEQ ID NO: 62; a VH CDR3 having an amino acid sequence of SEQ ID NO: 3; and a VH FR4 having an amino acid sequence of SEQ ID NO: 63;

a VH FR1 having an amino acid sequence of SEQ ID NO: 60; a VH CDR1 having an amino acid sequence of SEQ ID NO: 21; a VH FR2 having an amino acid sequence of SEQ ID NO: 61; a VH CDR2 having an amino acid sequence of SEQ ID NO: 22; a VH FR3 having an amino acid sequence of SEQ ID NO: 62; a VH CDR3 having an amino acid sequence of SEQ ID NO: 23; and a VH FR4 having an amino acid sequence of SEQ ID NO: 63;

a VH FR1 having an amino acid sequence of SEQ ID NO: 64; a VH CDR1 having an amino acid sequence selected from SEQ ID NO: 1 and 21; a VH FR2 having an amino acid sequence of SEQ ID NO: 65; a VH CDR2 having an amino acid sequence selected from SEQ ID NO: 2 and 22; a VH FR3 having an amino acid sequence of SEQ ID NO: 66; a VH CDR3 having an amino acid sequence selected from SEQ ID NO: 3 and 23; and a VH FR4 having an amino acid sequence of SEQ ID NO: 67;

a VH FR1 having an amino acid sequence of SEQ ID NO: 64; a VH CDR1 having an amino acid sequence of SEQ ID NO: 1; a VH FR2 having an amino acid sequence of SEQ ID NO: 65; a VH CDR2 having an amino acid sequence of SEQ ID NO: 2; a VH FR3 having an amino acid sequence of SEQ ID NO: 66; a VH CDR3 having an amino acid sequence of SEQ ID NO: 3; and a VH FR4 having an amino acid sequence of SEQ ID NO: 67; or a VH FR1 having an amino acid sequence of SEQ ID NO: 64; a VH CDR1 having an amino acid sequence of SEQ ID NO: 21; a VH FR2 having an amino acid sequence of SEQ ID NO: 65; a VH CDR2 having an amino acid sequence of SEQ ID NO: 22; a VH FR3 having an amino acid sequence of SEQ ID NO: 66; a VH CDR3 having an amino acid sequence of SEQ ID NO: 23; and a VH FR4 having an amino acid sequence of SEQ ID NO: 67.

In a particular embodiment, an isolated antibody of the invention, or antigen-binding fragment thereof, comprises an antibody heavy chain comprising amino acid sequence of SEQ ID NO:84.

Alternatively or additionally, in particular embodiments, an isolated antibody of the invention, or antigen-binding fragment thereof, comprises an antibody VL region comprising:

a VL FR1 having an amino acid sequence of SEQ ID NO: 68; a VL CDR1 having an amino acid sequence selected from SEQ ID NO: 4 and 24; a VL FR2 having an amino acid sequence of SEQ ID NO: 69; a VL CDR2 having an amino acid sequence selected from SEQ ID NO: 5 and 25; a VL FR3 having an amino acid sequence of SEQ ID NO: 70; a VL CDR3 having an amino acid sequence selected from SEQ ID NO: 6 and 26; and a VL FR4 having an amino acid sequence of SEQ ID NO: 71;

a VL FR1 having an amino acid sequence of SEQ ID NO: 68; a VL CDR1 having an amino acid sequence of SEQ ID NO: 4; a VL FR2 having an amino acid sequence of SEQ ID NO: 69; a VL CDR2 having an amino acid sequence of SEQ ID NO: 5; a VL FR3 having an amino acid sequence of SEQ ID NO: 70; a VL CDR3 having an amino acid sequence of SEQ ID NO: 6; and a VL FR4 having an amino acid sequence of SEQ ID NO: 71;

a VL FR1 having an amino acid sequence of SEQ ID NO: 68; a VL CDR1 having an amino acid sequence of SEQ ID NO: 24; a VL FR2 having an amino acid sequence of SEQ ID NO: 69; a VL CDR2 having an amino acid sequence of SEQ ID NO: 25; a VL FR3 having an amino acid sequence of SEQ ID NO: 70; a VL CDR3 having an amino acid sequence of SEQ ID NO: 26; and a VL FR4 having an amino acid sequence of SEQ ID NO: 71;

a VL FR1 having an amino acid sequence of SEQ ID NO: 72; a VL CDR1 having an amino acid sequence selected from SEQ ID NO: 4 and 24; a VL FR2 having an amino acid sequence of SEQ ID NO: 73; a VL CDR2 having an amino acid sequence selected from SEQ ID NO: 5 and 25; a VL FR3 having an amino acid sequence of SEQ ID NO: 74; a VL CDR3 having an amino acid sequence selected from SEQ ID NO: 6 and 26; and a VL FR4 having an amino acid sequence of SEQ ID NO: 75;

a VL FR1 having an amino acid sequence of SEQ ID NO: 72; a VL CDR1 having an amino acid sequence of SEQ ID NO: 4; a VL FR2 having an amino acid sequence of SEQ ID NO: 73; a VL CDR2 having an amino acid sequence of SEQ ID NO: 5; a VL FR3 having an amino acid sequence of SEQ ID NO: 74; a VL CDR3 having an amino acid sequence of SEQ ID NO: 6; and a VL FR4 having an amino acid sequence of SEQ ID NO: 75;

a VL FR1 having an amino acid sequence of SEQ ID NO: 72; a VL CDR1 having an amino acid sequence of SEQ ID NO: 24; a VL FR2 having an amino acid sequence of SEQ ID NO: 73; a VL CDR2 having an amino acid sequence of SEQ ID NO: 25; a VL FR3 having an amino acid sequence of SEQ ID NO: 74; a VL CDR3 having an amino acid sequence of SEQ ID NO: 26; and a VL FR4 having an amino acid sequence of SEQ ID NO: 75;

a VL FR1 having an amino acid sequence of SEQ ID NO: 76; a VL CDR1 having an amino acid sequence selected from SEQ ID NO: 4 and 24; a VL FR2 having an amino acid sequence of SEQ ID NO: 77; a VL CDR2 having an amino acid sequence selected from SEQ ID NO: 5 and 25; a VL FR3 having an amino acid sequence of SEQ ID NO: 78; a VL CDR3 having an amino acid sequence selected from SEQ ID NO: 6 and 26; and a VL FR4 having an amino acid sequence of SEQ ID NO: 79;

a VL FR1 having an amino acid sequence of SEQ ID NO: 76; a VL CDR1 having an amino acid sequence of SEQ ID NO: 4; a VL FR2 having an amino acid sequence of SEQ ID NO: 77; a VL CDR2 having an amino acid sequence of SEQ ID NO: 5; a VL FR3 having an amino acid sequence of SEQ ID NO: 78; a VL CDR3 having an amino acid sequence of SEQ ID NO: 6; and a VL FR4 having an amino acid sequence of SEQ ID NO: 79;

a VL FR1 having an amino acid sequence of SEQ ID NO: 76; a VL CDR1 having an amino acid sequence of SEQ ID NO: 24; a VL FR2 having an amino acid sequence of SEQ ID NO: 77; a VL CDR2 having an amino acid sequence of SEQ ID NO: 25; a VL FR3 having an amino acid sequence of SEQ ID NO: 78; a VL CDR3 having an amino acid sequence of SEQ ID NO: 26; and a VL FR4 having an amino acid sequence of SEQ ID NO: 79;

a VL FR1 having an amino acid sequence of SEQ ID NO: 80; a VL CDR1 having an amino acid sequence selected from SEQ ID NO: 4 and 24; a VL FR2 having an amino acid sequence of SEQ ID NO: 81; a VL CDR2 having an amino acid sequence selected from SEQ ID NO: 5 and 25; a VL FR3 having an amino acid sequence of SEQ ID NO: 82; a VL CDR3 having an amino acid sequence selected from SEQ ID NO: 6 and 26; and a VL FR4 having an amino acid sequence of SEQ ID NO: 83;

a VL FR1 having an amino acid sequence of SEQ ID NO: 80; a VL CDR1 having an amino acid sequence of SEQ ID NO: 4; a VL FR2 having an amino acid sequence of SEQ ID NO: 81; a VL CDR2 having an amino acid sequence of SEQ ID NO: 5; a VL FR3 having an amino acid sequence of SEQ ID NO: 82; a VL CDR3 having an amino acid sequence of SEQ ID NO: 6; and a VL FR4 having an amino acid sequence of SEQ ID NO: 83; or a VL FR1 having an amino acid sequence of SEQ ID NO: 80; a VL CDR1 having an amino acid sequence of SEQ ID NO: 24; a VL FR2 having an amino acid sequence of SEQ ID NO: 81; a VL CDR2 having an amino acid sequence of SEQ ID NO: 25; a VL FR3 having an amino acid sequence of SEQ ID NO: 82; a VL CDR3 having an amino acid sequence of SEQ ID NO: 26; and a VL FR4 having an amino acid sequence of SEQ ID NO: 83.

In a particular embodiment, an isolated antibody of the invention, or antigen-binding fragment thereof, comprises an antibody light chain comprising amino acid sequence of SEQ ID NO:85.

In a further particular embodiment, an isolated antibody of the invention, or antigen-binding fragment thereof, comprises an antibody heavy chain comprising amino acid sequence of SEQ ID NO:84, and an antibody light chain comprising amino acid sequence of SEQ ID NO:85.

In other embodiments, an isolated antibody of the invention, or antigen-binding fragment thereof, comprises an antibody VH region comprising:

a VH FR1 having an amino acid sequence of SEQ ID NO: 52; a VH CDR1 having an amino acid sequence selected from SEQ ID NO: 11 and 31; a VH FR2 having an amino acid sequence of SEQ ID NO: 53; a VH CDR2 having an amino acid sequence selected from SEQ ID NO: 12 and 32; a VH FR3 having an amino acid sequence of SEQ ID NO: 54; a VH CDR3 having an amino acid sequence selected from SEQ ID NO: 13 and 33; and a VH FR4 having an amino acid sequence of SEQ ID NO: 55;

a VH FR1 having an amino acid sequence of SEQ ID NO: 52; a VH CDR1 having an amino acid sequence of SEQ ID NO: 11; a VH FR2 having an amino acid sequence of SEQ ID NO: 53; a VH CDR2 having an amino acid sequence of SEQ ID NO: 12; a VH FR3 having an amino acid sequence of SEQ ID NO: 54; a VH CDR3 having an amino acid sequence of SEQ ID NO: 13; and a VH FR4 having an amino acid sequence of SEQ ID NO: 55;

a VH FR1 having an amino acid sequence of SEQ ID NO: 52; a VH CDR1 having an amino acid sequence of SEQ ID NO: 31; a VH FR2 having an amino acid sequence of SEQ ID NO: 53; a VH CDR2 having an amino acid sequence of SEQ ID NO: 32; a VH FR3 having an amino acid sequence of SEQ ID NO: 54; a VH CDR3 having an amino acid sequence of SEQ ID NO: 33; and a VH FR4 having an amino acid sequence of SEQ ID NO: 55;

a VH FR1 having an amino acid sequence of SEQ ID NO: 56; a VH CDR1 having an amino acid sequence selected from SEQ ID NO: 11 and 31; a VH FR2 having an amino acid sequence of SEQ ID NO: 57; a VH CDR2 having an amino acid sequence selected from SEQ ID NO: 12 and 32; a VH FR3 having an amino acid sequence of SEQ ID NO: 58; a VH CDR3 having an amino acid sequence selected from SEQ ID NO: 13 and 33; and a VH FR4 having an amino acid sequence of SEQ ID NO: 59;

a VH FR1 having an amino acid sequence of SEQ ID NO: 56; a VH CDR1 having an amino acid sequence of SEQ ID NO: 11; a VH FR2 having an amino acid sequence of SEQ ID NO: 57; a VH CDR2 having an amino acid sequence of SEQ ID NO: 12; a VH FR3 having an amino acid sequence of SEQ ID NO: 58; a VH CDR3 having an amino acid sequence of SEQ ID NO: 13; and a VH FR4 having an amino acid sequence of SEQ ID NO: 59;

a VH FR1 having an amino acid sequence of SEQ ID NO: 56; a VH CDR1 having an amino acid sequence of SEQ ID NO: 31; a VH FR2 having an amino acid sequence of SEQ ID NO: 57; a VH CDR2 having an amino acid sequence of SEQ ID NO: 32; a VH FR3 having an amino acid sequence of SEQ ID NO: 58; a VH CDR3 having an amino acid sequence of SEQ ID NO: 33; and a VH FR4 having an amino acid sequence of SEQ ID NO: 59;

a VH FR1 having an amino acid sequence of SEQ ID NO: 60; a VH CDR1 having an amino acid sequence selected from SEQ ID NO: 11 and 31; a VH FR2 having an amino acid sequence of SEQ ID NO: 61; a VH CDR2 having an amino acid sequence selected from SEQ ID NO: 12 and 32; a VH FR3 having an amino acid sequence of SEQ ID NO: 62; a VH CDR3 having an amino acid sequence selected from SEQ ID NO: 13 and 33; and a VH FR4 having an amino acid sequence of SEQ ID NO: 63;

a VH FR1 having an amino acid sequence of SEQ ID NO: 60; a VH CDR1 having an amino acid sequence of SEQ ID NO: 11; a VH FR2 having an amino acid sequence of SEQ ID NO: 61; a VH CDR2 having an amino acid sequence of SEQ ID NO: 12; a VH FR3 having an amino acid sequence of SEQ ID NO: 62; a VH CDR3 having an amino acid sequence of SEQ ID NO: 13; and a VH FR4 having an amino acid sequence of SEQ ID NO: 63;

a VH FR1 having an amino acid sequence of SEQ ID NO: 60; a VH CDR1 having an amino acid sequence of SEQ ID NO: 31; a VH FR2 having an amino acid sequence of SEQ ID NO: 61; a VH CDR2 having an amino acid sequence of SEQ ID NO: 32; a VH FR3 having an amino acid sequence of SEQ ID NO: 62; a VH CDR3 having an amino acid sequence of SEQ ID NO: 33; and a VH FR4 having an amino acid sequence of SEQ ID NO: 63;

a VH FR1 having an amino acid sequence of SEQ ID NO: 64; a VH CDR1 having an amino acid sequence selected from SEQ ID NO: 11 and 31; a VH FR2 having an amino acid sequence of SEQ ID NO: 65; a VH CDR2 having an amino acid sequence selected from SEQ ID NO: 12 and 32; a VH FR3 having an amino acid sequence of SEQ ID NO: 66; a VH CDR3 having an amino acid sequence selected from SEQ ID NO: 13 and 33; and a VH FR4 having an amino acid sequence of SEQ ID NO: 67;

a VH FR1 having an amino acid sequence of SEQ ID NO: 64; a VH CDR1 having an amino acid sequence of SEQ ID NO: 11; a VH FR2 having an amino acid sequence of SEQ ID NO: 65; a VH CDR2 having an amino acid sequence of SEQ ID NO: 12; a VH FR3 having an amino acid sequence of SEQ ID NO: 66; a VH CDR3 having an amino acid sequence of SEQ ID NO: 13; and a VH FR4 having an amino acid sequence of SEQ ID NO: 67; or a VH FR1 having an amino acid sequence of SEQ ID NO: 64; a VH CDR1 having an amino acid sequence of SEQ ID NO: 31; a VH FR2 having an amino acid sequence of SEQ ID NO: 65; a VH CDR2 having an amino acid sequence of SEQ ID NO: 32; a VH FR3 having an amino acid sequence of SEQ ID NO: 66; a VH CDR3 having an amino acid sequence of SEQ ID NO: 33; and a VH FR4 having an amino acid sequence of SEQ ID NO: 67.

Alternatively or additionally, in particular embodiments, an isolated antibody of the invention, or antigen-binding fragment thereof, comprises an antibody VL region comprising:

a VL FR1 having an amino acid sequence of SEQ ID NO: 68; a VL CDR1 having an amino acid sequence selected from SEQ ID NO: 14 and 34; a VL FR2 having an amino acid sequence of SEQ ID NO: 69; a VL CDR2 having an amino acid sequence selected from SEQ ID NO: 15 and 35; a VL FR3 having an amino acid sequence of SEQ ID NO: 70; a VL CDR3 having an amino acid sequence selected from SEQ ID NO: 16 and 36; and a VL FR4 having an amino acid sequence of SEQ ID NO: 71;

a VL FR1 having an amino acid sequence of SEQ ID NO: 68; a VL CDR1 having an amino acid sequence of SEQ ID NO: 14; a VL FR2 having an amino acid sequence of SEQ ID NO: 69; a VL CDR2 having an amino acid sequence of SEQ ID NO: 15; a VL FR3 having an amino acid sequence of SEQ ID NO: 70; a VL CDR3 having an amino acid sequence of SEQ ID NO: 16; and a VL FR4 having an amino acid sequence of SEQ ID NO: 71;

a VL FR1 having an amino acid sequence of SEQ ID NO: 68; a VL CDR1 having an amino acid sequence of SEQ ID NO: 34; a VL FR2 having an amino acid sequence of SEQ ID NO: 69; a VL CDR2 having an amino acid sequence of SEQ ID NO: 35; a VL FR3 having an amino acid sequence of SEQ ID NO: 70; a VL CDR3 having an amino acid sequence of SEQ ID NO: 36; and a VL FR4 having an amino acid sequence of SEQ ID NO: 71;

a VL FR1 having an amino acid sequence of SEQ ID NO: 72; a VL CDR1 having an amino acid sequence selected from SEQ ID NO: 14 and 34; a VL FR2 having an amino acid sequence of SEQ ID NO: 73; a VL CDR2 having an amino acid sequence selected from SEQ ID NO: 15 and 35; a VL FR3 having an amino acid sequence of SEQ ID NO: 74; a VL CDR3 having an amino acid sequence selected from SEQ ID NO: 16 and 36; and a VL FR4 having an amino acid sequence of SEQ ID NO: 75;

a VL FR1 having an amino acid sequence of SEQ ID NO: 72; a VL CDR1 having an amino acid sequence of SEQ ID NO: 14; a VL FR2 having an amino acid sequence of SEQ ID NO: 73; a VL CDR2 having an amino acid sequence of SEQ ID NO: 15; a VL FR3 having an amino acid sequence of SEQ ID NO: 74; a VL CDR3 having an amino acid sequence of SEQ ID NO: 16; and a VL FR4 having an amino acid sequence of SEQ ID NO: 75;

a VL FR1 having an amino acid sequence of SEQ ID NO: 72; a VL CDR1 having an amino acid sequence of SEQ ID NO: 34; a VL FR2 having an amino acid sequence of SEQ ID NO: 73; a VL CDR2 having an amino acid sequence of SEQ ID NO: 35; a VL FR3 having an amino acid sequence of SEQ ID NO: 74; a VL CDR3 having an amino acid sequence of SEQ ID NO: 36; and a VL FR4 having an amino acid sequence of SEQ ID NO: 75;

a VL FR1 having an amino acid sequence of SEQ ID NO: 76; a VL CDR1 having an amino acid sequence selected from SEQ ID NO: 14 and 34; a VL FR2 having an amino acid sequence of SEQ ID NO: 77; a VL CDR2 having an amino acid sequence selected from SEQ ID NO: 15 and 35; a VL FR3 having an amino acid sequence of SEQ ID NO: 78; a VL CDR3 having an amino acid sequence selected from SEQ ID NO: 16 and 36; and a VL FR4 having an amino acid sequence of SEQ ID NO: 79;

a VL FR1 having an amino acid sequence of SEQ ID NO: 76; a VL CDR1 having an amino acid sequence of SEQ ID NO: 14; a VL FR2 having an amino acid sequence of SEQ ID NO: 77; a VL CDR2 having an amino acid sequence of SEQ ID NO: 15; a VL FR3 having an amino acid sequence of SEQ ID NO: 78; a VL CDR3 having an amino acid sequence of SEQ ID NO: 16; and a VL FR4 having an amino acid sequence of SEQ ID NO: 79;

a VL FR1 having an amino acid sequence of SEQ ID NO: 76; a VL CDR1 having an amino acid sequence of SEQ ID NO: 34; a VL FR2 having an amino acid sequence of SEQ ID NO: 77; a VL CDR2 having an amino acid sequence of SEQ ID NO: 35; a VL FR3 having an amino acid sequence of SEQ ID NO: 78; a VL CDR3 having an amino acid sequence of SEQ ID NO: 36; and a VL FR4 having an amino acid sequence of SEQ ID NO: 79;

a VL FR1 having an amino acid sequence of SEQ ID NO: 80; a VL CDR1 having an amino acid sequence selected from SEQ ID NO: 14 and 34; a VL FR2 having an amino acid sequence of SEQ ID NO: 81; a VL CDR2 having an amino acid sequence selected from SEQ ID NO: 15 and 35;

a VL FR3 having an amino acid sequence of SEQ ID NO: 82; a VL CDR3 having an amino acid sequence selected from SEQ ID NO: 16 and 36; and a VL FR4 having an amino acid sequence of SEQ ID NO: 83;

a VL FR1 having an amino acid sequence of SEQ ID NO: 80; a VL CDR1 having an amino acid sequence of SEQ ID NO: 14; a VL FR2 having an amino acid sequence of SEQ ID NO: 81; a VL CDR2 having an amino acid sequence of SEQ ID NO: 15; a VL FR3 having an amino acid sequence of SEQ ID NO: 82; a VL CDR3 having an amino acid sequence of SEQ ID NO: 16; and a VL FR4 having an amino acid sequence of SEQ ID NO: 83; or a VL FR1 having an amino acid sequence of SEQ ID NO: 80; a VL CDR1 having an amino acid sequence of SEQ ID NO: 34; a VL FR2 having an amino acid sequence of SEQ ID NO: 81; a VL CDR2 having an amino acid sequence of SEQ ID NO: 35; a VL FR3 having an amino acid sequence of SEQ ID NO: 82; a VL CDR3 having an amino acid sequence of SEQ ID NO: 36; and a VL FR4 having an amino acid sequence of SEQ ID NO: 83. In some cases, a subject antibody comprises a constant region of an immunoglobulin (e.g., an Fc region). In some embodiments, the Fc region, if present, is a human Fc region. If constant regions are present, the antibody can contain both light chain and heavy chain constant regions. Suitable heavy chain constant regions include CH1, hinge, CH2, CH3, and CH4 regions.

An example of a suitable heavy chain Fc region is a human isotype IgG4 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab', F(ab')$_2$, and Fv, or as single chain antibodies in which heavy and light chain variable domains are linked through a spacer.

In some cases, the heavy chain region is of the isotype IgG4. In some of these embodiments, the hinge region comprises an S241P substitution. See, e.g., Angal et al. (1993) *Mol. Immunol.* 30:105. In some of these embodiments, the hinge region comprises an L236E (or L235E, using EU numbering; Kabat et al. (1991) *Sequences of Proteins of Immunological Interest, 5$^{th}$* Ed. U.S. Dept. Health and Human Services, Bethesda, Md., NIH Publication No. 91-3242) substitution. See, e.g., Reddy et al. (2000) *J. Immunol.* 164:1925; and Klechevsky et al. (2010) *Blood* 116:1685. In some of these embodiments, the hinge region comprises an S241P substitution and an L236E substitution.

The constant region amino acid sequence may be identical to the constant region amino acid sequence of the species from which it is derived (for example, human sequence), or may be at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to that constant region amino acid sequence. For example, the constant region amino acid sequence of an antibody of the invention may comprise one or more amino acid deletions, substitutions, or additions (for example one, two, three, four, five, six, seven, eight, nine, or ten amino acid deletions, substitutions, or additions) compared with the constant region amino acid sequence of the species from which it is derived.

For example, as described above, the amino acid sequence of the Fc hinge region of an antibody of the invention may be mutated to decrease the biological half-life of the antibody, or the amino acid sequence of the Fc region may be mutated to increase the biological half-life of the antibody.

It should be ensured that an antibody of the invention, or antigen-binding fragment thereof, lacks antibody-dependent cell-mediated cytotoxicity (ADCC) and complement-dependent cytotoxicity (CDC) so that the antibody, or fragment, can be used to negatively regulate T cell proliferation and/or function without depleting T cells as a result of ADCC or CDC.

For example, in some embodiments, the Fc region comprises a wild-type human IgG4 Fc sequence.

In other embodiments, the Fc region comprises a mutant human IgG4 Fc sequence with an S228P mutation to abolish Fab arm exchange (as shown in FIG. 20(A) for chimeric antibody Chim13E2IgG4 comprising heavy chain sequence 13E2IgG4mut).

In other embodiments, the Fc region comprises a wild-type human Ig kappa (IgK) chain C portion (13E2IgK) (as shown in FIG. 20(B) for chimeric antibody Chim13E2IgG4 comprising light chain sequence 13E2IgK).

The numbering of residues in the Fc region used for the human IgG4 Fc mutant described above is the standard numbering of the EU index as in Kabat (Kabat, E. A. et al., Sequences of proteins of immunological interest. 5th Edition—US Department of Health and Human Services, NIH publication n° 91-3242, pp 662, 680, 689 (1991)).

A subject antibody can comprise a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the antibody, where the antibody comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrrolysine or selenocysteine. Other terms that can be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); poly-butylmethacrylate; poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly (ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50,000 Da, e.g., from 5,000 Da to 40,000 Da, or from 25,000 to 40,000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a non-peptide synthetic polymer. In some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and can be found in, e.g., U.S. Pat. No. 5,849,860. PEG suitable for conjugation to a protein is generally soluble in water at room temperature, and has the general formula R(O—$CH_2$—$CH_2$)$_n$O—R, where R is hydrogen or a protective group such as an alkyl or an alkanol group, and where n is an integer from 1 to 1,000. Where R is a protective group, it generally has from 1 to 8 carbons.

In some embodiments, the PEG conjugated to the subject antibody is linear. In some embodiments, the PEG conjugated to the subject antibody is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., a subject antibody can comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine can also be used.

Addition of glycosylation sites to an antibody is conveniently accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers include bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable labels include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals.

A subject antibody can be labeled using standard techniques. For example, a subject antibody can be iodinated using chloramine T or 1,3,4,6-tetrachloro-3α,6α-diphenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques.

For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

In some embodiments, a subject antibody is conjugated to a therapeutic. Any of the subject antibodies disclosed herein can be used to form an antibody-agent conjugate. The agent can be attached to the N terminus of the light chain, the C terminus of the light chain, the N terminus of the heavy chain, or the C terminus of the heavy chain. In some embodiments, the agent is attached to the hinge of the antibody or to one or more other sites on the antibody. For a single chain antibody, the agent can be attached to the N or C terminus of the single chain antibody. The agent can be conjugated to the antibody directly or via a linker using techniques known to those skilled in the art. The linker can be cleavable or non-cleavable. Examples of such therapeutic agents (e.g., for use in therapy) are known to those skilled in the art.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., YPYDVPDYA; SEQ ID NO:41), FLAG (e.g., DYKDDDDK; SEQ ID NO:42), c-myc (e.g., EQKLISEEDL; SEQ ID NO:43), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion can also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:44), HisX6 (HHHHHH) (SEQ ID NO:45), c-myc (EQKLISEEDL) (SEQ ID NO:46), Flag (DYKDDDDK) (SEQ ID NO:42), StrepTag (WSHPQFEK) (SEQ ID NO:47), hemagglutinin, e.g., HA Tag (YPYDVPDYA; SEQ ID NO:41), glutathinone-S-transferase (GST), thioredoxin, cellulose binding domain, RYIRS (SEQ ID NO:48), Phe-His-His-Thr (SEQ ID NO:49), chitin binding domain, S-peptide, T7 peptide, SH2 domain, C-end RNA tag, WEAAAREACCRECCARA (SEQ ID NO:50), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

For nucleotide and amino acid sequences, the term "identical" or "identity" indicates the degree of identity between two nucleic acid or two amino acid sequences when optimally aligned and compared with appropriate insertions or deletions.

The percent identity between two sequences is a function of the number of identical positions shared by the sequences (i.e., % identity=number of identical positions/total number of positions multiplied by 100), taking into account the number of gaps, and the length of each gap, which need to be introduced for optimal alignment of the two sequences. The comparison of sequences and determination of percent identity between two sequences can be accomplished using a mathematical algorithm, as described below.

Percent identity between a query nucleic acid sequence and a subject nucleic acid sequence is the "Identities" value, expressed as a percentage, which is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

Percent identity between a query amino acid sequence and a subject amino acid sequence is the "Identities" value, expressed as a percentage, which is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

Methods of Producing a Subject Antibody

A subject antibody can be produced by any known method, e.g., conventional synthetic methods for protein synthesis; recombinant DNA methods; etc. In some embodiments, the subject antibody is produced by a method selected from the group consisting of recombinant production and chemical synthesis.

Where a subject antibody is a single chain polypeptide, it can be synthesized using standard chemical peptide synthesis techniques. Where a polypeptide is chemically synthesized, the synthesis can proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid can be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, repressor elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce an anti-LAG-3 antibody of the present disclosure (e.g., polynucleotides encoding a subject anti-LAG-3 antibody). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992). In other methods, antibodies of the invention can be produced in mice (see, for example, Laffleur et al "Production of human or humanized antibodies in mice", Methods Mol Biol. 2012; 901:149-59).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Nucleic Acid Molecules, Expression Vectors, and Host Cells

The present invention also provides nucleic acid molecules comprising nucleotide sequences encoding an anti-LAG-3 antibody of the invention, or antigen-binding fragment thereof.

In some embodiments, a nucleic acid molecule of the present disclosure encodes a subject anti-LAG-3 antibody comprising a heavy chain variable region that is at least 85%, 86%, 87%, 88%, 89%, 90%, 91%, 92%, 93%, 94%, 95%, 96%, 97%, 98% or 99% amino acid sequence identical to the amino acid sequence set forth in SEQ ID NO:7 or SEQ ID NO:17. In some embodiments, a nucleic acid molecule of the present disclosure encodes a subject anti-LAG-3 antibody comprising a heavy chain variable region comprising the amino acid sequence set forth in SEQ ID NO:7 or SEQ ID NO:17.

In some embodiments, a nucleic acid molecule of the present disclosure encodes a subject anti-LAG-3 antibody comprising a light chain variable region that is at least 85%, 86%, 87%, 88%, 89%, 90%, 91%, 92%, 93%, 94%, 95%, 96%, 97%, 98% or 99% amino acid sequence identical to the amino acid sequence set forth in SEQ ID NO:8 or SEQ ID NO:18. In some embodiments, a nucleic acid molecule of the present disclosure encodes a subject anti-LAG-3 antibody comprising a light chain variable region comprising the amino acid sequence set forth in SEQ ID NO:8 or SEQ ID NO:18.

In some embodiments, a nucleic acid molecule of the present disclosure encodes a subject anti-LAG-3 antibody comprising a heavy chain variable region comprising a CDR-H1, a CDR-H2, and a CDR-H3 of SEQ ID NO:1, SEQ ID NO:2, and SEQ ID NO:3, respectively.

In some embodiments, a nucleic acid molecule of the present disclosure encodes a subject anti-LAG-3 antibody comprising a light chain variable region comprising a CDR-L1, a CDR-L2, and a CDR-L3 of SEQ ID NO:4, SEQ ID NO:5, and SEQ ID NO:6, respectively.

In some embodiments, a nucleic acid molecule of the present disclosure encodes a subject anti-LAG-3 antibody comprising a heavy chain variable region comprising a CDR-H1, a CDR-H2, and a CDR-H3 of SEQ ID NO:11, SEQ ID NO:12, and SEQ ID NO:13, respectively.

In some embodiments, a nucleic acid molecule of the present disclosure encodes a subject anti-LAG-3 antibody comprising a light chain variable region comprising a CDR-L1, a CDR-L2, and a CDR-L3 of SEQ ID NO:14, SEQ ID NO:15, and SEQ ID NO:16, respectively.

In some embodiments, a nucleic acid molecule of the present disclosure encodes a subject anti-LAG-3 antibody comprising a heavy chain variable region comprising a CDR-H1, a CDR-H2, and a CDR-H3 of SEQ ID NO:21, SEQ ID NO:22, and SEQ ID NO:23, respectively.

In some embodiments, a nucleic acid molecule of the present disclosure encodes a subject anti-LAG-3 antibody comprising a light chain variable region comprising a CDR-L1, a CDR-L2, and a CDR-L3 of SEQ ID NO:24, SEQ ID NO:25, and SEQ ID NO:26, respectively.

In some embodiments, a nucleic acid molecule of the present disclosure encodes a subject anti-LAG-3 antibody comprising a heavy chain variable region comprising a CDR-H1, a CDR-H2, and a CDR-H3 of SEQ ID NO:31, SEQ ID NO:32, and SEQ ID NO:33, respectively.

In some embodiments, a nucleic acid molecule of the present disclosure encodes a subject anti-LAG-3 antibody comprising a light chain variable region comprising a CDR-L1, a CDR-L2, and a CDR-L3 of SEQ ID NO:34, SEQ ID NO:35, and SEQ ID NO:36, respectively.

In some embodiments, a nucleic acid molecule of the present disclosure encodes a subject anti-LAG-3 antibody comprising a light chain variable region and a heavy chain variable region.

A nucleic acid molecule encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. Suitable promoters for use in prokaryotic host cells include, but are not limited to, a bacteriophage T7 RNA polymerase promoter; a T3 promoter; a T5 promoter; a lambda P promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; a gpt promoter; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., *PNAS,* 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding the operator), a tryptophan promoter operator (when complexed with tryptophan, TrpR repressor protein has a conformation that binds the operator; in the absence of tryptophan, the TrpR repressor protein has a conformation that does not bind the operator), and a tac promoter operator (see, for example, deBoer et al. (1983) Proc. Natl. Acad. Sci. U.S.A. 80:21-25).

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*).

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Selection of the appropriate vector and promoter is well within the level of ordinary skill in the art.

A nucleic acid molecule encoding a subject antibody can be present in an expression vector and/or a cloning vector. The present disclosure provides a recombinant vector, which comprises a nucleic acid molecule encoding a subject antibody in a cloning vector. The present disclosure also provides a recombinant molecule, which comprises a nucleic acid molecule encoding a subject antibody operatively linked to appropriate regulatory sequence(s) in an expression vector to ensure expression of the encoded antibody. Where a subject antibody comprises two separate polypeptides, nucleic acid molecules encoding the two polypeptides can be cloned in the same or separate vectors to form one or more recombinant molecules. A recombinant molecule can include a selectable marker, an origin of replication, and other features that provide for replication and/or maintenance of the recombinant molecule.

Large numbers of suitable vectors and promoters are known to those of skill in the art; many are commercially available for generating a subject recombinant molecule. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host can be present. Suitable expression vectors include, but are not limited to, viral vectors. Examples of viral vectors include, but are not limited to, viral vectors based on: vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus (see, e.g., Miyoshi et al., PNAS 94:10319 23, 1997; Takahashi et al., J Virol 73:7812 7816, 1999), myeloproliferative sarcoma virus, and mammary tumor virus); and the like.

As noted above, a subject nucleic acid molecule comprises a nucleotide sequence encoding an anti-LAG-3 antibody of the present disclosure. In some embodiments, a subject nucleic acid molecule comprises a nucleotide sequence encoding heavy- and light-chain CDRs of a subject 13E2 or 34F4 antibody. In some embodiments, a subject nucleic acid molecule comprises a nucleotide sequence encoding heavy- and light-chain CDRs of a subject antibody, where the CDR-encoding sequences are interspersed with FR-encoding nucleotide sequences. In some embodiments, the FR-encoding nucleotide sequences are human FR-encoding nucleotide sequences.

Host Cells

The present disclosure provides isolated genetically modified host cells (e.g., in vitro cells) that are genetically modified with a subject nucleic acid molecule. In some embodiments, a subject isolated genetically modified host cell can produce a subject antibody. Such a cell is referred to as a recombinant cell. A recombinant cell comprises a recombinant molecule encoding a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61), CHO-M cells, CHO-DG44 cells (ATCC No. PTA-3356), and the like. In some embodiments, the host cell is a COS cell. In some embodiments, the host cell is a 293 cell. In some embodiments, the host cell is a CHO cell.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii,* and the like. In some embodiments, the host cell is a *Saccharomyces*. In some embodiments, the host cell is a *Pichia*.

Suitable prokaryotic cells include, but are not limited to, any of a variety of laboratory strains of *Escherichia coli, Bacillus* (e.g., *B. subtilis*), *Lactobacillus* sp., and the like. See, e.g., Carrier et al. (1992) *J. Immunol.* 148:1176-1181; U.S. Pat. No. 6,447,784; and Sizemore et al. (1995) *Science* 270:299-302. Typically, the laboratory strain is one that is non-pathogenic. In some embodiments, the host cell is *Escherichia coli*. In some embodiments, the host cell is *Bacillus subtilis*.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a phosphate buffer, a citrate buffer, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-am inopropanesulfonic acid (TAPS), etc.; a solubilizing agent; a detergent, e.g., a non-ionic detergent such as Tween-20, etc.; a protease inhibitor; glycerol; and the like.

Pharmaceutical Compositions

The present disclosure provides compositions, including pharmaceutical compositions comprising a subject antibody. In general, a pharmaceutical composition, also referred to herein as a formulation, comprises an effective amount of a subject antibody. An "effective amount" means a dosage sufficient to produce a desired result, e.g., reduction in an adverse symptom associated with an immune disorder, amelioration of a symptom of an immune disorder, slowing progression of an immune disorder, etc. Generally, the desired result is at least a reduction in a symptom of an immune disorder, as compared to a control.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers, pharmaceutically acceptable diluents, or other pharmaceutically acceptable excipients and can be formulated into preparations in solid, semi-solid, liquid or gaseous forms, such as tablets, capsules, powders, granules, ointments, solutions, suppositories, injections, inhalants and aerosols. In some embodiments, a pharmaceutical composition comprises a subject antibody and a pharmaceutically acceptable excipient.

In pharmaceutical dosage forms, a subject antibody can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying the antibody in an aqueous or nonaqueous solvent, such as vegetable or other similar oils, propylene glycol, synthetic aliphatic acid glycerides, injectable organic esters (e.g., ethyl oleate), esters of higher aliphatic acids or propylene glycol; and if desired, with conventional additives such as solubilizers, isotonic agents, suspending agents, emulsifying agents, stabilizers and preservatives. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Furthermore, the pharmaceutical composition of the present disclosure can comprise further agents such as dopamine or psychopharmacologic drugs, depending on the intended use of the pharmaceutical composition.

Pharmaceutical compositions comprising a subject antibody are prepared by mixing a subject antibody having the desired degree of purity with optional physiologically acceptable carriers, other excipients, stabilizers, surfactants, buffers and/or tonicity agents. Acceptable carriers, other excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition can be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents can be used for the production of pharmaceutical compositions for parenteral administration; see also Chen (1992) Drug Dev Ind Pharm 18, 1311-54.

Exemplary antibody concentrations in a subject pharmaceutical composition can range from about 1 mg/mL to about 200 mg/mL or from about 50 mg/mL to about 200 mg/mL, or from about 150 mg/mL to about 200 mg/mL.

An aqueous formulation of the antibody can be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent can be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions can be suitable. The term "isotonic" denotes a solution having the same tonicity as some other solution with which it is compared, such as a physiological salt solution or serum. Tonicity agents can be used in an amount of about 5 mM to about 350 mM, e.g., in an amount of 100 mM to 350 nM.

A surfactant can also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant can range from about 0.001% to about 1% w/v.

A lyoprotectant can also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM sucrose; and has a pH of 5.5; or 4) 75 mg/mL of a subject antibody; 0.04% Tween 20 w/v; 20 mM L-histidine; and 250 mM trehalose; and has a pH of 5.5; or 5) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.02% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like. Aerosol formulations such as nasal spray formulations include purified aqueous or other solutions of the active agent with preservative agents and isotonic agents. Such formulations are adjusted to a pH and isotonic state compatible with the nasal mucous membranes.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions can be provided wherein each dosage unit, for example, teaspoonful, tablespoonful, tablet or suppository, contains a predetermined amount of the composition. Similarly, unit dosage forms for injection or intravenous administration can comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-LAG-3 antibody of the present disclosure, calculated in an amount sufficient to produce the desired effect in association with a pharmaceutically acceptable diluent, carrier or vehicle. The specifications for a subject antibody can depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories can be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations can also contain preservatives such as, but not limited to, chlorobutanol and benzalkonium chloride. A surfactant can be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection can also be prepared. The preparation can also be emulsified or the antibody encapsulated in liposome vehicles.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations can be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations can be prevented by using appropriate additives, by controlling moisture content and by developing specific polymer matrix compositions.

Controlled release within the scope of the present disclosure can be taken to mean any one of a number of extended release dosage forms. The following terms can be considered to be substantially equivalent to controlled release, for the purposes of the present disclosure: continuous release, controlled release, delayed release, depot, extended release, gradual release, immediate release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, and sustained-action medications. Further discussions of these terms can be found in Lesczek Krowczynski, Extended-Release Dosage Forms, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release can be found in Agis F. Kydonieus, Controlled Release Technologies: Methods, Theory and Applications, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems can be found in Yie W. Chien, Novel Drug Delivery Systems, 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody can be administered in amounts from 1 ng/kg body weight to 20 mg/kg body weight per dose, for example from 0.001 to 10, 0.01 to 10, 0.1 to 10, 1 to 10, 0.001 to 1, 0.01 to 1, 0.1 to 1, 0.05 to 5, 0.05 to 0.5, or 0.5 to 5 mg/kg body weight. However, doses below or above this exemplary range are envisioned, especially considering the aforementioned factors. If the regimen is a continuous infusion, it may be in the range of 1 pg to 10 mg/kg of body weight per minute.

In some embodiments, a dose of a subject anti-LAG-3 antibody is in the range of 0.001 µg to 100 mg, for example 0.001 µg to 10 mg, 0.001 µg to 1 mg, 0.001 µg to 0.1 mg, 0.01 µg to 10 mg, 0.1 µg to 10 mg, 0.1 µg to 1 mg, or 0.1 µg to 0.1 mg, or 0.01 to 100 mg, 0.01 to 10 mg, 0.01 to 1 mg, 0.01 to 0.1 mg, 0.1 to 100 mg, 0.1 to 10 mg, 0.1 to 1 mg.

In some embodiments, the dosage can range, for example from about 0.0001 to 100 mg/kg, or from about 0.01 to 5 mg/kg (e.g., 0.02 to 5 mg/kg, 0.25 to 5 mg/kg, 0.5 to 5 mg/kg, 0.75 to 5 mg/kg, 1 to 5 mg/kg, 2 to 5 mg/kg, etc.) body weight. For example dosages can be 0.1, 1, or 10 mg/kg body weight or within the range of 0.01-10 mg/kg, or at least 0.1 mg/kg.

In particular embodiments, a dose of an anti-LAG-3 antibody of the invention, or fragment thereof, is up to 0.5 mg/kg body weight, for example in the range of 0.0001 to 0.5 mg/kg, 0.001 to 0.5 mg/kg, 0.01 to 0.5 mg/kg, 0.1 to 0.5 mg/kg, 0.0001 to 0.1 mg/kg, 0.001 to 0.1 mg/kg, 0.01 to 0.1 mg/kg body weight.

In some embodiments, a subject anti-LAG-3 antibody is administered in an amount that provides for a peak serum concentration of from about 0.001 µg/ml to about 1 mg/ml, for example 0.0001 µg/ml to 1 µg/ml, 0.001 µg/ml to 1 µg/ml, 0.001 µg/ml to 0.1 µg/ml, 0.01 to 1, or 0.01 to 0.1 µg/ml, or from about 0.005 µg/ml to about 1 µg/ml, or from about 0.1 µg/ml to about 1 µg/ml, or from about 1 µg/ml to about 2.5 µg/ml, from about 2.5 µg/ml to about 5 pg/ml, from about 5 µg/ml to about 7.5 µg/ml, from about 7.5 µg/ml to about 10 µg/ml, from about 10 µg/ml to about 25 µg/ml, from about 25 µg/ml to about 50 µg/ml, from about 50 pg/ml to about 100 µg/ml, from about 100 µg/ml to about 250 µg/ml, from about 250 µg/ml to about 500 µg/ml, from about 500 µg/ml to about 750 µg/ml, or from about 750 µg/ml to about 1000 µg/ml. In some embodiments, a subject anti-LAG-3 antibody is administered in an amount that provides for a peak serum concentration of greater than 1 mg/ml, e.g., from about 1 mg/ml to about 2 mg/ml, from about 2 mg/ml to about 5 mg/ml, or from about 5 mg/ml to about 10 mg/ml. In other embodiments, an anti-LAG-3 antibody of the invention, or fragment thereof, is administered in an amount that provides for a peak serum concentration of up to 1 µg/ml, for example in the range of 0.0001 µg/ml to 1 µg/ml, 0.001 pg/ml to 1 µg/ml, 0.01 µg/ml to 1 µg/ml, 0.1 to 1 µg/ml, 0.0001 µg/ml to 0.1 µg/ml, 0.001 pg/ml to 0.1 µg/ml, or 0.01 µg/ml to 0.1 µg/ml. Suitably such administration is by subcutaneous injection.

Individuals can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months.

Exemplary dosage schedules include 0.01 to 1 mg/kg, 0.01 to 0.1 mg/kg, 0.1 to 1 mg/kg, 1 to 10 mg/kg or 15 mg/kg on consecutive days, 0.02 to 20 mg/kg, for example 0.2 mg/kg, 0.5 mg/kg, 1 mg/kg, 5 mg/kg, 10 mg/kg, or 20 mg/kg on alternate days, or 0.1 to 100 mg/kg, for example 1 mg/kg, 10 mg/kg, 20 mg/kg, 30 mg/kg, 40 mg/kg, 50 mg/kg, or 60 mg/kg weekly. In some methods, two or more monoclonal antibodies with different binding specificities are administered simultaneously, in which case the dosage of each antibody administered falls within the ranges indicated. Progress can be monitored by periodic assessment.

The number of CD4+ and/or CD8+ T cells expressing LAG-3 in a subject is relatively low. It is expected that a single administration of an antibody of the invention (in particular, an antibody of the invention that has a serum half-life of at least two weeks and that lacks significant CDC and ADCC activity, such as a human IgG isotype antibody (which lacks CDC and ADCC activity), or an antibody that comprises one or more mutations to reduce or abolish CDC and ADCC activity) may be effective at inhibiting antigen-induced CD4+ and/or CD8+ T cell proliferation for at least several weeks. In view of this, a suitable treatment regimen may comprise administration of an antibody of the invention (for example 0.01 to 1 mg/kg of the antibody) once every four, six, eight, or ten weeks, or once every two or three months. Such treatment may be provided over a period of at least six months, or at least one, two, three, four, or five years, or longer, for example throughout the course of a disease that is treated by the administration, or throughout the lifetime of the subject.

Those of skill will readily appreciate that dose levels and administration schedules can vary as a function of the specific antibody, the severity of the symptoms and the susceptibility of the subject to side effects. Preferred dosages and administration schedules for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, intracranial, subcutaneous, intradermal, topical, intravenous, intraperitoneal, intraarterial (e.g., via the carotid artery), spinal or brain delivery, rectal, nasal, oral, and other enteral and parenteral routes of administration. Routes of administration can be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously. In some embodiments, a subject antibody composition is administered intrathecally.

An antibody of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By "treatment" is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an immune disorder. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, the host is an individual that has a complement system, such as a mammal, fish, or invertebrate. In some embodiments, the host is a complement system-containing mammal, fish, or invertebrate companion animal, agricultural animal, work animal, zoo animal, or lab animal. In some embodiments, the host is human.

The embodiments include compositions comprising a container suitable for containing a composition comprising a subject anti-LAG-3 antibody for administration to an individual. For example, a subject antibody can be disposed within a container suitable for containing a pharmaceutical composition. The container can be, for example, a bottle (e.g., with a closure device, such as a cap), a blister pack (e.g., which can provide for enclosure of one or more doses per blister), a vial, flexible packaging (e.g., sealed Mylar or plastic bags), an ampule (for single doses in solution), a dropper, a syringe, thin film, a tube and the like. In some embodiments, a container, such as a sterile container, comprises a subject pharmaceutical composition. In some embodiments the container is a bottle or a syringe. In some embodiments the container is a bottle. In some embodiments the container is a syringe.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Methods of Treatment

According to the invention there is also provided an antibody of the invention, or antigen-binding fragment thereof, or a pharmaceutical composition of the invention, for use as a medicament.

An antibody, fragment, or composition of the present invention may be utilised in any therapy where it is desired to increase the effects of LAG-3 in the subject.

The term "subject" includes any human or nonhuman animal. The term "nonhuman animal" includes all vertebrates, e.g., mammals and non-mammals, such as nonhuman primates, sheep, dogs, cats, cows, horses, chickens, amphibians, and reptiles, although mammals are preferred, such as non-human primates, sheep, dogs, cats, cows and horses.

The antibody, fragment, or composition may be used in any therapy where it is desired to negatively regulate T cell proliferation and/or function.

There is also provided according to the invention an antibody of the invention, or antigen-binding fragment thereof, or a pharmaceutical composition of the invention, for use in the treatment of a disorder associated with proliferation or activity of CD4+ and/or CD8+ T cells in a subject, or a disorder associated with decreased expression and/or activity of LAG-3 in a subject.

There is also provided according to the invention use of an antibody of the invention, or antigen-binding fragment thereof, or a pharmaceutical composition of the invention, in the manufacture of a medicament for the treatment of a disorder associated with proliferation or activity of CD4+ and/or CD8+ T cells in a subject, or disorder associated with decreased expression and/or activity of LAG-3 in a subject.

There is further provided according to the invention a method of treating a disorder associated with proliferation or activity of CD4+ and/or CD8+ T cells in a subject, or disorder associated with decreased expression and/or activity of LAG-3 in a subject, which comprises administering an effective amount of an antibody of the invention, or antigen-binding fragment thereof, or a pharmaceutical composition of the invention, to a subject in need of such treatment.

The disorder associated with proliferation or activity of CD4+ and/or CD8+ T cells may be an immune disorder, in particular a T-cell-mediated immune disorder, such as an inflammatory disease, or an autoimmune disorder.

The antibody, fragment or composition may be used to reduce the inflammatory process or to prevent the inflammatory process. In one embodiment there is provided an in vivo reduction of T cell proliferation or activation, in particular those involved in inappropriate inflammatory immune responses, for example recruited to the vicinity/location of such a response.

Reduction of T cell proliferation or activation, as employed herein, may be a reduction of 10, 20, 30, 40, 50, 60, 70, 80, 90 or more percent in comparison to before treatment or without treatment.

Advantageously, treatment with an antibody, fragment or composition according to the present invention, may allow a reduction in the T cell proliferation or activation, without reducing the patient's general level of T cells (unactivated T cells). This may result in fewer side effects, and prevent T cell depletion in the patient.

The immune disorder, may, for example be selected from the group consisting of infections (viral, bacterial, fungal and parasitic), endotoxic shock associated with infection, sepsis, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus) and Guillain-Barré syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia, or infertility related to lack of fetal-maternal tolerance.

An antibody, fragment, or composition of the invention may be used in any therapy where it is desired to inhibit binding of LAG-3 to MHC class II molecules, to antagonise MHC class II-activating signal into antigen-presenting cells (APCs), or to inhibit LAG-3-induced APC activation.

There is also provided according to the invention an antibody of the invention, or antigen-binding fragment thereof, or a pharmaceutical composition of the invention, for use in the treatment of a disorder associated with activation of APCs in a subject.

There is also provided according to the invention use of an antibody of the invention, or antigen-binding fragment thereof, or a pharmaceutical composition of the invention, in the manufacture of a medicament for the treatment of a disorder associated with activation of APCs in a subject.

There is further provided according to the invention a method of treating a disorder associated with activation of APCs in a subject, which comprises administering an effective amount of an antibody of the invention, or antigen-binding fragment thereof, or a pharmaceutical composition of the invention, to a subject in need of such treatment.

As used herein, the terms "treatment", "treating", "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment" as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

The terms "individual", "subject", "host", and "patient" used interchangeably herein includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

A "therapeutically effective amount" or "efficacious amount" refers to the amount of an anti-LAG-3 antibody that, when administered to a mammal or other subject for treating a disease, is sufficient to effect such treatment for the disease. The "therapeutically effective amount" will vary depending on the anti-LAG-3 antibody, the disease and its severity and the age, weight, etc., of the subject to be treated.

All publications mentioned herein are incorporated herein by reference to disclose and describe the methods and/or materials in connection with which the publications are cited.

Embodiments of the invention are now described, by way of example only, with reference to the accompanying drawings in which:

FIG. 1 shows amino acid sequence (SEQ ID NO:27) of mature human LAG-3 protein. The four extracellular Ig superfamily domains are at amino acid residues: 1-149 (D1); 150-239 (D2); 240-330 (D3); and 331-412 (D4). The amino acid sequence of the extra-loop structure of the D1 domain of human LAG-3 protein is shown underlined in bold (SEQ ID NO:40);

FIG. 2 shows a graphical representation of the $V_H$ CDR loops of monoclonal antibody 13E2 (Lefranc, M.-P. et al., Dev. Comp. Immunol., 27, 55-77 (2003));

FIG. 3 shows the amino acid sequence of the $V_H$ domain of monoclonal antibody 13E2 aligned with an encoding nucleic acid sequence;

FIG. 4 shows a graphical representation of the $V_L$ CDR loops of monoclonal antibody 13E2 (Lefranc, M.-P. et al., Dev. Comp. Immunol., 27, 55-77 (2003));

FIG. 5 shows the amino acid sequence of the $V_L$ domain of monoclonal antibody 13E2 aligned with an encoding nucleic acid sequence;

FIG. 6 shows a graphical representation of the $V_H$ CDR loops of monoclonal antibody 34F4 (Lefranc, M.-P. et al., Dev. Comp. Immunol., 27, 55-77 (2003));

FIG. 7 shows the amino acid sequence of the $V_H$ domain of monoclonal antibody 34F4 aligned with an encoding nucleic acid sequence;

FIG. 8 shows a graphical representation of the $V_L$ CDR loops of monoclonal antibody 34F4 (Lefranc, M.-P. et al., Dev. Comp. Immunol., 27, 55-77 (2003));

FIG. 9 shows the amino acid sequence of the $V_L$ domain of monoclonal antibody 34F4 aligned with an encoding nucleic acid sequence;

FIG. 10 shows the top V-D-J germline BLAST alignments for nucleotide sequence encoding the $V_H$ region of monoclonal antibody 13E2;

FIG. 11 shows the top V-J germline BLAST alignments for nucleotide sequence encoding the $V_L$ region of monoclonal antibody 13E2;

FIG. 12 shows the top V-D-J germline BLAST alignments for nucleotide sequence encoding the $V_H$ region of monoclonal antibody 34F4;

FIG. 13 shows the top V-J germline BLAST alignments for nucleotide sequence encoding the $V_L$ region of monoclonal antibody 34F4;

FIG. 15 shows the results of binding of different concentrations of agonistic anti-LAG-3 monoclonal antibodies 13E2 and 34F4, and antagonistic anti-LAG-3 monoclonal antibody 1764, to CD4+ and CD8+ primary cells (SEB-stimulated PBMCs), compared to an isotype control antibody (mIgG1), from a healthy donor (donor 1);

Figure 17:
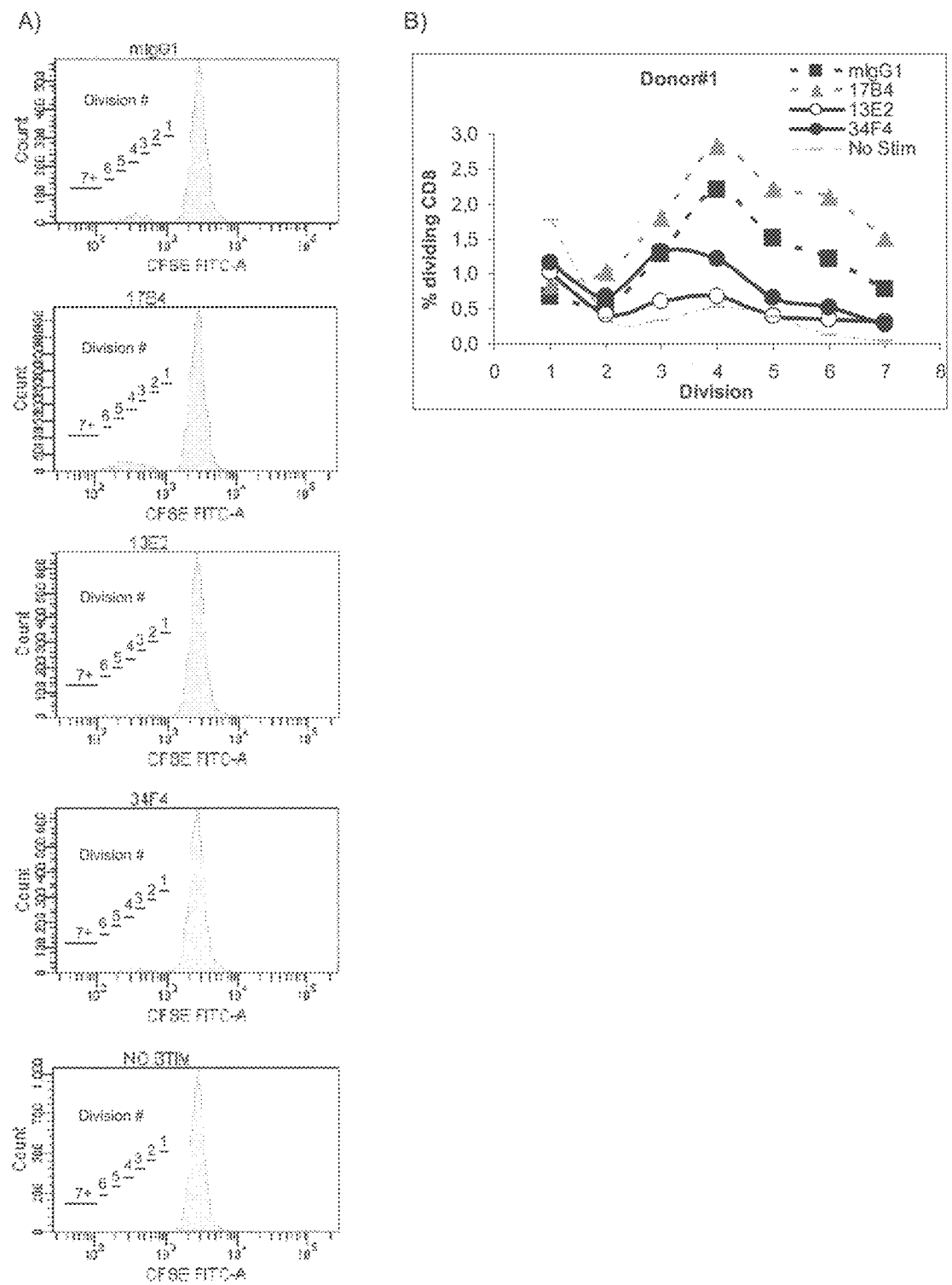
Figure 25:
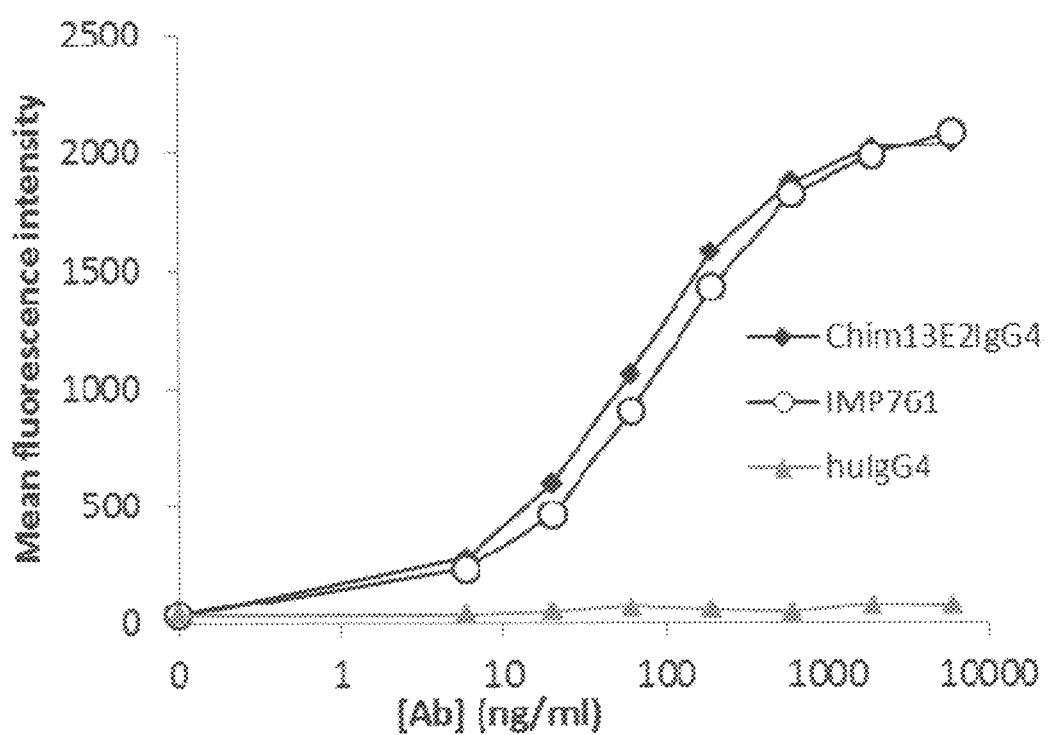
Figure 26:
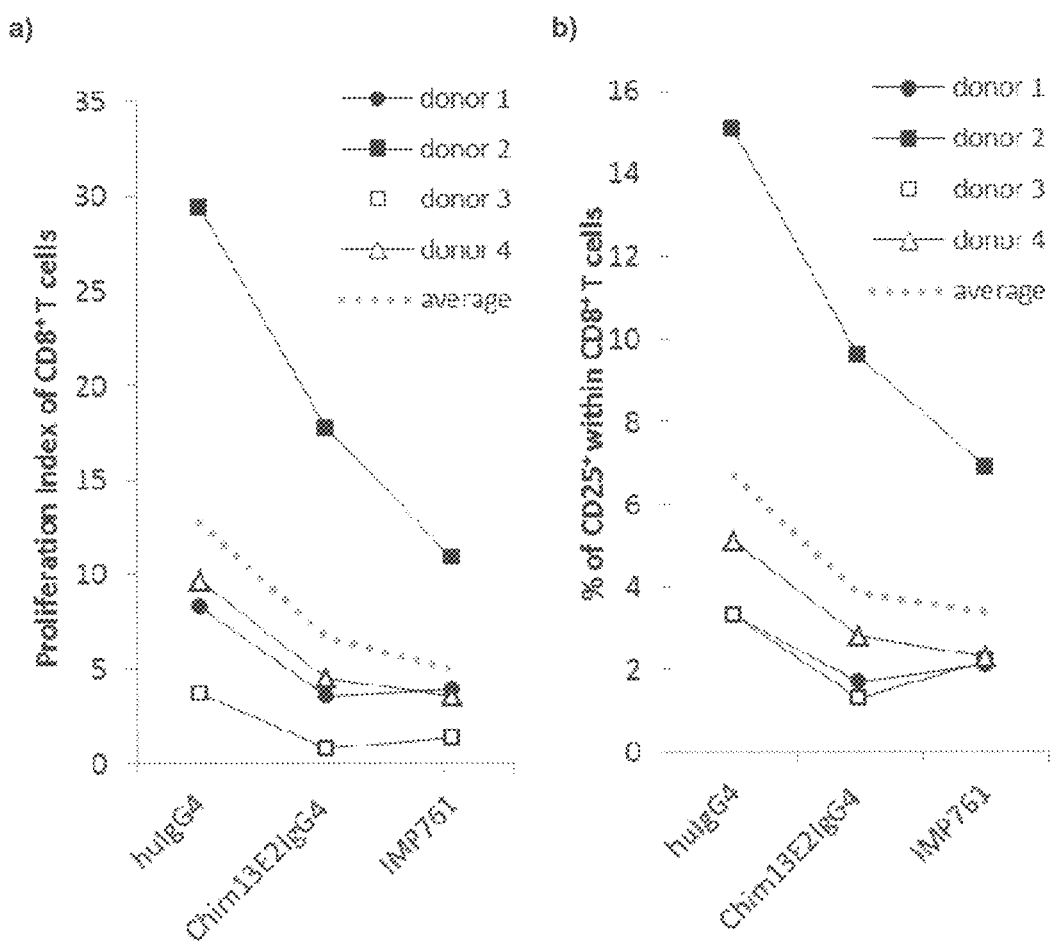
Figure 27:
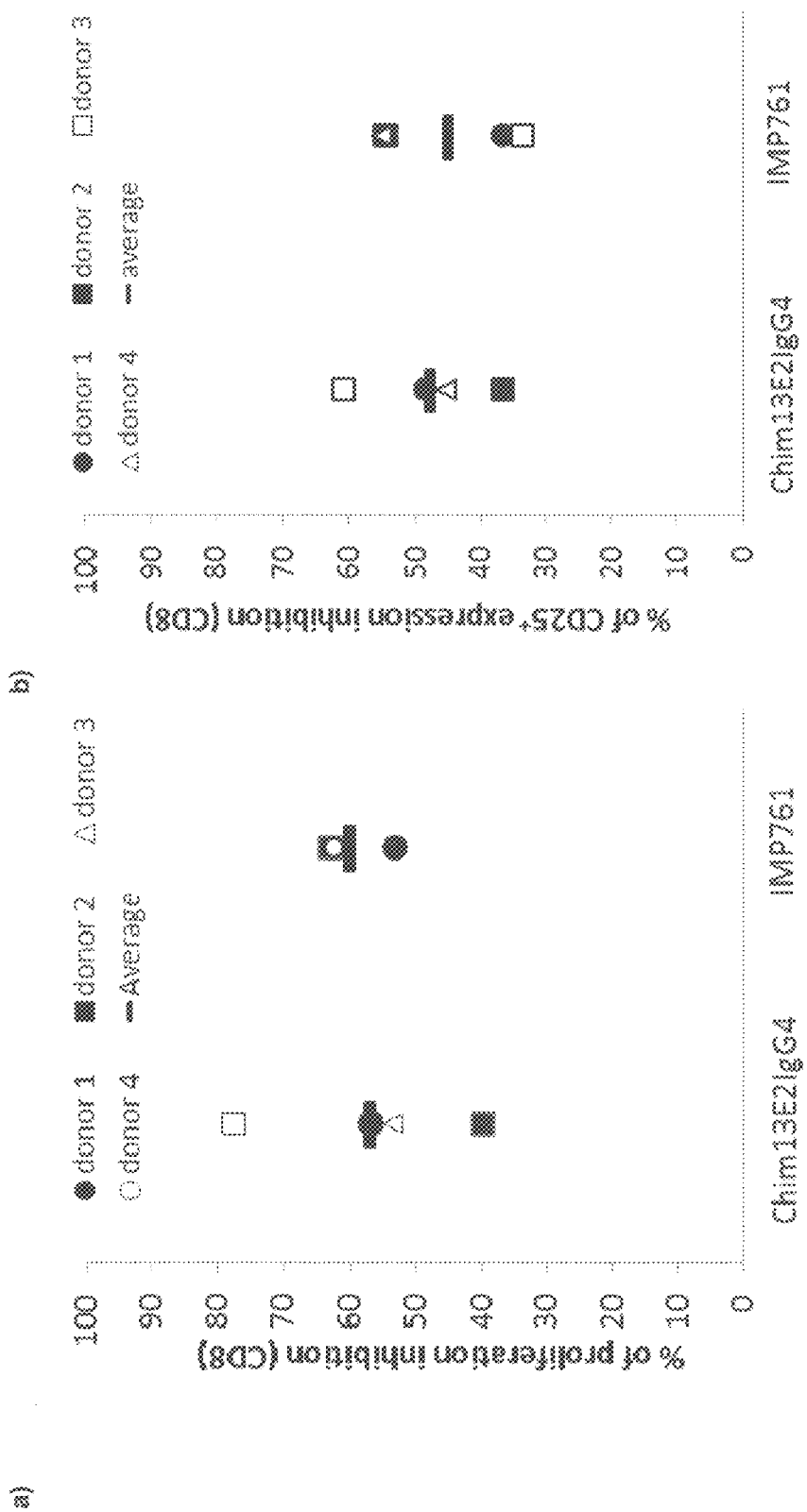
Figure 28:
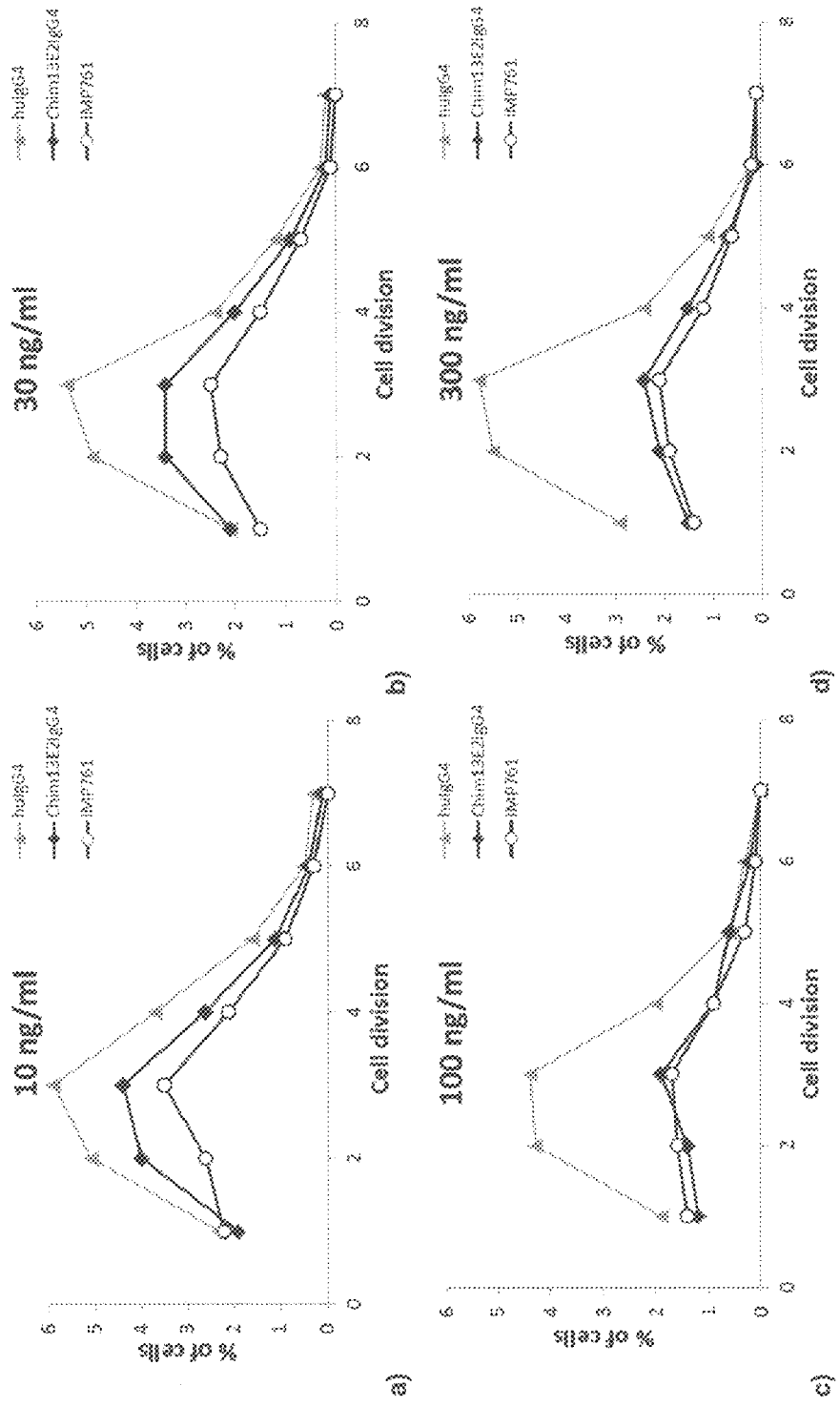

FIG. 16A shows the results of inhibition of binding of IMP321 (LAG-3Ig, 1 µg/ml) to MHC class II-positive B cells by different concentrations of agonistic anti-LAG-3 monoclonal antibodies 13E2 and 34F4, and antagonistic anti-LAG-3 monoclonal antibody 1764, compared to an isotype control antibody (mIgG1). FIG. 16B shows the results of inhibition of activation of THP-1 cells by IMP321 (20 ng/ml) in the presence of different concentrations of agonistic anti-LAG-3 monoclonal antibodies 13E2 and 34F4, and antagonistic anti-LAG-3 monoclonal antibody 1764, compared to an isotype control antibody (mIgG1);

FIG. 17(A) illustrates the CMV-induced proliferation profiles of the CD8+ T cells of one donor in the presence of mIgG1, 17B4, 13E2 or 34F4, analysed by flow cytometry and the gating strategy used for the assay described in Example 10. FIG. 17(B) shows the results of an assay for the inhibition of CD8+ T cell proliferation by antibodies 13E2, 34F4, and 1764, compared with the isotype control antibody (mIgG1) for the same donor. The baseline proliferation is also shown (No Stim);

FIG. 18 shows the results of an assay for the inhibition of CD4+ or CD8+ T cell proliferation by antibodies 13E2 or 34F4, compared with the isotype control antibody (mIgG1), in several different donors;

FIG. 19 shows the effect of different concentrations of agonistic anti-LAG-3 monoclonal antibodies 13E2 and 34F4 on CD8+ T cell proliferation;

FIG. 20 shows the heavy chain amino acid sequence of a chimeric 13E2-human IgG4 Fc antibody (the chimeric 13E2-human IgG4 Fc heavy chain amino acid sequence is referred to as 13E2IgG4mut in the figure), and the light chain amino acid sequence of a chimeric 13E2-human IgK antibody (the chimeric 13E2-human IgK light chain amino acid sequence is referred to as 13E2IgK in the figure);

FIG. 21 illustrates the different effects on T cells of depleting, antagonist, and agonist anti-LAG-3 antibodies;

FIG. 22 shows an alignment of the variable regions of humanized VH variants 1-4 ($VH_1$, $VH_2$, $VH_3$, and $VH_4$), and an alignment of the variable regions of humanized VL variants 1-4 ($VL_1$, $VL_2$, $VL_3$, and $VL_4$), with the corresponding sequence of the original mouse monoclonal antibody 13E2 (13E2 VH and 13E2 VL, respectively). CDR sequences are highlighted in grey. Changes in the humanized framework sequences of the variants, compared with the original mouse sequence, are shown underlined and in bold;

FIG. 23 shows the heavy chain amino acid sequence of a humanized 13E2-human IgG4 Fc antibody (IMP761) aligned with the chimeric 13E2-human IgG4 Fc heavy chain amino acid sequence (13E2IgG4mut) of antibody Chim13E2IgG4. The $V_H$ region is shown in bold, and the Fc region is shown highlighted. Amino acid residues of the humanized IMP761 sequence that differ from corresponding residues of the chimeric 13E2IgG4mut sequence are single underlined. CDR sequences (based on combined IMGT/Kabat CDR sequence identification) are shown double underlined;

FIG. 24 shows the light chain amino acid sequence of a humanized 13E2-human IgK antibody (IMP761) aligned with the chimeric 13E2-human IgK light chain amino acid sequence (13E2IgK) of antibody Chim13E2IgG4. The $V_L$ region is shown in bold, and the IgK region is shown highlighted. Amino acid residues of the humanized IMP761 sequence that differ from corresponding residues of the chimeric 13E2IgK sequence are single underlined. CDR sequences (based on the combined IMGT/Kabat CDR sequence identification) are shown double underlined;

FIG. 25 shows the results of an assay to test binding of the chimeric 13E2-human IgG4 Fc antibody (Chim13E2IgG4) and IMP761 to CHO-LAG-3+ cells;

FIG. 26 shows the results of an assay to test the effect of IMP761 and Chim13E2IgG4 on: (a) antigen-induced CD8+ T-cell proliferation; and (b) CD25 expression within CD8+ T cells;

FIG. 27 shows the effect of IMP761 and Chim13E2IgG4 on antigen-induced CD8+ T-cell proliferation, and CD25 expression, as a plot of: (a) the percentage inhibition of CD8+ T-cell proliferation; and (b) the percentage inhibition of CD25 expression within CD8+ T cells, compared to an isotype-matched control;

FIG. 28 shows the effect of different concentrations of IMP761 and Chim13E2IgG4 on antigen-induced CD8+ T-cell proliferation;

FIG. 29 shows the results of ADCC assays to determine whether IMP761 has cytotoxic activity against LAG-3- expressing cells, using: an ADCC Reporter Bioassay available from Promega (a); and an ADCC assay using IL-2-stimulated PBMCs as effector cells—the results are plotted as the percentage of: $CD4^+$ and $CD8^+$ T cells (b); or LAG-3+$CD4^+$ and LAG-3+$CD8^+$ T cells (c) in the PBMC population;

FIG. 30 shows the results of CDC assays using rabbit complement to determine whether IMP761 has cytotoxic activity against LAG-3-expressing cells—the results are plotted as the percentage of: (a) $CD4^+$ and $CD8^+$ T cells; or (b) LAG-3+$CD4^+$ and LAG-3+$CD8^+$ T cells, in the PBMC population; and FIG. 31 shows the results of an assay to determine whether IMP761 has cytotoxic activity against LAG-3-expressing cells after culturing antigen-stimulated PBMCs with the antibody for 3 days. The results are plotted as: (a) the percentage of $CD4^+$ and $CD8^+$ T cells in the PBMC population; and (b) the percentage of LAG-3+ cells in the $CD4^+$ and $CD8^+$ T cell subpopulation.

EXAMPLE 1

Generation of 13E2 anti-LAG-3 Monoclonal Antibody

To generate anti-LAG-3 antibodies, 15 Balb/c mice (referred to as mice numbers 1-15 below) were immunised according to the immunisation protocol described below.

Thirteen mice were each immunised with subcutaneous (s.c.) injections of 100 μg of IMP321 (LAG-3Ig), clinical grade lot S017/LC1/041011 (termed "LC1" below): 3 times (mouse no. 12); 4 times (mouse no. 9); 5 times (mice nos. 5 and 14); or 6 times (mice nos. 3, and 11) at Day 0, Day 15, Day 30, Day 50, Day 67 and Day 108. Mice nos. 1, 2, 4, 8, 10, 13 and 15 were immunised up to 4 additional times. In parallel, two mice (mouse no. 6 and mouse no. 7), used as controls, were immunised with 10 μg of LC1 in Complete Freund's Adjuvant (CFA) once at Day 0, and with the same dose of antigen in Incomplete Freund's Adjuvant (IFA) on Day 15, Day 30, Day 50, Day 67 and Day 108.

Twelve days after the 6th immunisation, serum of mice nos. 1, 2, 3, 4, 8, 10, 11, 13 and 15 was drawn (mice nos. 5, 9, 12 and 14 had already been sacrificed) and analyzed in an Enzyme-Linked Immunosorbent Assay (ELISA) using LAG-3 D1-D4 as coated antigen, purified anti-LAG-3 17B4 murine monoclonal antibody as reference, and a goat anti-mouse Ig-HRP as labelled secondary antibody, to determine the concentration of anti-LAG-3 antibodies present in the serum. The results are shown in Table 2 below:

TABLE 2

| Mouse No. | [Anti-LAG-3 Ab] μg/ml |
|---|---|
| 1 | 1049 |
| 2 | 281 |
| 3 | 423 |
| 4 | 193 |
| 6 | 131 |
| 7 | 394 |
| 8 | 242 |
| 10 | 275 |
| 11 | 506 |
| 13 | 188 |
| 15 | 848 |

After six immunisations, serum from several mice (including mouse no. 3) surprisingly gave better results than serum from the two positive control mice (nos. 6 and 7), even though these mice were immunised with IMP321 in the absence of CFA or IFA as adjuvant. This unconventional technique (i.e. immunisation with IMP321 in PBS, without using CFA or IFA as adjuvant) also gave good results compared with other experiments using LAG-3-expressing CHO cells in IFA (data not shown). Without being bound by theory, it is believed that this may be because IMP321 itself is an adjuvant, i.e. it directly triggers activation and maturation of dendritic cells.

The same serum samples were assessed for their ability to inhibit the binding of IMP321 to its ligand, MHC class II, expressed on Raji B cells. Ten microliters of a solution of 10 μg/ml of Alexa-Fluor488-conjugated IMP321 was preincubated with and without 5 μl of the serum collected from each mouse or naïve serum for 30 min at 4° C. Then Raji cells were added to a final volume of 50 μl and incubated for 30 minutes at 4° C. The cell-bound fluorescence was analyzed by flow cytometry.

Mouse no. 3 was selected because the serum from this mouse showed a high titre (423 μg/ml) in the D1-D4 serum ELISA assay (Table 1), and a strong capacity to inhibit the binding of IMP321 to MHC class $II^+$ Raji B cells.

Twelve days after the sixth immunisation, mouse no. 3 received an intravenous (i.v.) boost with 10 μg D1-D4 LAG-3 (with no Fc tail) recombinant protein (produced in CHO cells and purified). Three days after the i.v. boost injection, mouse no. 3 was sacrificed and the spleen was removed. The splenocytes were extracted by squeezing the pieces of spleen with a 5 ml syringe rubber plunger in a Petri dish containing complete serum-free DMEM. The splenocytes and Sp2/0 myeloma cells (cultivated in RPMI 1640+ 10% FCS+2 mM Glutamine+0.5% P/S) were washed in serum-free medium. The two cell types were mixed together in a ratio of 5:1 of splenocytes:myeloma, and then pelleted by centrifugation. The fusion agent (PEG-1500, Polyethylene Glycol solution 50% w/v in PBS, Roche 10783641001, 1 ml per $10^8$ cells) was pre-warmed at 37° C. and added to the cell pellet drop by drop. The cells were very gently resuspended, and diluted by doubling the volume after 90 seconds. The cells were further diluted at regular intervals to a final dilution of 1 to 15 over approximately 5 minutes. The cells were then centrifuged and resuspended in medium containing 10% FBS and incubated for approximately one hour at 37° C. The cells (10,000 cells/well) were then plated in 46 96-well plates in complete RPMI containing 10% of Ultralow Ig FBS (Gibco 16250), 2% HAT (Gibco 21060) and supplemented with 10% BM Condimed H1 (a supplement to the culture medium to support the growth of B-cell hybridomas after fusion and during cloning, Roche 11088947001), and cultured until screening.

The screening was performed by cytometry using CHO cells, with membrane-expressed LAG-3, to analyse the binding ability of antibodies present in the supernatants of growing hydridomas, revealed by a FITC-conjugated goat-anti mouse Ig. The positive hybridomas were expanded and rescreened on CHO LAG-$3^+$ cells, and wild type CHO cells. From this fusion, a total of 632 wells were screened by FACS analysis on LAG-3 expressing CHO cells (a yield of 14%). 4 hybridoma clones were found to stably express anti-LAG-3 antibody, including 13E2. The hybridoma was then subcloned by limiting dilution.

TABLE 3

| Fusion | N °5 |
|---|---|
| Splenocytes (millions) | 33 |
| Fusion characteristic | BM condimed H1, 10,000 cells/well |
| Number of wells to start with | 4416 |
| Number of wells with dividing cells that were screened | 632 |
| Recovery | 14% |
| Number of stable anti LAG-3 hybridomas | 4 |

EXAMPLE 2

Amino Acid Sequence of Variable Region of Antibody 13E2

$V_H$ Amino Acid Sequence:
(SEQ ID NO: 7)
QVTLKESGPGILQPSQTLSLTCSFS<u>GFSLS</u>TSGMGLGWIRQPSGKGLEWL TH<u>IWWDDIK</u>RYNPDLRSRLTISKDTSSSQIFLKIASVDTADTATYYC<u>ARI VEGSYSSSYFDV</u>WGAGTTVTVSS.

SEQ ID NO:7 is the amino acid sequence of the heavy chain variable ($V_H$) domain of antibody 13E2. The Complementarity Determining Regions (CDRs), as determined by the IMGT numbering system (Lefranc, M.-P. et al., Nucleic Acids Research, 27, 209-212 (1999)), are underlined. The CDRs, as determined by the Kabat numbering system, are shown in bold.

Figure 2:
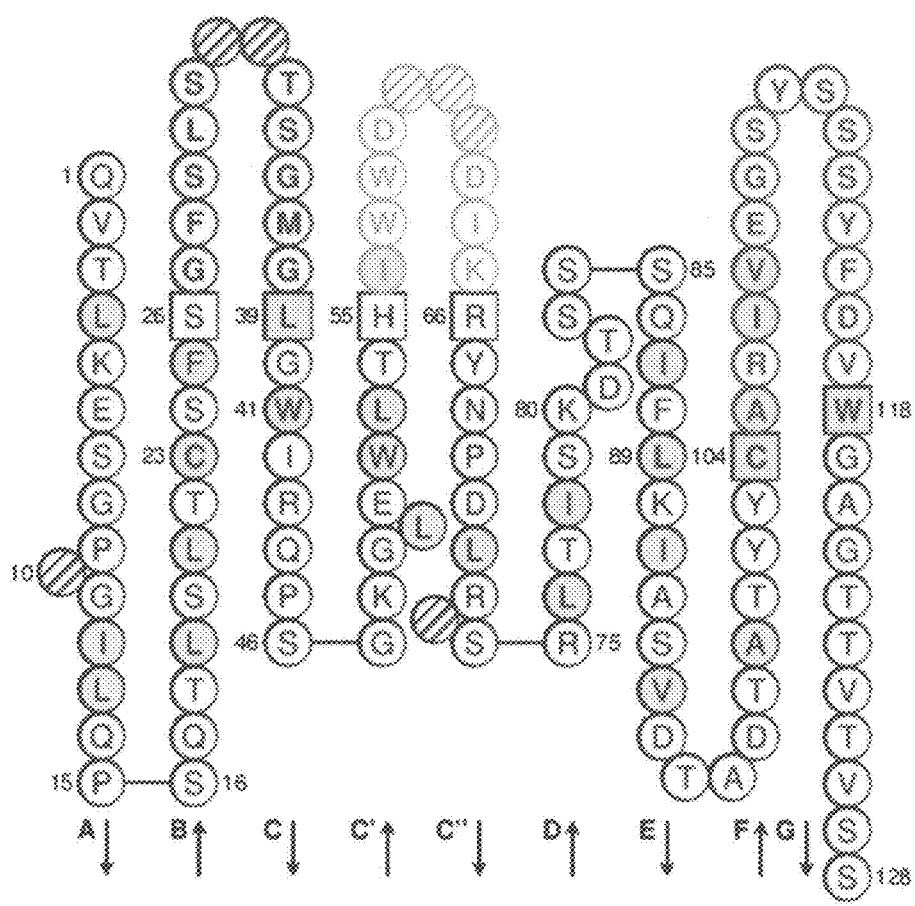

FIG. 2 shows a graphical representation of the $V_H$ CDR loops of monoclonal antibody 13E2 (Lefranc, M.-P. et al., Dev. Comp. Immunol., 27, 55-77 (2003)). Shaded circles (residue nos. 4, 12, 13, 19, 21, 23, 25, 41, 50, 52, 53, 71, 76, 78, 87, 89, 91, 94, 100) are hydrophobic (non-polar) residues in frameworks 1-3 at sites that are hydrophobic in the majority of antibodies. Squares are key residues at the start and end of each CDR. Amino acid residue nos. 23, 41, 89, 104, 118 in the framework are structurally conserved amino acids;

$V_L$ Amino Acid Sequence:
(SEQ ID NO: 8)
DIVMTQPHKFMSTSVEDRVTITCKAS<u>QDVIFD</u>VAWYQQKPGQSPKLLIY<u>S ASSRVS</u>GVPDRFTGSGSGTDFTFTISSVQAEDLAVYYC<u>QQHYSTPYT</u>FGG

GTTLEIK.

SEQ ID NO:8 is the amino acid sequence of the light chain variable ($V_L$) domain of antibody 13E2. The Complementarity Determining Regions (CDRs), as determined by the IMGT numbering system (Lefranc, M.-P. et al., Nucleic Acids Research, 27, 209-212 (1999)), are underlined. The CDRs, as determined by the Kabat numbering system, are shown in bold.

89, 104, 118 in the framework are structurally conserved amino acids.

EXAMPLE 3

Nucleic Acid Sequence Encoding the Variable Domains of Antibody 13E2

Nucleic acid sequence encoding the VH domain of monoclonal antibody 13E2 is shown in FIG. 3, and below:

(SEQ ID NO: 9)
CAGGTTACTCTGAAAGAGTCTGGCCCTGGGATATTGCAGCCCTCCCAGAC

CCTCAGTCTGACTTGTTCTTTCTCTGGGTTTTCACTGAGCACTTCTGGTA

TGGGTCTAGGCTGGATTCGTCAGCCATCAGGGAAGGGTCTGGAGTGGCTG

ACACACATTTGGTGGGATGATATCAAGCGCTATAACCCAGACCTGAGGAG

CCGACTGACTATCTCCAAGGATACCTCCAGCAGCCAGATTTTCCTCAAGA

TCGCCAGTGTGGACACTGCAGATACTGCCACATATTACTGTGCTCGAATA

GTGGAGGGTTCATACAGTAGTAGTTACTTCGATGTCTGGGGCGCAGGGAC

CACGGTCACCGTCTCCTCAG.

Nucleic acid BLAST alignment shows that nucleic acid sequence encoding the VH domain of monoclonal antibody 13E2 has significant identity to the sequence of the following germline genes: IGHV8-8*01, IGHV8-11*01, IGHV8-12*01, IGHD2-12*01, IGHD1-1*01, IGHJ1*01, IGHJ1*02, IGHJ1*03.

Figure 10:
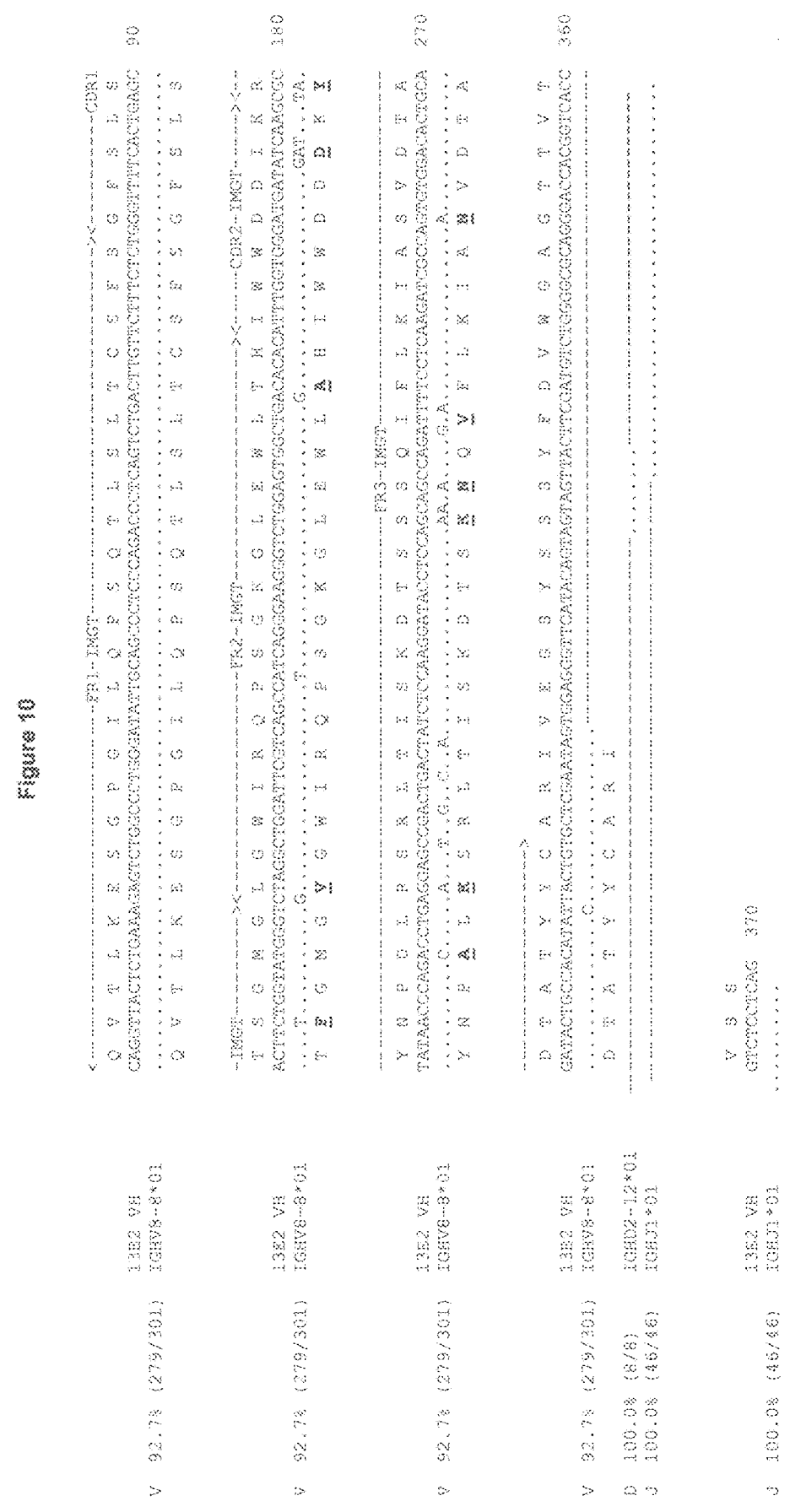

FIG. 10 shows an alignment of nucleic acid sequence encoding the VH domain of the 13E2 antibody with its top germline gene match. FIG. 10 shows that a portion comprising nucleotides 1-301 of the 13E2 VH region (which encompasses heavy chain framework regions FR1, FR2, and FR3) has 92.7% nucleic acid sequence identity with nucleic acid sequence of V gene IGHV8-8*01.

TABLE 4

13E2 VH and VL CDR Sequences

| Antibody | CDR-1 | CDR-2 | CDR-3 |
|---|---|---|---|
| 13E2 VH (IMGT numbering) | GFSLSTSGMG (SEQ ID NO: 1) | IWWDDIK (SEQ ID NO: 2) | ARIVEGSYSSSYFDV (SEQ ID NO: 3) |
| 13E2 VL (IMGT numbering) | QDVIFD (SEQ ID NO: 4) | SAS (SEQ ID NO: 5) | QQHYSTPYT (SEQ ID NO: 6) |
| 13E2 VH (Kabat numbering) | TSGMGLG (SEQ ID NO: 21) | HIWWDDIKRYNPDLRS (SEQ ID NO: 22) | IVEGSYSSSYFDV (SEQ ID NO: 23) |
| 13E2 VL (Kabat numbering) | KASQDVIFDVA (SEQ ID NO: 24) | SASSRVS (SEQ ID NO: 25) | QQHYSTPYT (SEQ ID NO: 26) |

Figure 4:
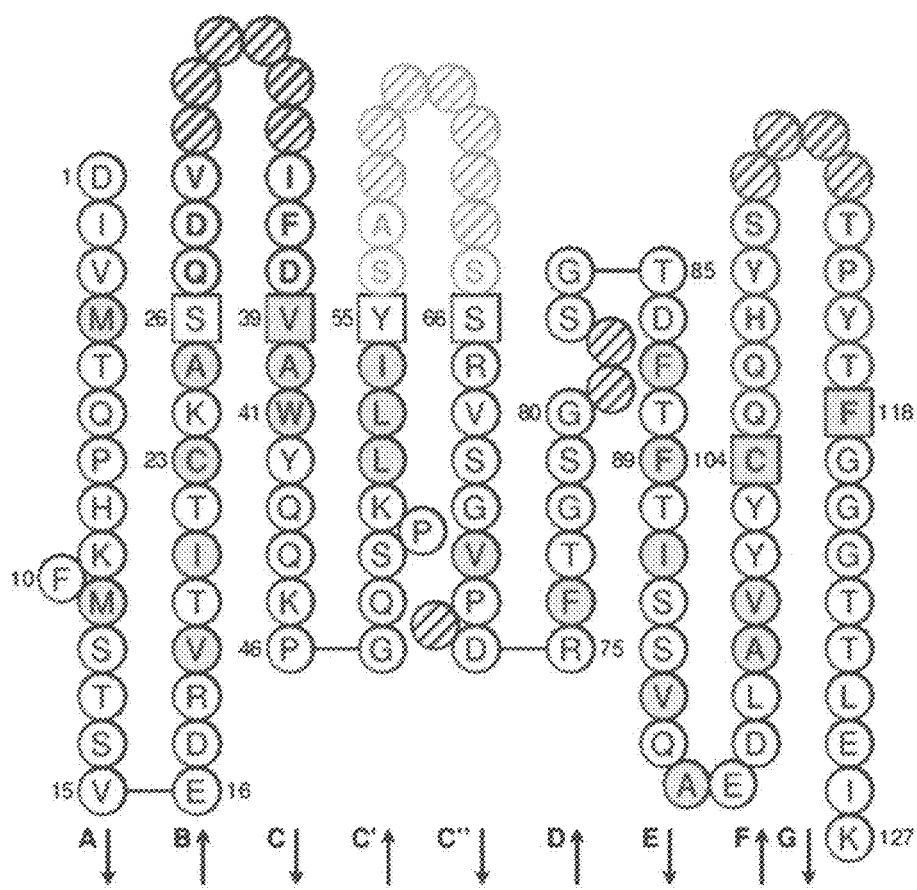

FIG. 4 shows a graphical representation of the $V_L$ CDR loops of monoclonal antibody 13E2 (Lefranc, M.-P. et al., Dev. Comp. Immunol., 27, 55-77 (2003)). Shaded circles (residue nos. 4, 11, 19, 21, 23, 25, 40, 41, 52, 53, 54, 71, 76, 87, 89, 91, 94, 96, 100, 101) are hydrophobic (non-polar) residues in frameworks 1-3 at sites that are hydrophobic in the majority of antibodies. Squares are key residues at the start and end of each CDR. Amino acids residue nos. 23, 41,

TABLE 5

Alignment summary between 13E2 VH and IGHV8-8*01

| | length | matches | mismatches | gaps | identity(%) |
|---|---|---|---|---|---|
| FR1-IMGT | 75 | 75 | 0 | 0 | 100 |
| CDR1-IMGT | 30 | 29 | 1 | 0 | 96.7 |

TABLE 5-continued

Alignment summary between 13E2 VH and IGHV8-8*01

| | length | matches | mismatches | gaps | identity(%) |
|---|---|---|---|---|---|
| FR2-IMGT | 51 | 48 | 3 | 0 | 94.1 |
| CDR2-IMGT | 21 | 18 | 3 | 0 | 85.7 |
| FR3-IMGT | 114 | 99 | 15 | 0 | 86.8 |
| CDR3-IMGT (germline) | 10 | 10 | 0 | 0 | 100 |
| Total | 301 | 279 | 22 | 0 | 92.7 |

Nucleic acid sequence encoding the VL domain of monoclonal antibody 13E2 is shown in FIG. 5, and below:

(SEQ ID NO: 10)
GACATTGTGATGACCCAGCCTCACAAATTCATGTCCACATCAGTGGAAGA

CAGGGTCACCATCACCTGCAAGGCCAGTCAGGATGTGATTTTTGATGTAG

CCTGGTATCAACAGAAACCAGGACAATCTCCTAAATTACTGATTTACTCG

GCATCCTCCCGGGTCAGTGGAGTCCCTGATCGCTTCACTGGCAGTGGATC

TGGGACGGATTTCACTTTCACCATCAGTAGTGTGCAGGCTGAAGACCTGG

CAGTTTATTACTGTCAGCAACACTATAGTACTCCGTACACGTTCGGAGGG

GGGACCACGCTGGAAATAAAAC.

Nucleic acid BLAST alignment shows that nucleic acid sequence encoding the VL domain of monoclonal antibody 13E2 has significant identity to the sequence of the following germline genes: IGKV6-17*01, IGKV6-25*01, IGKV6-23*01, IGKJ2*01, IGKJ2*03, IGKJ2*02.

Figure 11:
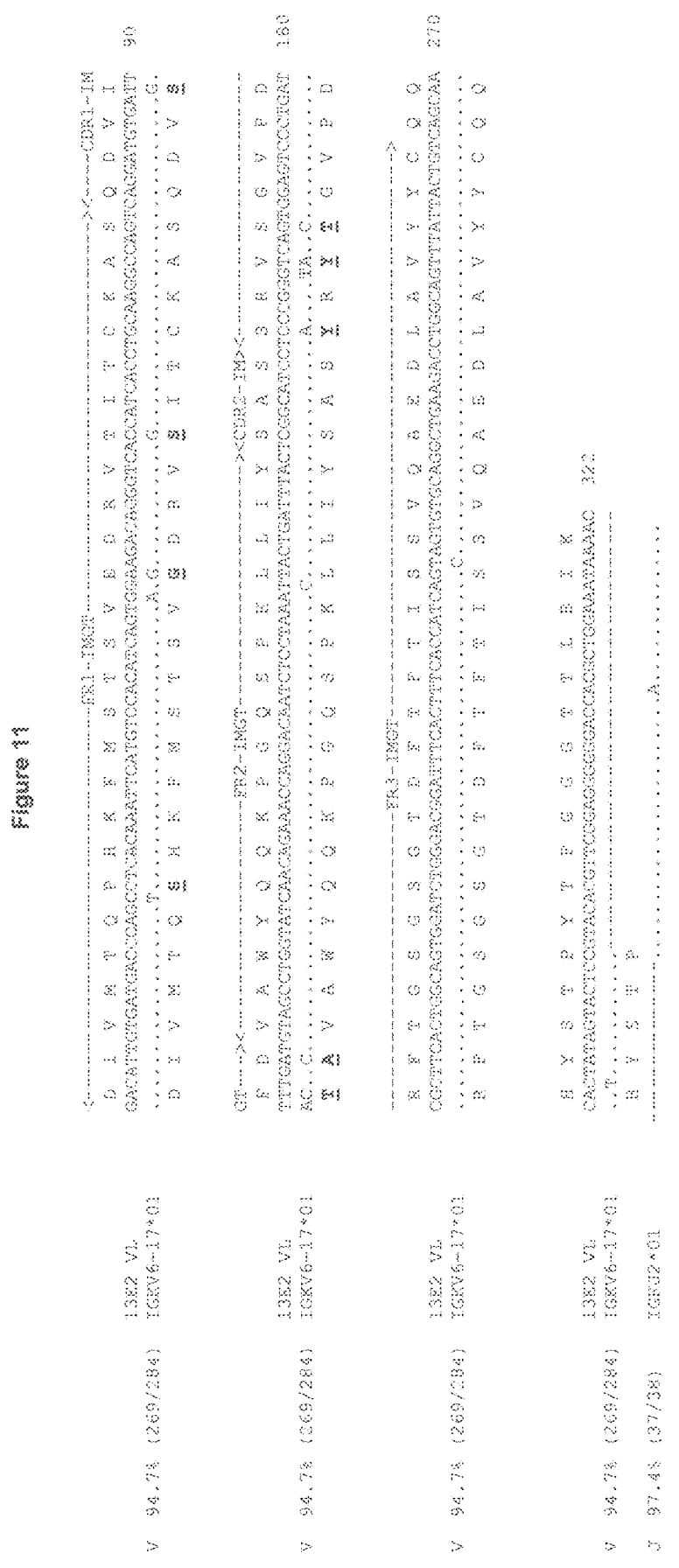

FIG. 11 shows an alignment of nucleic acid sequence encoding the VL domain of the 13E2 antibody with its top germline gene match. FIG. 11 shows that a portion comprising nucleotides 1-284 of the 13E2 VL region (which encompasses light chain framework regions FR1, FR2, and FR3) has 94.7% nucleic acid sequence identity with nucleic acid sequence of V gene IGKV6-17*01.

TABLE 6

Alignment summary between 13E2 VL and IGKV6-17*01

| | length | matches | mismatches | gaps | identity(%) |
|---|---|---|---|---|---|
| FR1-IMGT | 78 | 74 | 4 | 0 | 94.9 |
| CDR1-IMGT | 18 | 14 | 4 | 0 | 77.8 |
| FR2-IMGT | 51 | 50 | 1 | 0 | 98 |
| CDR2-IMGT | 9 | 9 | 0 | 0 | 100 |
| FR3-IMGT | 108 | 103 | 5 | 0 | 95.4 |
| CDR3-IMGT (germline) | 20 | 19 | 1 | 0 | 95 |
| Total | 284 | 269 | 15 | 0 | 94.7 |

EXAMPLE 4

Generation of 34F4 Anti-LAG-3 Monoclonal Antibody

4 Balb/c mice (referred to as mice nos. 1-4 below) were each immunised with four (mice nos. 2 and 4), or five (mice nos. 1 and 3) s.c. injections of 100 μg IMP321 (LAG-3Ig), clinical grade lot S017/LC1/041011 (termed "LC1" below), at Day 0, Day 14, Day 28, Day 43 and Day 70. An additional Balb/c mouse (referred to as mouse no. 5 below) was immunized with three s.c. injections of D1-D4 LAG-3.

Two weeks after the third injection, serum from each mouse was tested for anti-LAG-3 antibody content in an ELISA assay (as described in Example 1). The results are presented in Table 7 below:

TABLE 7

| Mouse No. | [Anti-LAG-3 Ab] μg/ml |
|---|---|
| 1 | 31 |
| 2 | 10 |
| 3 | 13 |
| 4 | 28 |
| 5 | 10 |

The ability of the serum from each mouse to inhibit binding of IMP321 to the Raji B cells was determined by FACS analysis (as described in Example 1).

As can be seen from Table 7, the antibody titres were low in all mice. None of the sera inhibited the binding of IMP321 to MHC class II$^+$ Raji B cells after three immunisations. No other bleeding was performed to test serum titres and inhibition capacity. The immunisation process was continued and mouse no. 3, which received five s.c. injections of LC1, was boosted with 10 μg of D1-D4 LAG-3 i.v. at Day 92.

Three days after the i.v. boost injection, 73 million splenocytes from mouse no. 3 were fused with 15 million Sp2/0 myeloma cells following the same procedure described in Example 1. The wells of 40 96-well plates were seeded with approximately 25,500 cells per well, and then cultured with supplementation of the culture medium with 10% BM Condimed Ht 2256 wells were screened by FACS analysis on LAG-3 expressing CHO cells (a yield of 59%). Two stable anti-LAG-3 hybridomas were selected, including 34F4 (see Table 8 below).

TABLE 8

| Fusion | N °17 |
|---|---|
| Splenocytes (millions) | 73 |
| Fusion characteristic | BM condimed H1, 25,000 cells/well |
| Number of wells to start with | 3840 |
| Number of wells with dividing cells that were screened | 2256 |
| Recovery | 59% |
| Number of stable anti LAG-3 hybridomas | 2 |

EXAMPLE 5

Amino Acid Sequence of Variable Region of Antibody 34F4

$V_H$ Amino Acid Sequence:

(SEQ ID NO: 17)
QVTLKESGPGILQPSQTLSLTCSFSGFSLNTSGMGVGWIRQPSGKGLEWL

THIWWDDVKRYNPALKSRLTISKDTSSSQVFLKIASVDTADTATYYCARI

EGDTYYDYYFDYWGQGVTLTVSS.

SEQ ID NO: 17 is the amino acid sequence of the heavy chain variable ($V_H$) domain of antibody 34F4. The Complementarity Determining Regions (CDRs), as determined by the IMGT numbering system (Lefranc, M.-P. et al., Nucleic Acids Research, 27, 209-212 (1999)), are underlined. The CDRs, as determined by the Kabat numbering system, are shown in bold.

Figure 6:
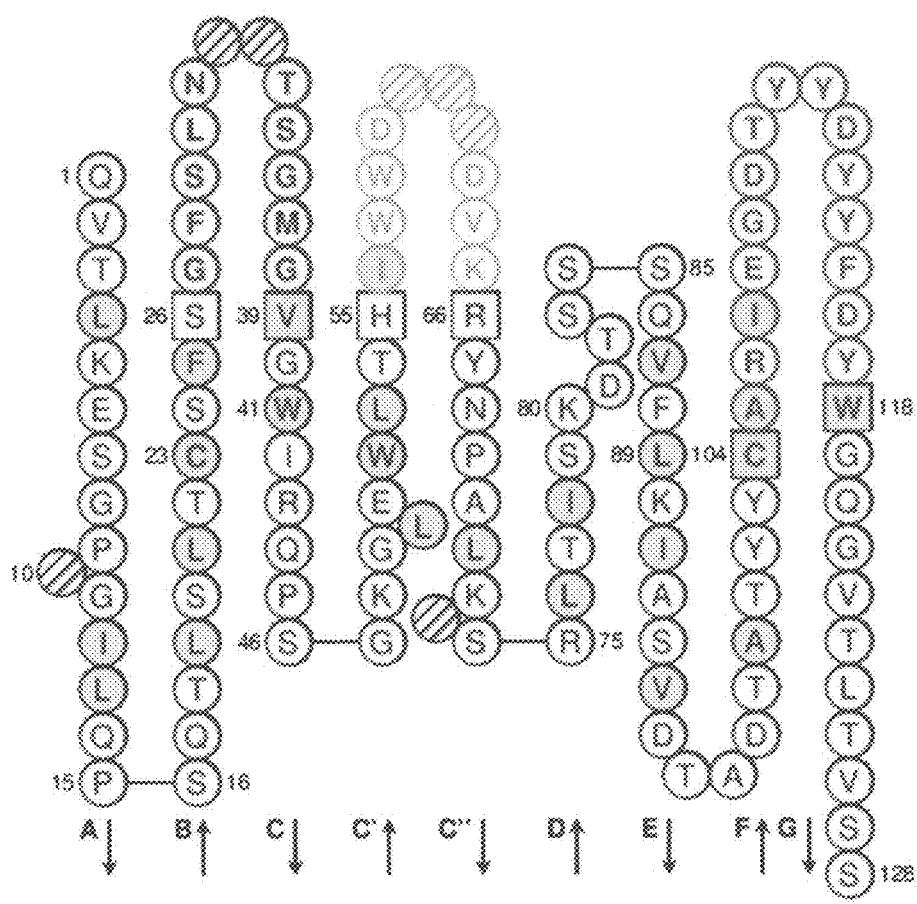

FIG. 6 shows a graphical representation of the V_H CDR loops of monoclonal antibody 34F4 (Lefranc, M.-P. et al., Dev. Comp. Immunol., 27, 55-77 (2003)). Shaded circles (residue nos. 4, 12, 13, 19, 21, 23, 25, 41, 50, 52, 53, 71, 76, 78, 87, 89, 91, 94, 100) are hydrophobic (non-polar) residues in frameworks 1-3 at sites that are hydrophobic in the majority of antibodies. Squares are key residues at the start and end of each CDR. Amino acid residue nos. 23, 41, 89, 104, 118 in the framework are structurally conserved amino acids.

V_L Amino Acid Sequence:
(SEQ ID NO: 18)
DIVMTQSHKLMSTSVGDGLSITCKASQDVSIAVVWYQQKPGQSPKLLIYS
ASFRYTGVPDRFTGSGSGTDFTFTISSVQAEDLAVYYCQQHYSIPWTFGG
GTKLEIK.

SEQ ID NO: 18 is the amino acid sequence of the light chain variable (V_L) domain of antibody 34F4. The Complementarity Determining Regions (CDRs), as determined by the IMGT numbering system (Lefranc, M.-P. et al., Nucleic Acids Research, 27, 209-212 (1999)), are underlined. The CDRs, as determined by the Kabat numbering system, are shown in bold.

ACACACATTTGGTGGGATGATGTCAAGCGCTATAATCCAGCCCTGAAGAG

CCGACTGACTATCTCCAAGGATACCTCCAGCAGCCAGGTATTCCTCAAGA

TCGCCAGTGTGGACACTGCAGATACTGCCACATACTACTGTGCTCGAATA

GAGGGGGATACTTACTACGACTATTACTTTGACTACTGGGGCCAAGGCGT

CACTCTCACAGTCTCCTCAG.

Nucleic acid BLAST alignment shows that nucleic acid sequence encoding the VH domain of monoclonal antibody 34F4 has significant identity to the sequence of the following germline genes: IGHV8-8*01, IGHV8-12*01, IGHV8-11*01, IGHD1-1*01, IGHD1-2*01, IGHD2-3*01, IGHJ2*01, IGHJ2*02, IGHJ2*03.

Figure 12:
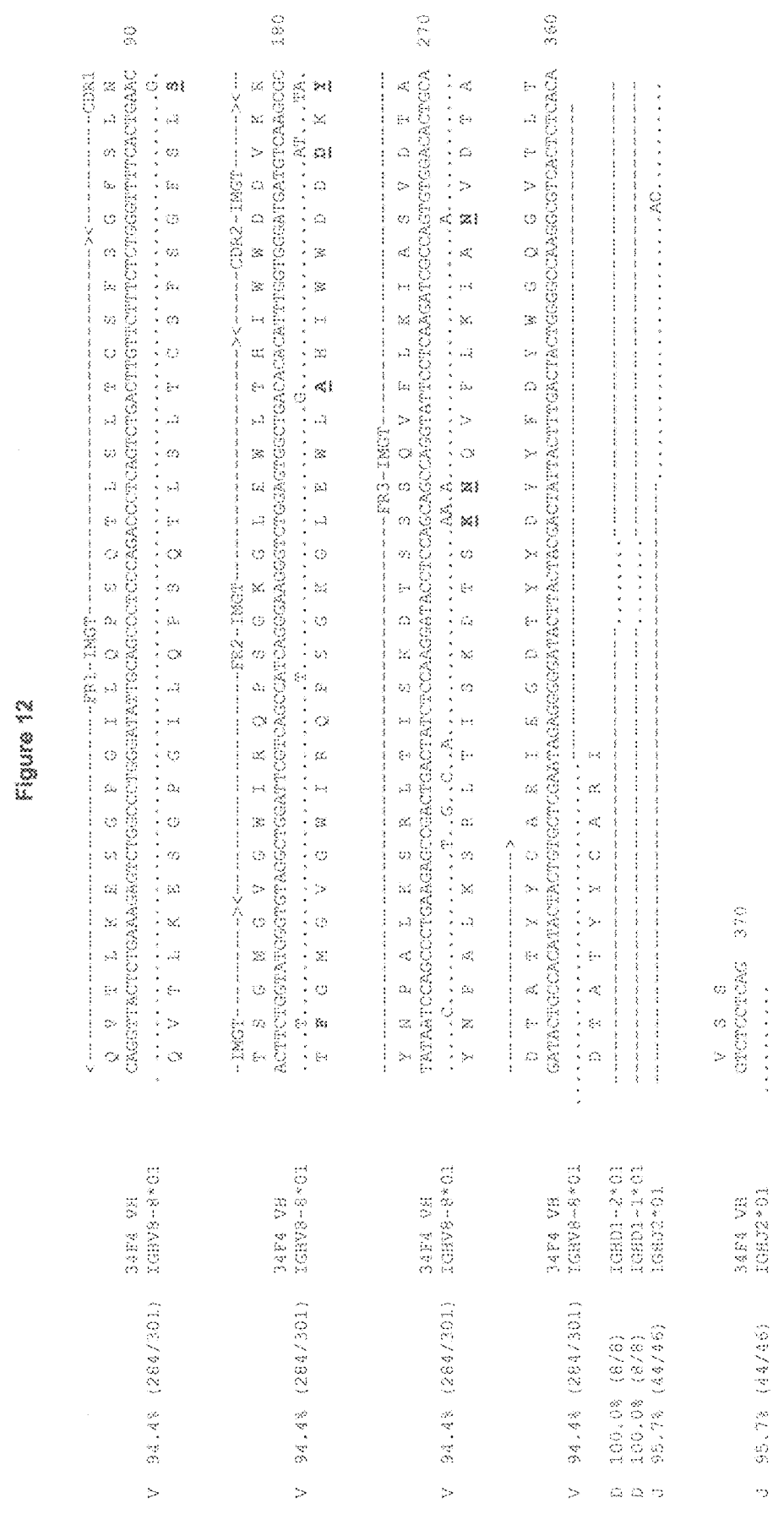

FIG. 12 shows an alignment of nucleic acid sequence encoding the VH domain of the 34F4 antibody with its top germline gene match. FIG. 12 shows that a portion comprising nucleotides 1-301 of the 34F4 VH region (which encompasses heavy chain framework regions FR1, FR2, and FR3) has 94.4% nucleic acid sequence identity with nucleic acid sequence of V gene IGHV8-8*01.

TABLE 9

34F4 VH and VL CDR Sequences

| Antibody | CDR-1 | CDR-2 | CDR-3 |
|---|---|---|---|
| 34F4 VH (IMGT numbering) | GFSLNTSGMG (SEQ ID NO: 11) | IWWDDVK (SEQ ID NO: 12) | ARIEGDTYYDYYFDY (SEQ ID NO: 13) |
| 34F4 VL (IMGT numbering) | QDVSIA (SEQ ID NO: 14) | SAS (SEQ ID NO: 15) | QQHYSIPWT (SEQ ID NO: 16) |
| 34F4 VH (Kabat numbering) | TSGMGVG (SEQ ID NO: 31) | HIWWDDVKRYNPALKS (SEQ ID NO: 32) | IEGDTYYDYYFDY (SEQ ID NO: 33) |
| 34F4 VL (Kabat numbering) | KASQDVSIAVV (SEQ ID NO: 34) | SASFRYT (SEQ ID NO: 35) | QQHYSIPWT (SEQ ID NO: 36) |

Figure 8:
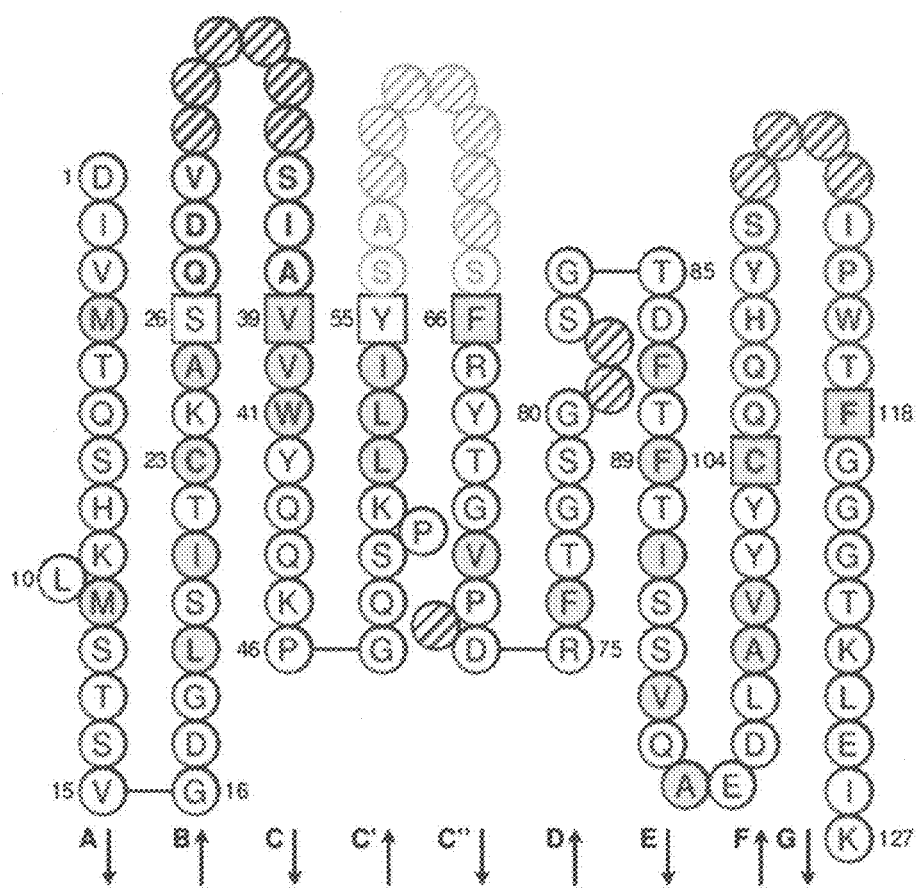

FIG. 8 shows a graphical representation of the V_L CDR loops of monoclonal antibody 34F4 (Lefranc, M.-P. et al., Dev. Comp. Immunol., 27, 55-77 (2003)). Shaded circles (residue nos. 4, 11, 19, 21, 23, 25, 40, 41, 52, 53, 54, 71, 76, 87, 89, 91, 94, 96, 100, 101) are hydrophobic (non-polar) residues in frameworks 1-3 at sites that are hydrophobic in the majority of antibodies. Squares are key residues at the start and end of each CDR. Amino acids residue nos. 23, 41, 89, 104, 118 in the framework are structurally conserved amino acids.

EXAMPLE 6

Nucleic Acid Sequence Encoding the Variable Domains of Antibody 34F4

Nucleic acid sequence encoding the VH domain of monoclonal antibody 34F4 is shown in FIG. 7, and below:

(SEQ ID NO: 19)
CAGGTTACTCTGAAAGAGTCTGGCCCTGGGATATTGCAGCCCTCCCAGAC

CCTCAGTCTGACTTGTTCTTTCTCTGGGTTTTCACTGAACACTTCTGGTA

TGGGTGTAGGCTGGATTCGTCAGCCATCAGGGAAGGGTCTGGAGTGGCTG

TABLE 10

Alignment summary between 34F4 VH and IGHV8-8*01

| | length | matches | mismatches | gaps | identity(%) |
|---|---|---|---|---|---|
| FR1-IMGT | 75 | 75 | 0 | 0 | 100 |
| CDR1-IMGT | 30 | 28 | 2 | 0 | 93.3 |
| FR2-IMGT | 51 | 49 | 2 | 0 | 96.1 |
| CDR2-IMGT | 21 | 19 | 2 | 0 | 90.5 |
| FR3-IMGT | 114 | 103 | 11 | 0 | 90.4 |
| CDR3-IMGT (germline) | 10 | 10 | 0 | 0 | 100 |
| Total | 301 | 284 | 17 | 0 | 94.4 |

Nucleic acid sequence encoding the VL domain of monoclonal antibody 34F4 is shown in FIG. 9, and below:

(SEQ ID NO: 20)
GACATTGTGATGACCCAGTCTCACAAACTCATGTCCACATCAGTTGGAGA

CGGGCTCAGCATCACCTGCAAGGCCAGTCAGGATGTGAGCATTGCTGTAG

TCTGGTATCAACAGAAACCAGGACAATCTCCTAAACTGCTGATTTACTCG

GCATCCTTCCGGTACACTGGAGTCCCTGATCGCTTCACTGGCAGTGGATC

-continued

TGGGACGGATTTCACTTTCACCATCAGCAGTGTGCAGGCTGAAGACCTGG

CAGTTTATTACTGTCAGCAACATTATAGTATTCCGTGGACGTTCGGTGGA

GGCACCAAGCTGGAAATCAAAC.

Nucleic acid BLAST alignment shows that nucleic acid sequence encoding the VL domain of monoclonal antibody 34F4 has significant identity to the sequence of the following germline genes: IGKV6-17*01, IGKV6-25*01, IGKV6-23*01, IGKJ1*01, IGKJ1*02, IGKJ2*01.

Figure 13:
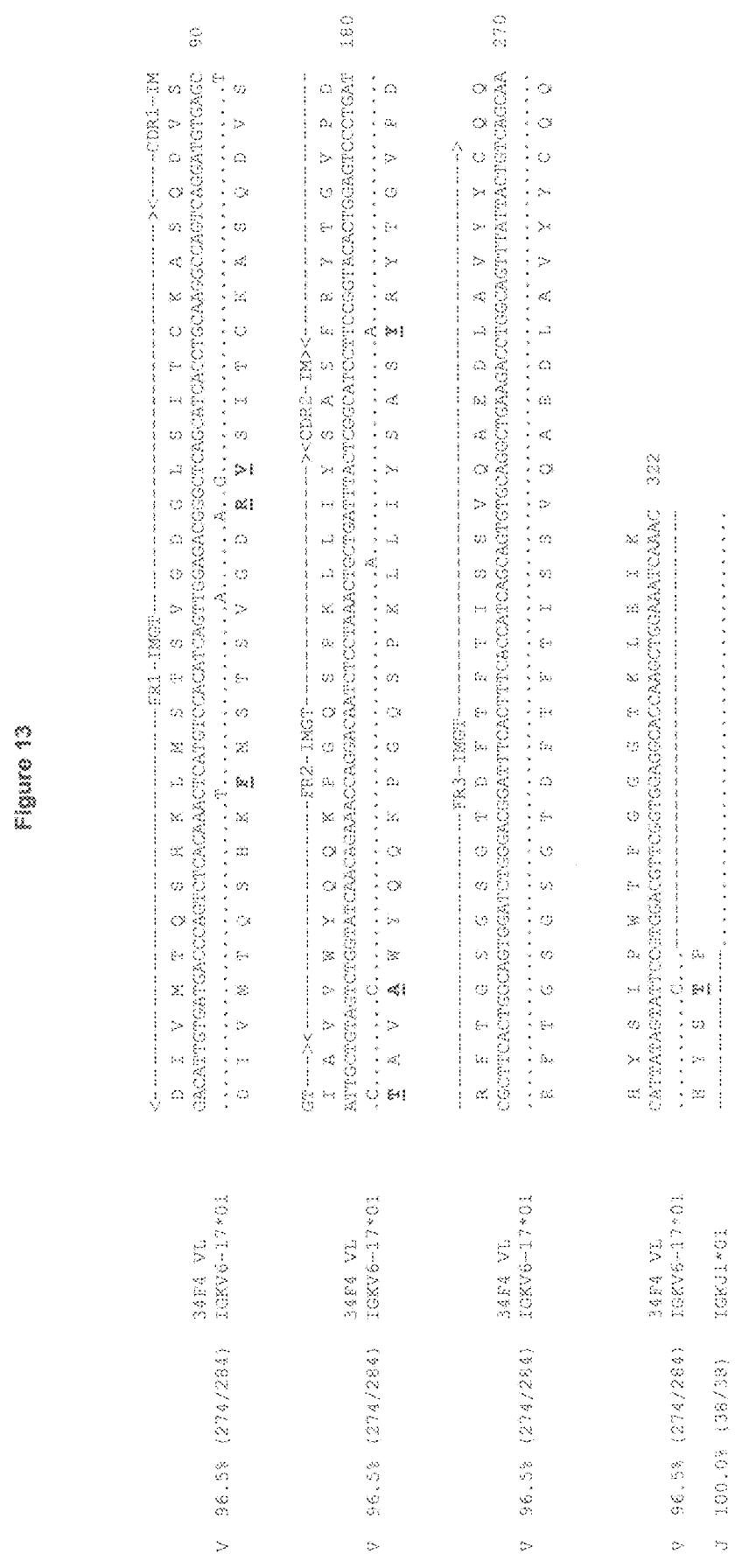

FIG. 13 shows an alignment of nucleic acid sequence encoding the VL domain of the 34F4 antibody with its top germline gene match. FIG. 13 shows that a portion comprising nucleotides 1-284 of the 34F4 VL region (which encompasses light chain framework regions FR1, FR2, and FR3) has 94.7% nucleic acid sequence identity with nucleic acid sequence of V gene IGKV6-17*01.

TABLE 11

Alignment summary between 34F4 VL and IGKV6-17*01

|  | length | matches | mismatches | gaps | identity(%) |
|---|---|---|---|---|---|
| FR1-IMGT | 78 | 74 | 4 | 0 | 94.9 |
| CDR1-IMGT | 18 | 16 | 2 | 0 | 88.9 |
| FR2-IMGT | 51 | 49 | 2 | 0 | 96.1 |
| CDR2-IMGT | 9 | 9 | 0 | 0 | 100 |
| FR3-IMGT | 108 | 107 | 1 | 0 | 99.1 |
| CDR3-IMGT (germline) | 20 | 19 | 1 | 0 | 95 |
| Total | 284 | 274 | 10 | 0 | 96.5 |

EXAMPLE 7

Binding of the Agonist 13E2 and 34F4 Monoclonal Antibodies to LAG-3+ Transfected, and Primary Cells, Compared to the 1764 Antagonist Monoclonal Antibody LAG-3+-transfected CHO cells, or SEB-stimulated PBMCs from a healthy donor were incubated with anti-LAG-3 monoclonal antibody, or an isotype control (mIgG1) for 30 minutes in PBS, BSA 0.5%, Azide 0.1% at 4° C. Cells were washed, and cell-bound antibody was revealed by a FITC-conjugated goat F(ab')2-anti-mouse Ig (H+L) (Coulter). The secondary antibody was washed away, and the CHO cells were directly analyzed by flow cytometry. The PBMCs were phenotyped using CD4-PE-Cy7 and CD8-APC-Cy7.

Binding to CHO LAG-3+ Cells

Figure 14:
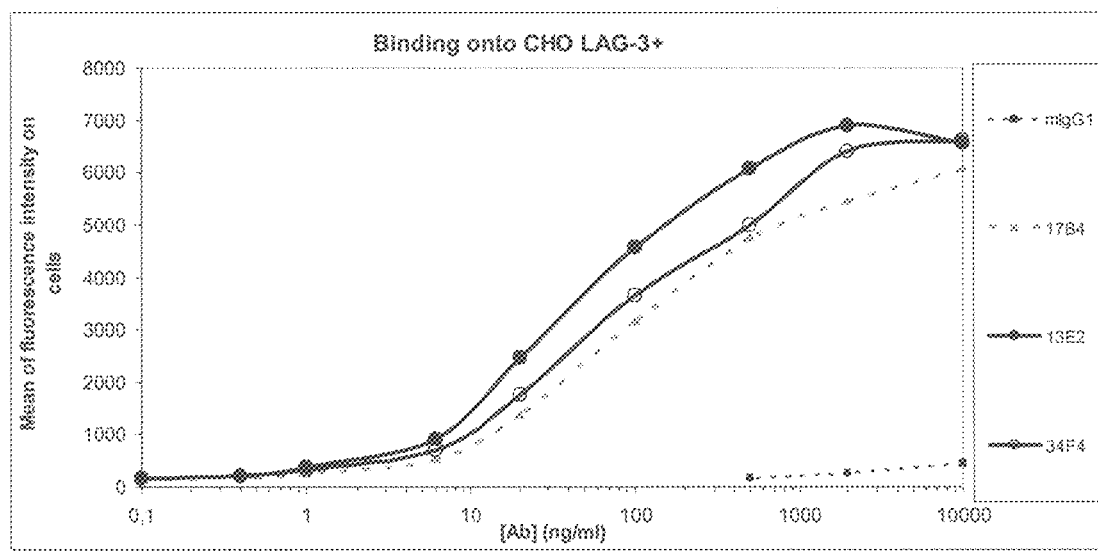
FIG. 14 shows the results of binding of different concentrations of agonistic anti-LAG-3 monoclonal antibodies 13E2 and 34F4, and antagonistic anti-LAG-3 monoclonal antibody 1764, to LAG-3-transfected Chinese hamster ovary (CHO) cells, compared to an isotype control antibody (mIgG1)

The results are presented as the mean of fluorescence intensity (MFI) of CHO cells transfected with human LAG-3-encoding plasmid as a function of antibody concentration. The results are shown in Table 12 below, and in FIG. 14.

TABLE 12

Binding to CHO LAG3+

| ng/ml | mIgG1 | 17B4 | 13E2 | 34F4 |
|---|---|---|---|---|
| 10000 | 440 | 6087 | 6578 | 6618 |
| 2000 | 251 | 5477 | 6904 | 6411 |
| 500 | 168 | 4759 | 6069 | 4988 |
| 100 | nd | 3170 | 4583 | 3653 |
| 20 | nd | 1378 | 2475 | 1763 |
| 6 | nd | 549 | 925 | 693 |
| 1 | nd | 247 | 379 | 329 |
| 0.4 | nd | 179 | 222 | 222 |
| 0 | 156 | 156 | 156 | 156 | nd = not determined

Based on the results in Table 12, the $EC_{50}$ value for binding of each antibody to LAG-3-expressing CHO cells is: 1764: 0.7 nM; 13E2: 0.3 nM; 34F4: 0.5 nM.

The mean $EC_{50}$ values from four independent experiments (data not shown) for binding of each antibody to LAG-3-expressing CHO cells is: 1764: 0.7 nM; 13E2: 0.4 nM; 34F4: 0.5 nM.

The mean, from the four independent experiments, of the 13E2 $EC_{50}$ value is 2.7 times the mean of the 1764 $EC_{50}$ value.

The mean, from the four independent experiments, of the 34F4 $EC_{50}$ value is 1.6 times the mean of the 1764 $EC_{50}$ value.

Binding to SEB-Stimulated PBMCs

The results are presented as the mean of fluorescence intensity on the CD4+ or CD8+ cells from PBMCs of a donor (Donor 1) stimulated for three days with 0.5 μg/ml SEB as a function of antibody concentration. The results for binding to CD4+ and CD8+ cells, for Donor 1, are shown in Table 13 below, and in FIG. 15.

TABLE 13

Binding on CD4 and CD8 (Donor 1)

| | CD4 | | | | | CD8 | | | |
|---|---|---|---|---|---|---|---|---|---|
| Antibody ng/ml | mIgG1 | 17B4 | 13E2 | 34F4 | ng/ml | mIgG1 | 17B4 | 13E2 | 34F4 |
| 10000 | 116 | 1598 | 1947 | 1787 | 10000 | 140 | 5142 | 5107 | 4719 |
| 2326 | 113 | 1944 | 1869 | 1662 | 2326 | 137 | 4826 | 4850 | 4455 |
| 541 | 116 | 1746 | 1601 | 1590 | 541 | 120 | 4092 | 4359 | 3867 |
| 126 | 109 | 1239 | 1491 | 1384 | 126 | 115 | 2837 | 3677 | 3302 |
| 29 | 108 | 675 | 1160 | 1139 | 29 | 110 | 1397 | 2432 | 2332 |
| 7 | 110 | 324 | 600 | 621 | 7 | 114 | 606 | 1131 | 1183 |
| 1.6 | 127 | 192 | 272 | 282 | 1.6 | 116 | 309 | 458 | 446 |
| 0.4 | 106 | 143 | 165 | 169 | 0.4 | 112 | 195 | 232 | 288 |
| 0 | 106 | 106 | 106 | 106 | 0 | 112 | 112 | 112 | 112 |

Based on the results given in Table 13, the $EC_{50}$ value for binding of each antibody to CD4+ cells is: 1764: 0.5 nM; 13E2: 0.1 nM; 34F4: 0.1 nM.

The mean $EC_{50}$ value from three donors (data not shown) for binding of each antibody to CD4+ cells is: 1764: 0.8 nM; 13E2: 0.2 nM; 34F4: 0.2 nM.

The mean of the 13E2 and 34F4 CD4+ $EC_{50}$ values from the three donors is 3.8 times the mean of the 1764 $EC_{50}$ value.

Based on the results given in Table 13, the EC50 value for binding of each antibody to CD8+ cells is: 1764: 0.7 nM; 13E2: 0.3 nM; 34F4: 0.2 nM.

The mean $EC_{50}$ value from three donors (data not shown) for binding of each antibody to CD8+ cells is: 1764: 1 nM; 13E2: 0.4 nM; 34F4: 0.5 nM.

The mean of the 13E2 and 34F4 CD8+$EC_{50}$ values from the three donors is 2.5 times the mean of the 1764 $EC_{50}$ value.

The results show that the 13E2 and 34F4 monoclonal antibodies each bind to CHO cells expressing LAG-3+, and to CD4+-T cells and CD8+-T cells, with a higher affinity than 1764.

Biacore analysis with LAG-3Ig on the chip and 1764 antibody in the running buffer gave the following results:

| | |
|---|---|
| ka (1/Ms) | $1.09 \times 10^6$ |
| kd (1/s) | $1.32 \times 10^{-4}$ |
| KD (M) | $1.21 \times 10^{-10}$ |

Biacore analysis with 1764 antibody on the chip and LAG-3Ig in the running buffer gave the following results:

| | |
|---|---|
| ka (1/Ms) | $2.22 \times 10^5$ |
| kd (1/s) | $8.18 \times 10^{-4}$ |
| KA (1/M) | $2.71 \times 10^8$ |
| KD (M) | $3.69 \times 10^{-9}$ |

EXAMPLE 8

Inhibition of Binding of IMP321 (LAG-3IG) to MHC Class II-Positive Cells by 13E2 and 34F4

Binding of an IMP321 conjugate (LAG-3Ig-Alexa 488) to MHC class II-positive B cells (Raji cells) was determined following pre-incubation of the conjugate (1 pg/ml at 4° C.) with an anti-LAG-3 monoclonal antibody (13E2, 34F4, or 1764), or an isotype control (mIgG1). Analysis of cell-bound fluorescence was carried out using fluorescence-activated cell sorting (FACS).

The mean fluorescence intensity (MFI) corresponding to the cell-bound LAG-3Ig as a function of antibody concentration is shown in Table 14 below, and in FIG. 16A.

TABLE 14

| MFI of sLAG-3Ig-Alexa 488 | | | | | |
|---|---|---|---|---|---|
| Antibody (ng/ml) | mIgG1 | 17B4 | 13E2 | 34F4 | Ratio Ab:IMP321-Alexa (1 µg/ml) |
| 11000 | 328 | −11 | −2 | −7 | 10:1 |
| 3300 | 359 | 13 | 20 | 18 | 3:1 |
| 990 | 361 | 35 | 37 | 35 | 1:1 |
| 297 | 373 | 73 | 51 | 46 | 0.3:1 |
| 89 | 324 | 214 | 179 | 185 | 0.1:1 |
| 27 | 254 | 260 | 207 | 258 | 0.03:1 |
| 0 | 284 | 284 | 284 | 284 | |

The results show that binding of IMP321 to Raji cells was inhibited by pre-incubation with each of the LAG-3-specific monoclonal antibodies.

EXAMPLE 9

Inhibition of IMP321 (LAG-3Ig)-Induced Monocyte Activation by 13E2 and 34F4

IMP321 (20 ng/ml) was preincubated with anti-LAG-3 monoclonal antibody 13E2, 34F4, or 17B4, or an isotype control (mIgG1), for 5 minutes at 37° C., before incubation of the mixture with THP-1 cells for 4 hours at 37° C. The amount of CCL4 secretion by the THP-1 cells was used to determine the level of monocyte activation.

The CCL4 concentration (expressed in pg/ml) as a function of Ab concentration is shown in Table 15 below, and in FIG. 16B.

TABLE 15

| Read-out [CCL4] in THP-1 monocytic cells supernatant (pg/ml) | | | | | |
|---|---|---|---|---|---|
| Antibody (ng/ml) | mIgG1 | 17B4 | 13E2 | 34F4 | Ratio Ab:IMP321 (20 ng/ml) |
| 20000 | 2901 | 860 | 97 | 130 | 1000:1 |
| 2000 | 2261 | 947 | 77 | 111 | 100:1 |
| 200 | 2222 | 860 | 94 | 135 | 10:1 |
| 20 | 2145 | 1548 | 224 | 338 | 1:1 |
| 2 | 2052 | 1963 | 1661 | 1798 | 0.10:1 |
| 0 | 2112 | 2112 | 2112 | 2112 | |

The results show that IMP321-induced monocyte activation is inhibited by pre-incubation of IMP321 with the antagonist anti-LAG-3 monoclonal antibody 17B4, and also by pre-incubation with the agonist monoclonal antibodies 13E2 and 34F4.

It was concluded from these results, and from the results in Example 8, that the agonist monoclonal antibodies 13E2 and 34F4, like the antagonist 17B4 monoclonal antibody, interact with or close to the MHC class II binding site of LAG-3, as shown by their ability to block the binding and the activity of LAG-3Ig (IMP321).

EXAMPLE 10

Inhibition of T Cell Proliferation by 13E2 and 34F4 Compared to 17E34

PBMCs from 3 healthy donors ($0.2 \times 10^6$ cells/well, at $1 \times 10^6$/ml in complete RPMI+10% FBS) were labelled with Carboxyfluorescein succinimidyl ester (CFSE) and incubated with a pool of peptides covering the sequence of CMV pp35 in the presence of monoclonal anti-LAG-3 antibody 13E2, 34F4, 1764, or an isotype control (mIgG1) (supraoptimal dose, 300 ng/ml for donor #1 and #2, 100 ng/ml for donor #3).

The T cell response was investigated by measuring the CFSE-based proliferation of CD4+ or CD8+ T cells on day 5. The FACS profiles of the CD8+ T cells of donor #1 in the presence of each different antibody, as well as the gating strategy, are shown in FIG. 17(A). FIG. 17(B) shows the percentage of CD8+ T cells under each division peak, as a function of cell division, for the same donor. The results for the 3 donors are shown in Table 16 below. The baseline proliferation without antigenic peptides (No stim) was also measured (see FIG. 17(A) lowest panel and Table 16). The CD4+ T cells of donor #1 did not display any CMV-specific proliferation, so the results for this population are not included.

TABLE 16

Percentage of CD4+ and CD8+ T cells under each division peak

| Division No. | 1 | 2 | 3 | 4 | 5 | 6 | 7 |
|---|---|---|---|---|---|---|---|
| Donor #1 CD8+ | | | | | | | |
| mIgG1 | 0.68 | 0.54 | 1.28 | 2.20 | 1.50 | 1.22 | 0.78 |
| 17B4 | 0.84 | 1.02 | 1.81 | 2.82 | 2.22 | 2.10 | 1.51 |
| 13E2 | 1.02 | 0.41 | 0.61 | 0.67 | 0.39 | 0.36 | 0.31 |
| 34F4 | 1.16 | 0.68 | 1.32 | 1.22 | 0.66 | 0.52 | 0.27 |
| No Stim | 1.77 | 0.36 | 0.33 | 0.52 | 0.38 | 0.13 | 0.04 |
| Donor #2 CD4+ | | | | | | | |
| mIgG1 | 1.90 | 2.26 | 2.67 | 1.84 | 0.78 | 0.20 | 0.18 |
| 17B4 | 1.87 | 2.44 | 2.47 | 1.72 | 0.69 | 0.17 | 0.14 |
| 13E2 | 1.72 | 1.89 | 2.04 | 1.35 | 0.64 | 0.21 | 0.16 |
| 34F4 | 1.61 | 1.88 | 2.01 | 1.34 | 0.60 | 0.16 | 0.15 |
| No Stim | 1.34 | 1.14 | 1.48 | 0.81 | 0.41 | 0.17 | 0.12 |
| Donor #2 CD8+ | | | | | | | |
| mIgG1 | 1.24 | 1.72 | 2.54 | 3.37 | 1.28 | 0.37 | 0.24 |
| 17B4 | 1.24 | 1.79 | 2.57 | 3.30 | 1.13 | 0.37 | 0.17 |
| 13E2 | 1.27 | 1.35 | 1.83 | 2.14 | 0.75 | 0.22 | 0.14 |
| 34F4 | 1.25 | 1.47 | 1.95 | 2.17 | 0.86 | 0.25 | 0.23 |
| No Stim | 0.77 | 0.92 | 1.03 | 1.22 | 0.33 | 0.22 | 0.10 |
| Donor #3 CD4+ | | | | | | | |
| mIgG1 | 2.93 | 2.85 | 4.32 | 8.18 | 5.03 | 2.1 | |
| 17B4 | 2.95 | 2.8 | 4.51 | 9.9 | 6.71 | 2.81 | |
| 13E2 | 3.42 | 2.62 | 3.01 | 4.66 | 2.53 | 1.07 | |
| No Stim | 2.77 | 2.07 | 2.79 | 3.71 | 1.71 | 0.5 | |
| Donor #3 CD8+ | | | | | | | |
| mIgG1 | 4.62 | 1.3 | 1.41 | 4.26 | 4.64 | 2.6 | |
| 17B4 | 4.74 | 1.63 | 1.56 | 4.24 | 4.56 | 2.67 | |
| 13E2 | 5.1 | 1.56 | 1.24 | 2.81 | 1.9 | 0.97 | |
| No Stim | 4.04 | 0.44 | 0.37 | 0.38 | 0.11 | 0.07 | |

The Proliferation Index (PI) (calculated as the sum of: the percentage of CD4+ or CD8+ T cells under each division peak, multiplied by the division number) is provided in Table 17. This index emphasises the percentages for cells which have experienced several rounds of division. Table 17 also records the percentage inhibition for each antibody compared with the isotype control (mIgG1) based on the PI values.

TABLE 17

Effect of antibodies 13E2 and 34F4 on CD4+ and CD8+ T cell proliferation compared to 17B4

| Donor No. | Antibody | PI (CD4) | % inhibition (CD4) | PI (CD8) | % inhibition (CD8) |
|---|---|---|---|---|---|
| 1 | mIgG1 | | | 34.64 | |
| | 17B4 | | | 53.80 | −55 |
| | 13E2 | | | 12.60 | 64 |
| | 34F4 | | | 19.65 | 43 |
| | No Stim | | | 8.54 | |
| 2 | mIgG1 | 28.16 | | 36.09 | |
| | 17B4 | 26.52 | 6 | 34.77 | 4 |
| | 13E2 | 22.59 | 20 | 24.09 | 33 |

TABLE 17-continued

Effect of antibodies 13E2 and 34F4 on CD4+ and CD8+ T cell proliferation compared to 17B4

| Donor No. | Antibody | PI (CD4) | % inhibition (CD4) | PI (CD8) | % inhibition (CD8) |
|---|---|---|---|---|---|
| | 34F4 | 21.76 | 23 | 26.13 | 28 |
| | No Stim | 15.20 | | 14.25 | |
| 3 | mIgG1 | 92.06 | | 67.29 | |
| | 17B4 | 112.09 | −22 | 68.46 | −2 |
| | 13E2 | 55.40 | 40 | 38.50 | 43 |
| | No Stim | 41.67 | | 8.52 | |

The results show that monoclonal antibodies 13E2 and 34F4 consistently inhibit the proliferation of CD4+ and CD8+ T cells induced by antigenic peptides, while monoclonal antibody 17B4 tends to have a minor positive effect at the tested concentration.

EXAMPLE 11

Inhibition of T Cell Proliferation by 13E2 and 34F4

PBMCs from 12 healthy donors (0.2×10⁶ cells/well, at 1×10⁶/ml in complete RPMI+10% FBS) were labelled with CFSE and incubated with a pool of peptides covering the sequence of CMV pp35 in the presence of monoclonal anti-LAG-3 antibody 13E2, 34F4, or an isotype control (mIgG1).

The T cell response was investigated by measuring the CFSE-based proliferation of CD4+ or CD8+ T cells on day 5. The percentage of CD4+ or CD8+ T cells under each division peak was calculated as a function of cell division, using the gating strategy illustrated in FIG. 17(A). The baseline proliferation without antigenic peptides (No stim) was also measured. The CD4+ T cells of donors #1, #5, and #12 did not display any CMV-specific proliferation, so the results for these samples are not included.

The Proliferation Index (PI) (calculated as the sum of: the percentage of CD4+ or CD8+ T cells under each division peak, multiplied by the division number) for each donor is provided in Table 18, and the results are plotted in FIG. 18. Table 18 also records the percentage inhibition for each antibody compared with the isotype control (mIgG1) based on the PI values.

TABLE 18

Effect of antibodies 13E2 and 34F4 on CD4+ and CD8+ T cell proliferation

| Donor No. | Antibody | PI (CD4) | % Inhibition (CD4) | PI (CD8) | % Inhibition (CD8) |
|---|---|---|---|---|---|
| 1 | mIgG1 | | | 34.64 | |
| | 13E2 | | | 12.60 | 64 |
| | 34F4 | | | 19.65 | 43 |
| | No Stim | | | 8.54 | |
| 2 | mIgG1 | 28.16 | | 36.09 | |
| | 13E2 | 22.59 | 20 | 24.09 | 33 |
| | 34F4 | 21.76 | 23 | 26.13 | 28 |
| | No Stim | 15.20 | | 14.25 | |
| 3 | mIgG1 | 92.06 | | 67.29 | |
| | 13E2 | 55.40 | 40 | 38.50 | 43 |
| | No Stim | 41.67 | | 8.52 | |
| 4 | mIgG1 | 10.10 | | 43.05 | |
| | 13E2 | 8.83 | 13 | 19.27 | 55 |
| | 34F4 | 9.39 | 7 | 19.32 | 55 |
| | No Stim | 6.14 | | 3.26 | |
| 5 | mIgG1 | | | 11.01 | |
| | 13E2 | | | 7.00 | 36 |

TABLE 18-continued

Effect of antibodies 13E2 and 34F4 on CD4+ and CD8+ T cell proliferation

| Donor No. | Antibody | PI (CD4) | % Inhibition (CD4) | PI (CD8) | % Inhibition (CD8) |
|---|---|---|---|---|---|
|  | 34F4 |  |  | 6.71 | 39 |
|  | No Stim |  |  | 3.08 |  |
| 6 | mIgG1 | 14.56 |  | 78.19 |  |
|  | 13E2 | 6.30 | 57 | 15.56 | 80 |
|  | 34F4 | 6.14 | 58 | 17.01 | 78 |
| 7 | mIgG1 | 36.25 |  | 31.62 |  |
|  | 13E2 | 18.90 | 48 | 12.95 | 59 |
|  | 34F4 | 32.00 | 12 | 21.99 | 30 |
|  | No Stim | 29.59 |  | 15.53 |  |
| 8 | mIgG1 | 6.20 |  | 10.96 |  |
|  | 13E2 | 4.32 | 30 | 6.77 | 38 |
|  | No Stim | 2.60 |  | 4.48 |  |
| 9 | mIgG1 | 7.60 |  | 10.44 |  |
|  | 13E2 | 4.63 | 39 | 6.57 | 37 |
|  | No Stim | 1.28 |  | 1.57 |  |
| 10 | mIgG1 | 15.80 |  | 75.10 |  |
|  | 34F4 | 11.70 | 26 | 25.50 | 66 |
|  | No Stim | 17.00 |  | 6.60 |  |
| 11 | mIgG1 | 15.19 |  | 19.14 |  |
|  | 13E2 | 5.51 | 64 | 12.77 | 33 |
|  | 34F4 | 4.96 | 67 | 1.73 | 91 |
| 12 | mIgG1 |  |  | 20.69 |  |
|  | 13E2 |  |  | 10.71 | 48 |
|  | No Stim |  |  | 10.71 |  |

Donor # 1, 2, 4, 5, 6, 7, 8, 9: 300 ng/ml; Donor # 3: 100 ng/ml; Donor # 10, 11, 12: 1000 ng/ml The mean values from these results are set out in Table 19.

TABLE 19

Effect of antibodies 13E2 and 34F4 on CD4+ and CD8+ T cell proliferation (donor averages)

| Mean of percentage inhibition | Mean of 11 donors tested with 13E2 | Mean of 8 donors tested with 34F4 | Mean of 7 donors tested with both antibodies 13E2 | Mean of 7 donors tested with both antibodies 34F4 |
|---|---|---|---|---|
| CD4 | 39% | 36% | 40% | 33% |
| CD8 | 48% | 55% | 52% | 52% |

The results show that monoclonal anti-LAG-3 antibodies 13E2 and 34F4 inhibit the proliferation of CD4+ and CD8+ T cells induced by antigenic peptides. The results suggest that the inhibitory effect of each antibody may be more pronounced for CD8+ T cells than for CD4+ T cells. In most of the donors tested, the effects of the 13E2 and 34F4 antibodies were very similar, so the antibodies appear to have comparable activity.

EXAMPLE 12

Dose-Response of Agonist Antibody on CD8+ T Cell Proliferation

CFSE-labelled PBMCs were stimulated by CMV peptide, as described above, in the presence of various concentrations of agonist anti-LAG-3 monoclonal antibody 13E2, 34F4, or an isotype control (mIgG1).

The T cell response was investigated by measuring CFSE-based proliferation of CD8+ T cells on day 5. The Proliferation Index (calculated as the sum of the percentage of CD8+ T cells under each division peak, multiplied by the division number) is provided in Table 20.

TABLE 20

Effect of 13E2 and 34F4 antibodies on CD8+ T cell proliferation

| Antibody (30 ng/ml) | Proliferation Index |
|---|---|
| mIgG1 | 69.9 |
| 13E2 | 26.2 |
| 34F4 | 16.4 |
| None | 95.3 |

Table 21 below records the CD8+ T cell Proliferation Index as a function of antibody concentration. The results in Table 21 are plotted in FIG. 19.

TABLE 21

Effect of different concentrations of antibody on CD8+ T cell proliferation

| Antibody concentration (ng/ml) | CD8+ T cell Proliferation Index | | |
|---|---|---|---|
|  | mIgG1 | 13E2 | 34F4 |
| 3000 | 82.9 | 17.6 | 14.9 |
| 952 | 72.9 | 13.7 | 10.5 |
| 302 | 69.9 | 16.4 | 26.2 |
| 96 | 65.3 | 19.6 | 13.7 |
| 30 | 87.4 | 14.4 | 22.8 |
| 10 | 78.2 | 50.4 | 46.2 |
| 3 | 77.8 | 59.2 | 66.6 |
| 0 | 95.3 | 95.3 | 95.3 |

The results show that a dose as low as 30 ng/ml of monoclonal anti-LAG-3 antibody 13E2, or 34F4, causes maximal inhibition of CD8+ T cell proliferation. The results also show that the effects of the antibodies were very similar.

EXAMPLE 13

Inhibition of CD8+ T Cell Proliferation by 34F4 is Reversed by Preincubation with IMP321

CFSE-labelled PBMCs from 2 donors were stimulated by CMV peptide, as described above, in the presence of various concentrations of 34F4 antibody. The 1 μg/ml dose of 34F4 was also assessed after neutralisation with a 10-fold excess of IMP321.

The T cell response was investigated by measuring the CFSE-based proliferation of CD8+ T cells on day 5. The percentage of inhibition of the proliferation of CD8+ T cells was calculated based on the percentage of dividing cells observed in the presence of 34F4 antibody, or 34F4 antibody and IMP321 (LAG-3Ig), compared to a control with or without IMP321.

The results are shown in Table 22 below.

TABLE 22

Effect of IMP321 on inhibition of CD8+ T cell proliferation by 34F4 antibody

| Incubation condition | Donor #1 Antibody concentration | | | Donor #2 Antibody concentration | | |
|---|---|---|---|---|---|---|
| | 1000 ng/ml | 100 ng/ml | 10 ng/ml | 1000 ng/ml | 100 ng/ml | 10 ng/ml |
| 34F4 | 64% | 68% | 44% | 65% | 35% | 41% |
| 34F4 + IMP321 | 0% | nd | nd | 41% | nd | nd |

The results show that pre-incubation of 34F4 antibody with IMP321 reverses the inhibitory effect of 34F4 antibody on proliferation of CD8+ T cells. This shows that the inhibition of CD8+ T cell proliferation mediated by 34F4 is dependent on binding of 34F4 antibody to LAG-3.

EXAMPLE 14

Inhibition of CD8+ T Cell Proliferation by 13E2 and 34F4 is not Reversed by IL-2

CFSE-labelled PBMCs were stimulated by CMV peptides, as described above, in the presence of 13E2 or 34F4 antibody, with or without IL-2.

The T cell response was investigated by measuring the CFSE-based proliferation of CD8+ T cells on day 5. The percentage of inhibition of the proliferation of CD8+ T cells was calculated based of the percentage of dividing cells observed in the presence of 13E2 or 34F4 antibody, with or without or IL-2, compared to an isotype control with or without IL-2.

The results are shown in Table 23 below.

TABLE 23

Effect of IL-2 on inhibition of CD8+ T cell proliferation by 13E2 and 34F4 antibody

| | Percentage of inhibition of CD8+ T cell proliferation | |
|---|---|---|
| Antibody | Without IL-2 | With IL-2 |
| 13E2 | 38% | 44% |
| 34F4 | 59% | 64% |

The results show that the addition of exogenous IL-2 was not able to overcome the inhibitory effect of 13E2 or 34F4 antibody on proliferation of CD8+ T cells. It is concluded from these results that antibodies 13E2 and 34F4 each directly inhibit signal 1 (response to the CMV antigen, a T-cell receptor dependent pathway) but not signal 2 (response to IL-2, that is help from CD4 cells) in CD8+ T cells.

EXAMPLE 15

Effect of 13E2 on T Cell Activation Marker Secretion

Peripheral blood mononuclear cells (PBMCs) include lymphocytes (T cells, B cells, and NK cells), monocytes, and dendritic cells. IFN-γ is predominantly secreted by activated CD4+ and CD8+ memory and effector T cells and by NK cells upon activation. After re-stimulation with specific antigen in vitro, secretion of IFN-γ is induced.

PBMCs from four healthy donors (0.2×10⁶ cells/well, at 1×10⁶/ml in complete RPMI+10% FBS) were labelled with CFSE, and incubated with a pool of peptides covering the sequence of CMV pp35 in the presence of monoclonal anti-LAG-3 antibody 13E2 or an isotype control (mIgG1). The T cell response was investigated by measuring the release of IFN-γ in cell supernatant on day 2. The concentration of IFN-γ, and the percentage inhibition of IFN-γ secretion by 13E2, is presented in Table 24 below.

TABLE 24

| Donor | Agonist/ Control | [IFN] (pg/ml) |
|---|---|---|
| Donor 1 | mIgG1 | 297 |
| | 13E2 | 226 |
| | % Inhibition | 24% |
| Donor 2 | mIgG1 | 1043 |
| | 13E2 | 255 |
| | % Inhibition | 76% |
| Donor 3 | mIgG1 | 499 |
| | 13E2 | 91 |
| | % Inhibition | 82% |
| Donor 4 | mIgG1 | 1151 |
| | 13E2 | 75 |
| | % Inhibition | 93% |

The results show that monoclonal antibody 13E2 inhibited the secretion of IFN-γ in each of the donors tested. This provides evidence that monoclonal antibody 13E2 inhibits activation of T cells.

EXAMPLE 16

Effect of 13E2 and 34F4 on T Cell Activation Marker Expression

PBMCs from four healthy donors (0.2×10⁶ cells/well, at 1×10⁶/ml in complete RPMI+10% FBS) were labelled with CFSE, and incubated with a pool of peptides covering the sequence of CMV pp35 in the presence of monoclonal anti-LAG-3 antibody 13E2 or 34F4, or an isotype control (mIgG1).

The T cell response was investigated by measuring the expression of CD25, as an activation marker, on CD8+ T cells on day 5. The percentage of CD8+ T cells expressing CD25, as well as the percentage inhibition of CD25 expression by 13E2 or 34F4, is presented in Table 25 below.

TABLE 25

| Donor | Agonist/ Control | % CD25+ in CD8+ T cells |
|---|---|---|
| Donor 1 | mIgG1 | 3.5 |
| | 13E2 | 1.2 |
| | % Inhibition | 66% |
| Donor 2 | mIgG1 | 6.6 |
| | 13E2 | 5 |
| | % Inhibition | 24% |
| Donor 3 | mIgG1 | 27.5 |
| | 34F4 | 8.8 |
| | % Inhibition | 68% |

TABLE 25-continued

| Donor | Agonist/Control | % CD25+ in CD8+ T cells |
|---|---|---|
| Donor 4 | mIgG1 | 9.2 |
| | 34F4 | 7.0 |
| | % Inhibition | 24% |

The results show that each monoclonal antibody, 13E2 and 34F4, significantly inhibited the expression of CD25 on CD8+ T cells. This provides evidence that each antibody inhibits activation of CD8+ T cells.

EXAMPLE 17

Chimeric 13E2-Human Antibody Sequences

Nucleotide sequences encoding the murine variable region of the 13E2 heavy and light chains were fused to sequences encoding the constant region of the human IgG4 heavy and Kappa light chains, respectively. These synthetic chimeric sequences were subcloned into an expression vector, and expressed in CHO cells grown in suspension.

The heavy chain amino acid sequence of a chimeric 13E2-human IgG4 Fc antibody is shown below, and in FIG. 20(A). The antibody comprises the $V_H$ domain of mouse monoclonal antibody 13E2, and a human IgG4 Fc portion with an S228P mutation (to abolish Fab arm exchange) (13E2IgG4mut). In the figure, the $V_H$ region is shown in bold, and the Fc region is shown highlighted.

```
13E2IgG4mut
                                           (SEQ ID NO: 30)
MGWTLVFLFLLSVTAGVHSQVTLKESGPGILQPSQTLSLTCSFSGFSLST
SGMGLGWIRQPSGKGLEWLTHIWWDDIKRYNPDLRSRLTISKDTSSSQIF
LKIASVDTADTATYYCARIVEGSYSSSYFDVWGAGTTVTVSSASTKGPSV
FPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVM
HEALHNHYTQKSLSLSLGK
```

The light chain amino acid sequence of a chimeric 13E2-human IgK antibody is shown below, and in FIG. 20(B). The antibody comprises the $V_L$ domain of monoclonal antibody 13E2, and a wild-type human Ig kappa (IgK) chain C portion (13E2IgK). In the figure, the $V_L$ region is shown in bold, and the IgK region is shown highlighted.

```
13E2IgK
                                           (SEQ ID NO: 37)
MVSSAQFLGLLLLCFQGTRCDIVMTQPHKFMSTSVEDRVTITCKASQDVI
FDVAWYQQKPGQSPKLLIYSASSRVSGVPDRFTGSGSGTDFTFTISSVQA
EDLAVYYCQQHYSTPYTFGGGTTLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC
```

A chimeric 13E2-human antibody (referred to as Chim13E2IgG4) comprises the chimeric heavy and light chains: 13E2IgG4mut; and 13E2IgK.

EXAMPLE 18

Humanized 13E2 Monoclonal Antibody (IMP761) Sequences

For optimal retention of CDR-loop conformation, combined IMGT/Kabat CDR sequence identification was used to graft CDRs from murine 13E2 to human frameworks in order to obtain a humanized version of 13E2. These synthetic chimeric sequences were subcloned into an expression vector, and expressed in CHO cells grown in suspension.

Heavy and light chain amino acid sequences of the humanized 13E2 monoclonal antibody (referred to as IMP761) are shown below. Variable domains are shown in bold, CDR sequences are shown underlined.

```
Amino acid sequence of IMP761 heavy chain
                                           (SEQ ID NO: 84)
MGWTLVFLFLLSVTAGVHSQITLKESGPTLVKPTQTLTLTCTFSGFSLST
SGMGLGWIRQPPGKTLEWLTHIWWDDIKRYNPDLRSRLSITKDTSKNQVV
LTMTNMDPLDTGTYYCARIVEGSYSSSYFDVWGQGTLVTVSSASTKGPSV
FPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVM
HEALHNHYTQKSLSLSLGK
```

Alignment of this sequence (IMP761 heavy chain) with the chimeric heavy chain sequence, 13E2IgG4mut, of Example 17 is shown in FIG. 23. In the figure, the $V_H$ region is shown in bold, and the Fc region is shown highlighted. Amino acid residues of the humanized IMP761 sequence that differ from corresponding residues of the chimeric 13E2IgG4mut sequence are single underlined. CDR sequences (based on the combined IMGT/Kabat CDR sequence identification) are shown double underlined. The changed residues in the humanized sequence are also set out in Table 26 below (as VH variant 4, $VH_4$, as well as the changed residues in three other humanized variants of the original 13E2 heavy chain sequence: VH variants 1, 2, and 3, $VH_1$, $VH_2$, and $VH_3$).

TABLE 26

| Heavy chain residue no. | 13E2 mouse heavy chain residue | Humanized residue | | | |
|---|---|---|---|---|---|
| | | $VH_1$ | $VH_2$ | $VH_3$ | $VH_4$ (IMP761) |
| 21 | V | | I | I | I |
| 26 | S | | | T | |
| 29 | G | A | A | T | T |
| 30 | I | L | L | L | L |
| 31 | L | V | V | V | V |

TABLE 26-continued

| Heavy chain residue no. | 13E2 mouse heavy chain residue | Humanized residue | | | |
|---|---|---|---|---|---|
| | | VH₁ | VH₂ | VH₃ | VH₄ (IMP761) |
| 32 | Q | K | K | K | K |
| 34 | S | T | T | T | T |
| 38 | S | T | T | T | T |
| 42 | S | T | | T | T |
| 62 | S | P | P | P | P |
| 65 | G | A | A | A | T |
| 69 | L | | | V | |
| 70 | T | A | A | | |
| 88 | L | | | V | |
| 89 | T | | | | S |
| 91 | S | | | R | T |
| 96 | S | K | K | K | K |
| 97 | S | | N | N | N |
| 99 | I | V | V | V | V |
| 100 | F | I | V | A | V |
| 102 | K | N | T | T | T |
| 103 | I | M | M | M | M |
| 104 | A | T | | T | T |
| 105 | S | N | N | N | N |
| 106 | V | M | M | M | M |
| 108 | T | P | P | P | P |
| 109 | A | V | V | L | L |
| 112 | A | | | G | G |
| 134 | A | Q | Q | Q | Q |
| 137 | T | | | L | L |

The heavy chain framework sequences of the humanized antibody (antibody IMP761) are:

```
                                        (SEQ ID NO: 64)
VH FR1: QITLKESGPTLVKPTQTLTLTCTFS;

(SEQ ID NO: 65)
VH FR2: WIRQPPGKTLEWLT;

(SEQ ID NO: 66)
VH FR3: RLSITKDTSKNQVVLTMTNMDPLDTGTYYC;
and (SEQ ID NO: 67)
VH FR4: WGQGTLVTVSS.
```

Amino acid sequence of IMP761 light chain
(SEQ ID NO: 85)
MVSSAQFLGLLLLCFQGTRCDIVMTQTPSSLSASVGDRVTITC<u>KASQDVI</u>
<u>FDVA</u>WYQQRPGQAPKLLIY<u>SASSRVS</u>GVPSRFSGSGSGTDFTLTISSLQP
EDFATYYC<u>QQHYSTPYT</u>FGQGTRLDIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Alignment of this sequence (IMP761 light chain) with the chimeric light chain sequence, 13E2IgK, of Example 17 is shown in FIG. 24. In the figure, the V_L region is shown in bold, and the IgK region is shown highlighted. Amino acid residues of the humanized IMP761 sequence that differ from corresponding residues of the chimeric 13E2IgK sequence are single underlined. CDR sequences (based on the combined IMGT/Kabat CDR sequence identification) are shown double underlined. The changed residues in the humanized sequence are set out in Table 27 below (as VL variant 3, VH₃, as well as the changed residues in three other humanized variants of the original 13E2 light chain sequence: VL variants 1, 2, and 4, VL₁, VL₂, and VL₄).

TABLE 27

| Light chain residue no. | 13E2 mouse light chain residue | Humanized residue | | | |
|---|---|---|---|---|---|
| | | VL₁ | VL₂ | VL₃ (IMP761) | VL₄ |
| 21 | D | | | | E |
| 23 | V | | Q | | |
| 24 | M | | | | L |
| 27 | P | S | S | T | S |
| 28 | H | P | P | P | P |
| 29 | K | D | S | S | D |
| 30 | F | S | S | S | S |
| 31 | M | L | L | L | L |
| 32 | S | A | | | A |
| 33 | T | V | A | A | V |
| 35 | V | L | | | L |
| 36 | E | G | G | G | G |
| 37 | D | E | | | E |
| 39 | V | A | | | A |
| 59 | K | | | R | |
| 60 | P | | | | A |
| 63 | S | P | A | A | |
| 69 | Y | | F | | |
| 80 | D | | | S | S |
| 83 | T | S | S | S | S |
| 93 | F | L | L | L | L |
| 96 | S | | | | D |
| 98 | V | L | L | L | L |

TABLE 27-continued

| Light chain residue no. | 13E2 mouse light chain residue | Humanized residue ||||
|---|---|---|---|---|---|
| | | VL$_1$ | VL$_2$ | VL$_3$ (IMP761) | VL$_4$ |
| 100 | A | | P | P | |
| 103 | L | V | F | F | V |
| 105 | V | | T | T | |
| 120 | G | Q | Q | Q | |
| 123 | T | K | K | R | K |
| 124 | L | | V | | V |
| 125 | E | | | D | |

The light chain framework sequences of the humanized antibody (antibody IMP761) are:

VL FR1: DIVMTQTPSSLSASVGDRVTITC; (SEQ ID NO: 64)

VL FR2: WYQQRPGQAPKLLIY; (SEQ ID NO: 65)

VL FR3: GVPSRFSGSGSGTDFTLTISSLQPEDFATYYC; (SEQ ID NO: 66)
and

VL FR4: FGQGTRLDIK (SEQ ID NO: 67)

EXAMPLE 19

Binding of Chimeric 13E2-Human Antibody (Chim13E2IgG4) and Humanized 13E2 Antibody (IMP761) to CHO-LAG-3+ Cells CHO cells expressing LAG-3 on their surface (0.05×10$^6$ cells/well in PBS, 0.5% BSA, 0.1% azide) were incubated with different concentrations of a chimeric 13E2-human antibody (referred to as Chim13E2IgG4) comprising the chimeric heavy and light chains described in Example 17 (heavy chain: 13E2IgG4mut; light chain: 13E2IgK), IMP761, or human IgG4 (as an isotype-matched negative control). Secondary antibody goat anti-human IgG-FITC was used to detect the presence of antibodies on the surface of the CHO-LAG-3+ cells. FITC mean fluorescence of intensity (MFI) was determined after analysis by flow cytometry.

The results are shown in Table 28 below, and in FIG. 25.

TABLE 28

| MFI FITC CHO cells ||||
|---|---|---|---|
| ng/ml | Chim13E2IgG4 | IMP761 | huigG4 |
| 6000 | 2039 | 2086 | 71 |
| 1905 | 2024 | 1989 | 77 |
| 605 | 1874 | 1821 | 46 |
| 192 | 1580 | 1429 | 59 |
| 61 | 1058 | 898 | 69 |
| 20 | 593 | 460 | 49 |
| 6 | 279 | 234 | 37 |
| 0 | 35 | 35 | 35 |

The results show that the humanized monoclonal antibody IMP761 binds to CHO cells expressing LAG-3 on their surface in a very similar manner to the chimeric antibody.

EXAMPLE 20

Binding Affinity of Chimeric 13E2-Human Antibody (Chim13E2IgG4) and Humanized 13E2 Antibody (IMP761) to Human LAG-3Ig Protein A Biacore™ surface plasmon resonance analysis was performed using the chimeric antibody Chim13E2IgG4 (comprising the chimeric heavy chain 13E2IgG4mut, and the chimeric light chain 13E2IgK, described in Example 17), or the humanized 13E2 antibody (IMP761) described in Example 18, covalently immobilized to a C1 sensor chip. The coating was performed in 10 mM sodium acetate, pH 5.0, to reach 13±1 RU. The recombinant human LAG-3Ig protein (IMP321) was then passed over the captured antibodies at 6 different concentrations, ranging from 0.078-2.5 nM, in analysis buffer (10 mM HEPES pH 7.4, 150 mM NaCl, 3 mM EDTA, 0.05% Tween 20) at 25° C., with regeneration in every cycle. The analysis was carried out on Biacore™ T200 and the data was fitted using the kinetic global fit (Langmuir 1:1) model. The kinetics parameters are recorded in Table 29, and represent the average of three runs.

TABLE 29

| Antibody | ka (M$^{-1}$s$^{-1}$) | kd (s$^{-1}$) | KD (pM) |
|---|---|---|---|
| Chim13E2IgG4 | 2.9 ± 0.2 × 10$^7$ | 6.4 ± 0.6 × 10$^{-4}$ | 21.9 ± 0.1 |
| IMP761 | 2.9 ± 0.2 × 10$^7$ | 6.6 ± 0.6 × 10$^{-4}$ | 22.8 ± 0.9 |

The results show that the humanized monoclonal antibody IMP761 has the same affinity to human LAG-3Ig protein as the chimeric antibody. Both antibodies display a very rapid association rate, which explains the high affinity of the 13E2-derived antibodies for LAG-3.

EXAMPLE 21

Effect of Humanized 13E2 Antibody (IMP761) on CD8$^+$ T Cell Proliferation and CD25 Expression Induced by Antigenic Stimulation CFSE-labelled PBMCs from healthy donors (0.2×10$^6$ cells/well in complete RPMI+10% FBS) were incubated with a pool of peptides covering the sequence of CMV pp35 in triplicate, with 300 ng/ml human IgG4 (isotype control), Chim13E2IgG4 or IMP761. The T cell response was evaluated by measuring the proliferation, evaluated using a proliferation index (calculated as the sum of the percentage of CD8$^+$ T cells under each division peak, multiplied by the division number), and the expression of CD25 at day 5 by flow cytometry. The percentage inhibition for each antibody, compared with the isotype-matched negative control (huIgG4), was calculated based on the proliferation index values, or the percentage of CD25$^+$ T cells within the CD8$^+$ T cell population.

The results are shown in Tables 30 and 31 below, and in FIGS. 26 and 27.

TABLE 30

| | | Proliferation index ||
|---|---|---|---|
| | | PI (CD8) | % inhibition |
| donor 1 | huIgG4 | 8.3 | |
| | Chim13E2IgG4 | 3.6 | 56.6 |
| | IMP761 | 3.9 | 53.0 |

TABLE 30-continued

Proliferation index

|  |  | PI (CD8) | % inhibition |
| --- | --- | --- | --- |
| donor 2 | huIgG4 | 29.4 | |
|  | Chim13E2IgG4 | 17.7 | 39.8 |
|  | IMP761 | 10.9 | 62.9 |
| donor 3 | huIgG4 | 3.7 | |
|  | Chim13E2IgG4 | 0.8 | 78.4 |
|  | IMP761 | 1.4 | 62.2 |
| donor 4 | huIgG4 | 9.7 | |
|  | Chim13E2IgG4 | 4.5 | 53.6 |
|  | IMP761 | 3.6 | 62.9 |
| Average | huIgG4 | 12.8 | |
|  | Chim13E2IgG4 | 6.7 | 57.1 |
|  | IMP761 | 5.0 | 60.2 |

TABLE 31

CD25 expression in CD8+ T cells

|  |  | % CD25 | % inhibition |
| --- | --- | --- | --- |
| donor 1 | huIgG4 | 3.3 | |
|  | Chim13E2IgG4 | 1.7 | 48.5 |
|  | IMP761 | 2.1 | 36.4 |
| donor 2 | huIgG4 | 15.1 | |
|  | Chim13E2IgG4 | 9.6 | 36.4 |
|  | IMP761 | 6.9 | 54.3 |
| donor 3 | huIgG4 | 3.3 | |
|  | Chim13E2IgG4 | 1.3 | 60.6 |
|  | IMP761 | 2.2 | 33.3 |
| donor 4 | huIgG4 | 5.1 | |
|  | Chim13E2IgG4 | 2.8 | 45.1 |
|  | IMP761 | 2.3 | 54.9 |
| Average | huIgG4 | 6.7 | |
|  | Chim13E2IgG4 | 3.9 | 47.7 |
|  | IMP761 | 3.4 | 44.7 |

The results show that the humanized monoclonal antibody IMP761 had a similar effect on inhibition of antigen-induced CD8+ T-cell proliferation, and CD25+ expression, as the chimeric antibody Chim13E2IgG4. Both antibodies caused, on average, approximately 60% inhibition of antigen-induced CD8+ T-cell proliferation, and approximately 45% inhibition of CD25+ T cells within the CD8+ T cell population.

EXAMPLE 22

Effect of Different Doses of Chimeric 13E2-Human Antibody (Chim13E2IgG4) and Humanized 13E2 Antibody (IMP761) on CD8+ T Cell Response CFSE-labelled PBMCs from healthy donors ($0.2 \times 10^6$ cells/well in complete RPMI+10% FBS) were incubated with a pool of peptides covering the sequence of CMV pp35 in triplicate, with different doses of Chim13E2IgG4, IMP761, or human IgG4 (an isotype-matched negative control). The T cell response was evaluated by measuring the proliferation (CFSE dilution) at day 5 by flow cytometry. The percentage of CD8+ T cells for each division number was calculated for the different antibody doses used.

The results are shown in Table 32 below, and in FIG. 28.

TABLE 32

| Antibody concentration (ng/ml) | Antibody | cell division | | | | | | |
| --- | --- | --- | --- | --- | --- | --- | --- | --- |
| | | 1 | 2 | 3 | 4 | 5 | 6 | 7 and more |
| 10 | huIgG4 | 2.3 | 5.1 | 5.9 | 3.7 | 1.6 | 0.5 | 0.3 |
|  | Chim13E2IgG4 | 1.9 | 4 | 4.4 | 2.6 | 1.1 | 0.4 | 0.1 |
|  | IMP761 | 2.2 | 2.6 | 3.5 | 2.1 | 0.9 | 0.3 | 0 |
| 30 | huIgG4 | 2.1 | 4.9 | 5.4 | 2.4 | 1.2 | 0.3 | 0.2 |
|  | Chim13E2IgG4 | 2.1 | 3.4 | 3.4 | 2 | 0.9 | 0.2 | 0.1 |
|  | IMP761 | 1.5 | 2.3 | 2.5 | 1.5 | 0.7 | 0.1 | 0 |
| 100 | huIgG4 | 1.9 | 4.3 | 4.4 | 2 | 0.6 | 0.3 | 0 |
|  | Chim13E2IgG4 | 1.2 | 1.4 | 1.9 | 0.9 | 0.6 | 0.2 | 0 |
|  | IMP761 | 1.4 | 1.6 | 1.7 | 0.9 | 0.3 | 0.1 | 0 |
| 300 | huIgG4 | 2.9 | 5.5 | 5.8 | 2.4 | 1.1 | 0.2 | 0.1 |
|  | Chim13E2IgG4 | 1.5 | 2.1 | 2.4 | 1.5 | 0.7 | 0.1 | 0.1 |
|  | IMP761 | 1.4 | 1.9 | 2.1 | 1.2 | 0.6 | 0.2 | 0.1 |
|  | Unstim | 1.2 | 0.1 | 0.1 | 0.1 | 0.1 | 0 | 0 |

The results show that the inhibitory effect of IMP761 and Chim13E2IgG4 on antigen-induced CD8+ T-cell proliferation was dose-dependent. In particular, the inhibitory effect of each antibody increased as the dose increased from 10 ng/ml to 100 ng/ml antibody. At 300 ng/ml antibody, the inhibitory effect was similar to that of 100 ng/ml antibody. The inhibitory effect of IMP761 was similar to that of Chim13E2IgG4 at all doses tested.

EXAMPLE 23

Humanized 13E2 Antibody (IMP761) does not Possess Cytotoxic Activity Against LAG-3-Expressing Cells Several types of assay were used to confirm that the humanized 13E2 antibody (IMP761) does not possess cytotoxic activity against LAG-3-expressing cells.
1) ADCC Reporter Bioassay (Promega, G7015)

In this assay, primary donor PBMC or NK cells are replaced with Jurkat cells stably expressing human FcγRIIIa (the high-affinity V158 receptor) and NFAT-responsive element driving expression of a luciferase reporter gene. If a test antibody has ADCC activity, it will bind together a target cell and the FcγRIIIa receptor of a Jurkat cell. Resulting activation of the signalling pathway downstream of the FcγRIIIa receptor results in NFAT pathway activation thereby inducing luciferase reporter gene expression. Luciferase activity is quantified by luminescence read-out.

LAG-3-transfected CHO and Jurkat cells, and PBMCs stimulated by SEB for 2 days to cause expression of LAG-3 (55% of the PBMCs were LAG-3$^+$), were used as targets cells to assay the ADCC activity of IMP761, compared with an isotype-matched negative control antibody, hIgG4 (recombinant mAb from BioRad). Anti-CD20 antibody and Raji cells, provided with the assay kit, were used as a positive control. The anti-CD20 antibody was also tested on SEB-stimulated PBMCs. The assays were carried out, following the manufacturer's instructions, using 75,000 effector cells with 12,500 target cells. After incubation for 6 hours at 37° C., Bio-Glo luciferase assay system was used, according to the manufacturer's instructions, to measure luminescence using a PerkinElmer EnVision 2103 luminometer (integration time of 0.5 sec/well).

The results are shown in Table 33 below, and in FIG. 29(a). The results are presented as the fold change in the relative luminescence unit (RLU), calculated by dividing the RLU obtained in the presence of the test antibody (at the maximal concentration recommended by the manufacturer, 3 µg/ml), by the RLU obtained without antibody.

TABLE 33

| Target cells | Fold change in RLU | | |
|---|---|---|---|
|  | anti-CD20 | hIgG4 | IMP761 |
| Raji | 36.8 |  |  |
| CHO-LAG3$^+$ |  | 1.4 | 1.1 |
| Jurkat WT |  | 2.3 | 0.9 |
| Jurkat-LAG3$^+$ |  | 2.5 | 1.2 |
| LAG3$^+$ PBMCs | 5.0 | 1.9 | 1.3 |

The results show that the fold change in RLU for IMP761 antibody was approximately 1-fold for each of the different target cells tested, irrespective of whether the target cell expresses LAG-3 or not. The fold change in RLU obtained for the isotype-matched negative control antibody, hIgG4, was slightly higher and ranged from a 1.4- to 2.5-fold for the different target cells. The positive control anti-CD20 antibody showed significant ADCC activity against the Raji cells (a B cell line), and against SEB-stimulated PBMCs, which contain a small percentage of B cells.

It was concluded from these results that the IMP761 antibody does not have any ADCC activity against LAG-3-expressing cells.

2) Conventional ADCC Assay

This assay uses PBMCs stimulated for one day in X-Vivo 10 medium (Lonza) with 100 IU/ml of IL-2 (Roche) and CFSE-labelled PBMCs, stimulated with SEB for two days to allow the expression of LAG-3 on T cells. The assay was carried out in X-Vivo 10 medium at a 50:1 effector:target ratio, with high dose (3 µg/ml) IMP761 or an isotype-matched negative control antibody, hIgG4. After 4 hours, the cell mixtures were harvested and stained for CD4, CD8, CD25 and LAG-3 using fluorochrome-conjugated antibodies. Cell viability in each blood cell population was then assessed by flow cytometry, after exclusion of cells which appeared positive for 7-Amino-Actinomycin D (7-AAD) staining, a fluorescent dye which labels cells which have lost their membranous integrity, a phenomenon which appears rapidly after cell death.

The results are shown in Table 34, and in FIGS. 29(b) and (c). The results are presented as the percentage of living CD4$^+$ or CD8$^+$ cells in the PBMC population (b), and the percentage of living LAG-3$^+$CD4$^+$ or LAG-3+CD8$^+$ cells in the PBMC population (c).

TABLE 34

|  | % living CD8$^+$ or CD4$^+$ cells in PBMC population | | | % living LAG-3$^+$CD8$^+$ or LAG-3$^+$CD4$^+$ cells in PBMC population | | |
|---|---|---|---|---|---|---|
|  | No Ab | hIgG4 | IMP761 | No Ab | hIgG4 | IMP761 |
| CD8$^+$ cells | 24.9 | 23.9 | 22.9 | 10.5 | 8.4 | 13.9 |
| CD4$^+$ cells | 43.3 | 41.0 | 44.1 | 14.0 | 9.0 | 17.1 |

The results show that IMP761 antibody does not reduce the percentage of CD8$^+$ or CD4$^+$ T cells in the PBMC population, or the percentage of LAG-3$^+$CD8$^+$ cytotoxic T cells, or LAG-3$^+$CD4$^+$ helper T cells in the PBMC population. The isotype-matched negative control antibody, hIgG4, caused a slight reduction in the viability of T cells in the PBMC population, especially of activated T cells expressing LAG-3.

It was concluded from these results that IMP761 antibody does not have any ADCC activity against LAG-3-expressing T cells.

3) CDC Assay

For CDC testing, SEB-stimulated cells, used as target cells, were incubated with 3 µg/ml of IMP761, an isotype-matched negative control antibody, hIgG4, a CDC-positive anti-CD3 control antibody (clone MEM-57, Cerdalane), or an isotype-matched negative control mouse antibody, mIgG2a, for 45 minutes in PBS, 0.5% BSA. Unbound antibodies were then washed away, and the cells were incubated with rabbit complement diluted by 3 volumes in RPMI medium for 1 hour at 37° C. The cells were stained for CD4, CD8, CD25 and LAG-3 using fluorochrome-conjugated antibodies. Cell viability in each blood cell population was then assessed by flow cytometry, after exclusion of cells labelled by 7-AAD.

The results are shown in Table 35, and in FIG. 30. The results are presented as the percentage of living CD4$^+$ or CD8$^+$ in the PBMC population (a), and the percentage of living LAG-3$^+$CD4$^+$ or LAG-3$^+$CD8$^+$ cells in the PBMC population (b).

TABLE 35

|  | % living CD8$^+$ or CD4$^+$ cells in PBMC population | | | | % living LAG3$^+$CD8$^+$ or LAG-3$^+$CD4$^+$ cells in PBMC population | | | |
|---|---|---|---|---|---|---|---|---|
|  | hIgG4 | IMP761 | mIgG2a | CD3 | hIgG4 | IMP761 | mIgG2a | CD3 |
| CD8$^+$ cells | 13.0 | 13.4 | 13.7 | 9.3 | 10.0 | 10.5 | 8.6 | 5.9 |
| CD4$^+$ cells | 35.8 | 36.6 | 32.9 | 26.9 | 13.3 | 13.9 | 12.1 | 8.9 |

The results show that IMP761 antibody does not reduce the percentage of CD8$^+$ or CD4$^+$ T cells in the PBMC population, or the percentage of LAG-3⁺CD8⁺ cytotoxic T cells, or LAG-3⁺CD4⁺ helper T cells in the PBMC population. As expected, the anti-CD3 positive control antibody did cause a decrease in the percentage of T cells in the PBMC population, and of activated T cells expressing LAG-3.

It was concluded from these results that IMP761 antibody does not have any CDC activity against LAG-3-expressing T cells.

4) Assessment of Cytotoxicity in T Cell Proliferation Assay

IMP761 antibody showed no cytotoxic activity in any of the short-term cytotoxicity assays described in (1)-(3) above. The cytotoxicity of IMP761 against LAG-3-expressing T cells was also evaluated after culturing antigen-stimulated PBMCs for several days. In a similar manner to the proliferation assays described in the previous examples, PBMCs from healthy donors ($0.2 \times 10^6$ cells/well in complete RPMI+10% FBS) were incubated in triplicate with a pool of peptides covering the sequence of CMV pp35, in the presence of 300 ng/ml IMP761, or human IgG4 (as an isotype-matched negative control). After three days, the percentage of CD8⁺ and CD4⁺ T cells gated in living lymphocytes, as well as the percentage of LAG-3⁺ cells in these T cell subsets, was measured by flow cytometry.

The results are shown in Table 36, and in FIG. 31.

TABLE 36

|  | % living CD8+ or CD4+ among lymphocytes | | | | % living LAG3+ among CD8+ or CD4+ lymphocytes | | | |
| --- | --- | --- | --- | --- | --- | --- | --- | --- |
|  | Donor 1 | | Donor 2 | | Donor 1 | | Donor 2 | |
|  | hIgG4 | IMP761 | hIgG4 | IMP761 | hIgG4 | IMP761 | hIgG4 | IMP761 |
| CD8+ cells | 13.9 | 13.9 | 36.3 | 36.2 | 3.2 | 3.8 | 0.9 | 1.2 |
| CD4+ cells | 35.8 | 36.6 | 35.3 | 35.3 | 2.6 | 3.4 | 2.5 | 2.8 |

The results show that IMP761 antibody does not reduce the percentage of CD8⁺ or CD4⁺ T cells in the lymphocyte population, or the percentage of LAG-3⁺CD8⁺ cytotoxic T cells, or LAG-3⁺CD4⁺ helper T cells in the lymphocyte population.

It was concluded from these results that IMP761 antibody does not show any cytotoxic activity against LAG-3-expressing T cells in this proliferation assay.

It was concluded from the results presented in this example that IMP761 antibody does not possess cytotoxic activity, so inhibition of antigen-induced T cell proliferation and activation by this antibody is not due to any cytotoxic activity against activated T cells.

The invention claimed is:

1. An isolated humanized antibody, or antigen-binding fragment thereof, that binds to lymphocyte activation gene-3 (LAG-3), comprising:
   a) an antibody VH region comprising a VH CDR1, a VH CDR2, and a VH CDR3, wherein the VH CDR1 has an amino acid sequence of SEQ ID NO:1, the VH CDR2 has an amino acid sequence of SEQ ID NO:2, and the VH CDR3 has an amino acid sequence of SEQ ID NO:3; and an antibody VL region comprising a VL CDR1, a VL CDR2, and a VL CDR3, wherein the VL CDR1 has an amino acid sequence of SEQ ID NO:4, the VL CDR2 has an amino acid sequence of SEQ ID NO:5, and the VL CDR3 has an amino acid sequence of SEQ ID NO:6; or
   b) an antibody VH region comprising a VH CDR1, a VH CDR2, and a VH CDR3, wherein the VH CDR1 has an amino acid sequence of SEQ ID NO:21, the VH CDR2 has an amino acid sequence of SEQ ID NO:22, and the VH CDR3 has an amino acid sequence of SEQ ID NO:23; and an antibody VL region comprising a VL CDR1, a VL CDR2, and a VL CDR3, wherein the VL CDR1 has an amino acid sequence of SEQ ID NO:24, the VL CDR2 has an amino acid sequence of SEQ ID NO:25, and the VL CDR3 has an amino acid sequence of SEQ ID NO:26; wherein:
   the antibody or antigen binding fragment thereof comprises a humanized light chain framework region which comprises:
   a VL framework region 1 (VL FR1) of SEQ ID NO: 68; a VL FR2 of SEQ ID NO: 69; a VL FR3 of SEQ ID NO: 70; and a VL FR4 of SEQ ID NO: 71;
   a VL framework region 1 (VL FR1) of SEQ ID NO: 72; a VL FR2 of SEQ ID NO: 73; a VL FR3 of SEQ ID NO: 74; and a VL FR4 of SEQ ID NO: 75;
   a VL framework region 1 (VL FR1) of SEQ ID NO: 76; a VL FR2 of SEQ ID NO: 77; a VL FR3 of SEQ ID NO: 78; and a VL FR4 of SEQ ID NO: 79; or
   a VL framework region 1 (VL FR1) of SEQ ID NO: 80; a VL FR2 of SEQ ID NO: 81; a VL FR3 of SEQ ID NO: 82; and a VL FR4 of SEQ ID NO: 83; and wherein the antibody or antigen binding fragment thereof comprises a humanized heavy chain framework region which comprises:
   a VH framework region I (VH FR1) of SEQ ID NO: 52; a VH FR2 of SEQ ID NO: 53; a VH FR3 of SEQ ID NO: 54; and a VH FR4 of SEQ ID NO: 55;
   a VH framework region 1 (VH FR1) of SEQ ID NO: 56; a VH FR2 of SEQ ID NO: 57; a VH FR3 of SEQ ID NO: 58; and a VH FR4 of SEQ ID NO: 59;
   a VH framework region 1 (VH FR1) of SEQ ID NO: 60; a VH FR2 of SEQ ID NO: 61; a VH FR3 of SEQ ID NO: 62; and a VH FR4 of SEQ ID NO: 63; or
   a VH framework region 1 (VH FR1) of SEQ ID NO: 64; a VH FR2 of SEQ ID NO: 65; a VH FR3 of SEQ ID NO: 66; and a VH FR4 of SEQ ID NO: 67.

2. An isolated humanized antibody, or antigen-binding fragment thereof, according to claim 1, which is a humanized monoclonal antibody, or antigen-binding fragment thereof.

3. An isolated humanized antibody, or antigen-binding fragment thereof, according to claim 1, which comprises an antibody VL region comprising:
   a VL FR1 having an amino acid sequence of SEQ ID NO: 68; a VL CDR1 having an amino acid sequence of SEQ ID NO: 4; a VL FR2 having an amino acid sequence of SEQ ID NO: 69; a VL CDR2 having an amino acid sequence of SEQ ID NO: 5; a VL FR3 having an amino acid sequence of SEQ ID NO: 70; a VL CDR3 having an amino acid sequence of SEQ ID NO: 6; and a VL FR4 having an amino acid sequence of SEQ ID NO: 71;
   a VL FR1 having an amino acid sequence of SEQ ID NO: 68; a VL CDR1 having an amino acid sequence of SEQ ID NO: 24; a VL FR2 having an amino acid sequence of SEQ ID NO: 69; a VL CDR2 having an amino acid sequence of SEQ ID NO: 25; a VL FR3 having an amino acid sequence of SEQ ID NO: 70; a VL CDR3 having an amino acid sequence of SEQ ID NO: 26; and a VL FR4 having an amino acid sequence of SEQ ID NO: 71;

a VL FR1 having an amino acid sequence of SEQ ID NO: 72; a VL CDR1 having an amino acid sequence of SEQ ID NO: 4; a VL FR2 having an amino acid sequence of SEQ ID NO: 73; a VL CDR2 having an amino acid sequence of SEQ ID NO: 5; a VL FR3 having an amino acid sequence of SEQ ID NO: 74; a VL CDR3 having an amino acid sequence of SEQ ID NO: 6; and a VL FR4 having an amino acid sequence of SEQ ID NO: 75;

a VL FR1 having an amino acid sequence of SEQ ID NO: 72; a VL CDR1 having an amino acid sequence of SEQ ID NO: 24; a VL FR2 having an amino acid sequence of SEQ ID NO: 73; a VL CDR2 having an amino acid sequence of SEQ ID NO: 25; a VL FR3 having an amino acid sequence of SEQ ID NO: 74; a VL CDR3 having an amino acid sequence of SEQ ID NO: 26; and a VL FR4 having an amino acid sequence of SEQ ID NO: 75;

a VL FR1 having an amino acid sequence of SEQ ID NO: 76; a VL CDR1 having an amino acid sequence of SEQ ID NO: 4; a VL FR2 having an amino acid sequence of SEQ ID NO: 77; a VL CDR2 having an amino acid sequence of SEQ ID NO: 5; a VL FR3 having an amino acid sequence of SEQ ID NO: 78; a VL CDR3 having an amino acid sequence of SEQ ID NO: 6; and a VL FR4 having an amino acid sequence of SEQ ID NO: 79;

a VL FR1 having an amino acid sequence of SEQ ID NO: 76; a VL CDR1 having an amino acid sequence of SEQ ID NO: 24; a VL FR2 having an amino acid sequence of SEQ ID NO: 77; a VL CDR2 having an amino acid sequence of SEQ ID NO: 25; a VL FR3 having an amino acid sequence of SEQ ID NO: 78; a VL CDR3 having an amino acid sequence of SEQ ID NO: 26; and a VL FR4 having an amino acid sequence of SEQ ID NO: 79;

a VL FR1 having an amino acid sequence of SEQ ID NO: 80; a VL CDR1 having an amino acid sequence of SEQ ID NO: 4; a VL FR2 having an amino acid sequence of SEQ ID NO: 81; a VL CDR2 having an amino acid sequence of SEQ ID NO: 5; a VL FR3 having an amino acid sequence of SEQ ID NO: 82; a VL CDR3 having an amino acid sequence of SEQ ID NO: 6; and a VL FR4 having an amino acid sequence of SEQ ID NO: 83; or a VL FR1 having an amino acid sequence of SEQ ID NO: 80; a VL CDR1 having an amino acid sequence of SEQ ID NO: 24; a VL FR2 having an amino acid sequence of SEQ ID NO: 81; a VL CDR2 having an amino acid sequence of SEQ ID NO: 25; a VL FR3 having an amino acid sequence of SEQ ID NO: 82; a VL CDR3 having an amino acid sequence of SEQ ID NO: 26; and a VL FR4 having an amino acid sequence of SEQ ID NO: 83.

4. An isolated humanized antibody, or antigen-binding fragment thereof, according to claim 1, which comprises an antibody VH region comprising:

a VH FR1 having an amino acid sequence of SEQ ID NO: 52; a VH CDR1 having an amino acid sequence of SEQ ID NO: 1; a VH FR2 having an amino acid sequence of SEQ ID NO: 53; a VH CDR2 having an amino acid sequence of SEQ ID NO: 2; a VH FR3 having an amino acid sequence of SEQ ID NO: 54; a VH CDR3 having an amino acid sequence of SEQ ID NO: 3; and a VH FR4 having an amino acid sequence of SEQ ID NO: 55;

a VH FR1 having an amino acid sequence of SEQ ID NO: 52; a VH CDR1 having an amino acid sequence of SEQ ID NO: 21; a VH FR2 having an amino acid sequence of SEQ ID NO: 53; a VH CDR2 having an amino acid sequence of SEQ ID NO: 22; a VH FR3 having an amino acid sequence of SEQ ID NO: 54; a VH CDR3 having an amino acid sequence of SEQ ID NO: 23; and a VH FR4 having an amino acid sequence of SEQ ID NO: 55;

a VH FR1 having an amino acid sequence of SEQ ID NO: 56; a VH CDR1 having an amino acid sequence of SEQ ID NO: 1; a VH FR2 having an amino acid sequence of SEQ ID NO: 57; a VH CDR2 having an amino acid sequence of SEQ ID NO: 2; a VH FR3 having an amino acid sequence of SEQ ID NO: 58; a VH CDR3 having an amino acid sequence of SEQ ID NO: 3; and a VH FR4 having an amino acid sequence of SEQ ID NO: 59;

a VH FR1 having an amino acid sequence of SEQ ID NO: 56; a VH CDR1 having an amino acid sequence of SEQ ID NO: 21; a VH FR2 having an amino acid sequence of SEQ ID NO: 57; a VH CDR2 having an amino acid sequence of SEQ ID NO: 22; a VH FR3 having an amino acid sequence of SEQ ID NO: 58; a VH CDR3 having an amino acid sequence of SEQ ID NO: 23; and a VH FR4 having an amino acid sequence of SEQ ID NO: 59;

a VH FR1 having an amino acid sequence of SEQ ID NO: 60; a VH CDR1 having an amino acid sequence of SEQ ID NO: 1; a VH FR2 having an amino acid sequence of SEQ ID NO: 61; a VH CDR2 having an amino acid sequence of SEQ ID NO: 2; a VH FR3 having an amino acid sequence of SEQ ID NO: 62; a VH CDR3 having an amino acid sequence of SEQ ID NO: 3; and a VH FR4 having an amino acid sequence of SEQ ID NO: 63;

a VH FR1 having an amino acid sequence of SEQ ID NO: 60; a VH CDR1 having an amino acid sequence of SEQ ID NO: 21; a VH FR2 having an amino acid sequence of SEQ ID NO: 61; a VH CDR2 having an amino acid sequence of SEQ ID NO: 22; a VH FR3 having an amino acid sequence of SEQ ID NO: 62; a VH CDR3 having an amino acid sequence of SEQ ID NO: 23; and a VH FR4 having an amino acid sequence of SEQ ID NO: 63;

a VH FR1 having an amino acid sequence of SEQ ID NO: 64; a VH CDR1 having an amino acid sequence of SEQ ID NO: 1; a VH FR2 having an amino acid sequence of SEQ ID NO: 65; a VH CDR2 having an amino acid sequence of SEQ ID NO: 2; a VH FR3 having an amino acid sequence of SEQ ID NO: 66; a VH CDR3 having an amino acid sequence of SEQ ID NO: 3; and a VH FR4 having an amino acid sequence of SEQ ID NO: 67; or a VH FR1 having an amino acid sequence of SEQ ID NO: 64; a VH CDR1 having an amino acid sequence of SEQ ID NO: 21; a VH FR2 having an amino acid sequence of SEQ ID NO: 65; a VH CDR2 having an amino acid sequence of SEQ ID NO: 22; a VH FR3 having an amino acid sequence of SEQ ID NO: 66; a VH CDR3 having an amino acid sequence of SEQ ID NO: 23; and a VH FR4 having an amino acid sequence of SEQ ID NO: 67.

5. An isolated antibody, or antigen-binding fragment thereof, that binds to lymphocyte activation gene-3 (LAG-3), which comprises:

an antibody VH region comprising: a VH FR1 having an amino acid sequence of SEQ ID NO: 64; a VH CDR1 having an amino acid sequence of SEQ ID NO: 1; a VH FR2 having an amino acid sequence of SEQ ID NO: 65; a VH CDR2 having an amino acid sequence of SEQ ID NO: 2; a VH FR3 having an amino acid sequence of SEQ ID NO: 66; a VH CDR3 having an amino acid sequence of SEQ ID NO: 3; and a VH FR4 having an amino acid sequence of SEQ ID NO: 67; and an antibody VL region comprising: a VL FR1 having an amino acid sequence of SEQ ID NO: 76; a VL CDR1 having an amino acid sequence of SEQ ID NO: 4; a VL FR2 having an amino acid sequence of SEQ ID NO: 77; a VL CDR2 having an amino acid sequence of SEQ ID NO: 5; a VL FR3 having an amino acid sequence of SEQ ID NO: 78; a VL CDR3 having an amino acid sequence of SEQ ID NO: 6; and a VL FR4 having an amino acid sequence of SEQ ID NO: 79.

6. An isolated antibody, or antigen-binding fragment thereof, that binds to lymphocyte activation gene-3 (LAG-3), which comprises:

an antibody VH region comprising: a VH FR1 having an amino acid sequence of SEQ ID NO: 64; a VH CDR1 having an amino acid sequence of SEQ ID NO: 21; a VH FR2 having an amino acid sequence of SEQ ID NO: 65; a VH CDR2 having an amino acid sequence of SEQ ID NO: 22; a VH FR3 having an amino acid sequence of SEQ ID NO: 66; a VH CDR3 having an amino acid sequence of SEQ ID NO: 23; and a VH FR4 having an amino acid sequence of SEQ ID NO: 67; and an antibody VL region comprising: a VL FR1 having an amino acid sequence of SEQ ID NO: 76; a VL CDR1 having an amino acid sequence of SEQ ID NO: 24; a VL FR2 having an amino acid sequence of SEQ ID NO: 77; a VL CDR2 having an amino acid sequence of SEQ ID NO: 25; a VL FR3 having an amino acid sequence of SEQ ID NO: 78; a VL CDR3 having an amino acid sequence of SEQ ID NO: 26; and a VL FR4 having an amino acid sequence of SEQ ID NO: 79.

7. An isolated humanized antibody, or antigen-binding fragment thereof, according to claim 1, which lacks complement-dependent cytotoxicity (CDC) and antibody-dependent cell-mediated cytotoxicity (ADCC) activity.

* * * * *

SEQUENCE LISTING

```
<160> NUMBER OF SEQ ID NOS: 85

<210> SEQ ID NO 1
<211> LENGTH: 10
<212> TYPE: PRT
<213> ORGANISM: Balb/c mouse

<400> SEQUENCE: 1

Gly Phe Ser Leu Ser Thr Ser Gly Met Gly
1               5                   10

<210> SEQ ID NO 2
<211> LENGTH: 7
<212> TYPE: PRT
<213> ORGANISM: Balb/c mouse

<400> SEQUENCE: 2

Ile Trp Trp Asp Asp Ile Lys
1               5

<210> SEQ ID NO 3
<211> LENGTH: 15
<212> TYPE: PRT
<213> ORGANISM: Balb/c mouse

<400> SEQUENCE: 3

Ala Arg Ile Val Glu Gly Ser Tyr Ser Ser Ser Tyr Phe Asp Val
1               5                   10                  15
```

<210> SEQ ID NO 4
<211> LENGTH: 6
<212> TYPE: PRT
<213> ORGANISM: Balb/c mouse

<400> SEQUENCE: 4

Gln Asp Val Ile Phe Asp
1               5

<210> SEQ ID NO 5
<211> LENGTH: 3
<212> TYPE: PRT
<213> ORGANISM: Balb/c mouse

<400> SEQUENCE: 5

Ser Ala Ser
1

<210> SEQ ID NO 6
<211> LENGTH: 9
<212> TYPE: PRT
<213> ORGANISM: Balb/c mouse

<400> SEQUENCE: 6

Gln Gln His Tyr Ser Thr Pro Tyr Thr
1               5

<210> SEQ ID NO 7
<211> LENGTH: 123
<212> TYPE: PRT
<213> ORGANISM: Balb/c mouse

<400> SEQUENCE: 7

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Gly Trp Ile Arg Gln Pro Ser Gly Lys Gly Leu Glu
        35                  40                  45

Trp Leu Thr His Ile Trp Trp Asp Asp Ile Lys Arg Tyr Asn Pro Asp
    50                  55                  60

Leu Arg Ser Arg Leu Thr Ile Ser Lys Asp Thr Ser Ser Ser Gln Ile
65                  70                  75                  80

Phe Leu Lys Ile Ala Ser Val Asp Thr Ala Asp Thr Ala Thr Tyr Tyr
                85                  90                  95

Cys Ala Arg Ile Val Glu Gly Ser Tyr Ser Ser Ser Tyr Phe Asp Val
            100                 105                 110

Trp Gly Ala Gly Thr Thr Val Thr Val Ser Ser
        115                 120

<210> SEQ ID NO 8
<211> LENGTH: 107
<212> TYPE: PRT
<213> ORGANISM: Balb/c mouse

<400> SEQUENCE: 8

Asp Ile Val Met Thr Gln Pro His Lys Phe Met Ser Thr Ser Val Glu
1               5                   10                  15

Asp Arg Val Thr Ile Thr Cys Lys Ala Ser Gln Asp Val Ile Phe Asp
            20                  25                  30

Val Ala Trp Tyr Gln Gln Lys Pro Gly Gln Ser Pro Lys Leu Leu Ile
        35                  40                  45

Tyr Ser Ala Ser Ser Arg Val Ser Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Thr Leu Glu Ile Lys
            100                 105

<210> SEQ ID NO 9
<211> LENGTH: 370
<212> TYPE: DNA
<213> ORGANISM: Balb/c mouse

<400> SEQUENCE: 9
caggttactc tgaaagagtc tggccctggg atattgcagc cctcccagac cctcagtctg    60
acttgttctt tctctgggtt ttcactgagc acttctggta tgggtctagg ctggattcgt   120
cagccatcag ggaagggtct ggagtggctg acacacattt ggtgggatga tatcaagcgc   180
tataacccag acctgaggag ccgactgact atctccaagg atacctccag cagccagatt   240
ttcctcaaga tcgccagtgt ggacactgca gatactgcca catattactg tgctcgaata   300
gtggagggtt catacagtag tagttacttc gatgtctggg gcgcaggggac cacggtcacc   360 gtctcctcag                                                          370

<210> SEQ ID NO 10
<211> LENGTH: 322
<212> TYPE: DNA
<213> ORGANISM: Balb/c mouse

<400> SEQUENCE: 10
gacattgtga tgacccagcc tcacaaattc atgtccacat cagtggaaga cagggtcacc    60
atcacctgca aggccagtca ggatgtgatt tttgatgtag cctggtatca acagaaacca   120
ggacaatctc ctaaattact gatttactcg gcatcctccc gggtcagtgg agtccctgat   180
cgcttcactg gcagtggatc tgggacggat ttcactttca ccatcagtag tgtgcaggct   240
gaagacctgg cagtttatta ctgtcagcaa cactatagta ctccgtacac gttcggaggg   300
gggaccacgc tggaaataaa ac                                            322

<210> SEQ ID NO 11
<211> LENGTH: 10
<212> TYPE: PRT
<213> ORGANISM: Balb/c mouse

<400> SEQUENCE: 11

Gly Phe Ser Leu Asn Thr Ser Gly Met Gly
1               5                   10

<210> SEQ ID NO 12
<211> LENGTH: 7
<212> TYPE: PRT
<213> ORGANISM: Balb/c mouse

<400> SEQUENCE: 12

Ile Trp Trp Asp Asp Val Lys
1               5

<210> SEQ ID NO 13
<211> LENGTH: 15
<212> TYPE: PRT
<213> ORGANISM: Balb/c mouse

<400> SEQUENCE: 13

Ala Arg Ile Glu Gly Asp Thr Tyr Tyr Asp Tyr Tyr Phe Asp Tyr
1               5                   10                  15

<210> SEQ ID NO 14
<211> LENGTH: 6
<212> TYPE: PRT
<213> ORGANISM: Balb/c mouse

<400> SEQUENCE: 14

Gln Asp Val Ser Ile Ala
1               5

<210> SEQ ID NO 15
<211> LENGTH: 3
<212> TYPE: PRT
<213> ORGANISM: Balb/c mouse

<400> SEQUENCE: 15

Ser Ala Ser
1

<210> SEQ ID NO 16
<211> LENGTH: 9
<212> TYPE: PRT
<213> ORGANISM: Balb/c mouse

<400> SEQUENCE: 16

Gln Gln His Tyr Ser Ile Pro Trp Thr
1               5

<210> SEQ ID NO 17
<211> LENGTH: 123
<212> TYPE: PRT
<213> ORGANISM: Balb/c mouse

<400> SEQUENCE: 17

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
                20                  25                  30

Gly Met Gly Val Gly Trp Ile Arg Gln Pro Ser Gly Lys Gly Leu Glu
        35                  40                  45

Trp Leu Thr His Ile Trp Trp Asp Asp Val Lys Arg Tyr Asn Pro Ala
    50                  55                  60

Leu Lys Ser Arg Leu Thr Ile Ser Lys Asp Thr Ser Ser Ser Gln Val
65                  70                  75                  80

Phe Leu Lys Ile Ala Ser Val Asp Thr Ala Asp Thr Ala Thr Tyr Tyr
                85                  90                  95

Cys Ala Arg Ile Glu Gly Asp Thr Tyr Tyr Asp Tyr Tyr Phe Asp Tyr
            100                 105                 110

Trp Gly Gln Gly Val Thr Leu Thr Val Ser Ser
        115                 120

<210> SEQ ID NO 18

```
<211> LENGTH: 107
<212> TYPE: PRT
<213> ORGANISM: Balb/c mouse

<400> SEQUENCE: 18

Asp Ile Val Met Thr Gln Ser His Lys Leu Met Ser Thr Ser Val Gly
1               5                   10                  15

Asp Gly Leu Ser Ile Thr Cys Lys Ala Ser Gln Asp Val Ser Ile Ala
            20                  25                  30

Val Val Trp Tyr Gln Lys Pro Gly Gln Ser Pro Lys Leu Leu Ile
        35                  40                  45

Tyr Ser Ala Ser Phe Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ile Pro Trp
                85                  90                  95

Thr Phe Gly Gly Gly Thr Lys Leu Glu Ile Lys
            100                 105

<210> SEQ ID NO 19
<211> LENGTH: 370
<212> TYPE: DNA
<213> ORGANISM: Balb/c mouse

<400> SEQUENCE: 19
caggttactc tgaaagagtc tggccctggg atattgcagc cctcccagac cctcagtctg      60
acttgttctt tctctgggtt ttcactgaac acttctggta tgggtgtagg ctggattcgt     120
cagccatcag ggaagggtct ggagtggctg acacacattt ggtgggatga tgtcaagcgc     180
tataatccag ccctgaagag ccgactgact atctccaagg atacctccag cagccaggta     240
ttcctcaaga tcgccagtgt ggacactgca gatactgcca catactactg tgctcgaata     300
gagggggata cttactacga ctattacttt gactactggg gccaaggcgt cactctcaca     360
gtctcctcag                                                            370

<210> SEQ ID NO 20
<211> LENGTH: 322
<212> TYPE: DNA
<213> ORGANISM: Balb/c mouse

<400> SEQUENCE: 20
gacattgtga tgacccagtc tcacaaactc atgtccacat cagttggaga cgggctcagc      60
atcacctgca aggccagtca ggatgtgagc attgctgtag tctggtatca acagaaacca     120
ggacaatctc ctaaactgct gatttactcg gcatccttcc ggtacactgg agtccctgat     180
cgcttcactg gcagtggatc tgggacggat ttcactttca ccatcagcag tgtgcaggct     240
gaagacctgg cagtttatta ctgtcagcaa cattatagta ttccgtggac gttcggtgga     300
ggcaccaagc tggaaatcaa ac                                              322

<210> SEQ ID NO 21
<211> LENGTH: 7
<212> TYPE: PRT
<213> ORGANISM: Balb/c mouse

<400> SEQUENCE: 21

Thr Ser Gly Met Gly Leu Gly
1               5
```

<210> SEQ ID NO 22
<211> LENGTH: 16
<212> TYPE: PRT
<213> ORGANISM: Balb/c mouse

<400> SEQUENCE: 22

His Ile Trp Trp Asp Asp Ile Lys Arg Tyr Asn Pro Asp Leu Arg Ser
1               5                   10                  15

<210> SEQ ID NO 23
<211> LENGTH: 13
<212> TYPE: PRT
<213> ORGANISM: Balb/c mouse

<400> SEQUENCE: 23

Ile Val Glu Gly Ser Tyr Ser Ser Ser Tyr Phe Asp Val
1               5                   10

<210> SEQ ID NO 24
<211> LENGTH: 11
<212> TYPE: PRT
<213> ORGANISM: Balb/c mouse

<400> SEQUENCE: 24

Lys Ala Ser Gln Asp Val Ile Phe Asp Val Ala
1               5                   10

<210> SEQ ID NO 25
<211> LENGTH: 7
<212> TYPE: PRT
<213> ORGANISM: Balb/c mouse

<400> SEQUENCE: 25

Ser Ala Ser Ser Arg Val Ser
1               5

<210> SEQ ID NO 26
<211> LENGTH: 9
<212> TYPE: PRT
<213> ORGANISM: Balb/c mouse

<400> SEQUENCE: 26

Gln Gln His Tyr Ser Thr Pro Tyr Thr
1               5

<210> SEQ ID NO 27
<211> LENGTH: 502
<212> TYPE: PRT
<213> ORGANISM: Homo sapiens

<400> SEQUENCE: 27

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

```
Ser Val Gly Pro Gly Gly Leu Arg Ser Gly Arg Leu Pro Leu Gln Pro
            85                  90                  95
Arg Val Gln Leu Asp Glu Arg Gly Arg Gln Gly Asp Phe Ser Leu
        100                 105                 110
Trp Leu Arg Pro Ala Arg Arg Ala Asp Ala Gly Glu Tyr Arg Ala Ala
            115                 120                 125
Val His Leu Arg Asp Arg Ala Leu Ser Cys Arg Leu Arg Leu Arg Leu
    130                 135                 140
Gly Gln Ala Ser Met Thr Ala Ser Pro Gly Ser Leu Arg Ala Ser
145                 150                 155                 160
Asp Trp Val Ile Leu Asn Cys Ser Phe Ser Arg Pro Asp Arg Pro Ala
            165                 170                 175
Ser Val His Trp Phe Arg Asn Arg Gly Gln Gly Arg Val Pro Val Arg
            180                 185                 190
Glu Ser Pro His His Leu Ala Glu Ser Phe Leu Phe Leu Pro Gln
        195                 200                 205
Val Ser Pro Met Asp Ser Gly Pro Trp Gly Cys Ile Leu Thr Tyr Arg
    210                 215                 220
Asp Gly Phe Asn Val Ser Ile Met Tyr Asn Leu Thr Val Leu Gly Leu
225                 230                 235                 240
Glu Pro Pro Thr Pro Leu Thr Val Tyr Ala Gly Ala Gly Ser Arg Val
            245                 250                 255
Gly Leu Pro Cys Arg Leu Pro Ala Gly Val Gly Thr Arg Ser Phe Leu
            260                 265                 270
Thr Ala Lys Trp Thr Pro Pro Gly Gly Gly Pro Asp Leu Leu Val Thr
            275                 280                 285
Gly Asp Asn Gly Asp Phe Thr Leu Arg Leu Glu Asp Val Ser Gln Ala
    290                 295                 300
Gln Ala Gly Thr Tyr Thr Cys His Ile His Leu Gln Glu Gln Gln Leu
305                 310                 315                 320
Asn Ala Thr Val Thr Leu Ala Ile Ile Thr Val Thr Pro Lys Ser Phe
            325                 330                 335
Gly Ser Pro Gly Ser Leu Gly Lys Leu Leu Cys Glu Val Thr Pro Val
            340                 345                 350
Ser Gly Gln Glu Arg Phe Val Trp Ser Ser Leu Asp Thr Pro Ser Gln
            355                 360                 365
Arg Ser Phe Ser Gly Pro Trp Leu Glu Ala Gln Glu Ala Gln Leu Leu
        370                 375                 380
Ser Gln Pro Trp Gln Cys Gln Leu Tyr Gln Gly Glu Arg Leu Leu Gly
385                 390                 395                 400
Ala Ala Val Tyr Phe Thr Glu Leu Ser Ser Pro Gly Ala Gln Arg Ser
            405                 410                 415
Gly Arg Ala Pro Gly Ala Leu Pro Ala Gly His Leu Leu Phe Leu
        420                 425                 430
Thr Leu Gly Val Leu Ser Leu Leu Leu Val Thr Gly Ala Phe Gly
            435                 440                 445
Phe His Leu Trp Arg Arg Gln Trp Arg Pro Arg Arg Phe Ser Ala Leu
    450                 455                 460
Glu Gln Gly Ile His Pro Gln Ala Gln Ser Lys Ile Glu Glu Leu Glu
465                 470                 475                 480
Gln Glu Pro Glu Pro Glu Pro Glu Pro Glu Pro Glu Pro Glu Pro Glu
            485                 490                 495
Pro Glu Pro Glu Gln Leu
```

-continued

<210> SEQ ID NO 28
<211> LENGTH: 149
<212> TYPE: PRT
<213> ORGANISM: Homo sapiens

<400> SEQUENCE: 28

```
Leu Gln Pro Gly Ala Glu Val Pro Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met
145
```

<210> SEQ ID NO 29
<211> LENGTH: 90
<212> TYPE: PRT
<213> ORGANISM: Homo sapiens

<400> SEQUENCE: 29

```
Thr Ala Ser Pro Pro Gly Ser Leu Arg Ala Ser Asp Trp Val Ile Leu
1               5                   10                  15

Asn Cys Ser Phe Ser Arg Pro Asp Arg Pro Ala Ser Val His Trp Phe
                20                  25                  30

Arg Asn Arg Gly Gln Gly Arg Val Pro Val Arg Glu Ser Pro His His
            35                  40                  45

His Leu Ala Glu Ser Phe Leu Phe Leu Pro Gln Val Ser Pro Met Asp
        50                  55                  60

Ser Gly Pro Trp Gly Cys Ile Leu Thr Tyr Arg Asp Gly Phe Asn Val
65                  70                  75                  80

Ser Ile Met Tyr Asn Leu Thr Val Leu Gly
                85                  90
```

<210> SEQ ID NO 30
<211> LENGTH: 469
<212> TYPE: PRT
<213> ORGANISM: Artificial
<220> FEATURE:
<223> OTHER INFORMATION: VH domain of mouse monoclonal antibody 13E2,
      and a human IgG4 Fc portion with an S228P mutation

<400> SEQUENCE: 30

```
Met Gly Trp Thr Leu Val Phe Leu Phe Leu Leu Ser Val Thr Ala Gly
1               5                   10                  15
```

```
Val His Ser Gln Val Thr Leu Lys Glu Ser Gly Pro Gly Ile Leu Gln
             20                  25                  30

Pro Ser Gln Thr Leu Ser Leu Thr Cys Ser Phe Ser Gly Phe Ser Leu
             35                  40                  45

Ser Thr Ser Gly Met Gly Leu Gly Trp Ile Arg Gln Pro Ser Gly Lys
 50                  55                  60

Gly Leu Glu Trp Leu Thr His Ile Trp Trp Asp Asp Ile Lys Arg Tyr
 65                  70                  75                  80

Asn Pro Asp Leu Arg Ser Arg Leu Thr Ile Ser Lys Asp Thr Ser Ser
                 85                  90                  95

Ser Gln Ile Phe Leu Lys Ile Ala Ser Val Asp Thr Ala Asp Thr Ala
             100                 105                 110

Thr Tyr Tyr Cys Ala Arg Ile Val Glu Gly Ser Tyr Ser Ser Ser Tyr
             115                 120                 125

Phe Asp Val Trp Gly Ala Gly Thr Thr Val Thr Val Ser Ser Ala Ser
         130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
             165                 170                 175

Glu Pro Val Thr Val Ser Trp Asn Ser Gly Ala Leu Thr Ser Gly Val
             180                 185                 190

His Thr Phe Pro Ala Val Leu Gln Ser Ser Gly Leu Tyr Ser Leu Ser
         195                 200                 205

Ser Val Val Thr Val Pro Ser Ser Leu Gly Thr Lys Thr Tyr Thr
             210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Pro Cys Pro Ala Pro Glu Phe
             245                 250                 255

Leu Gly Gly Pro Ser Val Phe Leu Phe Pro Pro Lys Pro Lys Asp Thr
             260                 265                 270

Leu Met Ile Ser Arg Thr Pro Glu Val Thr Cys Val Val Val Asp Val
             275                 280                 285

Ser Gln Glu Asp Pro Glu Val Gln Phe Asn Trp Tyr Val Asp Gly Val
290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
             325                 330                 335

Asn Gly Lys Glu Tyr Lys Cys Lys Val Ser Asn Lys Gly Leu Pro Ser
             340                 345                 350

Ser Ile Glu Lys Thr Ile Ser Lys Ala Lys Gly Gln Pro Arg Glu Pro
         355                 360                 365

Gln Val Tyr Thr Leu Pro Pro Ser Gln Glu Glu Met Thr Lys Asn Gln
     370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
             405                 410                 415

Pro Pro Val Leu Asp Ser Asp Gly Ser Phe Phe Leu Tyr Ser Arg Leu
             420                 425                 430
```

```
Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys
465

<210> SEQ ID NO 31
<211> LENGTH: 7
<212> TYPE: PRT
<213> ORGANISM: Balb/c mouse

<400> SEQUENCE: 31

Thr Ser Gly Met Gly Val Gly
1               5

<210> SEQ ID NO 32
<211> LENGTH: 16
<212> TYPE: PRT
<213> ORGANISM: Balb/c mouse

<400> SEQUENCE: 32

His Ile Trp Trp Asp Asp Val Lys Arg Tyr Asn Pro Ala Leu Lys Ser
1               5                   10                  15

<210> SEQ ID NO 33
<211> LENGTH: 13
<212> TYPE: PRT
<213> ORGANISM: Balb/c mouse

<400> SEQUENCE: 33

Ile Glu Gly Asp Thr Tyr Tyr Asp Tyr Tyr Phe Asp Tyr
1               5                   10

<210> SEQ ID NO 34
<211> LENGTH: 11
<212> TYPE: PRT
<213> ORGANISM: Balb/c mouse

<400> SEQUENCE: 34

Lys Ala Ser Gln Asp Val Ser Ile Ala Val Val
1               5                   10

<210> SEQ ID NO 35
<211> LENGTH: 7
<212> TYPE: PRT
<213> ORGANISM: Balb/c mouse

<400> SEQUENCE: 35

Ser Ala Ser Phe Arg Tyr Thr
1               5

<210> SEQ ID NO 36
<211> LENGTH: 9
<212> TYPE: PRT
<213> ORGANISM: Balb/c mouse

<400> SEQUENCE: 36

Gln Gln His Tyr Ser Ile Pro Trp Thr
1               5

<210> SEQ ID NO 37
<211> LENGTH: 234
<212> TYPE: PRT
```

<213> ORGANISM: Artificial
<220> FEATURE:
<223> OTHER INFORMATION: VL domain of monoclonal antibody 13E2, and a wild-type human Ig kappa (IgK) chain C portion

<400> SEQUENCE: 37

Met Val Ser Ser Ala Gln Phe Leu Gly Leu Leu Leu Cys Phe Gln
1               5                   10                  15

Gly Thr Arg Cys Asp Ile Val Met Thr Gln Pro His Lys Phe Met Ser
                20                  25                  30

Thr Ser Val Glu Asp Arg Val Thr Ile Thr Cys Lys Ala Ser Gln Asp
            35                  40                  45

Val Ile Phe Asp Val Ala Trp Tyr Gln Gln Lys Pro Gly Gln Ser Pro
    50                  55                  60

Lys Leu Leu Ile Tyr Ser Ala Ser Ser Arg Val Ser Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Ser Thr Pro Tyr Thr Phe Gly Gly Gly Thr Thr Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 38
<211> LENGTH: 525
<212> TYPE: PRT
<213> ORGANISM: Homo sapiens

<400> SEQUENCE: 38

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly

```
                100                 105                    110
Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
                195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
                275                 280                 285

Gly Thr Arg Ser Phe Leu Thr Ala Lys Trp Thr Pro Pro Gly Gly Gly
                290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
                355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
                420                 425                 430

Pro Gly Ala Gln Arg Ser Gly Arg Ala Pro Gly Ala Leu Pro Ala Gly
                435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Pro Glu Gln Leu
                515                 520                 525
```

<210> SEQ ID NO 39
<211> LENGTH: 91
<212> TYPE: PRT
<213> ORGANISM: Homo sapiens

<400> SEQUENCE: 39

Leu Glu Pro Pro Thr Pro Leu Thr Val Tyr Ala Gly Ala Gly Ser Arg
1               5                   10                  15

Val Gly Leu Pro Cys Arg Leu Pro Ala Gly Val Gly Thr Arg Ser Phe
            20                  25                  30

Leu Thr Ala Lys Trp Thr Pro Pro Gly Gly Gly Pro Asp Leu Leu Val
        35                  40                  45

Thr Gly Asp Asn Gly Asp Phe Thr Leu Arg Leu Glu Asp Val Ser Gln
    50                  55                  60

Ala Gln Ala Gly Thr Tyr Thr Cys His Ile His Leu Gln Glu Gln Gln
65                  70                  75                  80

Leu Asn Ala Thr Val Thr Leu Ala Ile Ile Thr
                85                  90

<210> SEQ ID NO 40
<211> LENGTH: 30
<212> TYPE: PRT
<213> ORGANISM: Homo sapiens

<400> SEQUENCE: 40

Gly Pro Pro Ala Ala Ala Pro Gly His Pro Leu Ala Pro Gly Pro His
1               5                   10                  15

Pro Ala Ala Pro Ser Ser Trp Gly Pro Arg Pro Arg Arg Tyr
            20                  25                  30

<210> SEQ ID NO 41
<211> LENGTH: 9
<212> TYPE: PRT
<213> ORGANISM: Artificial
<220> FEATURE:
<223> OTHER INFORMATION: Hemagglutinin epitope tag

<400> SEQUENCE: 41

Tyr Pro Tyr Asp Val Pro Asp Tyr Ala
1               5

<210> SEQ ID NO 42
<211> LENGTH: 8
<212> TYPE: PRT
<213> ORGANISM: Artificial
<220> FEATURE:
<223> OTHER INFORMATION: FLAG epitope tag

<400> SEQUENCE: 42

Asp Tyr Lys Asp Asp Asp Asp Lys
1               5

<210> SEQ ID NO 43
<211> LENGTH: 10
<212> TYPE: PRT
<213> ORGANISM: Artificial
<220> FEATURE:
<223> OTHER INFORMATION: c-myc epitope tag

<400> SEQUENCE: 43

Glu Gln Lys Leu Ile Ser Glu Glu Asp Leu
1               5                   10

```
<210> SEQ ID NO 44
<211> LENGTH: 5
<212> TYPE: PRT
<213> ORGANISM: Artificial
<220> FEATURE:
<223> OTHER INFORMATION: His5 affinity domain

<400> SEQUENCE: 44

His His His His His
1               5

<210> SEQ ID NO 45
<211> LENGTH: 6
<212> TYPE: PRT
<213> ORGANISM: Artificial
<220> FEATURE:
<223> OTHER INFORMATION: HisX6 affinity domain

<400> SEQUENCE: 45

His His His His His His
1               5

<210> SEQ ID NO 46
<211> LENGTH: 10
<212> TYPE: PRT
<213> ORGANISM: Artificial
<220> FEATURE:
<223> OTHER INFORMATION: c-myc affinity domain

<400> SEQUENCE: 46

Glu Gln Lys Leu Ile Ser Glu Glu Asp Leu
1               5                   10

<210> SEQ ID NO 47
<211> LENGTH: 8
<212> TYPE: PRT
<213> ORGANISM: Artificial
<220> FEATURE:
<223> OTHER INFORMATION: StrepTag affinity domain

<400> SEQUENCE: 47

Trp Ser His Pro Gln Phe Glu Lys
1               5

<210> SEQ ID NO 48
<211> LENGTH: 5
<212> TYPE: PRT
<213> ORGANISM: Artificial
<220> FEATURE:
<223> OTHER INFORMATION: Affinity domain

<400> SEQUENCE: 48

Arg Tyr Ile Arg Ser
1               5

<210> SEQ ID NO 49
<211> LENGTH: 4
<212> TYPE: PRT
<213> ORGANISM: Artificial
<220> FEATURE:
<223> OTHER INFORMATION: Affinity domain

<400> SEQUENCE: 49

Phe His His Thr
1
```

-continued

```
<210> SEQ ID NO 50
<211> LENGTH: 17
<212> TYPE: PRT
<213> ORGANISM: Artificial
<220> FEATURE:
<223> OTHER INFORMATION: Affinity domain

<400> SEQUENCE: 50

Trp Glu Ala Ala Ala Arg Glu Ala Cys Cys Arg Glu Cys Cys Ala Arg
1               5                   10                  15

Ala

<210> SEQ ID NO 51
<211> LENGTH: 82
<212> TYPE: PRT
<213> ORGANISM: Homo sapiens

<400> SEQUENCE: 51

Val Thr Pro Lys Ser Phe Gly Ser Pro Gly Ser Leu Gly Lys Leu Leu
1               5                   10                  15

Cys Glu Val Thr Pro Val Ser Gly Gln Glu Arg Phe Val Trp Ser Ser
            20                  25                  30

Leu Asp Thr Pro Ser Gln Arg Ser Phe Ser Gly Pro Trp Leu Glu Ala
        35                  40                  45

Gln Glu Ala Gln Leu Leu Ser Gln Pro Trp Gln Cys Gln Leu Tyr Gln
    50                  55                  60

Gly Glu Arg Leu Leu Gly Ala Ala Val Tyr Phe Thr Glu Leu Ser Ser
65                  70                  75                  80

Pro Gly

<210> SEQ ID NO 52
<211> LENGTH: 25
<212> TYPE: PRT
<213> ORGANISM: Artificial
<220> FEATURE:
<223> OTHER INFORMATION: Humanized framework sequence

<400> SEQUENCE: 52

Gln Val Thr Leu Lys Glu Ser Gly Pro Ala Leu Val Lys Pro Thr Gln
1               5                   10                  15

Thr Leu Thr Leu Thr Cys Thr Phe Ser
            20                  25

<210> SEQ ID NO 53
<211> LENGTH: 14
<212> TYPE: PRT
<213> ORGANISM: Artificial
<220> FEATURE:
<223> OTHER INFORMATION: Humanized framework sequence

<400> SEQUENCE: 53

Trp Ile Arg Gln Pro Pro Gly Lys Ala Leu Glu Trp Leu Ala
1               5                   10

<210> SEQ ID NO 54
<211> LENGTH: 30
<212> TYPE: PRT
<213> ORGANISM: Artificial
<220> FEATURE:
<223> OTHER INFORMATION: Humanized framework sequence

<400> SEQUENCE: 54
```

-continued

Arg Leu Thr Ile Ser Lys Asp Thr Ser Lys Ser Gln Val Ile Leu Asn
1               5                   10                  15

Met Thr Asn Met Asp Pro Val Asp Thr Ala Tyr Tyr Cys
            20                  25                  30

<210> SEQ ID NO 55
<211> LENGTH: 11
<212> TYPE: PRT
<213> ORGANISM: Artificial
<220> FEATURE:
<223> OTHER INFORMATION: Humanized framework sequence

<400> SEQUENCE: 55

Trp Gly Gln Gly Thr Thr Val Thr Val Ser Ser
1               5                   10

<210> SEQ ID NO 56
<211> LENGTH: 25
<212> TYPE: PRT
<213> ORGANISM: Artificial
<220> FEATURE:
<223> OTHER INFORMATION: Humanized framework sequence

<400> SEQUENCE: 56

Gln Ile Thr Leu Lys Glu Ser Gly Pro Ala Leu Val Lys Pro Thr Gln
1               5                   10                  15

Thr Leu Thr Leu Thr Cys Ser Phe Ser
            20                  25

<210> SEQ ID NO 57
<211> LENGTH: 14
<212> TYPE: PRT
<213> ORGANISM: Artificial
<220> FEATURE:
<223> OTHER INFORMATION: Humanized framework sequence

<400> SEQUENCE: 57

Trp Ile Arg Gln Pro Pro Gly Lys Ala Leu Glu Trp Leu Ala
1               5                   10

<210> SEQ ID NO 58
<211> LENGTH: 30
<212> TYPE: PRT
<213> ORGANISM: Artificial
<220> FEATURE:
<223> OTHER INFORMATION: Humanized framework sequence

<400> SEQUENCE: 58

Arg Leu Thr Ile Ser Lys Asp Thr Ser Lys Asn Gln Val Val Leu Thr
1               5                   10                  15

Met Ala Asn Met Asp Pro Val Asp Thr Ala Thr Tyr Tyr Cys
            20                  25                  30

<210> SEQ ID NO 59
<211> LENGTH: 11
<212> TYPE: PRT
<213> ORGANISM: Artificial
<220> FEATURE:
<223> OTHER INFORMATION: Humanized framework sequence

<400> SEQUENCE: 59

Trp Gly Gln Gly Thr Thr Val Thr Val Ser Ser
1               5                   10

<210> SEQ ID NO 60

```
<211> LENGTH: 25
<212> TYPE: PRT
<213> ORGANISM: Artificial
<220> FEATURE:
<223> OTHER INFORMATION: Humanized framework sequence

<400> SEQUENCE: 60

Gln Ile Thr Leu Lys Glu Thr Gly Pro Thr Leu Val Lys Pro Thr Gln
1               5                   10                  15

Thr Leu Thr Leu Thr Cys Thr Phe Ser
            20                  25

<210> SEQ ID NO 61
<211> LENGTH: 14
<212> TYPE: PRT
<213> ORGANISM: Artificial
<220> FEATURE:
<223> OTHER INFORMATION: Humanized framework sequence

<400> SEQUENCE: 61

Trp Ile Arg Gln Pro Pro Gly Lys Ala Leu Glu Trp Val Thr
1               5                   10

<210> SEQ ID NO 62
<211> LENGTH: 30
<212> TYPE: PRT
<213> ORGANISM: Artificial
<220> FEATURE:
<223> OTHER INFORMATION: Humanized framework sequence

<400> SEQUENCE: 62

Arg Val Thr Ile Arg Lys Asp Thr Ser Lys Asn Gln Val Ala Leu Thr
1               5                   10                  15

Met Thr Asn Met Asp Pro Leu Asp Thr Gly Thr Tyr Tyr Cys
            20                  25                  30

<210> SEQ ID NO 63
<211> LENGTH: 11
<212> TYPE: PRT
<213> ORGANISM: Artificial
<220> FEATURE:
<223> OTHER INFORMATION: Humanized framework sequence

<400> SEQUENCE: 63

Trp Gly Gln Gly Thr Leu Val Thr Val Ser Ser
1               5                   10

<210> SEQ ID NO 64
<211> LENGTH: 25
<212> TYPE: PRT
<213> ORGANISM: Artificial
<220> FEATURE:
<223> OTHER INFORMATION: Humanized framework sequence

<400> SEQUENCE: 64

Gln Ile Thr Leu Lys Glu Ser Gly Pro Thr Leu Val Lys Pro Thr Gln
1               5                   10                  15

Thr Leu Thr Leu Thr Cys Thr Phe Ser
            20                  25

<210> SEQ ID NO 65
<211> LENGTH: 14
<212> TYPE: PRT
<213> ORGANISM: Artificial
<220> FEATURE:
<223> OTHER INFORMATION: Humanized framework sequence
```

```
<400> SEQUENCE: 65

Trp Ile Arg Gln Pro Pro Gly Lys Thr Leu Glu Trp Leu Thr
1               5                   10

<210> SEQ ID NO 66
<211> LENGTH: 30
<212> TYPE: PRT
<213> ORGANISM: Artificial
<220> FEATURE:
<223> OTHER INFORMATION: Humanized framework sequence

<400> SEQUENCE: 66

Arg Leu Ser Ile Thr Lys Asp Thr Ser Lys Asn Gln Val Val Leu Thr
1               5                   10                  15

Met Thr Asn Met Asp Pro Leu Asp Thr Gly Thr Tyr Tyr Cys
            20                  25                  30

<210> SEQ ID NO 67
<211> LENGTH: 11
<212> TYPE: PRT
<213> ORGANISM: Artificial
<220> FEATURE:
<223> OTHER INFORMATION: Humanized framework sequence

<400> SEQUENCE: 67

Trp Gly Gln Gly Thr Leu Val Thr Val Ser Ser
1               5                   10

<210> SEQ ID NO 68
<211> LENGTH: 23
<212> TYPE: PRT
<213> ORGANISM: Artificial
<220> FEATURE:
<223> OTHER INFORMATION: Humanized framework sequence

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 69
<211> LENGTH: 15
<212> TYPE: PRT
<213> ORGANISM: Artificial
<220> FEATURE:
<223> OTHER INFORMATION: Humanized framework sequence

<400> SEQUENCE: 69

Trp Tyr Gln Gln Lys Pro Gly Gln Pro Pro Lys Leu Leu Ile Tyr
1               5                   10                  15

<210> SEQ ID NO 70
<211> LENGTH: 32
<212> TYPE: PRT
<213> ORGANISM: Artificial
<220> FEATURE:
<223> OTHER INFORMATION: Humanized framework sequence

<400> SEQUENCE: 70

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 71
<211> LENGTH: 10
<212> TYPE: PRT
<213> ORGANISM: Artificial
<220> FEATURE:
<223> OTHER INFORMATION: Humanized framework sequence

<400> SEQUENCE: 71

Phe Gly Gln Gly Thr Lys Leu Glu Ile Lys
1               5                   10

<210> SEQ ID NO 72
<211> LENGTH: 23
<212> TYPE: PRT
<213> ORGANISM: Artificial
<220> FEATURE:
<223> OTHER INFORMATION: Humanized framework sequence

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 73
<211> LENGTH: 15
<212> TYPE: PRT
<213> ORGANISM: Artificial
<220> FEATURE:
<223> OTHER INFORMATION: Humanized framework sequence

<400> SEQUENCE: 73

Trp Tyr Gln Gln Lys Pro Gly Gln Ala Pro Lys Leu Leu Ile Phe
1               5                   10                  15

<210> SEQ ID NO 74
<211> LENGTH: 32
<212> TYPE: PRT
<213> ORGANISM: Artificial
<220> FEATURE:
<223> OTHER INFORMATION: Humanized framework sequence

<400> SEQUENCE: 74

Gly Val Pro Ser Arg Phe Ser Gly Ser Gly Ser Gly Thr Asp Phe Thr
1               5                   10                  15

Leu Thr Leu Ser Ser Leu Gln Pro Glu Asp Phe Ala Thr Tyr Tyr Cys
            20                  25                  30

<210> SEQ ID NO 75
<211> LENGTH: 10
<212> TYPE: PRT
<213> ORGANISM: Artificial
<220> FEATURE:
<223> OTHER INFORMATION: Humanized framework sequence

<400> SEQUENCE: 75

Phe Gly Gln Gly Thr Lys Val Glu Ile Lys
1               5                   10

<210> SEQ ID NO 76
<211> LENGTH: 23
<212> TYPE: PRT
<213> ORGANISM: Artificial
<220> FEATURE:
<223> OTHER INFORMATION: Humanized framework sequence

<400> SEQUENCE: 76

Asp Ile Val Met Thr Gln Thr Pro Ser Ser Leu Ser Ala Ser Val Gly
1               5                   10                  15

Asp Arg Val Thr Ile Thr Cys
            20

<210> SEQ ID NO 77
<211> LENGTH: 15
<212> TYPE: PRT
<213> ORGANISM: Artificial
<220> FEATURE:
<223> OTHER INFORMATION: Humanized framework sequence

<400> SEQUENCE: 77

Trp Tyr Gln Gln Arg Pro Gly Gln Ala Pro Lys Leu Leu Ile Tyr
1               5                   10                  15

<210> SEQ ID NO 78
<211> LENGTH: 32
<212> TYPE: PRT
<213> ORGANISM: Artificial
<220> FEATURE:
<223> OTHER INFORMATION: Humanized framework sequence

<400> SEQUENCE: 78

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 79
<211> LENGTH: 10
<212> TYPE: PRT
<213> ORGANISM: Artificial
<220> FEATURE:
<223> OTHER INFORMATION: Humanized framework sequence

<400> SEQUENCE: 79

Phe Gly Gln Gly Thr Arg Leu Asp Ile Lys
1               5                   10

<210> SEQ ID NO 80
<211> LENGTH: 23
<212> TYPE: PRT
<213> ORGANISM: Artificial
<220> FEATURE:
<223> OTHER INFORMATION: Humanized framework sequence

<400> SEQUENCE: 80

Glu Ile Val Leu Thr Gln Ser Pro Asp Ser Leu Ala Val Ser Leu Gly
1               5                   10                  15

Glu Arg Ala Thr Ile Asn Cys
            20

<210> SEQ ID NO 81
<211> LENGTH: 15
<212> TYPE: PRT
<213> ORGANISM: Artificial
<220> FEATURE:
<223> OTHER INFORMATION: Humanized framework sequence

<400> SEQUENCE: 81

Trp Tyr Gln Gln Lys Ala Gly Gln Ser Pro Lys Leu Leu Ile Tyr
1               5                   10                  15

```
<210> SEQ ID NO 82
<211> LENGTH: 32
<212> TYPE: PRT
<213> ORGANISM: Artificial
<220> FEATURE:
<223> OTHER INFORMATION: Humanized framework sequence

<400> SEQUENCE: 82

Gly Val Pro Asp Arg Phe Ser Gly Ser Gly Ser Gly Thr Asp Phe Thr
1               5                   10                  15

Leu Thr Ile Asp Ser Leu Gln Ala Glu Asp Val Ala Val Tyr Tyr Cys
            20                  25                  30

<210> SEQ ID NO 83
<211> LENGTH: 10
<212> TYPE: PRT
<213> ORGANISM: Artificial
<220> FEATURE:
<223> OTHER INFORMATION: Humanized framework sequence

<400> SEQUENCE: 83

Phe Gly Gly Gly Thr Lys Val Glu Ile Lys
1               5                   10

<210> SEQ ID NO 84
<211> LENGTH: 469
<212> TYPE: PRT
<213> ORGANISM: Artificial
<220> FEATURE:
<223> OTHER INFORMATION: Heavy chain amino acid sequences of humanized
      13E2 monoclonal antibody

<400> SEQUENCE: 84

Met Gly Trp Thr Leu Val Phe Leu Phe Leu Leu Ser Val Thr Ala Gly
1               5                   10                  15

Val His Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Gly Leu Gly Trp Ile Arg Gln Pro Pro Gly Lys
    50                  55                  60

Thr Leu Glu Trp Leu Thr His Ile Trp Trp Asp Asp Ile Lys Arg Tyr
65                  70                  75                  80

Asn Pro Asp Leu Arg Ser Arg Leu Ser Ile Thr Lys Asp Thr Ser Lys
                85                  90                  95

Asn Gln Val Val Leu Thr Met Thr Asn Met Asp Pro Leu Asp Thr Gly
            100                 105                 110

Thr Tyr Tyr Cys Ala Arg Ile Val Glu Gly Ser Tyr Ser Ser Ser Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205
```

Ser Val Val Thr Val Pro Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Pro Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys
465

<210> SEQ ID NO 85
<211> LENGTH: 234
<212> TYPE: PRT
<213> ORGANISM: Artificial
<220> FEATURE:
<223> OTHER INFORMATION: Light chain amino acid sequence of humanized
      13E2 monoclonal antibody

<400> SEQUENCE: 85

Met Val Ser Ser Ala Gln Phe Leu Gly Leu Leu Leu Cys Phe Gln
1               5                   10                  15

Gly Thr Arg Cys Asp Ile Val Met Thr Gln Thr Pro Ser Ser Leu Ser
            20                  25                  30

Ala Ser Val Gly Asp Arg Val Thr Ile Thr Cys Lys Ala Ser Gln Asp
        35                  40                  45

Val Ile Phe Asp Val Ala Trp Tyr Gln Gln Arg Pro Gly Gln Ala Pro
    50                  55                  60

Lys Leu Leu Ile Tyr Ser Ala Ser Ser Arg Val Ser Gly Val Pro Ser
65                  70                  75                  80

Arg Phe Ser Gly Ser Gly Ser Gly Thr Asp Phe Thr Leu Thr Ile Ser

```
                85                    90                    95

Ser Leu Gln Pro Glu Asp Phe Ala Thr Tyr Tyr Cys Gln Gln His Tyr
            100                 105                 110

Ser Thr Pro Tyr Thr Phe Gly Gln Gly Thr Arg Leu Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```